(12) United States Patent
Cavaco Paulo et al.

(10) Patent No.: US 10,709,655 B2
(45) Date of Patent: *Jul. 14, 2020

(54) PEPTIDE COMPOSITION AND RESPECTIVE USES

(71) Applicant: UNIVERSIDADE DO MINHO, Braga (PT)

(72) Inventors: Artur Manuel Cavaco Paulo, Braga (PT); Celia Freitas Da Cruz, Guimaraes (PT); Margarida Maria Macedo Francesko Fernandes, Braga (PT)

(73) Assignee: UNIVERSIDADE DO MINHO, Braga (PT)

( * ) Notice: Subject to any disclaimer, the term of this patent is extended or adjusted under 35 U.S.C. 154(b) by 0 days.

This patent is subject to a terminal disclaimer.

(21) Appl. No.: 15/030,313

(22) PCT Filed: Oct. 16, 2014

(86) PCT No.: PCT/IB2014/065375
§ 371 (c)(1),
(2) Date: Apr. 18, 2016

(87) PCT Pub. No.: WO2015/056216
PCT Pub. Date: Apr. 23, 2015

(65) Prior Publication Data
US 2016/0271043 A1 Sep. 22, 2016

(30) Foreign Application Priority Data
Oct. 18, 2013 (PT) .......................... 107244

(51) Int. Cl.
*A61K 8/64* (2006.01)
*A61Q 5/06* (2006.01)
*A61Q 5/00* (2006.01)
*A61Q 5/04* (2006.01)

(52) U.S. Cl.
CPC ............... *A61K 8/64* (2013.01); *A61K 8/645* (2013.01); *A61Q 5/002* (2013.01); *A61Q 5/04* (2013.01); *A61Q 5/06* (2013.01); *A61Q 5/065* (2013.01); *A61K 2800/30* (2013.01)

(58) Field of Classification Search
CPC ...... A61K 2800/30; A61K 8/64; A61K 8/645; A61Q 5/002; A61Q 5/04; A61Q 5/06; A61Q 5/065
See application file for complete search history.

(56) References Cited

U.S. PATENT DOCUMENTS

| 5,028,419 A | 7/1991 | Pigiet |
| 5,635,170 A | 6/1997 | Lang et al. |
| 2010/0272666 A1 | 10/2010 | Breakspear et al. |

FOREIGN PATENT DOCUMENTS

| EP | 0488242 | 6/1992 | |
| EP | 1705188 A1 | 9/2006 | |
| FR | 2 706 300 A1 | 12/1994 | |
| FR | 2876286 A1 | 4/2006 | |
| JP | H06 56889 A | 3/1994 | |
| JP | WO 2005049834 A1 * | 6/2005 | ............... A61K 8/64 |
| PT | 103484 | 11/2007 | |
| WO | WO 97/11672 | 4/1997 | |
| WO | WO 2000/023039 | 4/2000 | |
| WO | WO 2000/051556 | 9/2000 | |
| WO | WO 2000/064405 | 11/2000 | |
| WO | WO 2004/048399 A2 | 6/2004 | |
| WO | WO 2005/049834 A1 | 6/2005 | |
| WO | WO 2006/001536 | 1/2006 | |
| WO | WO 2008/081348 | 7/2008 | |
| WO | WO 2011/072991 A1 | 6/2011 | |
| WO | WO 2012/13593 | 2/2012 | |

OTHER PUBLICATIONS

English Translation of Description for WO2005049834, accessed on Nov. 14, 2016.*
Dow, Carbowax Sentry Polyethylene Glycols, published online 2011.*
Naturally Curly, http://www.naturallycurly.com/curlreading/kinky-hair-type-4a/ingredients-commonly-used-in-hair-care-products-peg-modified-materials/, published online Jun. 8, 2010.*
Application No. JP2003-393014, publication No. is JP2005-151849, english translation of Description, published 2005.*
Application No. JP2003-393014, publication No. is JP2005-151849, english translation of Abstract, published 2005.*
Uniprot protein database, protein Type II hair keratin 1, protein accession Q9NSB5, accessed on Aug. 28, 2017.*
Anna Marabotti, The misuse of terms in scientific literature, vol. 26 No. 19 2010, p. 2498, Bioinformatics.*
Uniprot Protein Database, protein Accession P26371, accessed on Nov. 8, 2019.*
Uniprot Protein Database, protein Accession Q9NSB5, accessed on Nov. 8, 2019.*
International Search Report and Written Opinion in corresponding PCT Application No. PCT/IB2014/065375, dated Jun. 7, 2015.
International Preliminary Report on Patentability in corresponding PCT Application No. PCT/IB2014/065375, dated Apr. 19, 2016.
Fernandes, Margarida M., et al. "Keratin-based peptide: biological evaluation and strengthening properties on relaxed hair." International journal of cosmetic science 34.4 (2012): 338-346.

* cited by examiner

*Primary Examiner* — Rachael E Bredefeld
*Assistant Examiner* — Erinne R Dabkowski
(74) *Attorney, Agent, or Firm* — Leason Ellis LLP

(57) ABSTRACT

The present invention provides a composition that comprises at least one peptide with a sequence length of 6-12 amino acids, where 2-5 of those amino acids are cysteines for the treatment of the hair, including animal and human hair, without the use of chemicals harmful to the hair fiber and consumer health and uses of said compositions in shampoo, lotion, serum, cream, conditioner, foam, elixir, oil, aerosol or mask.

11 Claims, No Drawings
Specification includes a Sequence Listing.

SEQUENCE LISTING

<160> NUMBER OF SEQ ID NOS: 1239

<210> SEQ ID NO 1
<211> LENGTH: 10
<212> TYPE: PRT
<213> ORGANISM: Homo sapiens

<400> SEQUENCE: 1

Ala Pro Cys Ala Pro Arg Pro Ser Cys Gly
1               5                   10

<210> SEQ ID NO 2
<211> LENGTH: 10
<212> TYPE: PRT

-continued

<213> ORGANISM: Homo sapiens

<400> SEQUENCE: 2

Glu Ala Cys Val Pro Ser Val Pro Cys Pro
1               5                   10

<210> SEQ ID NO 3
<211> LENGTH: 10
<212> TYPE: PRT
<213> ORGANISM: Homo sapiens

<400> SEQUENCE: 3

Glu Ser Cys Gly Thr Ala Ser Gly Cys Ala
1               5                   10

<210> SEQ ID NO 4
<211> LENGTH: 10
<212> TYPE: PRT
<213> ORGANISM: Homo sapiens

<400> SEQUENCE: 4

Gly Leu Cys Ala Gly Thr Ser Ala Cys Leu
1               5                   10

<210> SEQ ID NO 5
<211> LENGTH: 10
<212> TYPE: PRT
<213> ORGANISM: Homo sapiens

<400> SEQUENCE: 5

Gly Val Cys Gly Pro Ser Pro Pro Cys Ile
1               5                   10

<210> SEQ ID NO 6
<211> LENGTH: 10
<212> TYPE: PRT
<213> ORGANISM: Homo sapiens

<400> SEQUENCE: 6

His Gly Cys Thr Leu Pro Gly Ala Cys Asn
1               5                   10

<210> SEQ ID NO 7
<211> LENGTH: 10
<212> TYPE: PRT
<213> ORGANISM: Homo sapiens

<400> SEQUENCE: 7

His Ser Cys Thr Leu Pro Gly Ala Cys Asn
1               5                   10

<210> SEQ ID NO 8
<211> LENGTH: 10
<212> TYPE: PRT
<213> ORGANISM: Homo sapiens

<400> SEQUENCE: 8

Lys Asp Cys Leu Gln Asn Ser Leu Cys Glu
1               5                   10

<210> SEQ ID NO 9
<211> LENGTH: 10
<212> TYPE: PRT
<213> ORGANISM: Homo sapiens

```
<400> SEQUENCE: 9

Leu Pro Cys Leu Pro Ala Ala Ser Cys Gly
1               5                   10

<210> SEQ ID NO 10
<211> LENGTH: 10
<212> TYPE: PRT
<213> ORGANISM: Homo sapiens

<400> SEQUENCE: 10

Leu Pro Cys Tyr Phe Thr Gly Ser Cys Asn
1               5                   10

<210> SEQ ID NO 11
<211> LENGTH: 10
<212> TYPE: PRT
<213> ORGANISM: Homo sapiens

<400> SEQUENCE: 11

Asn Phe Cys Leu Pro Ser Leu Ser Cys Arg
1               5                   10

<210> SEQ ID NO 12
<211> LENGTH: 10
<212> TYPE: PRT
<213> ORGANISM: Homo sapiens

<400> SEQUENCE: 12

Asn Pro Cys Ala Thr Thr Asn Ala Cys Asp
1               5                   10

<210> SEQ ID NO 13
<211> LENGTH: 10
<212> TYPE: PRT
<213> ORGANISM: Homo sapiens

<400> SEQUENCE: 13

Asn Pro Cys Ala Thr Thr Asn Ala Cys Glu
1               5                   10

<210> SEQ ID NO 14
<211> LENGTH: 10
<212> TYPE: PRT
<213> ORGANISM: Homo sapiens

<400> SEQUENCE: 14

Asn Pro Cys Ala Thr Thr Asn Ala Cys Ser
1               5                   10

<210> SEQ ID NO 15
<211> LENGTH: 10
<212> TYPE: PRT
<213> ORGANISM: Homo sapiens

<400> SEQUENCE: 15

Asn Pro Cys Gly Leu Arg Ala Arg Cys Gly
1               5                   10

<210> SEQ ID NO 16
<211> LENGTH: 10
<212> TYPE: PRT
<213> ORGANISM: Homo sapiens

<400> SEQUENCE: 16
```

Asn Pro Cys Gly Pro Arg Ser Arg Cys Gly
1               5                  10

<210> SEQ ID NO 17
<211> LENGTH: 10
<212> TYPE: PRT
<213> ORGANISM: Homo sapiens

<400> SEQUENCE: 17

Asn Pro Cys Ser Thr Pro Ala Ser Cys Thr
1               5                  10

<210> SEQ ID NO 18
<211> LENGTH: 10
<212> TYPE: PRT
<213> ORGANISM: Homo sapiens

<400> SEQUENCE: 18

Asn Pro Cys Ser Thr Ser Pro Ser Cys Val
1               5                  10

<210> SEQ ID NO 19
<211> LENGTH: 10
<212> TYPE: PRT
<213> ORGANISM: Homo sapiens

<400> SEQUENCE: 19

Pro Ala Cys Thr Ser Ser Ser Pro Cys Ser
1               5                  10

<210> SEQ ID NO 20
<211> LENGTH: 10
<212> TYPE: PRT
<213> ORGANISM: Homo sapiens

<400> SEQUENCE: 20

Ser Lys Cys His Glu Ser Thr Val Cys Pro
1               5                  10

<210> SEQ ID NO 21
<211> LENGTH: 10
<212> TYPE: PRT
<213> ORGANISM: Homo sapiens

<400> SEQUENCE: 21

Ser Pro Cys Val Pro Arg Thr Val Cys Val
1               5                  10

<210> SEQ ID NO 22
<211> LENGTH: 10
<212> TYPE: PRT
<213> ORGANISM: Homo sapiens

<400> SEQUENCE: 22

Ser Ser Cys Ser Val Glu Thr Ala Cys Leu
1               5                  10

<210> SEQ ID NO 23
<211> LENGTH: 10
<212> TYPE: PRT
<213> ORGANISM: Homo sapiens

<400> SEQUENCE: 23

Ser Val Cys Ser Ser Gly Val Asn Cys Arg
1               5                  10

<210> SEQ ID NO 24
<211> LENGTH: 10
<212> TYPE: PRT
<213> ORGANISM: Homo sapiens

<400> SEQUENCE: 24

Thr Ala Cys Pro Leu Pro Gly Thr Cys His
1               5                   10

<210> SEQ ID NO 25
<211> LENGTH: 10
<212> TYPE: PRT
<213> ORGANISM: Homo sapiens

<400> SEQUENCE: 25

Thr Asn Cys Ser Pro Arg Pro Ile Cys Val
1               5                   10

<210> SEQ ID NO 26
<211> LENGTH: 10
<212> TYPE: PRT
<213> ORGANISM: Homo sapiens

<400> SEQUENCE: 26

Thr Ser Cys Val Pro Pro Ala Pro Cys Thr
1               5                   10

<210> SEQ ID NO 27
<211> LENGTH: 10
<212> TYPE: PRT
<213> ORGANISM: Homo sapiens

<400> SEQUENCE: 27

Thr Thr Cys Thr Ser Ser Asn Thr Cys Glu
1               5                   10

<210> SEQ ID NO 28
<211> LENGTH: 10
<212> TYPE: PRT
<213> ORGANISM: Homo sapiens

<400> SEQUENCE: 28

Val Pro Cys Val Pro Ser Val Pro Cys Thr
1               5                   10

<210> SEQ ID NO 29
<211> LENGTH: 10
<212> TYPE: PRT
<213> ORGANISM: Homo sapiens

<400> SEQUENCE: 29

Ala Thr Cys Gly Pro Ser Ala Cys Ile Thr
1               5                   10

<210> SEQ ID NO 30
<211> LENGTH: 10
<212> TYPE: PRT
<213> ORGANISM: Homo sapiens

<400> SEQUENCE: 30

Gly Pro Cys Ile Ser Asn Pro Cys Gly Leu
1               5                   10

```
<210> SEQ ID NO 31
<211> LENGTH: 10
<212> TYPE: PRT
<213> ORGANISM: Homo sapiens

<400> SEQUENCE: 31

Gly Pro Cys Leu Ser Asn Pro Cys Thr Ser
1               5                   10

<210> SEQ ID NO 32
<211> LENGTH: 10
<212> TYPE: PRT
<213> ORGANISM: Homo sapiens

<400> SEQUENCE: 32

Gly Ser Cys Val Thr Asn Pro Cys Gly Pro
1               5                   10

<210> SEQ ID NO 33
<211> LENGTH: 10
<212> TYPE: PRT
<213> ORGANISM: Homo sapiens

<400> SEQUENCE: 33

Leu Thr Cys Phe Ser Ile Thr Cys Ser Ser
1               5                   10

<210> SEQ ID NO 34
<211> LENGTH: 10
<212> TYPE: PRT
<213> ORGANISM: Homo sapiens

<400> SEQUENCE: 34

Asn Pro Cys Ser Thr Pro Ser Cys Thr Thr
1               5                   10

<210> SEQ ID NO 35
<211> LENGTH: 10
<212> TYPE: PRT
<213> ORGANISM: Homo sapiens

<400> SEQUENCE: 35

Pro Ser Cys Val Thr Ala Pro Cys Ala Pro
1               5                   10

<210> SEQ ID NO 36
<211> LENGTH: 10
<212> TYPE: PRT
<213> ORGANISM: Homo sapiens

<400> SEQUENCE: 36

Ser Asp Cys Ser Ser Thr His Cys Ser Pro
1               5                   10

<210> SEQ ID NO 37
<211> LENGTH: 10
<212> TYPE: PRT
<213> ORGANISM: Homo sapiens

<400> SEQUENCE: 37

Ser Leu Cys Leu Pro Pro Thr Cys His Thr
1               5                   10

<210> SEQ ID NO 38
<211> LENGTH: 10
```

-continued

```
<212> TYPE: PRT
<213> ORGANISM: Homo sapiens

<400> SEQUENCE: 38

Ser Leu Cys Asn Leu Gly Ser Cys Gly Pro
1               5                   10

<210> SEQ ID NO 39
<211> LENGTH: 10
<212> TYPE: PRT
<213> ORGANISM: Homo sapiens

<400> SEQUENCE: 39

Ser Pro Cys Leu Val Gly Asn Cys Ala Trp
1               5                   10

<210> SEQ ID NO 40
<211> LENGTH: 10
<212> TYPE: PRT
<213> ORGANISM: Homo sapiens

<400> SEQUENCE: 40

Thr Ala Cys Leu Pro Gly Thr Cys Ala Thr
1               5                   10

<210> SEQ ID NO 41
<211> LENGTH: 10
<212> TYPE: PRT
<213> ORGANISM: Homo sapiens

<400> SEQUENCE: 41

Thr Ser Cys Leu Pro Ala Leu Cys Leu Pro
1               5                   10

<210> SEQ ID NO 42
<211> LENGTH: 10
<212> TYPE: PRT
<213> ORGANISM: Homo sapiens

<400> SEQUENCE: 42

Thr Ser Cys Ser Ser Arg Pro Cys Val Pro
1               5                   10

<210> SEQ ID NO 43
<211> LENGTH: 10
<212> TYPE: PRT
<213> ORGANISM: Homo sapiens

<400> SEQUENCE: 43

Thr Thr Cys Gly Gly Gly Ser Cys Gly Val
1               5                   10

<210> SEQ ID NO 44
<211> LENGTH: 10
<212> TYPE: PRT
<213> ORGANISM: Homo sapiens

<400> SEQUENCE: 44

Val Asn Cys Arg Pro Glu Leu Cys Leu Gly
1               5                   10

<210> SEQ ID NO 45
<211> LENGTH: 10
<212> TYPE: PRT
<213> ORGANISM: Homo sapiens
```

```
<400> SEQUENCE: 45

Tyr Val Cys Gln Pro Met Ala Cys Leu Pro
1               5                   10

<210> SEQ ID NO 46
<211> LENGTH: 10
<212> TYPE: PRT
<213> ORGANISM: Homo sapiens

<400> SEQUENCE: 46

Ala Phe Ser Cys Ile Ser Ala Cys Gly Pro
1               5                   10

<210> SEQ ID NO 47
<211> LENGTH: 10
<212> TYPE: PRT
<213> ORGANISM: Homo sapiens

<400> SEQUENCE: 47

Gly Ser Val Cys Ser Ala Pro Cys Asn Gly
1               5                   10

<210> SEQ ID NO 48
<211> LENGTH: 10
<212> TYPE: PRT
<213> ORGANISM: Homo sapiens

<400> SEQUENCE: 48

Gly Val Val Cys Gly Asp Leu Cys Ala Ser
1               5                   10

<210> SEQ ID NO 49
<211> LENGTH: 10
<212> TYPE: PRT
<213> ORGANISM: Homo sapiens

<400> SEQUENCE: 49

Gly Val Val Cys Gly Asp Leu Cys Val Ser
1               5                   10

<210> SEQ ID NO 50
<211> LENGTH: 10
<212> TYPE: PRT
<213> ORGANISM: Homo sapiens

<400> SEQUENCE: 50

Leu Thr Gly Cys Leu Leu Pro Cys Tyr Phe
1               5                   10

<210> SEQ ID NO 51
<211> LENGTH: 10
<212> TYPE: PRT
<213> ORGANISM: Homo sapiens

<400> SEQUENCE: 51

Asn Glu Asp Cys Lys Leu Pro Cys Asn Pro
1               5                   10

<210> SEQ ID NO 52
<211> LENGTH: 10
<212> TYPE: PRT
<213> ORGANISM: Homo sapiens

<400> SEQUENCE: 52
```

Asn Phe Ser Cys Val Ser Ala Cys Gly Pro
1               5                   10

<210> SEQ ID NO 53
<211> LENGTH: 10
<212> TYPE: PRT
<213> ORGANISM: Homo sapiens

<400> SEQUENCE: 53

Pro Pro Thr Cys His Thr Ala Cys Pro Leu
1               5                   10

<210> SEQ ID NO 54
<211> LENGTH: 10
<212> TYPE: PRT
<213> ORGANISM: Homo sapiens

<400> SEQUENCE: 54

Pro Gln Pro Cys Ala Thr Ala Cys Lys Pro
1               5                   10

<210> SEQ ID NO 55
<211> LENGTH: 10
<212> TYPE: PRT
<213> ORGANISM: Homo sapiens

<400> SEQUENCE: 55

Ser Glu Asp Cys Lys Leu Pro Cys Asn Pro
1               5                   10

<210> SEQ ID NO 56
<211> LENGTH: 10
<212> TYPE: PRT
<213> ORGANISM: Homo sapiens

<400> SEQUENCE: 56

Ser Leu Gly Cys Arg Thr Ser Cys Ser Ser
1               5                   10

<210> SEQ ID NO 57
<211> LENGTH: 10
<212> TYPE: PRT
<213> ORGANISM: Homo sapiens

<400> SEQUENCE: 57

Ser Leu Ser Cys Arg Thr Ser Cys Ser Ser
1               5                   10

<210> SEQ ID NO 58
<211> LENGTH: 10
<212> TYPE: PRT
<213> ORGANISM: Homo sapiens

<400> SEQUENCE: 58

Ser Ser Ser Cys Pro Leu Gly Cys Thr Met
1               5                   10

<210> SEQ ID NO 59
<211> LENGTH: 10
<212> TYPE: PRT
<213> ORGANISM: Homo sapiens

<400> SEQUENCE: 59

Thr Gly Ser Cys Asn Ser Pro Cys Leu Val

```
1               5                   10
```

<210> SEQ ID NO 60
<211> LENGTH: 10
<212> TYPE: PRT
<213> ORGANISM: Homo sapiens

<400> SEQUENCE: 60

```
Thr Ser Ser Cys Pro Leu Gly Cys Thr Met
1               5                   10
```

<210> SEQ ID NO 61
<211> LENGTH: 10
<212> TYPE: PRT
<213> ORGANISM: Homo sapiens

<400> SEQUENCE: 61

```
Val Gly Ser Cys Gly Ser Ser Cys Arg Lys
1               5                   10
```

<210> SEQ ID NO 62
<211> LENGTH: 10
<212> TYPE: PRT
<213> ORGANISM: Homo sapiens

<400> SEQUENCE: 62

```
Val Gly Val Cys Gly Gly Ser Cys Lys Arg
1               5                   10
```

<210> SEQ ID NO 63
<211> LENGTH: 10
<212> TYPE: PRT
<213> ORGANISM: Homo sapiens

<400> SEQUENCE: 63

```
Val Ser Asn Cys Asn Trp Phe Cys Glu Gly
1               5                   10
```

<210> SEQ ID NO 64
<211> LENGTH: 10
<212> TYPE: PRT
<213> ORGANISM: Homo sapiens

<400> SEQUENCE: 64

```
Ala Cys Gly Pro Arg Pro Gly Arg Cys Cys
1               5                   10
```

<210> SEQ ID NO 65
<211> LENGTH: 10
<212> TYPE: PRT
<213> ORGANISM: Homo sapiens

<400> SEQUENCE: 65

```
Ala Cys Gly Pro Arg Pro Ser Arg Cys Cys
1               5                   10
```

<210> SEQ ID NO 66
<211> LENGTH: 10
<212> TYPE: PRT
<213> ORGANISM: Homo sapiens

<400> SEQUENCE: 66

```
Cys Ala Pro Arg Pro Ser Cys Gly Pro Cys
1               5                   10
```

<210> SEQ ID NO 67
<211> LENGTH: 10
<212> TYPE: PRT
<213> ORGANISM: Homo sapiens

<400> SEQUENCE: 67

Cys Glu Pro Cys Ser Ala Tyr Val Ile Cys
1               5                   10

<210> SEQ ID NO 68
<211> LENGTH: 10
<212> TYPE: PRT
<213> ORGANISM: Homo sapiens

<400> SEQUENCE: 68

Cys Gly Leu Arg Ala Arg Cys Gly Pro Cys
1               5                   10

<210> SEQ ID NO 69
<211> LENGTH: 10
<212> TYPE: PRT
<213> ORGANISM: Homo sapiens

<400> SEQUENCE: 69

Cys Gly Pro Arg Pro Gly Arg Cys Cys Ile
1               5                   10

<210> SEQ ID NO 70
<211> LENGTH: 10
<212> TYPE: PRT
<213> ORGANISM: Homo sapiens

<400> SEQUENCE: 70

Cys Gly Pro Arg Pro Ser Arg Cys Cys Ile
1               5                   10

<210> SEQ ID NO 71
<211> LENGTH: 10
<212> TYPE: PRT
<213> ORGANISM: Homo sapiens

<400> SEQUENCE: 71

Cys Gly Pro Arg Ser Arg Cys Gly Pro Cys
1               5                   10

<210> SEQ ID NO 72
<211> LENGTH: 10
<212> TYPE: PRT
<213> ORGANISM: Homo sapiens

<400> SEQUENCE: 72

Cys Gly Thr Ser Gln Lys Gly Cys Cys Asn
1               5                   10

<210> SEQ ID NO 73
<211> LENGTH: 10
<212> TYPE: PRT
<213> ORGANISM: Homo sapiens

<400> SEQUENCE: 73

Cys His Gly Cys Thr Leu Pro Gly Ala Cys
1               5                   10

<210> SEQ ID NO 74

```
<210> SEQ ID NO 74
<211> LENGTH: 10
<212> TYPE: PRT
<213> ORGANISM: Homo sapiens

<400> SEQUENCE: 74

Cys His Ser Cys Thr Leu Pro Gly Ala Cys
1               5                   10

<210> SEQ ID NO 75
<211> LENGTH: 10
<212> TYPE: PRT
<213> ORGANISM: Homo sapiens

<400> SEQUENCE: 75

Cys Leu Pro Cys Leu Pro Ala Ala Ser Cys
1               5                   10

<210> SEQ ID NO 76
<211> LENGTH: 10
<212> TYPE: PRT
<213> ORGANISM: Homo sapiens

<400> SEQUENCE: 76

Cys Leu Pro Pro Thr Cys His Thr Ala Cys
1               5                   10

<210> SEQ ID NO 77
<211> LENGTH: 10
<212> TYPE: PRT
<213> ORGANISM: Homo sapiens

<400> SEQUENCE: 77

Cys Leu Ser Asn Pro Cys Thr Ser Cys Val
1               5                   10

<210> SEQ ID NO 78
<211> LENGTH: 10
<212> TYPE: PRT
<213> ORGANISM: Homo sapiens

<400> SEQUENCE: 78

Cys Leu Val Gly Asn Cys Ala Trp Cys Glu
1               5                   10

<210> SEQ ID NO 79
<211> LENGTH: 10
<212> TYPE: PRT
<213> ORGANISM: Homo sapiens

<400> SEQUENCE: 79

Cys Asn Pro Cys Ser Thr Pro Ala Ser Cys
1               5                   10

<210> SEQ ID NO 80
<211> LENGTH: 10
<212> TYPE: PRT
<213> ORGANISM: Homo sapiens

<400> SEQUENCE: 80

Cys Asn Pro Cys Ser Thr Pro Ser Cys Thr
1               5                   10

<210> SEQ ID NO 81
<211> LENGTH: 10
<212> TYPE: PRT
```

<213> ORGANISM: Homo sapiens

<400> SEQUENCE: 81

Cys Asn Pro Cys Ser Thr Ser Pro Ser Cys
1               5                   10

<210> SEQ ID NO 82
<211> LENGTH: 10
<212> TYPE: PRT
<213> ORGANISM: Homo sapiens

<400> SEQUENCE: 82

Cys Asn Ser Pro Cys Leu Val Gly Asn Cys
1               5                   10

<210> SEQ ID NO 83
<211> LENGTH: 10
<212> TYPE: PRT
<213> ORGANISM: Homo sapiens

<400> SEQUENCE: 83

Cys Arg Thr Ser Cys Ser Ser Arg Pro Cys
1               5                   10

<210> SEQ ID NO 84
<211> LENGTH: 10
<212> TYPE: PRT
<213> ORGANISM: Homo sapiens

<400> SEQUENCE: 84

Cys Ser Leu Lys Glu His Cys Ser Ala Cys
1               5                   10

<210> SEQ ID NO 85
<211> LENGTH: 10
<212> TYPE: PRT
<213> ORGANISM: Homo sapiens

<400> SEQUENCE: 85

Cys Ser Pro Arg Pro Ile Cys Val Pro Cys
1               5                   10

<210> SEQ ID NO 86
<211> LENGTH: 10
<212> TYPE: PRT
<213> ORGANISM: Homo sapiens

<400> SEQUENCE: 86

Cys Ser Ser Thr Met Ser Tyr Ser Cys Cys
1               5                   10

<210> SEQ ID NO 87
<211> LENGTH: 10
<212> TYPE: PRT
<213> ORGANISM: Homo sapiens

<400> SEQUENCE: 87

Cys Ser Thr Pro Ala Ser Cys Thr Ser Cys
1               5                   10

<210> SEQ ID NO 88
<211> LENGTH: 10
<212> TYPE: PRT
<213> ORGANISM: Homo sapiens

```
<400> SEQUENCE: 88

Cys Ser Thr Pro Ser Cys Thr Thr Cys Val
1               5                   10

<210> SEQ ID NO 89
<211> LENGTH: 10
<212> TYPE: PRT
<213> ORGANISM: Homo sapiens

<400> SEQUENCE: 89

Cys Thr Ser Cys Val Pro Pro Ala Pro Cys
1               5                   10

<210> SEQ ID NO 90
<211> LENGTH: 10
<212> TYPE: PRT
<213> ORGANISM: Homo sapiens

<400> SEQUENCE: 90

Cys Thr Ser Ser Asn Thr Cys Glu Pro Cys
1               5                   10

<210> SEQ ID NO 91
<211> LENGTH: 10
<212> TYPE: PRT
<213> ORGANISM: Homo sapiens

<400> SEQUENCE: 91

Cys Val Pro Pro Ala Pro Cys Thr Pro Cys
1               5                   10

<210> SEQ ID NO 92
<211> LENGTH: 10
<212> TYPE: PRT
<213> ORGANISM: Homo sapiens

<400> SEQUENCE: 92

Cys Val Pro Pro Ser Cys His Gly Cys Thr
1               5                   10

<210> SEQ ID NO 93
<211> LENGTH: 10
<212> TYPE: PRT
<213> ORGANISM: Homo sapiens

<400> SEQUENCE: 93

Cys Val Pro Pro Ser Cys His Ser Cys Thr
1               5                   10

<210> SEQ ID NO 94
<211> LENGTH: 10
<212> TYPE: PRT
<213> ORGANISM: Homo sapiens

<400> SEQUENCE: 94

Asp Cys Lys Leu Pro Cys Asn Pro Cys Ala
1               5                   10

<210> SEQ ID NO 95
<211> LENGTH: 10
<212> TYPE: PRT
<213> ORGANISM: Homo sapiens

<400> SEQUENCE: 95
```

```
Asp Cys Lys Leu Pro Cys Asn Pro Cys Ser
1               5                   10
```

<210> SEQ ID NO 96
<211> LENGTH: 10
<212> TYPE: PRT
<213> ORGANISM: Homo sapiens

<400> SEQUENCE: 96

```
Pro Cys Gly Thr Ser Gln Lys Gly Cys Cys
1               5                   10
```

<210> SEQ ID NO 97
<211> LENGTH: 10
<212> TYPE: PRT
<213> ORGANISM: Homo sapiens

<400> SEQUENCE: 97

```
Pro Cys Leu Ser Asn Pro Cys Thr Ser Cys
1               5                   10
```

<210> SEQ ID NO 98
<211> LENGTH: 10
<212> TYPE: PRT
<213> ORGANISM: Homo sapiens

<400> SEQUENCE: 98

```
Pro Cys Leu Val Gly Asn Cys Ala Trp Cys
1               5                   10
```

<210> SEQ ID NO 99
<211> LENGTH: 10
<212> TYPE: PRT
<213> ORGANISM: Homo sapiens

<400> SEQUENCE: 99

```
Pro Cys Asn Pro Cys Ser Thr Pro Ser Cys
1               5                   10
```

<210> SEQ ID NO 100
<211> LENGTH: 10
<212> TYPE: PRT
<213> ORGANISM: Homo sapiens

<400> SEQUENCE: 100

```
Pro Cys Ser Thr Pro Ser Cys Thr Thr Cys
1               5                   10
```

<210> SEQ ID NO 101
<211> LENGTH: 10
<212> TYPE: PRT
<213> ORGANISM: Homo sapiens

<400> SEQUENCE: 101

```
Pro Cys Thr Thr Cys Gly Pro Thr Cys Gly
1               5                   10
```

<210> SEQ ID NO 102
<211> LENGTH: 10
<212> TYPE: PRT
<213> ORGANISM: Homo sapiens

<400> SEQUENCE: 102

```
Pro Cys Val Pro Pro Ser Cys His Gly Cys
1               5                   10
```

<210> SEQ ID NO 103
<211> LENGTH: 10
<212> TYPE: PRT
<213> ORGANISM: Homo sapiens

<400> SEQUENCE: 103

Pro Cys Val Pro Pro Ser Cys His Ser Cys
1               5                   10

<210> SEQ ID NO 104
<211> LENGTH: 10
<212> TYPE: PRT
<213> ORGANISM: Homo sapiens

<400> SEQUENCE: 104

Ser Cys Cys Leu Pro Ser Leu Gly Cys Arg
1               5                   10

<210> SEQ ID NO 105
<211> LENGTH: 10
<212> TYPE: PRT
<213> ORGANISM: Homo sapiens

<400> SEQUENCE: 105

Ser Cys Ser Glu Glu Leu Gln Cys Cys Gln
1               5                   10

<210> SEQ ID NO 106
<211> LENGTH: 10
<212> TYPE: PRT
<213> ORGANISM: Homo sapiens

<400> SEQUENCE: 106

Ser Cys Ser Pro Cys Ser Thr Thr Cys Thr
1               5                   10

<210> SEQ ID NO 107
<211> LENGTH: 10
<212> TYPE: PRT
<213> ORGANISM: Homo sapiens

<400> SEQUENCE: 107

Ala Ser Cys Ser Thr Ser Gly Thr Cys Gly
1               5                   10

<210> SEQ ID NO 108
<211> LENGTH: 10
<212> TYPE: PRT
<213> ORGANISM: Homo sapiens

<400> SEQUENCE: 108

Ala Ser Cys Tyr Ile Pro Val Gly Cys Gln
1               5                   10

<210> SEQ ID NO 109
<211> LENGTH: 10
<212> TYPE: PRT
<213> ORGANISM: Homo sapiens

<400> SEQUENCE: 109

Ala Ser Cys Tyr Val Pro Val Ser Cys Gln
1               5                   10

```
<210> SEQ ID NO 110
<211> LENGTH: 10
<212> TYPE: PRT
<213> ORGANISM: Homo sapiens

<400> SEQUENCE: 110

Ala Val Cys Thr Leu Pro Ser Ser Cys Gln
1               5                   10

<210> SEQ ID NO 111
<211> LENGTH: 10
<212> TYPE: PRT
<213> ORGANISM: Homo sapiens

<400> SEQUENCE: 111

Asp Leu Cys Pro Thr Ser Val Ser Cys Gly
1               5                   10

<210> SEQ ID NO 112
<211> LENGTH: 10
<212> TYPE: PRT
<213> ORGANISM: Homo sapiens

<400> SEQUENCE: 112

Glu Ile Cys Trp Glu Pro Thr Ser Cys Gln
1               5                   10

<210> SEQ ID NO 113
<211> LENGTH: 10
<212> TYPE: PRT
<213> ORGANISM: Homo sapiens

<400> SEQUENCE: 113

Glu Thr Cys Gly Glu Pro Thr Ser Cys Gln
1               5                   10

<210> SEQ ID NO 114
<211> LENGTH: 10
<212> TYPE: PRT
<213> ORGANISM: Homo sapiens

<400> SEQUENCE: 114

Glu Thr Cys Asn Glu Thr Thr Ser Cys Gln
1               5                   10

<210> SEQ ID NO 115
<211> LENGTH: 10
<212> TYPE: PRT
<213> ORGANISM: Homo sapiens

<400> SEQUENCE: 115

Glu Thr Cys Trp Arg Pro Asn Ser Cys Gln
1               5                   10

<210> SEQ ID NO 116
<211> LENGTH: 10
<212> TYPE: PRT
<213> ORGANISM: Homo sapiens

<400> SEQUENCE: 116

Gly Tyr Cys Gly Tyr Arg Pro Phe Cys Phe
1               5                   10

<210> SEQ ID NO 117
<211> LENGTH: 10
```

```
<212> TYPE: PRT
<213> ORGANISM: Homo sapiens

<400> SEQUENCE: 117

Lys Thr Cys Trp Glu Pro Ala Ser Cys Gln
1               5                   10

<210> SEQ ID NO 118
<211> LENGTH: 10
<212> TYPE: PRT
<213> ORGANISM: Homo sapiens

<400> SEQUENCE: 118

Lys Thr Cys Trp Glu Pro Thr Ser Cys Gln
1               5                   10

<210> SEQ ID NO 119
<211> LENGTH: 10
<212> TYPE: PRT
<213> ORGANISM: Homo sapiens

<400> SEQUENCE: 119

Leu Asp Cys Val Asp Thr Thr Pro Cys Lys
1               5                   10

<210> SEQ ID NO 120
<211> LENGTH: 10
<212> TYPE: PRT
<213> ORGANISM: Homo sapiens

<400> SEQUENCE: 120

Leu Gly Cys Gly Tyr Gly Ser Phe Cys Gly
1               5                   10

<210> SEQ ID NO 121
<211> LENGTH: 10
<212> TYPE: PRT
<213> ORGANISM: Homo sapiens

<400> SEQUENCE: 121

Asn Ser Cys Gly Tyr Gly Ser Gly Cys Gly
1               5                   10

<210> SEQ ID NO 122
<211> LENGTH: 10
<212> TYPE: PRT
<213> ORGANISM: Homo sapiens

<400> SEQUENCE: 122

Asn Tyr Cys Pro Ser Asn Thr Met Cys Glu
1               5                   10

<210> SEQ ID NO 123
<211> LENGTH: 10
<212> TYPE: PRT
<213> ORGANISM: Homo sapiens

<400> SEQUENCE: 123

Pro Ala Cys Val Thr Ser Tyr Ser Cys Arg
1               5                   10

<210> SEQ ID NO 124
<211> LENGTH: 10
<212> TYPE: PRT
<213> ORGANISM: Homo sapiens
```

```
<400> SEQUENCE: 124

Pro Asp Cys His Val Glu Gly Thr Cys Leu
1               5                   10

<210> SEQ ID NO 125
<211> LENGTH: 10
<212> TYPE: PRT
<213> ORGANISM: Homo sapiens

<400> SEQUENCE: 125

Pro Asp Cys Arg Val Glu Gly Thr Cys Leu
1               5                   10

<210> SEQ ID NO 126
<211> LENGTH: 10
<212> TYPE: PRT
<213> ORGANISM: Homo sapiens

<400> SEQUENCE: 126

Pro Ile Cys Ser Glu Pro Ser Pro Cys Ser
1               5                   10

<210> SEQ ID NO 127
<211> LENGTH: 10
<212> TYPE: PRT
<213> ORGANISM: Homo sapiens

<400> SEQUENCE: 127

Pro Ile Cys Tyr Ile Phe Lys Pro Cys Gln
1               5                   10

<210> SEQ ID NO 128
<211> LENGTH: 10
<212> TYPE: PRT
<213> ORGANISM: Homo sapiens

<400> SEQUENCE: 128

Pro Leu Cys Tyr Ile Ser Asn Ser Cys Gln
1               5                   10

<210> SEQ ID NO 129
<211> LENGTH: 10
<212> TYPE: PRT
<213> ORGANISM: Homo sapiens

<400> SEQUENCE: 129

Pro Pro Cys Gly Gln Pro Thr Pro Cys Ser
1               5                   10

<210> SEQ ID NO 130
<211> LENGTH: 10
<212> TYPE: PRT
<213> ORGANISM: Homo sapiens

<400> SEQUENCE: 130

Pro Pro Cys His Ile Pro Gln Pro Cys Val
1               5                   10

<210> SEQ ID NO 131
<211> LENGTH: 10
<212> TYPE: PRT
<213> ORGANISM: Homo sapiens

<400> SEQUENCE: 131
```

Pro Ser Cys Gly Arg Leu Ala Ser Cys Gly
1               5                   10

<210> SEQ ID NO 132
<211> LENGTH: 10
<212> TYPE: PRT
<213> ORGANISM: Homo sapiens

<400> SEQUENCE: 132

Pro Ser Cys Ser Glu Ser Ser Ile Cys Gln
1               5                   10

<210> SEQ ID NO 133
<211> LENGTH: 10
<212> TYPE: PRT
<213> ORGANISM: Homo sapiens

<400> SEQUENCE: 133

Pro Ser Cys Ser Glu Val Thr Ser Cys Pro
1               5                   10

<210> SEQ ID NO 134
<211> LENGTH: 10
<212> TYPE: PRT
<213> ORGANISM: Homo sapiens

<400> SEQUENCE: 134

Pro Ser Cys Ser Thr Ser Gly Thr Cys Gly
1               5                   10

<210> SEQ ID NO 135
<211> LENGTH: 10
<212> TYPE: PRT
<213> ORGANISM: Homo sapiens

<400> SEQUENCE: 135

Pro Ser Cys Ser Val Ser Ser Gly Cys Gln
1               5                   10

<210> SEQ ID NO 136
<211> LENGTH: 10
<212> TYPE: PRT
<213> ORGANISM: Homo sapiens

<400> SEQUENCE: 136

Pro Ser Cys Thr Glu Ser Asp Ser Cys Lys
1               5                   10

<210> SEQ ID NO 137
<211> LENGTH: 10
<212> TYPE: PRT
<213> ORGANISM: Homo sapiens

<400> SEQUENCE: 137

Pro Ser Cys Tyr Gln Thr Ser Ser Cys Gly
1               5                   10

<210> SEQ ID NO 138
<211> LENGTH: 10
<212> TYPE: PRT
<213> ORGANISM: Homo sapiens

<400> SEQUENCE: 138

Pro Thr Cys Phe Leu Leu Asn Ser Cys Gln

```
                1               5                   10

<210> SEQ ID NO 139
<211> LENGTH: 10
<212> TYPE: PRT
<213> ORGANISM: Homo sapiens

<400> SEQUENCE: 139

Pro Thr Cys Ser Val Thr Ser Ser Cys Gln
1               5                   10

<210> SEQ ID NO 140
<211> LENGTH: 10
<212> TYPE: PRT
<213> ORGANISM: Homo sapiens

<400> SEQUENCE: 140

Pro Thr Cys Trp Leu Leu Asn Asn Cys His
1               5                   10

<210> SEQ ID NO 141
<211> LENGTH: 10
<212> TYPE: PRT
<213> ORGANISM: Homo sapiens

<400> SEQUENCE: 141

Pro Thr Cys Tyr Gln Arg Thr Ser Cys Val
1               5                   10

<210> SEQ ID NO 142
<211> LENGTH: 10
<212> TYPE: PRT
<213> ORGANISM: Homo sapiens

<400> SEQUENCE: 142

Pro Thr Cys Tyr Arg Arg Thr Ser Cys Val
1               5                   10

<210> SEQ ID NO 143
<211> LENGTH: 10
<212> TYPE: PRT
<213> ORGANISM: Homo sapiens

<400> SEQUENCE: 143

Pro Thr Cys Tyr Val Val Lys Arg Cys Pro
1               5                   10

<210> SEQ ID NO 144
<211> LENGTH: 10
<212> TYPE: PRT
<213> ORGANISM: Homo sapiens

<400> SEQUENCE: 144

Pro Val Cys Phe Glu Ala Thr Ile Cys Glu
1               5                   10

<210> SEQ ID NO 145
<211> LENGTH: 10
<212> TYPE: PRT
<213> ORGANISM: Homo sapiens

<400> SEQUENCE: 145

Pro Val Cys Phe Glu Ala Thr Val Cys Glu
1               5                   10
```

<210> SEQ ID NO 146
<211> LENGTH: 10
<212> TYPE: PRT
<213> ORGANISM: Homo sapiens

<400> SEQUENCE: 146

Pro Val Cys Ser Arg Pro Ala Ser Cys Ser
1               5                   10

<210> SEQ ID NO 147
<211> LENGTH: 10
<212> TYPE: PRT
<213> ORGANISM: Homo sapiens

<400> SEQUENCE: 147

Pro Val Cys Ser Trp Val Pro Ala Cys Ser
1               5                   10

<210> SEQ ID NO 148
<211> LENGTH: 10
<212> TYPE: PRT
<213> ORGANISM: Homo sapiens

<400> SEQUENCE: 148

Gln Thr Cys Asn Glu Ser Ser Tyr Cys Leu
1               5                   10

<210> SEQ ID NO 149
<211> LENGTH: 10
<212> TYPE: PRT
<213> ORGANISM: Homo sapiens

<400> SEQUENCE: 149

Gln Thr Cys Trp Glu Pro Thr Ser Cys Gln
1               5                   10

<210> SEQ ID NO 150
<211> LENGTH: 10
<212> TYPE: PRT
<213> ORGANISM: Homo sapiens

<400> SEQUENCE: 150

Ser Phe Cys Arg Leu Gly Tyr Gly Cys Gly
1               5                   10

<210> SEQ ID NO 151
<211> LENGTH: 10
<212> TYPE: PRT
<213> ORGANISM: Homo sapiens

<400> SEQUENCE: 151

Ser Phe Cys Arg Arg Gly Ser Gly Cys Gly
1               5                   10

<210> SEQ ID NO 152
<211> LENGTH: 10
<212> TYPE: PRT
<213> ORGANISM: Homo sapiens

<400> SEQUENCE: 152

Ser Leu Cys Gly Tyr Gly Tyr Gly Cys Gly
1               5                   10

<210> SEQ ID NO 153

```
<211> LENGTH: 10
<212> TYPE: PRT
<213> ORGANISM: Homo sapiens

<400> SEQUENCE: 153

Ser Leu Cys Ser Thr Glu Val Ser Cys Gly
1               5                   10

<210> SEQ ID NO 154
<211> LENGTH: 10
<212> TYPE: PRT
<213> ORGANISM: Homo sapiens

<400> SEQUENCE: 154

Ser Asn Cys Phe Gly Gln Leu Asn Cys Leu
1               5                   10

<210> SEQ ID NO 155
<211> LENGTH: 10
<212> TYPE: PRT
<213> ORGANISM: Homo sapiens

<400> SEQUENCE: 155

Ser Pro Cys Gly Gln Pro Thr Pro Cys Ser
1               5                   10

<210> SEQ ID NO 156
<211> LENGTH: 10
<212> TYPE: PRT
<213> ORGANISM: Homo sapiens

<400> SEQUENCE: 156

Ser Ser Cys Asp Gln Ser Ser Ser Cys Ala
1               5                   10

<210> SEQ ID NO 157
<211> LENGTH: 10
<212> TYPE: PRT
<213> ORGANISM: Homo sapiens

<400> SEQUENCE: 157

Ser Ser Cys Gly Gln Ser Ser Ser Cys Ala
1               5                   10

<210> SEQ ID NO 158
<211> LENGTH: 10
<212> TYPE: PRT
<213> ORGANISM: Homo sapiens

<400> SEQUENCE: 158

Ser Val Cys Pro Glu Pro Val Ser Cys Pro
1               5                   10

<210> SEQ ID NO 159
<211> LENGTH: 10
<212> TYPE: PRT
<213> ORGANISM: Homo sapiens

<400> SEQUENCE: 159

Thr Phe Cys Ser Phe Asp Lys Ser Cys Arg
1               5                   10

<210> SEQ ID NO 160
<211> LENGTH: 10
<212> TYPE: PRT
```

<213> ORGANISM: Homo sapiens

<400> SEQUENCE: 160

Thr Ile Cys Ser Ser Asp Lys Ser Cys Arg
1               5                   10

<210> SEQ ID NO 161
<211> LENGTH: 10
<212> TYPE: PRT
<213> ORGANISM: Homo sapiens

<400> SEQUENCE: 161

Thr Leu Cys Val Glu Ser Ser Pro Cys His
1               5                   10

<210> SEQ ID NO 162
<211> LENGTH: 10
<212> TYPE: PRT
<213> ORGANISM: Homo sapiens

<400> SEQUENCE: 162

Thr Pro Cys Tyr Gln Gln Ser Ser Cys Gln
1               5                   10

<210> SEQ ID NO 163
<211> LENGTH: 10
<212> TYPE: PRT
<213> ORGANISM: Homo sapiens

<400> SEQUENCE: 163

Val Thr Cys Ser Arg Gln Thr Thr Cys Ile
1               5                   10

<210> SEQ ID NO 164
<211> LENGTH: 10
<212> TYPE: PRT
<213> ORGANISM: Homo sapiens

<400> SEQUENCE: 164

Tyr Gly Cys Gly Tyr Gly Ser Gly Cys Gly
1               5                   10

<210> SEQ ID NO 165
<211> LENGTH: 10
<212> TYPE: PRT
<213> ORGANISM: Homo sapiens

<400> SEQUENCE: 165

Tyr Gly Cys Gly Tyr Gly Ser Gly Cys Arg
1               5                   10

<210> SEQ ID NO 166
<211> LENGTH: 10
<212> TYPE: PRT
<213> ORGANISM: Homo sapiens

<400> SEQUENCE: 166

Tyr Gly Cys Ile His Ser Thr His Cys Gly
1               5                   10

<210> SEQ ID NO 167
<211> LENGTH: 10
<212> TYPE: PRT
<213> ORGANISM: Homo sapiens

```
<400> SEQUENCE: 167

Ala Ala Cys Glu Pro Ser Ala Cys Gln Ser
1               5                   10

<210> SEQ ID NO 168
<211> LENGTH: 10
<212> TYPE: PRT
<213> ORGANISM: Homo sapiens

<400> SEQUENCE: 168

Ala Ala Cys Glu Pro Ser Pro Cys Gln Ser
1               5                   10

<210> SEQ ID NO 169
<211> LENGTH: 10
<212> TYPE: PRT
<213> ORGANISM: Homo sapiens

<400> SEQUENCE: 169

Ala Ala Cys Thr Met Ser Val Cys Ser Ser
1               5                   10

<210> SEQ ID NO 170
<211> LENGTH: 10
<212> TYPE: PRT
<213> ORGANISM: Homo sapiens

<400> SEQUENCE: 170

Ala Asp Cys Leu Gly Gly Ile Cys Leu Pro
1               5                   10

<210> SEQ ID NO 171
<211> LENGTH: 10
<212> TYPE: PRT
<213> ORGANISM: Homo sapiens

<400> SEQUENCE: 171

Ala Leu Cys Leu Pro Ser Ser Cys His Ser
1               5                   10

<210> SEQ ID NO 172
<211> LENGTH: 10
<212> TYPE: PRT
<213> ORGANISM: Homo sapiens

<400> SEQUENCE: 172

Ala Leu Cys Ser Pro Ser Thr Cys Gln Leu
1               5                   10

<210> SEQ ID NO 173
<211> LENGTH: 10
<212> TYPE: PRT
<213> ORGANISM: Homo sapiens

<400> SEQUENCE: 173

Ala Pro Cys Leu Ala Leu Val Cys Ala Pro
1               5                   10

<210> SEQ ID NO 174
<211> LENGTH: 10
<212> TYPE: PRT
<213> ORGANISM: Homo sapiens

<400> SEQUENCE: 174
```

Ala Pro Cys Leu Ser Leu Val Cys Thr Pro
1               5                   10

<210> SEQ ID NO 175
<211> LENGTH: 10
<212> TYPE: PRT
<213> ORGANISM: Homo sapiens

<400> SEQUENCE: 175

Ala Pro Cys Leu Thr Leu Val Cys Thr Pro
1               5                   10

<210> SEQ ID NO 176
<211> LENGTH: 10
<212> TYPE: PRT
<213> ORGANISM: Homo sapiens

<400> SEQUENCE: 176

Ala Pro Cys Val Ala Leu Leu Cys Arg Pro
1               5                   10

<210> SEQ ID NO 177
<211> LENGTH: 10
<212> TYPE: PRT
<213> ORGANISM: Homo sapiens

<400> SEQUENCE: 177

Ala Ser Cys Gly Ser Leu Leu Cys Arg Pro
1               5                   10

<210> SEQ ID NO 178
<211> LENGTH: 10
<212> TYPE: PRT
<213> ORGANISM: Homo sapiens

<400> SEQUENCE: 178

Ala Ser Cys Leu Ser Phe Leu Cys Arg Pro
1               5                   10

<210> SEQ ID NO 179
<211> LENGTH: 10
<212> TYPE: PRT
<213> ORGANISM: Homo sapiens

<400> SEQUENCE: 179

Ala Ser Cys Val Ser Leu Leu Cys Arg Pro
1               5                   10

<210> SEQ ID NO 180
<211> LENGTH: 10
<212> TYPE: PRT
<213> ORGANISM: Homo sapiens

<400> SEQUENCE: 180

Ala Val Cys Glu Pro Ser Pro Cys Gln Ser
1               5                   10

<210> SEQ ID NO 181
<211> LENGTH: 10
<212> TYPE: PRT
<213> ORGANISM: Homo sapiens

<400> SEQUENCE: 181

Ala Val Cys Leu Pro Val Ser Cys Gln Ser
1               5                   10

<210> SEQ ID NO 182
<211> LENGTH: 10
<212> TYPE: PRT
<213> ORGANISM: Homo sapiens

<400> SEQUENCE: 182

Ala Val Cys Val Pro Val Arg Cys Gln Ser
1               5                   10

<210> SEQ ID NO 183
<211> LENGTH: 10
<212> TYPE: PRT
<213> ORGANISM: Homo sapiens

<400> SEQUENCE: 183

Ala Val Cys Val Pro Val Ser Cys Gln Ser
1               5                   10

<210> SEQ ID NO 184
<211> LENGTH: 10
<212> TYPE: PRT
<213> ORGANISM: Homo sapiens

<400> SEQUENCE: 184

Asp Leu Cys Ser Pro Ser Thr Cys Gln Leu
1               5                   10

<210> SEQ ID NO 185
<211> LENGTH: 10
<212> TYPE: PRT
<213> ORGANISM: Homo sapiens

<400> SEQUENCE: 185

Asp Ser Cys Gly Ser Ser Cys Gly Pro
1               5                   10

<210> SEQ ID NO 186
<211> LENGTH: 10
<212> TYPE: PRT
<213> ORGANISM: Homo sapiens

<400> SEQUENCE: 186

Asp Ser Cys Val Gln Ser Asn Cys Phe Pro
1               5                   10

<210> SEQ ID NO 187
<211> LENGTH: 10
<212> TYPE: PRT
<213> ORGANISM: Homo sapiens

<400> SEQUENCE: 187

Phe Asn Cys Ser Thr Arg Asn Cys Ser Ser
1               5                   10

<210> SEQ ID NO 188
<211> LENGTH: 10
<212> TYPE: PRT
<213> ORGANISM: Homo sapiens

<400> SEQUENCE: 188

Gly Gly Cys Gly Ser Tyr Gly Cys Ser Gln
1               5                   10

-continued

```
<210> SEQ ID NO 189
<211> LENGTH: 10
<212> TYPE: PRT
<213> ORGANISM: Homo sapiens

<400> SEQUENCE: 189

Gly Ser Cys Gly Phe Gly Ser Cys Tyr Gly
1               5                   10

<210> SEQ ID NO 190
<211> LENGTH: 10
<212> TYPE: PRT
<213> ORGANISM: Homo sapiens

<400> SEQUENCE: 190

Gly Ser Cys Ser Ser Arg Lys Cys Phe Ser
1               5                   10

<210> SEQ ID NO 191
<211> LENGTH: 10
<212> TYPE: PRT
<213> ORGANISM: Homo sapiens

<400> SEQUENCE: 191

Gly Val Cys Leu Pro Ser Thr Cys Pro His
1               5                   10

<210> SEQ ID NO 192
<211> LENGTH: 10
<212> TYPE: PRT
<213> ORGANISM: Homo sapiens

<400> SEQUENCE: 192

His Ser Cys Glu Gly Tyr Leu Cys Tyr Ser
1               5                   10

<210> SEQ ID NO 193
<211> LENGTH: 10
<212> TYPE: PRT
<213> ORGANISM: Homo sapiens

<400> SEQUENCE: 193

Ile Val Cys Ala Ala Pro Ser Cys Gln Ser
1               5                   10

<210> SEQ ID NO 194
<211> LENGTH: 10
<212> TYPE: PRT
<213> ORGANISM: Homo sapiens

<400> SEQUENCE: 194

Lys Thr Cys Ser Thr Thr Gly Cys Asp Pro
1               5                   10

<210> SEQ ID NO 195
<211> LENGTH: 10
<212> TYPE: PRT
<213> ORGANISM: Homo sapiens

<400> SEQUENCE: 195

Leu Ala Cys Val Ser Gln Pro Cys Gln Ser
1               5                   10

<210> SEQ ID NO 196
<211> LENGTH: 10
```

```
<212> TYPE: PRT
<213> ORGANISM: Homo sapiens

<400> SEQUENCE: 196

Leu Gly Cys Gly Tyr Gly Gly Cys Gly Tyr
1               5                   10

<210> SEQ ID NO 197
<211> LENGTH: 10
<212> TYPE: PRT
<213> ORGANISM: Homo sapiens

<400> SEQUENCE: 197

Leu Ser Cys Gly Ser Arg Ser Cys Ser Ser
1               5                   10

<210> SEQ ID NO 198
<211> LENGTH: 10
<212> TYPE: PRT
<213> ORGANISM: Homo sapiens

<400> SEQUENCE: 198

Leu Val Cys Thr Pro Val Ser Cys Val Ser
1               5                   10

<210> SEQ ID NO 199
<211> LENGTH: 10
<212> TYPE: PRT
<213> ORGANISM: Homo sapiens

<400> SEQUENCE: 199

Asn Gly Cys Gln Glu Thr Tyr Cys Glu Pro
1               5                   10

<210> SEQ ID NO 200
<211> LENGTH: 10
<212> TYPE: PRT
<213> ORGANISM: Homo sapiens

<400> SEQUENCE: 200

Asn Ser Cys Arg Ser Leu Ser Cys Gly Ser
1               5                   10

<210> SEQ ID NO 201
<211> LENGTH: 10
<212> TYPE: PRT
<213> ORGANISM: Homo sapiens

<400> SEQUENCE: 201

Pro Ala Cys Val Ile Ser Thr Cys Pro Arg
1               5                   10

<210> SEQ ID NO 202
<211> LENGTH: 10
<212> TYPE: PRT
<213> ORGANISM: Homo sapiens

<400> SEQUENCE: 202

Pro Gly Cys Leu Asn Gln Ser Cys Gly Ser
1               5                   10

<210> SEQ ID NO 203
<211> LENGTH: 10
<212> TYPE: PRT
<213> ORGANISM: Homo sapiens
```

-continued

<400> SEQUENCE: 203

Pro Pro Cys Gly Thr Ala Pro Cys Leu Thr
1               5                   10

<210> SEQ ID NO 204
<211> LENGTH: 10
<212> TYPE: PRT
<213> ORGANISM: Homo sapiens

<400> SEQUENCE: 204

Pro Pro Cys Thr Thr Ala Leu Cys Arg Pro
1               5                   10

<210> SEQ ID NO 205
<211> LENGTH: 10
<212> TYPE: PRT
<213> ORGANISM: Homo sapiens

<400> SEQUENCE: 205

Pro Pro Cys Tyr Leu Val Ser Cys Thr Pro
1               5                   10

<210> SEQ ID NO 206
<211> LENGTH: 10
<212> TYPE: PRT
<213> ORGANISM: Homo sapiens

<400> SEQUENCE: 206

Pro Arg Cys Thr Arg Pro Ile Cys Glu Pro
1               5                   10

<210> SEQ ID NO 207
<211> LENGTH: 10
<212> TYPE: PRT
<213> ORGANISM: Homo sapiens

<400> SEQUENCE: 207

Pro Ser Cys Pro Val Ser Ser Cys Ala Gln
1               5                   10

<210> SEQ ID NO 208
<211> LENGTH: 10
<212> TYPE: PRT
<213> ORGANISM: Homo sapiens

<400> SEQUENCE: 208

Pro Ser Cys Gln Pro Ser Val Cys Val Pro
1               5                   10

<210> SEQ ID NO 209
<211> LENGTH: 10
<212> TYPE: PRT
<213> ORGANISM: Homo sapiens

<400> SEQUENCE: 209

Pro Ser Cys Ser Val Ser Asn Cys Tyr Gln
1               5                   10

<210> SEQ ID NO 210
<211> LENGTH: 10
<212> TYPE: PRT
<213> ORGANISM: Homo sapiens

<400> SEQUENCE: 210

```
Pro Ser Cys Ser Val Ser Ser Cys Ala Gln
1               5                   10

<210> SEQ ID NO 211
<211> LENGTH: 10
<212> TYPE: PRT
<213> ORGANISM: Homo sapiens

<400> SEQUENCE: 211

Pro Ser Cys Thr Ser Val Leu Cys Arg Pro
1               5                   10

<210> SEQ ID NO 212
<211> LENGTH: 10
<212> TYPE: PRT
<213> ORGANISM: Homo sapiens

<400> SEQUENCE: 212

Pro Thr Cys Lys Ser Pro Ser Cys Glu Pro
1               5                   10

<210> SEQ ID NO 213
<211> LENGTH: 10
<212> TYPE: PRT
<213> ORGANISM: Homo sapiens

<400> SEQUENCE: 213

Pro Thr Cys Val Ile Ser Ser Cys Pro Arg
1               5                   10

<210> SEQ ID NO 214
<211> LENGTH: 10
<212> TYPE: PRT
<213> ORGANISM: Homo sapiens

<400> SEQUENCE: 214

Pro Thr Cys Val Ile Ser Thr Cys Pro Arg
1               5                   10

<210> SEQ ID NO 215
<211> LENGTH: 10
<212> TYPE: PRT
<213> ORGANISM: Homo sapiens

<400> SEQUENCE: 215

Pro Thr Cys Tyr Gln Thr Ile Cys Phe Arg
1               5                   10

<210> SEQ ID NO 216
<211> LENGTH: 10
<212> TYPE: PRT
<213> ORGANISM: Homo sapiens

<400> SEQUENCE: 216

Pro Val Cys Gly Gly Val Ser Cys His Thr
1               5                   10

<210> SEQ ID NO 217
<211> LENGTH: 10
<212> TYPE: PRT
<213> ORGANISM: Homo sapiens

<400> SEQUENCE: 217

Pro Val Cys Gly Arg Val Ser Cys His Thr
```

<210> SEQ ID NO 218
<211> LENGTH: 10
<212> TYPE: PRT
<213> ORGANISM: Homo sapiens

<400> SEQUENCE: 218

Pro Val Cys Asn Lys Pro Val Cys Phe Val
1               5                   10

<210> SEQ ID NO 219
<211> LENGTH: 10
<212> TYPE: PRT
<213> ORGANISM: Homo sapiens

<400> SEQUENCE: 219

Pro Val Cys Pro Thr Pro Thr Cys Ser Val
1               5                   10

<210> SEQ ID NO 220
<211> LENGTH: 10
<212> TYPE: PRT
<213> ORGANISM: Homo sapiens

<400> SEQUENCE: 220

Pro Val Cys Arg Ser Thr Tyr Cys Val Pro
1               5                   10

<210> SEQ ID NO 221
<211> LENGTH: 10
<212> TYPE: PRT
<213> ORGANISM: Homo sapiens

<400> SEQUENCE: 221

Pro Val Cys Ser Lys Ser Val Cys Tyr Val
1               5                   10

<210> SEQ ID NO 222
<211> LENGTH: 10
<212> TYPE: PRT
<213> ORGANISM: Homo sapiens

<400> SEQUENCE: 222

Pro Val Cys Ser Arg Pro Ala Cys Tyr Ser
1               5                   10

<210> SEQ ID NO 223
<211> LENGTH: 10
<212> TYPE: PRT
<213> ORGANISM: Homo sapiens

<400> SEQUENCE: 223

Pro Val Cys Tyr Val Pro Thr Cys Ser Glu
1               5                   10

<210> SEQ ID NO 224
<211> LENGTH: 10
<212> TYPE: PRT
<213> ORGANISM: Homo sapiens

<400> SEQUENCE: 224

Gln Phe Cys Leu Ser Lys Ser Cys Gln Pro
1               5                   10

<210> SEQ ID NO 225
<211> LENGTH: 10
<212> TYPE: PRT
<213> ORGANISM: Homo sapiens

<400> SEQUENCE: 225

Arg Pro Cys Glu Arg Thr Ala Cys Gln Ser
1               5                   10

<210> SEQ ID NO 226
<211> LENGTH: 10
<212> TYPE: PRT
<213> ORGANISM: Homo sapiens

<400> SEQUENCE: 226

Arg Ser Cys Gln Thr Ser Phe Cys Gly Phe
1               5                   10

<210> SEQ ID NO 227
<211> LENGTH: 10
<212> TYPE: PRT
<213> ORGANISM: Homo sapiens

<400> SEQUENCE: 227

Arg Ser Cys Ser Ser Leu Gly Cys Gly Ser
1               5                   10

<210> SEQ ID NO 228
<211> LENGTH: 10
<212> TYPE: PRT
<213> ORGANISM: Homo sapiens

<400> SEQUENCE: 228

Arg Ser Cys Tyr Ser Val Gly Cys Gly Ser
1               5                   10

<210> SEQ ID NO 229
<211> LENGTH: 10
<212> TYPE: PRT
<213> ORGANISM: Homo sapiens

<400> SEQUENCE: 229

Arg Val Cys Leu Pro Gly Ser Cys Asp Ser
1               5                   10

<210> SEQ ID NO 230
<211> LENGTH: 10
<212> TYPE: PRT
<213> ORGANISM: Homo sapiens

<400> SEQUENCE: 230

Ser Phe Cys Gly Phe Pro Ser Cys Ser Thr
1               5                   10

<210> SEQ ID NO 231
<211> LENGTH: 10
<212> TYPE: PRT
<213> ORGANISM: Homo sapiens

<400> SEQUENCE: 231

Ser Phe Cys Gly Tyr Pro Ser Cys Ser Thr
1               5                   10

<210> SEQ ID NO 232

```
<211> LENGTH: 10
<212> TYPE: PRT
<213> ORGANISM: Homo sapiens

<400> SEQUENCE: 232

Ser Gly Cys Asp Pro Ala Ser Cys Gln Pro
1               5                   10

<210> SEQ ID NO 233
<211> LENGTH: 10
<212> TYPE: PRT
<213> ORGANISM: Homo sapiens

<400> SEQUENCE: 233

Ser Gly Cys Gly Gly Ser Gly Cys Gly Gly
1               5                   10

<210> SEQ ID NO 234
<211> LENGTH: 10
<212> TYPE: PRT
<213> ORGANISM: Homo sapiens

<400> SEQUENCE: 234

Ser Gly Cys Gln Pro Ser Ser Cys Leu Ala
1               5                   10

<210> SEQ ID NO 235
<211> LENGTH: 10
<212> TYPE: PRT
<213> ORGANISM: Homo sapiens

<400> SEQUENCE: 235

Ser His Cys Gln Pro Pro His Cys Gln Leu
1               5                   10

<210> SEQ ID NO 236
<211> LENGTH: 10
<212> TYPE: PRT
<213> ORGANISM: Homo sapiens

<400> SEQUENCE: 236

Ser Ile Cys Gln Pro Ala Thr Cys Val Ala
1               5                   10

<210> SEQ ID NO 237
<211> LENGTH: 10
<212> TYPE: PRT
<213> ORGANISM: Homo sapiens

<400> SEQUENCE: 237

Ser Leu Cys Val Pro Val Ser Cys Arg Pro
1               5                   10

<210> SEQ ID NO 238
<211> LENGTH: 10
<212> TYPE: PRT
<213> ORGANISM: Homo sapiens

<400> SEQUENCE: 238

Ser Asn Cys Leu Pro Thr Ser Cys Gln Pro
1               5                   10

<210> SEQ ID NO 239
<211> LENGTH: 10
<212> TYPE: PRT
```

<213> ORGANISM: Homo sapiens

<400> SEQUENCE: 239

Ser Pro Cys Leu Val Ser Ser Cys Gln Pro
1               5                   10

<210> SEQ ID NO 240
<211> LENGTH: 10
<212> TYPE: PRT
<213> ORGANISM: Homo sapiens

<400> SEQUENCE: 240

Ser Pro Cys Gln Gln Ser Ser Cys Gln Glu
1               5                   10

<210> SEQ ID NO 241
<211> LENGTH: 10
<212> TYPE: PRT
<213> ORGANISM: Homo sapiens

<400> SEQUENCE: 241

Ser Pro Cys Gln Gln Ser Tyr Cys Val Pro
1               5                   10

<210> SEQ ID NO 242
<211> LENGTH: 10
<212> TYPE: PRT
<213> ORGANISM: Homo sapiens

<400> SEQUENCE: 242

Ser Pro Cys Ser Pro Ala Val Cys Val Ser
1               5                   10

<210> SEQ ID NO 243
<211> LENGTH: 10
<212> TYPE: PRT
<213> ORGANISM: Homo sapiens

<400> SEQUENCE: 243

Ser Arg Cys Gln Gln Pro Ser Cys Gln Pro
1               5                   10

<210> SEQ ID NO 244
<211> LENGTH: 10
<212> TYPE: PRT
<213> ORGANISM: Homo sapiens

<400> SEQUENCE: 244

Ser Arg Cys Tyr Arg Pro His Cys Gly Gln
1               5                   10

<210> SEQ ID NO 245
<211> LENGTH: 10
<212> TYPE: PRT
<213> ORGANISM: Homo sapiens

<400> SEQUENCE: 245

Ser Ser Cys Ala Pro Ile Tyr Cys Arg Arg
1               5                   10

<210> SEQ ID NO 246
<211> LENGTH: 10
<212> TYPE: PRT
<213> ORGANISM: Homo sapiens

<400> SEQUENCE: 246

Ser Ser Cys Ala Pro Val Tyr Cys Arg Arg
1               5                   10

<210> SEQ ID NO 247
<211> LENGTH: 10
<212> TYPE: PRT
<213> ORGANISM: Homo sapiens

<400> SEQUENCE: 247

Ser Ser Cys Gly Lys Gly Gly Cys Gly Ser
1               5                   10

<210> SEQ ID NO 248
<211> LENGTH: 10
<212> TYPE: PRT
<213> ORGANISM: Homo sapiens

<400> SEQUENCE: 248

Ser Ser Cys Gly Lys Arg Gly Cys Gly Ser
1               5                   10

<210> SEQ ID NO 249
<211> LENGTH: 10
<212> TYPE: PRT
<213> ORGANISM: Homo sapiens

<400> SEQUENCE: 249

Ser Ser Cys Leu Pro Val Ser Cys Arg Pro
1               5                   10

<210> SEQ ID NO 250
<211> LENGTH: 10
<212> TYPE: PRT
<213> ORGANISM: Homo sapiens

<400> SEQUENCE: 250

Ser Ser Cys Gln Pro Ala Tyr Cys Thr Ser
1               5                   10

<210> SEQ ID NO 251
<211> LENGTH: 10
<212> TYPE: PRT
<213> ORGANISM: Homo sapiens

<400> SEQUENCE: 251

Ser Ser Cys Gln Pro Ser Tyr Cys Arg Gln
1               5                   10

<210> SEQ ID NO 252
<211> LENGTH: 10
<212> TYPE: PRT
<213> ORGANISM: Homo sapiens

<400> SEQUENCE: 252

Ser Ser Cys Gln Pro Val Val Cys Glu Pro
1               5                   10

<210> SEQ ID NO 253
<211> LENGTH: 10
<212> TYPE: PRT
<213> ORGANISM: Homo sapiens

<400> SEQUENCE: 253

Ser Ser Cys Thr Ala Val Val Cys Arg Pro
1               5                   10

<210> SEQ ID NO 254
<211> LENGTH: 10
<212> TYPE: PRT
<213> ORGANISM: Homo sapiens

<400> SEQUENCE: 254

Ser Ser Cys Tyr Gln Pro Phe Cys Arg Ser
1               5                   10

<210> SEQ ID NO 255
<211> LENGTH: 10
<212> TYPE: PRT
<213> ORGANISM: Homo sapiens

<400> SEQUENCE: 255

Ser Ser Cys Tyr Arg Pro Ile Cys Gly Ser
1               5                   10

<210> SEQ ID NO 256
<211> LENGTH: 10
<212> TYPE: PRT
<213> ORGANISM: Homo sapiens

<400> SEQUENCE: 256

Ser Ser Cys Tyr Arg Pro Thr Cys Gly Ser
1               5                   10

<210> SEQ ID NO 257
<211> LENGTH: 10
<212> TYPE: PRT
<213> ORGANISM: Homo sapiens

<400> SEQUENCE: 257

Ser Val Cys Met Ser Gly Ser Cys Gln Ala
1               5                   10

<210> SEQ ID NO 258
<211> LENGTH: 10
<212> TYPE: PRT
<213> ORGANISM: Homo sapiens

<400> SEQUENCE: 258

Ser Val Cys Ser Asp Gln Gly Cys Asp Gln
1               5                   10

<210> SEQ ID NO 259
<211> LENGTH: 10
<212> TYPE: PRT
<213> ORGANISM: Homo sapiens

<400> SEQUENCE: 259

Ser Val Cys Ser Asp Gln Gly Cys Gly Leu
1               5                   10

<210> SEQ ID NO 260
<211> LENGTH: 10
<212> TYPE: PRT
<213> ORGANISM: Homo sapiens

<400> SEQUENCE: 260

Ser Val Cys Ser Asp Gln Gly Cys Gly Gln
1               5                   10

```
<210> SEQ ID NO 261
<211> LENGTH: 10
<212> TYPE: PRT
<213> ORGANISM: Homo sapiens

<400> SEQUENCE: 261

Ser Val Cys Ser Asp Gln Gly Cys Ser Gln
1               5                   10

<210> SEQ ID NO 262
<211> LENGTH: 10
<212> TYPE: PRT
<213> ORGANISM: Homo sapiens

<400> SEQUENCE: 262

Ser Val Cys Ser Asp Gln Ser Cys Gly Gln
1               5                   10

<210> SEQ ID NO 263
<211> LENGTH: 10
<212> TYPE: PRT
<213> ORGANISM: Homo sapiens

<400> SEQUENCE: 263

Ser Val Cys Ser His Gln Gly Cys Gly Gln
1               5                   10

<210> SEQ ID NO 264
<211> LENGTH: 10
<212> TYPE: PRT
<213> ORGANISM: Homo sapiens

<400> SEQUENCE: 264

Ser Val Cys Ser His Gln Gly Cys Gly Arg
1               5                   10

<210> SEQ ID NO 265
<211> LENGTH: 10
<212> TYPE: PRT
<213> ORGANISM: Homo sapiens

<400> SEQUENCE: 265

Ser Val Cys Val Pro Val Ser Cys Arg Pro
1               5                   10

<210> SEQ ID NO 266
<211> LENGTH: 10
<212> TYPE: PRT
<213> ORGANISM: Homo sapiens

<400> SEQUENCE: 266

Ser Tyr Cys Arg Gln Ala Ser Cys Val Ser
1               5                   10

<210> SEQ ID NO 267
<211> LENGTH: 10
<212> TYPE: PRT
<213> ORGANISM: Homo sapiens

<400> SEQUENCE: 267

Thr Ala Cys Glu Pro Ser Ala Cys Gln Ser
1               5                   10
```

```
<210> SEQ ID NO 268
<211> LENGTH: 10
<212> TYPE: PRT
<213> ORGANISM: Homo sapiens

<400> SEQUENCE: 268

Thr Ile Cys Thr Ala Ser Pro Cys Gln Pro
1               5                   10

<210> SEQ ID NO 269
<211> LENGTH: 10
<212> TYPE: PRT
<213> ORGANISM: Homo sapiens

<400> SEQUENCE: 269

Thr Ser Cys Pro Glu Thr Ser Cys Leu Pro
1               5                   10

<210> SEQ ID NO 270
<211> LENGTH: 10
<212> TYPE: PRT
<213> ORGANISM: Homo sapiens

<400> SEQUENCE: 270

Thr Ser Cys Gln Met Thr Asn Cys Glu Gln
1               5                   10

<210> SEQ ID NO 271
<211> LENGTH: 10
<212> TYPE: PRT
<213> ORGANISM: Homo sapiens

<400> SEQUENCE: 271

Thr Ser Cys Gln Pro Val His Cys Glu Thr
1               5                   10

<210> SEQ ID NO 272
<211> LENGTH: 10
<212> TYPE: PRT
<213> ORGANISM: Homo sapiens

<400> SEQUENCE: 272

Thr Ser Cys Gln Pro Val Leu Cys Lys Ser
1               5                   10

<210> SEQ ID NO 273
<211> LENGTH: 10
<212> TYPE: PRT
<213> ORGANISM: Homo sapiens

<400> SEQUENCE: 273

Thr Ser Cys Gln Pro Val Leu Cys Val Pro
1               5                   10

<210> SEQ ID NO 274
<211> LENGTH: 10
<212> TYPE: PRT
<213> ORGANISM: Homo sapiens

<400> SEQUENCE: 274

Thr Ser Cys Val Gly Phe Val Cys Gln Pro
1               5                   10

<210> SEQ ID NO 275
<211> LENGTH: 10
```

```
<212> TYPE: PRT
<213> ORGANISM: Homo sapiens

<400> SEQUENCE: 275

Thr Ser Cys Val Ser Asn Pro Cys Gln Val
1               5                   10

<210> SEQ ID NO 276
<211> LENGTH: 10
<212> TYPE: PRT
<213> ORGANISM: Homo sapiens

<400> SEQUENCE: 276

Thr Thr Cys Phe Gln Pro Thr Cys Val Ser
1               5                   10

<210> SEQ ID NO 277
<211> LENGTH: 10
<212> TYPE: PRT
<213> ORGANISM: Homo sapiens

<400> SEQUENCE: 277

Thr Thr Cys Phe Gln Pro Thr Cys Val Thr
1               5                   10

<210> SEQ ID NO 278
<211> LENGTH: 10
<212> TYPE: PRT
<213> ORGANISM: Homo sapiens

<400> SEQUENCE: 278

Thr Thr Cys Phe Gln Pro Thr Cys Val Tyr
1               5                   10

<210> SEQ ID NO 279
<211> LENGTH: 10
<212> TYPE: PRT
<213> ORGANISM: Homo sapiens

<400> SEQUENCE: 279

Thr Thr Cys Ile Ser Asn Pro Cys Ser Thr
1               5                   10

<210> SEQ ID NO 280
<211> LENGTH: 10
<212> TYPE: PRT
<213> ORGANISM: Homo sapiens

<400> SEQUENCE: 280

Thr Trp Cys Gln Gly Ser Ser Cys Gln Pro
1               5                   10

<210> SEQ ID NO 281
<211> LENGTH: 10
<212> TYPE: PRT
<213> ORGANISM: Homo sapiens

<400> SEQUENCE: 281

Val Gly Cys Gln Ser Ser Val Cys Val Pro
1               5                   10

<210> SEQ ID NO 282
<211> LENGTH: 10
<212> TYPE: PRT
<213> ORGANISM: Homo sapiens
```

<400> SEQUENCE: 282

Val Pro Cys Gln Pro Ser Thr Cys Val Phe
1               5                   10

<210> SEQ ID NO 283
<211> LENGTH: 10
<212> TYPE: PRT
<213> ORGANISM: Homo sapiens

<400> SEQUENCE: 283

Val Ser Cys Glu Pro Ser Pro Cys Gln Ser
1               5                   10

<210> SEQ ID NO 284
<211> LENGTH: 10
<212> TYPE: PRT
<213> ORGANISM: Homo sapiens

<400> SEQUENCE: 284

Val Ser Cys Gly Gly Pro Ile Cys Leu Pro
1               5                   10

<210> SEQ ID NO 285
<211> LENGTH: 10
<212> TYPE: PRT
<213> ORGANISM: Homo sapiens

<400> SEQUENCE: 285

Val Ser Cys Lys Pro Val Leu Cys Val Ala
1               5                   10

<210> SEQ ID NO 286
<211> LENGTH: 10
<212> TYPE: PRT
<213> ORGANISM: Homo sapiens

<400> SEQUENCE: 286

Val Ser Cys Pro Ser Thr Ser Cys Arg Pro
1               5                   10

<210> SEQ ID NO 287
<211> LENGTH: 10
<212> TYPE: PRT
<213> ORGANISM: Homo sapiens

<400> SEQUENCE: 287

Val Ser Cys Gln Ser Ser Val Cys Met Pro
1               5                   10

<210> SEQ ID NO 288
<211> LENGTH: 10
<212> TYPE: PRT
<213> ORGANISM: Homo sapiens

<400> SEQUENCE: 288

Val Ser Cys Thr Arg Ile Val Cys Val Ala
1               5                   10

<210> SEQ ID NO 289
<211> LENGTH: 10
<212> TYPE: PRT
<213> ORGANISM: Homo sapiens

<400> SEQUENCE: 289

Val Thr Cys Glu Pro Ser Pro Cys Gln Ser
1               5                   10

<210> SEQ ID NO 290
<211> LENGTH: 10
<212> TYPE: PRT
<213> ORGANISM: Homo sapiens

<400> SEQUENCE: 290

Val Thr Cys Gln Thr Thr Val Cys Arg Pro
1               5                   10

<210> SEQ ID NO 291
<211> LENGTH: 10
<212> TYPE: PRT
<213> ORGANISM: Homo sapiens

<400> SEQUENCE: 291

Tyr Gly Cys Gly Tyr Glu Gly Cys Arg Tyr
1               5                   10

<210> SEQ ID NO 292
<211> LENGTH: 10
<212> TYPE: PRT
<213> ORGANISM: Homo sapiens

<400> SEQUENCE: 292

Ala Gly Ser Cys Gln Pro Ser Cys Ser Glu
1               5                   10

<210> SEQ ID NO 293
<211> LENGTH: 10
<212> TYPE: PRT
<213> ORGANISM: Homo sapiens

<400> SEQUENCE: 293

Ala Leu Leu Cys Arg Pro Leu Cys Gly Val
1               5                   10

<210> SEQ ID NO 294
<211> LENGTH: 10
<212> TYPE: PRT
<213> ORGANISM: Homo sapiens

<400> SEQUENCE: 294

Ala Leu Val Cys Glu Pro Val Cys Leu Arg
1               5                   10

<210> SEQ ID NO 295
<211> LENGTH: 10
<212> TYPE: PRT
<213> ORGANISM: Homo sapiens

<400> SEQUENCE: 295

Ala Thr Ile Cys Glu Pro Ser Cys Ser Val
1               5                   10

<210> SEQ ID NO 296
<211> LENGTH: 10
<212> TYPE: PRT
<213> ORGANISM: Homo sapiens

<400> SEQUENCE: 296

Ala Thr Thr Cys Glu Pro Ser Cys Ser Val

```
1               5                   10

<210> SEQ ID NO 297
<211> LENGTH: 10
<212> TYPE: PRT
<213> ORGANISM: Homo sapiens

<400> SEQUENCE: 297

Ala Thr Val Cys Glu Pro Ser Cys Ser Val
1               5                   10

<210> SEQ ID NO 298
<211> LENGTH: 10
<212> TYPE: PRT
<213> ORGANISM: Homo sapiens

<400> SEQUENCE: 298

Glu Gly Thr Cys Leu Pro Pro Cys Tyr Leu
1               5                   10

<210> SEQ ID NO 299
<211> LENGTH: 10
<212> TYPE: PRT
<213> ORGANISM: Homo sapiens

<400> SEQUENCE: 299

Phe Ser Thr Cys Arg Pro Ser Cys Ser Gly
1               5                   10

<210> SEQ ID NO 300
<211> LENGTH: 10
<212> TYPE: PRT
<213> ORGANISM: Homo sapiens

<400> SEQUENCE: 300

Gly Phe Val Cys Gln Pro Met Cys Ser His
1               5                   10

<210> SEQ ID NO 301
<211> LENGTH: 10
<212> TYPE: PRT
<213> ORGANISM: Homo sapiens

<400> SEQUENCE: 301

Gly Leu Asp Cys Gly Tyr Gly Cys Gly Tyr
1               5                   10

<210> SEQ ID NO 302
<211> LENGTH: 10
<212> TYPE: PRT
<213> ORGANISM: Homo sapiens

<400> SEQUENCE: 302

Gly Leu Gly Cys Gly Tyr Gly Cys Gly Tyr
1               5                   10

<210> SEQ ID NO 303
<211> LENGTH: 10
<212> TYPE: PRT
<213> ORGANISM: Homo sapiens

<400> SEQUENCE: 303

Gly Leu Gly Cys Ser Tyr Gly Cys Gly His
1               5                   10
```

<210> SEQ ID NO 304
<211> LENGTH: 10
<212> TYPE: PRT
<213> ORGANISM: Homo sapiens

<400> SEQUENCE: 304

Gly Leu Gly Cys Ser Tyr Gly Cys Gly Leu
1               5                   10

<210> SEQ ID NO 305
<211> LENGTH: 10
<212> TYPE: PRT
<213> ORGANISM: Homo sapiens

<400> SEQUENCE: 305

Gly Ser Gly Cys Gly Tyr Gly Cys Gly Tyr
1               5                   10

<210> SEQ ID NO 306
<211> LENGTH: 10
<212> TYPE: PRT
<213> ORGANISM: Homo sapiens

<400> SEQUENCE: 306

Gly Thr Gly Cys Gly Tyr Gly Cys Gly Tyr
1               5                   10

<210> SEQ ID NO 307
<211> LENGTH: 10
<212> TYPE: PRT
<213> ORGANISM: Homo sapiens

<400> SEQUENCE: 307

Gly Val Ser Cys His Thr Thr Cys Tyr Arg
1               5                   10

<210> SEQ ID NO 308
<211> LENGTH: 10
<212> TYPE: PRT
<213> ORGANISM: Homo sapiens

<400> SEQUENCE: 308

Gly Tyr Ala Cys Asn Phe Pro Cys Ser Tyr
1               5                   10

<210> SEQ ID NO 309
<211> LENGTH: 10
<212> TYPE: PRT
<213> ORGANISM: Homo sapiens

<400> SEQUENCE: 309

Gly Tyr Gly Cys Gly Tyr Gly Cys Gly Phe
1               5                   10

<210> SEQ ID NO 310
<211> LENGTH: 10
<212> TYPE: PRT
<213> ORGANISM: Homo sapiens

<400> SEQUENCE: 310

His Ser Pro Cys Gln Ala Ser Cys Tyr Val
1               5                   10

<210> SEQ ID NO 311

```
<211> LENGTH: 10
<212> TYPE: PRT
<213> ORGANISM: Homo sapiens

<400> SEQUENCE: 311

His Thr Ser Cys Ser Pro Ala Cys Gln Pro
1               5                   10

<210> SEQ ID NO 312
<211> LENGTH: 10
<212> TYPE: PRT
<213> ORGANISM: Homo sapiens

<400> SEQUENCE: 312

His Thr Ser Cys Ser Ser Gly Cys Gln Pro
1               5                   10

<210> SEQ ID NO 313
<211> LENGTH: 10
<212> TYPE: PRT
<213> ORGANISM: Homo sapiens

<400> SEQUENCE: 313

Ile Arg Trp Cys His Pro Asp Cys His Val
1               5                   10

<210> SEQ ID NO 314
<211> LENGTH: 10
<212> TYPE: PRT
<213> ORGANISM: Homo sapiens

<400> SEQUENCE: 314

Ile Arg Trp Cys Arg Pro Asp Cys Arg Val
1               5                   10

<210> SEQ ID NO 315
<211> LENGTH: 10
<212> TYPE: PRT
<213> ORGANISM: Homo sapiens

<400> SEQUENCE: 315

Ile Ser Ser Cys Gly Thr Gly Cys Gly Ile
1               5                   10

<210> SEQ ID NO 316
<211> LENGTH: 10
<212> TYPE: PRT
<213> ORGANISM: Homo sapiens

<400> SEQUENCE: 316

Lys Gly Gly Cys Gly Ser Gly Cys Gly Gly
1               5                   10

<210> SEQ ID NO 317
<211> LENGTH: 10
<212> TYPE: PRT
<213> ORGANISM: Homo sapiens

<400> SEQUENCE: 317

Lys Gly Gly Cys Gly Ser Ser Cys Ser Gln
1               5                   10

<210> SEQ ID NO 318
<211> LENGTH: 10
<212> TYPE: PRT
```

<213> ORGANISM: Homo sapiens

<400> SEQUENCE: 318

Leu Val Thr Cys Gln Asp Ser Cys Gly Ser
1               5                   10

<210> SEQ ID NO 319
<211> LENGTH: 10
<212> TYPE: PRT
<213> ORGANISM: Homo sapiens

<400> SEQUENCE: 319

Leu Val Thr Cys Gln Glu Ser Cys Gln Pro
1               5                   10

<210> SEQ ID NO 320
<211> LENGTH: 10
<212> TYPE: PRT
<213> ORGANISM: Homo sapiens

<400> SEQUENCE: 320

Met Ser Ile Cys Ser Ser Ala Cys Thr Asp
1               5                   10

<210> SEQ ID NO 321
<211> LENGTH: 10
<212> TYPE: PRT
<213> ORGANISM: Homo sapiens

<400> SEQUENCE: 321

Met Ser Ile Cys Ser Ser Ala Cys Thr Asn
1               5                   10

<210> SEQ ID NO 322
<211> LENGTH: 10
<212> TYPE: PRT
<213> ORGANISM: Homo sapiens

<400> SEQUENCE: 322

Met Ser Val Cys Ser Ser Ala Cys Ser Asp
1               5                   10

<210> SEQ ID NO 323
<211> LENGTH: 10
<212> TYPE: PRT
<213> ORGANISM: Homo sapiens

<400> SEQUENCE: 323

Pro Ala Ile Cys Glu Pro Ser Cys Ser Val
1               5                   10

<210> SEQ ID NO 324
<211> LENGTH: 10
<212> TYPE: PRT
<213> ORGANISM: Homo sapiens

<400> SEQUENCE: 324

Pro Ala Ser Cys Gln Lys Ser Cys Tyr Arg
1               5                   10

<210> SEQ ID NO 325
<211> LENGTH: 10
<212> TYPE: PRT
<213> ORGANISM: Homo sapiens

<400> SEQUENCE: 325

Pro Ile Tyr Cys Arg Arg Thr Cys Tyr His
1               5                   10

<210> SEQ ID NO 326
<211> LENGTH: 10
<212> TYPE: PRT
<213> ORGANISM: Homo sapiens

<400> SEQUENCE: 326

Pro Asn Ser Cys Gln Thr Leu Cys Val Glu
1               5                   10

<210> SEQ ID NO 327
<211> LENGTH: 10
<212> TYPE: PRT
<213> ORGANISM: Homo sapiens

<400> SEQUENCE: 327

Pro Gln Pro Cys Val Pro Thr Cys Phe Leu
1               5                   10

<210> SEQ ID NO 328
<211> LENGTH: 10
<212> TYPE: PRT
<213> ORGANISM: Homo sapiens

<400> SEQUENCE: 328

Pro Ser Ala Cys Gln Ser Gly Cys Thr Ser
1               5                   10

<210> SEQ ID NO 329
<211> LENGTH: 10
<212> TYPE: PRT
<213> ORGANISM: Homo sapiens

<400> SEQUENCE: 329

Pro Ser Pro Cys Glu Pro Ser Cys Ser Glu
1               5                   10

<210> SEQ ID NO 330
<211> LENGTH: 10
<212> TYPE: PRT
<213> ORGANISM: Homo sapiens

<400> SEQUENCE: 330

Pro Ser Pro Cys Gln Ala Ser Cys Tyr Ile
1               5                   10

<210> SEQ ID NO 331
<211> LENGTH: 10
<212> TYPE: PRT
<213> ORGANISM: Homo sapiens

<400> SEQUENCE: 331

Pro Ser Pro Cys Gln Ser Gly Cys Ile Ser
1               5                   10

<210> SEQ ID NO 332
<211> LENGTH: 10
<212> TYPE: PRT
<213> ORGANISM: Homo sapiens

<400> SEQUENCE: 332

Pro Ser Pro Cys Gln Ser Gly Cys Thr Asp
1               5                   10

<210> SEQ ID NO 333
<211> LENGTH: 10
<212> TYPE: PRT
<213> ORGANISM: Homo sapiens

<400> SEQUENCE: 333

Pro Ser Pro Cys Gln Ser Gly Cys Thr Ser
1               5                   10

<210> SEQ ID NO 334
<211> LENGTH: 10
<212> TYPE: PRT
<213> ORGANISM: Homo sapiens

<400> SEQUENCE: 334

Pro Thr Ala Cys Gln Pro Thr Cys Tyr Gln
1               5                   10

<210> SEQ ID NO 335
<211> LENGTH: 10
<212> TYPE: PRT
<213> ORGANISM: Homo sapiens

<400> SEQUENCE: 335

Pro Thr Ala Cys Gln Pro Thr Cys Tyr Arg
1               5                   10

<210> SEQ ID NO 336
<211> LENGTH: 10
<212> TYPE: PRT
<213> ORGANISM: Homo sapiens

<400> SEQUENCE: 336

Pro Thr Pro Cys Ser Thr Thr Cys Arg Thr
1               5                   10

<210> SEQ ID NO 337
<211> LENGTH: 10
<212> TYPE: PRT
<213> ORGANISM: Homo sapiens

<400> SEQUENCE: 337

Pro Thr Ser Cys Gln Lys Ser Cys Tyr Arg
1               5                   10

<210> SEQ ID NO 338
<211> LENGTH: 10
<212> TYPE: PRT
<213> ORGANISM: Homo sapiens

<400> SEQUENCE: 338

Pro Thr Ser Cys Gln Pro Ser Cys Glu Ser
1               5                   10

<210> SEQ ID NO 339
<211> LENGTH: 10
<212> TYPE: PRT
<213> ORGANISM: Homo sapiens

<400> SEQUENCE: 339

Pro Thr Ser Cys Gln Thr Ser Cys Thr Leu
1               5                   10

<210> SEQ ID NO 340
<211> LENGTH: 10
<212> TYPE: PRT
<213> ORGANISM: Homo sapiens

<400> SEQUENCE: 340

Pro Val Ile Cys Glu Pro Ser Cys Ser Val
1               5                   10

<210> SEQ ID NO 341
<211> LENGTH: 10
<212> TYPE: PRT
<213> ORGANISM: Homo sapiens

<400> SEQUENCE: 341

Pro Val Ser Cys Val Pro Val Cys Ser Gly
1               5                   10

<210> SEQ ID NO 342
<211> LENGTH: 10
<212> TYPE: PRT
<213> ORGANISM: Homo sapiens

<400> SEQUENCE: 342

Pro Val Thr Cys Val Pro Arg Cys Thr Arg
1               5                   10

<210> SEQ ID NO 343
<211> LENGTH: 10
<212> TYPE: PRT
<213> ORGANISM: Homo sapiens

<400> SEQUENCE: 343

Pro Val Tyr Cys Arg Arg Thr Cys Tyr His
1               5                   10

<210> SEQ ID NO 344
<211> LENGTH: 10
<212> TYPE: PRT
<213> ORGANISM: Homo sapiens

<400> SEQUENCE: 344

Pro Val Tyr Cys Arg Arg Thr Cys Tyr Tyr
1               5                   10

<210> SEQ ID NO 345
<211> LENGTH: 10
<212> TYPE: PRT
<213> ORGANISM: Homo sapiens

<400> SEQUENCE: 345

Pro Val Tyr Cys Val Pro Val Cys Ser Gly
1               5                   10

<210> SEQ ID NO 346
<211> LENGTH: 10
<212> TYPE: PRT
<213> ORGANISM: Homo sapiens

<400> SEQUENCE: 346

Gln Pro Gly Cys Glu Ser Pro Cys Glu Pro
1               5                   10

```
<210> SEQ ID NO 347
<211> LENGTH: 10
<212> TYPE: PRT
<213> ORGANISM: Homo sapiens

<400> SEQUENCE: 347

Gln Gln Ser Cys Val Ser Ser Cys Arg Arg
1               5                   10

<210> SEQ ID NO 348
<211> LENGTH: 10
<212> TYPE: PRT
<213> ORGANISM: Homo sapiens

<400> SEQUENCE: 348

Gln Thr Ser Cys Gly Ser Ser Cys Gly Gln
1               5                   10

<210> SEQ ID NO 349
<211> LENGTH: 10
<212> TYPE: PRT
<213> ORGANISM: Homo sapiens

<400> SEQUENCE: 349

Gln Thr Thr Cys His Pro Ser Cys Gly Met
1               5                   10

<210> SEQ ID NO 350
<211> LENGTH: 10
<212> TYPE: PRT
<213> ORGANISM: Homo sapiens

<400> SEQUENCE: 350

Gln Thr Thr Cys Arg Pro Ser Cys Gly Val
1               5                   10

<210> SEQ ID NO 351
<211> LENGTH: 10
<212> TYPE: PRT
<213> ORGANISM: Homo sapiens

<400> SEQUENCE: 351

Arg Gly Gly Cys Gly Ser Gly Cys Gly Gly
1               5                   10

<210> SEQ ID NO 352
<211> LENGTH: 10
<212> TYPE: PRT
<213> ORGANISM: Homo sapiens

<400> SEQUENCE: 352

Arg Leu Ala Cys Tyr Ser Leu Cys Ser Gly
1               5                   10

<210> SEQ ID NO 353
<211> LENGTH: 10
<212> TYPE: PRT
<213> ORGANISM: Homo sapiens

<400> SEQUENCE: 353

Arg Pro Ala Cys Tyr Arg Pro Cys Tyr Ser
1               5                   10

<210> SEQ ID NO 354
<211> LENGTH: 10
```

<212> TYPE: PRT
<213> ORGANISM: Homo sapiens

<400> SEQUENCE: 354

Arg Pro Phe Cys Phe Arg Arg Cys Tyr Ser
1               5                   10

<210> SEQ ID NO 355
<211> LENGTH: 10
<212> TYPE: PRT
<213> ORGANISM: Homo sapiens

<400> SEQUENCE: 355

Arg Pro Ile Cys Arg Pro Ile Cys Ser Gly
1               5                   10

<210> SEQ ID NO 356
<211> LENGTH: 10
<212> TYPE: PRT
<213> ORGANISM: Homo sapiens

<400> SEQUENCE: 356

Arg Pro Leu Cys Tyr Arg Arg Cys Tyr Ser
1               5                   10

<210> SEQ ID NO 357
<211> LENGTH: 10
<212> TYPE: PRT
<213> ORGANISM: Homo sapiens

<400> SEQUENCE: 357

Arg Ser Pro Cys Gln Ala Ser Cys Tyr Val
1               5                   10

<210> SEQ ID NO 358
<211> LENGTH: 10
<212> TYPE: PRT
<213> ORGANISM: Homo sapiens

<400> SEQUENCE: 358

Arg Val Ser Cys His Thr Thr Cys Tyr Arg
1               5                   10

<210> SEQ ID NO 359
<211> LENGTH: 10
<212> TYPE: PRT
<213> ORGANISM: Homo sapiens

<400> SEQUENCE: 359

Ser Ala Ile Cys Arg Pro Thr Cys Pro Arg
1               5                   10

<210> SEQ ID NO 360
<211> LENGTH: 10
<212> TYPE: PRT
<213> ORGANISM: Homo sapiens

<400> SEQUENCE: 360

Ser Asp Ser Cys Lys Arg Asp Cys Lys Lys
1               5                   10

<210> SEQ ID NO 361
<211> LENGTH: 10
<212> TYPE: PRT
<213> ORGANISM: Homo sapiens

<400> SEQUENCE: 361

Ser Glu Gly Cys Gly Ser Gly Cys Gly Gly
1               5                   10

<210> SEQ ID NO 362
<211> LENGTH: 10
<212> TYPE: PRT
<213> ORGANISM: Homo sapiens

<400> SEQUENCE: 362

Ser Phe Leu Cys Arg Pro Ala Cys Ser Arg
1               5                   10

<210> SEQ ID NO 363
<211> LENGTH: 10
<212> TYPE: PRT
<213> ORGANISM: Homo sapiens

<400> SEQUENCE: 363

Ser Gly Gly Cys Gly Ser Gly Cys Gly Gly
1               5                   10

<210> SEQ ID NO 364
<211> LENGTH: 10
<212> TYPE: PRT
<213> ORGANISM: Homo sapiens

<400> SEQUENCE: 364

Ser Gly Gly Cys Gly Ser Ser Cys Gly Gly
1               5                   10

<210> SEQ ID NO 365
<211> LENGTH: 10
<212> TYPE: PRT
<213> ORGANISM: Homo sapiens

<400> SEQUENCE: 365

Ser Gly Ser Cys Gln Ala Ala Cys Gly Gln
1               5                   10

<210> SEQ ID NO 366
<211> LENGTH: 10
<212> TYPE: PRT
<213> ORGANISM: Homo sapiens

<400> SEQUENCE: 366

Ser Leu Leu Cys His Pro Val Cys Lys Ser
1               5                   10

<210> SEQ ID NO 367
<211> LENGTH: 10
<212> TYPE: PRT
<213> ORGANISM: Homo sapiens

<400> SEQUENCE: 367

Ser Leu Leu Cys His Pro Val Cys Arg Ser
1               5                   10

<210> SEQ ID NO 368
<211> LENGTH: 10
<212> TYPE: PRT
<213> ORGANISM: Homo sapiens

<400> SEQUENCE: 368

Ser Leu Leu Cys Arg Pro Ala Cys Ser Pro
1               5                   10

<210> SEQ ID NO 369
<211> LENGTH: 10
<212> TYPE: PRT
<213> ORGANISM: Homo sapiens

<400> SEQUENCE: 369

Ser Leu Leu Cys Arg Pro Ala Cys Ser Arg
1               5                   10

<210> SEQ ID NO 370
<211> LENGTH: 10
<212> TYPE: PRT
<213> ORGANISM: Homo sapiens

<400> SEQUENCE: 370

Ser Leu Leu Cys Arg Pro Ile Cys Arg Pro
1               5                   10

<210> SEQ ID NO 371
<211> LENGTH: 10
<212> TYPE: PRT
<213> ORGANISM: Homo sapiens

<400> SEQUENCE: 371

Ser Leu Leu Cys Arg Pro Met Cys Ser Arg
1               5                   10

<210> SEQ ID NO 372
<211> LENGTH: 10
<212> TYPE: PRT
<213> ORGANISM: Homo sapiens

<400> SEQUENCE: 372

Ser Leu Leu Cys Arg Pro Thr Cys Ser Arg
1               5                   10

<210> SEQ ID NO 373
<211> LENGTH: 10
<212> TYPE: PRT
<213> ORGANISM: Homo sapiens

<400> SEQUENCE: 373

Ser Leu Leu Cys Arg Pro Val Cys Gln Pro
1               5                   10

<210> SEQ ID NO 374
<211> LENGTH: 10
<212> TYPE: PRT
<213> ORGANISM: Homo sapiens

<400> SEQUENCE: 374

Ser Leu Leu Cys Arg Pro Val Cys Arg Pro
1               5                   10

<210> SEQ ID NO 375
<211> LENGTH: 10
<212> TYPE: PRT
<213> ORGANISM: Homo sapiens

<400> SEQUENCE: 375

Ser Leu Leu Cys Arg Pro Val Cys Arg Ser

```
1               5                  10

<210> SEQ ID NO 376
<211> LENGTH: 10
<212> TYPE: PRT
<213> ORGANISM: Homo sapiens

<400> SEQUENCE: 376

Ser Leu Leu Cys Arg Pro Val Cys Ser Arg
1               5                  10

<210> SEQ ID NO 377
<211> LENGTH: 10
<212> TYPE: PRT
<213> ORGANISM: Homo sapiens

<400> SEQUENCE: 377

Ser Asn Pro Cys Gln Val Thr Cys Ser Arg
1               5                  10

<210> SEQ ID NO 378
<211> LENGTH: 10
<212> TYPE: PRT
<213> ORGANISM: Homo sapiens

<400> SEQUENCE: 378

Ser Arg Gly Cys Gly Ser Gly Cys Gly Gly
1               5                  10

<210> SEQ ID NO 379
<211> LENGTH: 10
<212> TYPE: PRT
<213> ORGANISM: Homo sapiens

<400> SEQUENCE: 379

Ser Arg Ser Cys Gln Ser Pro Cys Tyr Arg
1               5                  10

<210> SEQ ID NO 380
<211> LENGTH: 10
<212> TYPE: PRT
<213> ORGANISM: Homo sapiens

<400> SEQUENCE: 380

Ser Arg Ser Cys Gln Ser Ser Cys Tyr Arg
1               5                  10

<210> SEQ ID NO 381
<211> LENGTH: 10
<212> TYPE: PRT
<213> ORGANISM: Homo sapiens

<400> SEQUENCE: 381

Ser Ser Gly Cys Gly Tyr Gly Cys Gly Tyr
1               5                  10

<210> SEQ ID NO 382
<211> LENGTH: 10
<212> TYPE: PRT
<213> ORGANISM: Homo sapiens

<400> SEQUENCE: 382

Ser Ser Gly Cys Pro Met Ala Cys Pro Gly
1               5                  10
```

<210> SEQ ID NO 383
<211> LENGTH: 10
<212> TYPE: PRT
<213> ORGANISM: Homo sapiens

<400> SEQUENCE: 383

Ser Ser Ile Cys Gln Pro Ile Cys Ser Glu
1               5                   10

<210> SEQ ID NO 384
<211> LENGTH: 10
<212> TYPE: PRT
<213> ORGANISM: Homo sapiens

<400> SEQUENCE: 384

Ser Ser Pro Cys His Thr Ser Cys Tyr Tyr
1               5                   10

<210> SEQ ID NO 385
<211> LENGTH: 10
<212> TYPE: PRT
<213> ORGANISM: Homo sapiens

<400> SEQUENCE: 385

Ser Ser Pro Cys Gln Pro Thr Cys Tyr Val
1               5                   10

<210> SEQ ID NO 386
<211> LENGTH: 10
<212> TYPE: PRT
<213> ORGANISM: Homo sapiens

<400> SEQUENCE: 386

Ser Ser Pro Cys Gln Gln Ser Cys Tyr Val
1               5                   10

<210> SEQ ID NO 387
<211> LENGTH: 10
<212> TYPE: PRT
<213> ORGANISM: Homo sapiens

<400> SEQUENCE: 387

Ser Ser Pro Cys Gln Thr Ser Cys Tyr Arg
1               5                   10

<210> SEQ ID NO 388
<211> LENGTH: 10
<212> TYPE: PRT
<213> ORGANISM: Homo sapiens

<400> SEQUENCE: 388

Ser Ser Ser Cys Gln Gln Ser Cys Arg Val
1               5                   10

<210> SEQ ID NO 389
<211> LENGTH: 10
<212> TYPE: PRT
<213> ORGANISM: Homo sapiens

<400> SEQUENCE: 389

Ser Thr Val Cys Gln Pro Ala Cys Gly Val
1               5                   10

<210> SEQ ID NO 390

```
<211> LENGTH: 10
<212> TYPE: PRT
<213> ORGANISM: Homo sapiens

<400> SEQUENCE: 390

Thr Asp Asn Cys Gln Glu Thr Cys Gly Glu
1               5                   10

<210> SEQ ID NO 391
<211> LENGTH: 10
<212> TYPE: PRT
<213> ORGANISM: Homo sapiens

<400> SEQUENCE: 391

Thr Gln Pro Cys Tyr Glu Pro Cys Leu Pro
1               5                   10

<210> SEQ ID NO 392
<211> LENGTH: 10
<212> TYPE: PRT
<213> ORGANISM: Homo sapiens

<400> SEQUENCE: 392

Thr Ser Ser Cys Gly Thr Gly Cys Gly Ile
1               5                   10

<210> SEQ ID NO 393
<211> LENGTH: 10
<212> TYPE: PRT
<213> ORGANISM: Homo sapiens

<400> SEQUENCE: 393

Thr Ser Ser Cys Gln Pro Ser Cys Gly Arg
1               5                   10

<210> SEQ ID NO 394
<211> LENGTH: 10
<212> TYPE: PRT
<213> ORGANISM: Homo sapiens

<400> SEQUENCE: 394

Thr Ser Ser Cys Thr Thr Pro Cys Tyr Gln
1               5                   10

<210> SEQ ID NO 395
<211> LENGTH: 10
<212> TYPE: PRT
<213> ORGANISM: Homo sapiens

<400> SEQUENCE: 395

Thr Ser Val Cys Leu Pro Gly Cys Leu Asn
1               5                   10

<210> SEQ ID NO 396
<211> LENGTH: 10
<212> TYPE: PRT
<213> ORGANISM: Homo sapiens

<400> SEQUENCE: 396

Thr Thr Val Cys Leu Pro Gly Cys Leu Asn
1               5                   10

<210> SEQ ID NO 397
<211> LENGTH: 10
<212> TYPE: PRT
```

```
<213> ORGANISM: Homo sapiens

<400> SEQUENCE: 397

Val Ala Asn Cys Gln Ala Pro Cys Ser Thr
1               5                   10

<210> SEQ ID NO 398
<211> LENGTH: 10
<212> TYPE: PRT
<213> ORGANISM: Homo sapiens

<400> SEQUENCE: 398

Val Asp Asp Cys Pro Glu Ser Cys Trp Pro
1               5                   10

<210> SEQ ID NO 399
<211> LENGTH: 10
<212> TYPE: PRT
<213> ORGANISM: Homo sapiens

<400> SEQUENCE: 399

Val Lys Arg Cys Pro Ser Val Cys Pro Glu
1               5                   10

<210> SEQ ID NO 400
<211> LENGTH: 10
<212> TYPE: PRT
<213> ORGANISM: Homo sapiens

<400> SEQUENCE: 400

Val Ser Ser Cys Gln Pro Ser Cys Ser Glu
1               5                   10

<210> SEQ ID NO 401
<211> LENGTH: 10
<212> TYPE: PRT
<213> ORGANISM: Homo sapiens

<400> SEQUENCE: 401

Tyr Glu Gly Cys Arg Tyr Gly Cys Gly His
1               5                   10

<210> SEQ ID NO 402
<211> LENGTH: 10
<212> TYPE: PRT
<213> ORGANISM: Homo sapiens

<400> SEQUENCE: 402

Tyr Gly Arg Cys Arg His Gly Cys His Ser
1               5                   10

<210> SEQ ID NO 403
<211> LENGTH: 10
<212> TYPE: PRT
<213> ORGANISM: Homo sapiens

<400> SEQUENCE: 403

Tyr Gly Tyr Cys Arg Pro Ser Cys Tyr Gly
1               5                   10

<210> SEQ ID NO 404
<211> LENGTH: 10
<212> TYPE: PRT
<213> ORGANISM: Homo sapiens
```

-continued

```
<400> SEQUENCE: 404

Tyr Arg Asp Cys Gln Lys Thr Cys Trp Glu
1               5                   10

<210> SEQ ID NO 405
<211> LENGTH: 10
<212> TYPE: PRT
<213> ORGANISM: Homo sapiens

<400> SEQUENCE: 405

Tyr Arg Gly Cys Gln Glu Ile Cys Trp Glu
1               5                   10

<210> SEQ ID NO 406
<211> LENGTH: 10
<212> TYPE: PRT
<213> ORGANISM: Homo sapiens

<400> SEQUENCE: 406

Tyr Arg Gly Cys Gln Glu Thr Cys Trp Arg
1               5                   10

<210> SEQ ID NO 407
<211> LENGTH: 10
<212> TYPE: PRT
<213> ORGANISM: Homo sapiens

<400> SEQUENCE: 407

Tyr Arg Gly Cys Gln Gln Thr Cys Trp Glu
1               5                   10

<210> SEQ ID NO 408
<211> LENGTH: 10
<212> TYPE: PRT
<213> ORGANISM: Homo sapiens

<400> SEQUENCE: 408

Tyr Arg Ser Cys Arg Pro Ser Cys Tyr Gly
1               5                   10

<210> SEQ ID NO 409
<211> LENGTH: 10
<212> TYPE: PRT
<213> ORGANISM: Homo sapiens

<400> SEQUENCE: 409

Gly Gly Val Cys Gly Pro Ser Pro Pro Cys
1               5                   10

<210> SEQ ID NO 410
<211> LENGTH: 10
<212> TYPE: PRT
<213> ORGANISM: Homo sapiens

<400> SEQUENCE: 410

Gly Val Cys Gly Pro Ser Pro Pro Cys Ile
1               5                   10

<210> SEQ ID NO 411
<211> LENGTH: 10
<212> TYPE: PRT
<213> ORGANISM: Homo sapiens

<400> SEQUENCE: 411
```

Val Cys Gly Pro Ser Pro Pro Cys Ile Thr
1               5                   10

<210> SEQ ID NO 412
<211> LENGTH: 10
<212> TYPE: PRT
<213> ORGANISM: Homo sapiens

<400> SEQUENCE: 412

Cys Gly Pro Ser Pro Pro Cys Ile Thr Thr
1               5                   10

<210> SEQ ID NO 413
<211> LENGTH: 10
<212> TYPE: PRT
<213> ORGANISM: Homo sapiens

<400> SEQUENCE: 413

Cys Ala Pro Ile Tyr Cys Arg Arg Thr Cys
1               5                   10

<210> SEQ ID NO 414
<211> LENGTH: 10
<212> TYPE: PRT
<213> ORGANISM: Homo sapiens

<400> SEQUENCE: 414

Cys Ala Pro Ser Pro Cys Gln Ala Ser Cys
1               5                   10

<210> SEQ ID NO 415
<211> LENGTH: 10
<212> TYPE: PRT
<213> ORGANISM: Homo sapiens

<400> SEQUENCE: 415

Cys Ala Pro Ser Pro Cys Gln Pro Ala Cys
1               5                   10

<210> SEQ ID NO 416
<211> LENGTH: 10
<212> TYPE: PRT
<213> ORGANISM: Homo sapiens

<400> SEQUENCE: 416

Cys Ala Pro Val Tyr Cys Arg Arg Thr Cys
1               5                   10

<210> SEQ ID NO 417
<211> LENGTH: 10
<212> TYPE: PRT
<213> ORGANISM: Homo sapiens

<400> SEQUENCE: 417

Cys Ala Ser Ser Pro Cys Gln Gln Ala Cys
1               5                   10

<210> SEQ ID NO 418
<211> LENGTH: 10
<212> TYPE: PRT
<213> ORGANISM: Homo sapiens

<400> SEQUENCE: 418

Cys Ala Ser Ser Ser Cys Gln Pro Ala Cys
1               5                   10

<210> SEQ ID NO 419
<211> LENGTH: 10
<212> TYPE: PRT
<213> ORGANISM: Homo sapiens

<400> SEQUENCE: 419

Cys Ala Ser Ser Cys Gln Gln Ser Cys
1               5                   10

<210> SEQ ID NO 420
<211> LENGTH: 10
<212> TYPE: PRT
<213> ORGANISM: Homo sapiens

<400> SEQUENCE: 420

Cys Cys Gly Asn Phe Ser Ser His Ser Cys
1               5                   10

<210> SEQ ID NO 421
<211> LENGTH: 10
<212> TYPE: PRT
<213> ORGANISM: Homo sapiens

<400> SEQUENCE: 421

Cys Cys Gly Tyr Gly Gly Leu Gly Cys Gly
1               5                   10

<210> SEQ ID NO 422
<211> LENGTH: 10
<212> TYPE: PRT
<213> ORGANISM: Homo sapiens

<400> SEQUENCE: 422

Cys Cys Asn Tyr Tyr Gly Asn Ser Cys Gly
1               5                   10

<210> SEQ ID NO 423
<211> LENGTH: 10
<212> TYPE: PRT
<213> ORGANISM: Homo sapiens

<400> SEQUENCE: 423

Cys Cys Asn Tyr Tyr Arg Asn Ser Cys Gly
1               5                   10

<210> SEQ ID NO 424
<211> LENGTH: 10
<212> TYPE: PRT
<213> ORGANISM: Homo sapiens

<400> SEQUENCE: 424

Cys Cys Ser Arg Asn Phe Ser Ser Cys Ser
1               5                   10

<210> SEQ ID NO 425
<211> LENGTH: 10
<212> TYPE: PRT
<213> ORGANISM: Homo sapiens

<400> SEQUENCE: 425

Cys Asp Ala Gly Ser Cys Gln Pro Ser Cys
1               5                   10

```
<210> SEQ ID NO 426
<211> LENGTH: 10
<212> TYPE: PRT
<213> ORGANISM: Homo sapiens

<400> SEQUENCE: 426

Cys Asp Pro Cys Ser Leu Gln Glu Gly Cys
1               5                   10

<210> SEQ ID NO 427
<211> LENGTH: 10
<212> TYPE: PRT
<213> ORGANISM: Homo sapiens

<400> SEQUENCE: 427

Cys Asp Pro Ser Pro Cys Glu Pro Ser Cys
1               5                   10

<210> SEQ ID NO 428
<211> LENGTH: 10
<212> TYPE: PRT
<213> ORGANISM: Homo sapiens

<400> SEQUENCE: 428

Cys Asp Pro Val Ile Cys Glu Pro Ser Cys
1               5                   10

<210> SEQ ID NO 429
<211> LENGTH: 10
<212> TYPE: PRT
<213> ORGANISM: Homo sapiens

<400> SEQUENCE: 429

Cys Asp Gln Gly Leu Cys Gln Glu Thr Cys
1               5                   10

<210> SEQ ID NO 430
<211> LENGTH: 10
<212> TYPE: PRT
<213> ORGANISM: Homo sapiens

<400> SEQUENCE: 430

Cys Glu Ala Thr Thr Cys Glu Pro Ser Cys
1               5                   10

<210> SEQ ID NO 431
<211> LENGTH: 10
<212> TYPE: PRT
<213> ORGANISM: Homo sapiens

<400> SEQUENCE: 431

Cys Glu Leu Pro Cys Gly Thr Pro Ser Cys
1               5                   10

<210> SEQ ID NO 432
<211> LENGTH: 10
<212> TYPE: PRT
<213> ORGANISM: Homo sapiens

<400> SEQUENCE: 432

Cys Glu Pro Ala Ile Cys Glu Pro Ser Cys
1               5                   10

<210> SEQ ID NO 433
<211> LENGTH: 10
```

<212> TYPE: PRT
<213> ORGANISM: Homo sapiens

<400> SEQUENCE: 433

Cys Glu Pro Pro Cys Gly Thr Ala Pro Cys
1               5                   10

<210> SEQ ID NO 434
<211> LENGTH: 10
<212> TYPE: PRT
<213> ORGANISM: Homo sapiens

<400> SEQUENCE: 434

Cys Glu Pro Pro Cys Ser Ala Pro Ser Cys
1               5                   10

<210> SEQ ID NO 435
<211> LENGTH: 10
<212> TYPE: PRT
<213> ORGANISM: Homo sapiens

<400> SEQUENCE: 435

Cys Glu Pro Arg Ser Cys Ala Ser Ser Cys
1               5                   10

<210> SEQ ID NO 436
<211> LENGTH: 10
<212> TYPE: PRT
<213> ORGANISM: Homo sapiens

<400> SEQUENCE: 436

Cys Glu Pro Ser Ala Cys Gln Ser Gly Cys
1               5                   10

<210> SEQ ID NO 437
<211> LENGTH: 10
<212> TYPE: PRT
<213> ORGANISM: Homo sapiens

<400> SEQUENCE: 437

Cys Glu Pro Ser Cys Ser Val Ser Asn Cys
1               5                   10

<210> SEQ ID NO 438
<211> LENGTH: 10
<212> TYPE: PRT
<213> ORGANISM: Homo sapiens

<400> SEQUENCE: 438

Cys Glu Pro Ser Cys Ser Val Ser Ser Cys
1               5                   10

<210> SEQ ID NO 439
<211> LENGTH: 10
<212> TYPE: PRT
<213> ORGANISM: Homo sapiens

<400> SEQUENCE: 439

Cys Glu Pro Ser Pro Cys Gln Ser Gly Cys
1               5                   10

<210> SEQ ID NO 440
<211> LENGTH: 10
<212> TYPE: PRT
<213> ORGANISM: Homo sapiens

```
<400> SEQUENCE: 440

Cys Glu Pro Thr Ala Cys Gln Pro Thr Cys
1               5                   10

<210> SEQ ID NO 441
<211> LENGTH: 10
<212> TYPE: PRT
<213> ORGANISM: Homo sapiens

<400> SEQUENCE: 441

Cys Glu Pro Thr Ser Cys Gln Thr Ser Cys
1               5                   10

<210> SEQ ID NO 442
<211> LENGTH: 10
<212> TYPE: PRT
<213> ORGANISM: Homo sapiens

<400> SEQUENCE: 442

Cys Glu Pro Val Cys Leu Arg Pro Val Cys
1               5                   10

<210> SEQ ID NO 443
<211> LENGTH: 10
<212> TYPE: PRT
<213> ORGANISM: Homo sapiens

<400> SEQUENCE: 443

Cys Glu Thr Ser Ser Cys Gln Pro Arg Cys
1               5                   10

<210> SEQ ID NO 444
<211> LENGTH: 10
<212> TYPE: PRT
<213> ORGANISM: Homo sapiens

<400> SEQUENCE: 444

Cys Glu Thr Thr Cys Phe Gln Pro Thr Cys
1               5                   10

<210> SEQ ID NO 445
<211> LENGTH: 10
<212> TYPE: PRT
<213> ORGANISM: Homo sapiens

<400> SEQUENCE: 445

Cys Phe Gln Pro Thr Cys Val Ser Ser Cys
1               5                   10

<210> SEQ ID NO 446
<211> LENGTH: 10
<212> TYPE: PRT
<213> ORGANISM: Homo sapiens

<400> SEQUENCE: 446

Cys Phe Gln Pro Thr Cys Val Thr Ser Cys
1               5                   10

<210> SEQ ID NO 447
<211> LENGTH: 10
<212> TYPE: PRT
<213> ORGANISM: Homo sapiens

<400> SEQUENCE: 447
```

```
Cys Phe Gln Pro Thr Cys Val Tyr Ser Cys
1               5                   10
```

<210> SEQ ID NO 448
<211> LENGTH: 10
<212> TYPE: PRT
<213> ORGANISM: Homo sapiens

<400> SEQUENCE: 448

```
Cys Gly Cys Gly Phe Arg Arg Leu Gly Cys
1               5                   10
```

<210> SEQ ID NO 449
<211> LENGTH: 10
<212> TYPE: PRT
<213> ORGANISM: Homo sapiens

<400> SEQUENCE: 449

```
Cys Gly Cys Gly Tyr Arg Gly Leu Asp Cys
1               5                   10
```

<210> SEQ ID NO 450
<211> LENGTH: 10
<212> TYPE: PRT
<213> ORGANISM: Homo sapiens

<400> SEQUENCE: 450

```
Cys Gly Cys Asn Gly Tyr Tyr Gly Cys Tyr
1               5                   10
```

<210> SEQ ID NO 451
<211> LENGTH: 10
<212> TYPE: PRT
<213> ORGANISM: Homo sapiens

<400> SEQUENCE: 451

```
Cys Gly Phe Gly Ser Cys Tyr Gly Cys Gly
1               5                   10
```

<210> SEQ ID NO 452
<211> LENGTH: 10
<212> TYPE: PRT
<213> ORGANISM: Homo sapiens

<400> SEQUENCE: 452

```
Cys Gly Gly Ser Gly Cys Gly Gly Ser Cys
1               5                   10
```

<210> SEQ ID NO 453
<211> LENGTH: 10
<212> TYPE: PRT
<213> ORGANISM: Homo sapiens

<400> SEQUENCE: 453

```
Cys Gly Gly Ser Gly Ser Ser Cys Cys Val
1               5                   10
```

<210> SEQ ID NO 454
<211> LENGTH: 10
<212> TYPE: PRT
<213> ORGANISM: Homo sapiens

<400> SEQUENCE: 454

```
Cys Gly Gly Val Ser Cys His Thr Thr Cys
```

```
1               5                   10

<210> SEQ ID NO 455
<211> LENGTH: 10
<212> TYPE: PRT
<213> ORGANISM: Homo sapiens

<400> SEQUENCE: 455

Cys Gly Lys Gly Gly Cys Gly Ser Cys Gly
1               5                   10

<210> SEQ ID NO 456
<211> LENGTH: 10
<212> TYPE: PRT
<213> ORGANISM: Homo sapiens

<400> SEQUENCE: 456

Cys Gly Lys Arg Gly Cys Gly Ser Cys Gly
1               5                   10

<210> SEQ ID NO 457
<211> LENGTH: 10
<212> TYPE: PRT
<213> ORGANISM: Homo sapiens

<400> SEQUENCE: 457

Cys Gly Gln Asp Leu Cys Gln Glu Thr Cys
1               5                   10

<210> SEQ ID NO 458
<211> LENGTH: 10
<212> TYPE: PRT
<213> ORGANISM: Homo sapiens

<400> SEQUENCE: 458

Cys Gly Gln Thr Ser Cys Gly Ser Ser Cys
1               5                   10

<210> SEQ ID NO 459
<211> LENGTH: 10
<212> TYPE: PRT
<213> ORGANISM: Homo sapiens

<400> SEQUENCE: 459

Cys Gly Gln Val Leu Cys Gln Glu Thr Cys
1               5                   10

<210> SEQ ID NO 460
<211> LENGTH: 10
<212> TYPE: PRT
<213> ORGANISM: Homo sapiens

<400> SEQUENCE: 460

Cys Gly Arg Asp Leu Cys Gln Glu Thr Cys
1               5                   10

<210> SEQ ID NO 461
<211> LENGTH: 10
<212> TYPE: PRT
<213> ORGANISM: Homo sapiens

<400> SEQUENCE: 461

Cys Gly Arg Val Ser Cys His Thr Thr Cys
1               5                   10
```

<210> SEQ ID NO 462
<211> LENGTH: 10
<212> TYPE: PRT
<213> ORGANISM: Homo sapiens

<400> SEQUENCE: 462

Cys Gly Ser Cys Gly Phe Gly Ser Cys Tyr
1               5                   10

<210> SEQ ID NO 463
<211> LENGTH: 10
<212> TYPE: PRT
<213> ORGANISM: Homo sapiens

<400> SEQUENCE: 463

Cys Gly Ser Cys Gly Gly Ser Lys Gly Cys
1               5                   10

<210> SEQ ID NO 464
<211> LENGTH: 10
<212> TYPE: PRT
<213> ORGANISM: Homo sapiens

<400> SEQUENCE: 464

Cys Gly Ser Gly Cys Gly Val Pro Val Cys
1               5                   10

<210> SEQ ID NO 465
<211> LENGTH: 10
<212> TYPE: PRT
<213> ORGANISM: Homo sapiens

<400> SEQUENCE: 465

Cys Gly Ser Leu Leu Cys Arg Pro Thr Cys
1               5                   10

<210> SEQ ID NO 466
<211> LENGTH: 10
<212> TYPE: PRT
<213> ORGANISM: Homo sapiens

<400> SEQUENCE: 466

Cys Gly Ser Arg Cys Tyr Val Pro Val Cys
1               5                   10

<210> SEQ ID NO 467
<211> LENGTH: 10
<212> TYPE: PRT
<213> ORGANISM: Homo sapiens

<400> SEQUENCE: 467

Cys Gly Ser Ser Ser Cys Gly Pro Gln Cys
1               5                   10

<210> SEQ ID NO 468
<211> LENGTH: 10
<212> TYPE: PRT
<213> ORGANISM: Homo sapiens

<400> SEQUENCE: 468

Cys Gly Ser Val Cys Ser Asp Gln Gly Cys
1               5                   10

<210> SEQ ID NO 469

```
<211> LENGTH: 10
<212> TYPE: PRT
<213> ORGANISM: Homo sapiens

<400> SEQUENCE: 469

Cys Gly Ser Val Cys Ser Asp Gln Ser Cys
1               5                   10

<210> SEQ ID NO 470
<211> LENGTH: 10
<212> TYPE: PRT
<213> ORGANISM: Homo sapiens

<400> SEQUENCE: 470

Cys Gly Ser Val Cys Ser His Gln Gly Cys
1               5                   10

<210> SEQ ID NO 471
<211> LENGTH: 10
<212> TYPE: PRT
<213> ORGANISM: Homo sapiens

<400> SEQUENCE: 471

Cys Gly Ser Tyr Gly Cys Ser Gln Cys Ser
1               5                   10

<210> SEQ ID NO 472
<211> LENGTH: 10
<212> TYPE: PRT
<213> ORGANISM: Homo sapiens

<400> SEQUENCE: 472

Cys Gly Val Cys Leu Pro Ser Thr Cys Pro
1               5                   10

<210> SEQ ID NO 473
<211> LENGTH: 10
<212> TYPE: PRT
<213> ORGANISM: Homo sapiens

<400> SEQUENCE: 473

Cys Gly Tyr Glu Gly Cys Arg Tyr Gly Cys
1               5                   10

<210> SEQ ID NO 474
<211> LENGTH: 10
<212> TYPE: PRT
<213> ORGANISM: Homo sapiens

<400> SEQUENCE: 474

Cys Gly Tyr Gly Cys Gly Tyr Gly Cys Gly
1               5                   10

<210> SEQ ID NO 475
<211> LENGTH: 10
<212> TYPE: PRT
<213> ORGANISM: Homo sapiens

<400> SEQUENCE: 475

Cys Gly Tyr Gly Gly Cys Gly Tyr Gly Cys
1               5                   10

<210> SEQ ID NO 476
<211> LENGTH: 10
<212> TYPE: PRT
```

```
<213> ORGANISM: Homo sapiens

<400> SEQUENCE: 476

Cys Gly Tyr Gly Ser Phe Cys Gly Cys Gly
1               5                   10

<210> SEQ ID NO 477
<211> LENGTH: 10
<212> TYPE: PRT
<213> ORGANISM: Homo sapiens

<400> SEQUENCE: 477

Cys Gly Tyr Gly Ser Gly Cys Gly Cys Gly
1               5                   10

<210> SEQ ID NO 478
<211> LENGTH: 10
<212> TYPE: PRT
<213> ORGANISM: Homo sapiens

<400> SEQUENCE: 478

Cys His Pro Ser Cys Gly Met Ser Ser Cys
1               5                   10

<210> SEQ ID NO 479
<211> LENGTH: 10
<212> TYPE: PRT
<213> ORGANISM: Homo sapiens

<400> SEQUENCE: 479

Cys His Pro Ser Cys Ser Ile Ser Ser Cys
1               5                   10

<210> SEQ ID NO 480
<211> LENGTH: 10
<212> TYPE: PRT
<213> ORGANISM: Homo sapiens

<400> SEQUENCE: 480

Cys His Pro Thr Cys Tyr Gln Thr Ile Cys
1               5                   10

<210> SEQ ID NO 481
<211> LENGTH: 10
<212> TYPE: PRT
<213> ORGANISM: Homo sapiens

<400> SEQUENCE: 481

Cys His Thr Ser Cys Ser Pro Ala Cys Gln
1               5                   10

<210> SEQ ID NO 482
<211> LENGTH: 10
<212> TYPE: PRT
<213> ORGANISM: Homo sapiens

<400> SEQUENCE: 482

Cys His Thr Ser Cys Ser Ser Gly Cys Gln
1               5                   10

<210> SEQ ID NO 483
<211> LENGTH: 10
<212> TYPE: PRT
<213> ORGANISM: Homo sapiens
```

```
<400> SEQUENCE: 483

Cys His Thr Thr Cys Tyr Arg Pro Ala Cys
1               5                   10

<210> SEQ ID NO 484
<211> LENGTH: 10
<212> TYPE: PRT
<213> ORGANISM: Homo sapiens

<400> SEQUENCE: 484

Cys His Thr Thr Cys Tyr Arg Pro Thr Cys
1               5                   10

<210> SEQ ID NO 485
<211> LENGTH: 10
<212> TYPE: PRT
<213> ORGANISM: Homo sapiens

<400> SEQUENCE: 485

Cys Ile His Ser Pro Cys Gln Ala Ser Cys
1               5                   10

<210> SEQ ID NO 486
<211> LENGTH: 10
<212> TYPE: PRT
<213> ORGANISM: Homo sapiens

<400> SEQUENCE: 486

Cys Ile His Ser Thr His Cys Gly Cys Asn
1               5                   10

<210> SEQ ID NO 487
<211> LENGTH: 10
<212> TYPE: PRT
<213> ORGANISM: Homo sapiens

<400> SEQUENCE: 487

Cys Ile Arg Ser Pro Cys Gln Ala Ser Cys
1               5                   10

<210> SEQ ID NO 488
<211> LENGTH: 10
<212> TYPE: PRT
<213> ORGANISM: Homo sapiens

<400> SEQUENCE: 488

Cys Ile Ser Ser Cys Tyr Arg Pro Gln Cys
1               5                   10

<210> SEQ ID NO 489
<211> LENGTH: 10
<212> TYPE: PRT
<213> ORGANISM: Homo sapiens

<400> SEQUENCE: 489

Cys Ile Ser Ser Pro Cys Gln Gln Ser Cys
1               5                   10

<210> SEQ ID NO 490
<211> LENGTH: 10
<212> TYPE: PRT
<213> ORGANISM: Homo sapiens

<400> SEQUENCE: 490
```

```
Cys Lys Pro Cys Ser Ser Gln Ser Ser Cys
1               5                   10
```

<210> SEQ ID NO 491
<211> LENGTH: 10
<212> TYPE: PRT
<213> ORGANISM: Homo sapiens

<400> SEQUENCE: 491

```
Cys Lys Pro Ser Cys Ser Gln Ser Ser Cys
1               5                   10
```

<210> SEQ ID NO 492
<211> LENGTH: 10
<212> TYPE: PRT
<213> ORGANISM: Homo sapiens

<400> SEQUENCE: 492

```
Cys Lys Pro Val Cys Phe Lys Pro Ile Cys
1               5                   10
```

<210> SEQ ID NO 493
<211> LENGTH: 10
<212> TYPE: PRT
<213> ORGANISM: Homo sapiens

<400> SEQUENCE: 493

```
Cys Lys Pro Val Cys Tyr Val Pro Thr Cys
1               5                   10
```

<210> SEQ ID NO 494
<211> LENGTH: 10
<212> TYPE: PRT
<213> ORGANISM: Homo sapiens

<400> SEQUENCE: 494

```
Cys Lys Pro Val Ser Cys Val Pro Val Cys
1               5                   10
```

<210> SEQ ID NO 495
<211> LENGTH: 10
<212> TYPE: PRT
<213> ORGANISM: Homo sapiens

<400> SEQUENCE: 495

```
Cys Lys Pro Val Tyr Cys Val Pro Val Cys
1               5                   10
```

<210> SEQ ID NO 496
<211> LENGTH: 10
<212> TYPE: PRT
<213> ORGANISM: Homo sapiens

<400> SEQUENCE: 496

```
Cys Lys Thr Val Tyr Cys Lys Pro Ile Cys
1               5                   10
```

<210> SEQ ID NO 497
<211> LENGTH: 10
<212> TYPE: PRT
<213> ORGANISM: Homo sapiens

<400> SEQUENCE: 497

```
Cys Leu Asn Gln Ser Cys Gly Ser Asn Cys
1               5                   10
```

```
<210> SEQ ID NO 498
<211> LENGTH: 10
<212> TYPE: PRT
<213> ORGANISM: Homo sapiens

<400> SEQUENCE: 498

Cys Leu Asn Gln Ser Cys Gly Ser Ser Cys
1               5                   10

<210> SEQ ID NO 499
<211> LENGTH: 10
<212> TYPE: PRT
<213> ORGANISM: Homo sapiens

<400> SEQUENCE: 499

Cys Leu Pro Gly Cys Leu Asn Gln Ser Cys
1               5                   10

<210> SEQ ID NO 500
<211> LENGTH: 10
<212> TYPE: PRT
<213> ORGANISM: Homo sapiens

<400> SEQUENCE: 500

Cys Leu Pro Gly Ser Cys Asp Ser Cys Ser
1               5                   10

<210> SEQ ID NO 501
<211> LENGTH: 10
<212> TYPE: PRT
<213> ORGANISM: Homo sapiens

<400> SEQUENCE: 501

Cys Leu Pro Pro Cys Tyr Leu Val Ser Cys
1               5                   10

<210> SEQ ID NO 502
<211> LENGTH: 10
<212> TYPE: PRT
<213> ORGANISM: Homo sapiens

<400> SEQUENCE: 502

Cys Leu Pro Thr Ser Cys Gln Pro Ser Cys
1               5                   10

<210> SEQ ID NO 503
<211> LENGTH: 10
<212> TYPE: PRT
<213> ORGANISM: Homo sapiens

<400> SEQUENCE: 503

Cys Leu Ser Phe Leu Cys Arg Pro Ala Cys
1               5                   10

<210> SEQ ID NO 504
<211> LENGTH: 10
<212> TYPE: PRT
<213> ORGANISM: Homo sapiens

<400> SEQUENCE: 504

Cys Leu Val Ser Ser Cys Gln Pro Ser Cys
1               5                   10
```

```
<210> SEQ ID NO 505
<211> LENGTH: 10
<212> TYPE: PRT
<213> ORGANISM: Homo sapiens

<400> SEQUENCE: 505

Cys Met Pro Ser Pro Cys Gln Pro Ala Cys
1               5                   10

<210> SEQ ID NO 506
<211> LENGTH: 10
<212> TYPE: PRT
<213> ORGANISM: Homo sapiens

<400> SEQUENCE: 506

Cys Met Ser Gly Ser Cys Gln Ala Ala Cys
1               5                   10

<210> SEQ ID NO 507
<211> LENGTH: 10
<212> TYPE: PRT
<213> ORGANISM: Homo sapiens

<400> SEQUENCE: 507

Cys Asn Glu Ser Ser Tyr Cys Leu Pro Cys
1               5                   10

<210> SEQ ID NO 508
<211> LENGTH: 10
<212> TYPE: PRT
<213> ORGANISM: Homo sapiens

<400> SEQUENCE: 508

Cys Pro Ala Ser Cys Val Ser Leu Leu Cys
1               5                   10

<210> SEQ ID NO 509
<211> LENGTH: 10
<212> TYPE: PRT
<213> ORGANISM: Homo sapiens

<400> SEQUENCE: 509

Cys Pro Met Ala Cys Pro Gly Ser Pro Cys
1               5                   10

<210> SEQ ID NO 510
<211> LENGTH: 10
<212> TYPE: PRT
<213> ORGANISM: Homo sapiens

<400> SEQUENCE: 510

Cys Pro Ser Ser Cys Thr Ala Val Val Cys
1               5                   10

<210> SEQ ID NO 511
<211> LENGTH: 10
<212> TYPE: PRT
<213> ORGANISM: Homo sapiens

<400> SEQUENCE: 511

Cys Pro Val Thr Cys Glu Pro Ser Pro Cys
1               5                   10

<210> SEQ ID NO 512
<211> LENGTH: 10
```

```
<212> TYPE: PRT
<213> ORGANISM: Homo sapiens

<400> SEQUENCE: 512

Cys Gln Ala Ala Cys Glu Pro Ser Ala Cys
1               5                   10

<210> SEQ ID NO 513
<211> LENGTH: 10
<212> TYPE: PRT
<213> ORGANISM: Homo sapiens

<400> SEQUENCE: 513

Cys Gln Ala Ala Cys Glu Pro Ser Pro Cys
1               5                   10

<210> SEQ ID NO 514
<211> LENGTH: 10
<212> TYPE: PRT
<213> ORGANISM: Homo sapiens

<400> SEQUENCE: 514

Cys Gln Ala Ala Cys Gly Gln Ser Val Cys
1               5                   10

<210> SEQ ID NO 515
<211> LENGTH: 10
<212> TYPE: PRT
<213> ORGANISM: Homo sapiens

<400> SEQUENCE: 515

Cys Gln Ala Pro Cys Ser Thr Lys Asn Cys
1               5                   10

<210> SEQ ID NO 516
<211> LENGTH: 10
<212> TYPE: PRT
<213> ORGANISM: Homo sapiens

<400> SEQUENCE: 516

Cys Gln Ala Val Cys Glu Pro Ser Pro Cys
1               5                   10

<210> SEQ ID NO 517
<211> LENGTH: 10
<212> TYPE: PRT
<213> ORGANISM: Homo sapiens

<400> SEQUENCE: 517

Cys Gln Asp Ser Cys Gly Ser Ser Ser Cys
1               5                   10

<210> SEQ ID NO 518
<211> LENGTH: 10
<212> TYPE: PRT
<213> ORGANISM: Homo sapiens

<400> SEQUENCE: 518

Cys Gln His Ser Ser Cys Gln Pro Thr Cys
1               5                   10

<210> SEQ ID NO 519
<211> LENGTH: 10
<212> TYPE: PRT
<213> ORGANISM: Homo sapiens
```

<400> SEQUENCE: 519

Cys Gln Ile Ser Ser Cys Gly Thr Gly Cys
1               5                   10

<210> SEQ ID NO 520
<211> LENGTH: 10
<212> TYPE: PRT
<213> ORGANISM: Homo sapiens

<400> SEQUENCE: 520

Cys Gln Lys Ser Ser Cys Gln Pro Ala Cys
1               5                   10

<210> SEQ ID NO 521
<211> LENGTH: 10
<212> TYPE: PRT
<213> ORGANISM: Homo sapiens

<400> SEQUENCE: 521

Cys Gln Pro Met Cys Ser His Ala Ala Cys
1               5                   10

<210> SEQ ID NO 522
<211> LENGTH: 10
<212> TYPE: PRT
<213> ORGANISM: Homo sapiens

<400> SEQUENCE: 522

Cys Gln Pro Pro Cys Thr Thr Ala Leu Cys
1               5                   10

<210> SEQ ID NO 523
<211> LENGTH: 10
<212> TYPE: PRT
<213> ORGANISM: Homo sapiens

<400> SEQUENCE: 523

Cys Gln Pro Ser Cys Glu Ser Ser Phe Cys
1               5                   10

<210> SEQ ID NO 524
<211> LENGTH: 10
<212> TYPE: PRT
<213> ORGANISM: Homo sapiens

<400> SEQUENCE: 524

Cys Gln Pro Ser Cys Ser Glu Ser Thr Cys
1               5                   10

<210> SEQ ID NO 525
<211> LENGTH: 10
<212> TYPE: PRT
<213> ORGANISM: Homo sapiens

<400> SEQUENCE: 525

Cys Gln Pro Ser Cys Thr Ser Val Leu Cys
1               5                   10

<210> SEQ ID NO 526
<211> LENGTH: 10
<212> TYPE: PRT
<213> ORGANISM: Homo sapiens

<400> SEQUENCE: 526

Cys Gln Pro Thr Cys Gly Gly Ser Ser Cys
1               5                   10

<210> SEQ ID NO 527
<211> LENGTH: 10
<212> TYPE: PRT
<213> ORGANISM: Homo sapiens

<400> SEQUENCE: 527

Cys Gln Pro Thr Cys Ser Arg Pro Ser Cys
1               5                   10

<210> SEQ ID NO 528
<211> LENGTH: 10
<212> TYPE: PRT
<213> ORGANISM: Homo sapiens

<400> SEQUENCE: 528

Cys Gln Pro Val Cys Pro Thr Pro Thr Cys
1               5                   10

<210> SEQ ID NO 529
<211> LENGTH: 10
<212> TYPE: PRT
<213> ORGANISM: Homo sapiens

<400> SEQUENCE: 529

Cys Gln Pro Val Leu Cys Lys Ser Ser Cys
1               5                   10

<210> SEQ ID NO 530
<211> LENGTH: 10
<212> TYPE: PRT
<213> ORGANISM: Homo sapiens

<400> SEQUENCE: 530

Cys Gln Pro Val Val Cys Glu Pro Ser Cys
1               5                   10

<210> SEQ ID NO 531
<211> LENGTH: 10
<212> TYPE: PRT
<213> ORGANISM: Homo sapiens

<400> SEQUENCE: 531

Cys Gln Gln Pro Ser Cys Gln Pro Ala Cys
1               5                   10

<210> SEQ ID NO 532
<211> LENGTH: 10
<212> TYPE: PRT
<213> ORGANISM: Homo sapiens

<400> SEQUENCE: 532

Cys Gln Gln Ser Cys Arg Val Pro Val Cys
1               5                   10

<210> SEQ ID NO 533
<211> LENGTH: 10
<212> TYPE: PRT
<213> ORGANISM: Homo sapiens

<400> SEQUENCE: 533

Cys Gln Gln Ser Cys Tyr Val Pro Val Cys

```
1               5                  10
```

<210> SEQ ID NO 534
<211> LENGTH: 10
<212> TYPE: PRT
<213> ORGANISM: Homo sapiens

<400> SEQUENCE: 534

```
Cys Gln Gln Ser Gly Cys Gln Pro Ala Cys
1               5                  10
```

<210> SEQ ID NO 535
<211> LENGTH: 10
<212> TYPE: PRT
<213> ORGANISM: Homo sapiens

<400> SEQUENCE: 535

```
Cys Gln Gln Ser Ser Cys His Pro Ala Cys
1               5                  10
```

<210> SEQ ID NO 536
<211> LENGTH: 10
<212> TYPE: PRT
<213> ORGANISM: Homo sapiens

<400> SEQUENCE: 536

```
Cys Gln Gln Ser Ser Cys Lys Pro Ala Cys
1               5                  10
```

<210> SEQ ID NO 537
<211> LENGTH: 10
<212> TYPE: PRT
<213> ORGANISM: Homo sapiens

<400> SEQUENCE: 537

```
Cys Gln Gln Ser Ser Cys Gln Leu Ala Cys
1               5                  10
```

<210> SEQ ID NO 538
<211> LENGTH: 10
<212> TYPE: PRT
<213> ORGANISM: Homo sapiens

<400> SEQUENCE: 538

```
Cys Gln Gln Ser Ser Cys Gln Pro Ala Cys
1               5                  10
```

<210> SEQ ID NO 539
<211> LENGTH: 10
<212> TYPE: PRT
<213> ORGANISM: Homo sapiens

<400> SEQUENCE: 539

```
Cys Gln Gln Ser Ser Cys Gln Pro Thr Cys
1               5                  10
```

<210> SEQ ID NO 540
<211> LENGTH: 10
<212> TYPE: PRT
<213> ORGANISM: Homo sapiens

<400> SEQUENCE: 540

```
Cys Gln Gln Ser Ser Cys Gln Ser Ala Cys
1               5                  10
```

<210> SEQ ID NO 541
<211> LENGTH: 10
<212> TYPE: PRT
<213> ORGANISM: Homo sapiens

<400> SEQUENCE: 541

Cys Gln Gln Ser Ser Cys Val Ser Cys Val
1               5                   10

<210> SEQ ID NO 542
<211> LENGTH: 10
<212> TYPE: PRT
<213> ORGANISM: Homo sapiens

<400> SEQUENCE: 542

Cys Gln Gln Ser Tyr Cys Val Pro Val Cys
1               5                   10

<210> SEQ ID NO 543
<211> LENGTH: 10
<212> TYPE: PRT
<213> ORGANISM: Homo sapiens

<400> SEQUENCE: 543

Cys Gln Ser Gly Cys Ile Ser Ser Cys Thr
1               5                   10

<210> SEQ ID NO 544
<211> LENGTH: 10
<212> TYPE: PRT
<213> ORGANISM: Homo sapiens

<400> SEQUENCE: 544

Cys Gln Ser Gly Cys Thr Asp Ser Cys Thr
1               5                   10

<210> SEQ ID NO 545
<211> LENGTH: 10
<212> TYPE: PRT
<213> ORGANISM: Homo sapiens

<400> SEQUENCE: 545

Cys Gln Ser Gly Cys Thr Ser Ser Cys Thr
1               5                   10

<210> SEQ ID NO 546
<211> LENGTH: 10
<212> TYPE: PRT
<213> ORGANISM: Homo sapiens

<400> SEQUENCE: 546

Cys Gln Ser Ser Cys Tyr Arg Pro Thr Cys
1               5                   10

<210> SEQ ID NO 547
<211> LENGTH: 10
<212> TYPE: PRT
<213> ORGANISM: Homo sapiens

<400> SEQUENCE: 547

Cys Gln Ser Val Cys Tyr Gln Pro Thr Cys
1               5                   10

<210> SEQ ID NO 548

<210> SEQ ID NO 548
<211> LENGTH: 10
<212> TYPE: PRT
<213> ORGANISM: Homo sapiens

<400> SEQUENCE: 548

Cys Gln Ser Val Tyr Cys Gln Pro Thr Cys
1               5                   10

<210> SEQ ID NO 549
<211> LENGTH: 10
<212> TYPE: PRT
<213> ORGANISM: Homo sapiens

<400> SEQUENCE: 549

Cys Gln Thr Ala Cys Glu Pro Ser Ala Cys
1               5                   10

<210> SEQ ID NO 550
<211> LENGTH: 10
<212> TYPE: PRT
<213> ORGANISM: Homo sapiens

<400> SEQUENCE: 550

Cys Gln Thr Ser Ser Cys Gly Thr Gly Cys
1               5                   10

<210> SEQ ID NO 551
<211> LENGTH: 10
<212> TYPE: PRT
<213> ORGANISM: Homo sapiens

<400> SEQUENCE: 551

Cys Gln Thr Thr Cys His Pro Ser Cys Gly
1               5                   10

<210> SEQ ID NO 552
<211> LENGTH: 10
<212> TYPE: PRT
<213> ORGANISM: Homo sapiens

<400> SEQUENCE: 552

Cys Gln Thr Thr Cys Arg Pro Ser Cys Gly
1               5                   10

<210> SEQ ID NO 553
<211> LENGTH: 10
<212> TYPE: PRT
<213> ORGANISM: Homo sapiens

<400> SEQUENCE: 553

Cys Gln Thr Thr Cys Tyr Arg Thr Thr Cys
1               5                   10

<210> SEQ ID NO 554
<211> LENGTH: 10
<212> TYPE: PRT
<213> ORGANISM: Homo sapiens

<400> SEQUENCE: 554

Cys Gln Thr Thr Arg Cys Arg Thr Thr Cys
1               5                   10

<210> SEQ ID NO 555
<211> LENGTH: 10
<212> TYPE: PRT

<213> ORGANISM: Homo sapiens

<400> SEQUENCE: 555

Cys Gln Val Thr Cys Glu Pro Ser Pro Cys
1               5                   10

<210> SEQ ID NO 556
<211> LENGTH: 10
<212> TYPE: PRT
<213> ORGANISM: Homo sapiens

<400> SEQUENCE: 556

Cys Arg Asn Thr Ser Cys Gln Pro Thr Cys
1               5                   10

<210> SEQ ID NO 557
<211> LENGTH: 10
<212> TYPE: PRT
<213> ORGANISM: Homo sapiens

<400> SEQUENCE: 557

Cys Arg Pro Ala Cys Ser Pro Leu Ala Cys
1               5                   10

<210> SEQ ID NO 558
<211> LENGTH: 10
<212> TYPE: PRT
<213> ORGANISM: Homo sapiens

<400> SEQUENCE: 558

Cys Arg Pro Ala Cys Ser Arg Leu Ala Cys
1               5                   10

<210> SEQ ID NO 559
<211> LENGTH: 10
<212> TYPE: PRT
<213> ORGANISM: Homo sapiens

<400> SEQUENCE: 559

Cys Arg Pro Ala Cys Ser Arg Pro Ala Cys
1               5                   10

<210> SEQ ID NO 560
<211> LENGTH: 10
<212> TYPE: PRT
<213> ORGANISM: Homo sapiens

<400> SEQUENCE: 560

Cys Arg Pro Met Cys Ser Arg Pro Ala Cys
1               5                   10

<210> SEQ ID NO 561
<211> LENGTH: 10
<212> TYPE: PRT
<213> ORGANISM: Homo sapiens

<400> SEQUENCE: 561

Cys Arg Pro Ser Cys Gly Gln Thr Thr Cys
1               5                   10

<210> SEQ ID NO 562
<211> LENGTH: 10
<212> TYPE: PRT
<213> ORGANISM: Homo sapiens

<400> SEQUENCE: 562

Cys Arg Pro Ser Cys Gly Val Ser Ser Cys
1               5                   10

<210> SEQ ID NO 563
<211> LENGTH: 10
<212> TYPE: PRT
<213> ORGANISM: Homo sapiens

<400> SEQUENCE: 563

Cys Arg Pro Ser Cys Ser Ile Ser Ser Cys
1               5                   10

<210> SEQ ID NO 564
<211> LENGTH: 10
<212> TYPE: PRT
<213> ORGANISM: Homo sapiens

<400> SEQUENCE: 564

Cys Arg Pro Ser Cys Ser Gln Thr Thr Cys
1               5                   10

<210> SEQ ID NO 565
<211> LENGTH: 10
<212> TYPE: PRT
<213> ORGANISM: Homo sapiens

<400> SEQUENCE: 565

Cys Arg Pro Ser Tyr Cys Gly Gln Ser Cys
1               5                   10

<210> SEQ ID NO 566
<211> LENGTH: 10
<212> TYPE: PRT
<213> ORGANISM: Homo sapiens

<400> SEQUENCE: 566

Cys Arg Pro Ser Tyr Cys Ile Ser Ser Cys
1               5                   10

<210> SEQ ID NO 567
<211> LENGTH: 10
<212> TYPE: PRT
<213> ORGANISM: Homo sapiens

<400> SEQUENCE: 567

Cys Arg Pro Ser Tyr Cys Gln Thr Thr Cys
1               5                   10

<210> SEQ ID NO 568
<211> LENGTH: 10
<212> TYPE: PRT
<213> ORGANISM: Homo sapiens

<400> SEQUENCE: 568

Cys Arg Pro Thr Cys Ser Arg Leu Ala Cys
1               5                   10

<210> SEQ ID NO 569
<211> LENGTH: 10
<212> TYPE: PRT
<213> ORGANISM: Homo sapiens

<400> SEQUENCE: 569

Cys Arg Pro Thr Cys Ser Ser Gly Ser Cys
1               5                   10

<210> SEQ ID NO 570
<211> LENGTH: 10
<212> TYPE: PRT
<213> ORGANISM: Homo sapiens

<400> SEQUENCE: 570

Cys Arg Pro Thr Ser Cys Gln Asn Thr Cys
1               5                   10

<210> SEQ ID NO 571
<211> LENGTH: 10
<212> TYPE: PRT
<213> ORGANISM: Homo sapiens

<400> SEQUENCE: 571

Cys Arg Pro Val Cys Arg Ser Thr Tyr Cys
1               5                   10

<210> SEQ ID NO 572
<211> LENGTH: 10
<212> TYPE: PRT
<213> ORGANISM: Homo sapiens

<400> SEQUENCE: 572

Cys Arg Pro Val Cys Ser Arg Pro Ala Cys
1               5                   10

<210> SEQ ID NO 573
<211> LENGTH: 10
<212> TYPE: PRT
<213> ORGANISM: Homo sapiens

<400> SEQUENCE: 573

Cys Arg Pro Val Thr Cys Val Pro Arg Cys
1               5                   10

<210> SEQ ID NO 574
<211> LENGTH: 10
<212> TYPE: PRT
<213> ORGANISM: Homo sapiens

<400> SEQUENCE: 574

Cys Arg Gln Ser Ser Cys Gln Pro Ala Cys
1               5                   10

<210> SEQ ID NO 575
<211> LENGTH: 10
<212> TYPE: PRT
<213> ORGANISM: Homo sapiens

<400> SEQUENCE: 575

Cys Arg Thr Thr Cys Phe His Pro Ile Cys
1               5                   10

<210> SEQ ID NO 576
<211> LENGTH: 10
<212> TYPE: PRT
<213> ORGANISM: Homo sapiens

<400> SEQUENCE: 576

Cys Arg Thr Thr Cys Phe Gln Pro Thr Cys
1               5                   10

<210> SEQ ID NO 577
<211> LENGTH: 10
<212> TYPE: PRT
<213> ORGANISM: Homo sapiens

<400> SEQUENCE: 577

Cys Arg Thr Thr Cys Tyr Arg Pro Ser Cys
1               5                   10

<210> SEQ ID NO 578
<211> LENGTH: 10
<212> TYPE: PRT
<213> ORGANISM: Homo sapiens

<400> SEQUENCE: 578

Cys Arg Thr Thr Tyr Cys Arg Pro Ser Cys
1               5                   10

<210> SEQ ID NO 579
<211> LENGTH: 10
<212> TYPE: PRT
<213> ORGANISM: Homo sapiens

<400> SEQUENCE: 579

Cys Arg Val Thr Cys Glu Pro Ser Pro Cys
1               5                   10

<210> SEQ ID NO 580
<211> LENGTH: 10
<212> TYPE: PRT
<213> ORGANISM: Homo sapiens

<400> SEQUENCE: 580

Cys Arg Tyr Gly Cys Gly His Arg Gly Cys
1               5                   10

<210> SEQ ID NO 581
<211> LENGTH: 10
<212> TYPE: PRT
<213> ORGANISM: Homo sapiens

<400> SEQUENCE: 581

Cys Ser Ala Pro Cys Val Ala Leu Leu Cys
1               5                   10

<210> SEQ ID NO 582
<211> LENGTH: 10
<212> TYPE: PRT
<213> ORGANISM: Homo sapiens

<400> SEQUENCE: 582

Cys Ser Asp Asp Ser Gly Ser Cys Cys Gln
1               5                   10

<210> SEQ ID NO 583
<211> LENGTH: 10
<212> TYPE: PRT
<213> ORGANISM: Homo sapiens

<400> SEQUENCE: 583

Cys Ser Glu Asp Ser Ser Ser Cys Cys Gln
1               5                   10

```
<210> SEQ ID NO 584
<211> LENGTH: 10
<212> TYPE: PRT
<213> ORGANISM: Homo sapiens

<400> SEQUENCE: 584

Cys Ser Glu Asp Ser Tyr Ser Cys Cys Gln
1               5                   10

<210> SEQ ID NO 585
<211> LENGTH: 10
<212> TYPE: PRT
<213> ORGANISM: Homo sapiens

<400> SEQUENCE: 585

Cys Ser Glu Gly Cys Gly Ser Gly Cys Gly
1               5                   10

<210> SEQ ID NO 586
<211> LENGTH: 10
<212> TYPE: PRT
<213> ORGANISM: Homo sapiens

<400> SEQUENCE: 586

Cys Ser Glu Ser Ser Pro Ser Cys Cys Gln
1               5                   10

<210> SEQ ID NO 587
<211> LENGTH: 10
<212> TYPE: PRT
<213> ORGANISM: Homo sapiens

<400> SEQUENCE: 587

Cys Ser Glu Ser Ser Ser Ser Cys Cys Gln
1               5                   10

<210> SEQ ID NO 588
<211> LENGTH: 10
<212> TYPE: PRT
<213> ORGANISM: Homo sapiens

<400> SEQUENCE: 588

Cys Ser Phe Asp Lys Ser Cys Arg Cys Gly
1               5                   10

<210> SEQ ID NO 589
<211> LENGTH: 10
<212> TYPE: PRT
<213> ORGANISM: Homo sapiens

<400> SEQUENCE: 589

Cys Ser Gly Ala Ser Ser Leu Cys Cys Gln
1               5                   10

<210> SEQ ID NO 590
<211> LENGTH: 10
<212> TYPE: PRT
<213> ORGANISM: Homo sapiens

<400> SEQUENCE: 590

Cys Ser Gly Ala Ser Ser Pro Cys Cys Gln
1               5                   10

<210> SEQ ID NO 591
<211> LENGTH: 10
```

```
<212> TYPE: PRT
<213> ORGANISM: Homo sapiens

<400> SEQUENCE: 591

Cys Ser Gly Ala Ser Ser Ser Cys Cys Gln
1               5                   10

<210> SEQ ID NO 592
<211> LENGTH: 10
<212> TYPE: PRT
<213> ORGANISM: Homo sapiens

<400> SEQUENCE: 592

Cys Ser Gly Ala Ser Thr Ser Cys Cys Gln
1               5                   10

<210> SEQ ID NO 593
<211> LENGTH: 10
<212> TYPE: PRT
<213> ORGANISM: Homo sapiens

<400> SEQUENCE: 593

Cys Ser Gly Gly Cys Gly Ser Gly Cys Gly
1               5                   10

<210> SEQ ID NO 594
<211> LENGTH: 10
<212> TYPE: PRT
<213> ORGANISM: Homo sapiens

<400> SEQUENCE: 594

Cys Ser Gly Gly Cys Gly Ser Ser Cys Gly
1               5                   10

<210> SEQ ID NO 595
<211> LENGTH: 10
<212> TYPE: PRT
<213> ORGANISM: Homo sapiens

<400> SEQUENCE: 595

Cys Ser Gly Ile Ser Ser Ser Cys Cys Gln
1               5                   10

<210> SEQ ID NO 596
<211> LENGTH: 10
<212> TYPE: PRT
<213> ORGANISM: Homo sapiens

<400> SEQUENCE: 596

Cys Ser Lys Asp Ser Ser Ser Cys Cys Gln
1               5                   10

<210> SEQ ID NO 597
<211> LENGTH: 10
<212> TYPE: PRT
<213> ORGANISM: Homo sapiens

<400> SEQUENCE: 597

Cys Ser Lys Gly Ala Cys Gly Ser Cys Gly
1               5                   10

<210> SEQ ID NO 598
<211> LENGTH: 10
<212> TYPE: PRT
<213> ORGANISM: Homo sapiens
```

<400> SEQUENCE: 598

Cys Ser Leu Ser Cys Gly Ser Arg Ser Cys
1               5                   10

<210> SEQ ID NO 599
<211> LENGTH: 10
<212> TYPE: PRT
<213> ORGANISM: Homo sapiens

<400> SEQUENCE: 599

Cys Ser Gln Asp Leu Cys Gln Glu Thr Cys
1               5                   10

<210> SEQ ID NO 600
<211> LENGTH: 10
<212> TYPE: PRT
<213> ORGANISM: Homo sapiens

<400> SEQUENCE: 600

Cys Ser Arg Gly Cys Gly Ser Gly Cys Gly
1               5                   10

<210> SEQ ID NO 601
<211> LENGTH: 10
<212> TYPE: PRT
<213> ORGANISM: Homo sapiens

<400> SEQUENCE: 601

Cys Ser Arg Leu Ser Ser Ala Cys Cys Gly
1               5                   10

<210> SEQ ID NO 602
<211> LENGTH: 10
<212> TYPE: PRT
<213> ORGANISM: Homo sapiens

<400> SEQUENCE: 602

Cys Ser Ser Cys Gly Lys Gly Gly Cys Gly
1               5                   10

<210> SEQ ID NO 603
<211> LENGTH: 10
<212> TYPE: PRT
<213> ORGANISM: Homo sapiens

<400> SEQUENCE: 603

Cys Ser Ser Cys Gly Lys Arg Gly Cys Gly
1               5                   10

<210> SEQ ID NO 604
<211> LENGTH: 10
<212> TYPE: PRT
<213> ORGANISM: Homo sapiens

<400> SEQUENCE: 604

Cys Ser Ser Asp Lys Ser Cys Arg Cys Gly
1               5                   10

<210> SEQ ID NO 605
<211> LENGTH: 10
<212> TYPE: PRT
<213> ORGANISM: Homo sapiens

<400> SEQUENCE: 605

Cys Ser Ser Gly Asn Phe Ser Ser Cys Cys
1               5                   10

<210> SEQ ID NO 606
<211> LENGTH: 10
<212> TYPE: PRT
<213> ORGANISM: Homo sapiens

<400> SEQUENCE: 606

Cys Ser Ser Ser Gly Cys Gly Ser Phe Cys
1               5                   10

<210> SEQ ID NO 607
<211> LENGTH: 10
<212> TYPE: PRT
<213> ORGANISM: Homo sapiens

<400> SEQUENCE: 607

Cys Ser Ser Ser Gly Cys Gly Ser Ser Cys
1               5                   10

<210> SEQ ID NO 608
<211> LENGTH: 10
<212> TYPE: PRT
<213> ORGANISM: Homo sapiens

<400> SEQUENCE: 608

Cys Ser Thr Pro Cys Tyr Gln Pro Ile Cys
1               5                   10

<210> SEQ ID NO 609
<211> LENGTH: 10
<212> TYPE: PRT
<213> ORGANISM: Homo sapiens

<400> SEQUENCE: 609

Cys Ser Thr Thr Cys Arg Thr Ser Ser Cys
1               5                   10

<210> SEQ ID NO 610
<211> LENGTH: 10
<212> TYPE: PRT
<213> ORGANISM: Homo sapiens

<400> SEQUENCE: 610

Cys Ser Trp Val Pro Ala Cys Ser Cys Thr
1               5                   10

<210> SEQ ID NO 611
<211> LENGTH: 10
<212> TYPE: PRT
<213> ORGANISM: Homo sapiens

<400> SEQUENCE: 611

Cys Thr Phe Ser Pro Cys Gln Gln Ala Cys
1               5                   10

<210> SEQ ID NO 612
<211> LENGTH: 10
<212> TYPE: PRT
<213> ORGANISM: Homo sapiens

<400> SEQUENCE: 612

Cys Thr Met Ser Val Cys Ser Ser Ala Cys

-continued

```
<210> SEQ ID NO 613
<211> LENGTH: 10
<212> TYPE: PRT
<213> ORGANISM: Homo sapiens

<400> SEQUENCE: 613

Cys Thr Arg Pro Ile Cys Glu Pro Cys Arg
1               5                   10

<210> SEQ ID NO 614
<211> LENGTH: 10
<212> TYPE: PRT
<213> ORGANISM: Homo sapiens

<400> SEQUENCE: 614

Cys Thr Ser Ser Pro Cys Gln His Ala Cys
1               5                   10

<210> SEQ ID NO 615
<211> LENGTH: 10
<212> TYPE: PRT
<213> ORGANISM: Homo sapiens

<400> SEQUENCE: 615

Cys Thr Ser Ser Pro Cys Gln Gln Ala Cys
1               5                   10

<210> SEQ ID NO 616
<211> LENGTH: 10
<212> TYPE: PRT
<213> ORGANISM: Homo sapiens

<400> SEQUENCE: 616

Cys Thr Ser Ser Pro Cys Gln Gln Ser Cys
1               5                   10

<210> SEQ ID NO 617
<211> LENGTH: 10
<212> TYPE: PRT
<213> ORGANISM: Homo sapiens

<400> SEQUENCE: 617

Cys Thr Ser Ser Ser Cys Gln Gln Ala Cys
1               5                   10

<210> SEQ ID NO 618
<211> LENGTH: 10
<212> TYPE: PRT
<213> ORGANISM: Homo sapiens

<400> SEQUENCE: 618

Cys Val Ala Leu Leu Cys Arg Pro Leu Cys
1               5                   10

<210> SEQ ID NO 619
<211> LENGTH: 10
<212> TYPE: PRT
<213> ORGANISM: Homo sapiens

<400> SEQUENCE: 619

Cys Val Ala Leu Val Cys Glu Pro Val Cys
1               5                   10
```

<210> SEQ ID NO 620
<211> LENGTH: 10
<212> TYPE: PRT
<213> ORGANISM: Homo sapiens

<400> SEQUENCE: 620

Cys Val Phe Ser Ser Cys Asn Thr Thr Cys
1               5                   10

<210> SEQ ID NO 621
<211> LENGTH: 10
<212> TYPE: PRT
<213> ORGANISM: Homo sapiens

<400> SEQUENCE: 621

Cys Val Gly Phe Val Cys Gln Pro Met Cys
1               5                   10

<210> SEQ ID NO 622
<211> LENGTH: 10
<212> TYPE: PRT
<213> ORGANISM: Homo sapiens

<400> SEQUENCE: 622

Cys Val Pro Arg Cys Thr Arg Pro Ile Cys
1               5                   10

<210> SEQ ID NO 623
<211> LENGTH: 10
<212> TYPE: PRT
<213> ORGANISM: Homo sapiens

<400> SEQUENCE: 623

Cys Val Pro Ser Pro Cys Gln Val Ala Cys
1               5                   10

<210> SEQ ID NO 624
<211> LENGTH: 10
<212> TYPE: PRT
<213> ORGANISM: Homo sapiens

<400> SEQUENCE: 624

Cys Val Pro Ser Arg Cys Gln Ala Ser Cys
1               5                   10

<210> SEQ ID NO 625
<211> LENGTH: 10
<212> TYPE: PRT
<213> ORGANISM: Homo sapiens

<400> SEQUENCE: 625

Cys Val Pro Ser Ser Cys Gln Ala Ser Cys
1               5                   10

<210> SEQ ID NO 626
<211> LENGTH: 10
<212> TYPE: PRT
<213> ORGANISM: Homo sapiens

<400> SEQUENCE: 626

Cys Val Pro Val Cys Asn Lys Pro Val Cys
1               5                   10

<210> SEQ ID NO 627

```
<211> LENGTH: 10
<212> TYPE: PRT
<213> ORGANISM: Homo sapiens

<400> SEQUENCE: 627

Cys Val Pro Val Cys Ser Lys Ser Val Cys
1               5                   10

<210> SEQ ID NO 628
<211> LENGTH: 10
<212> TYPE: PRT
<213> ORGANISM: Homo sapiens

<400> SEQUENCE: 628

Cys Val Pro Val Arg Cys Lys Pro Val Cys
1               5                   10

<210> SEQ ID NO 629
<211> LENGTH: 10
<212> TYPE: PRT
<213> ORGANISM: Homo sapiens

<400> SEQUENCE: 629

Cys Val Ser Leu Leu Cys Arg Pro Ala Cys
1               5                   10

<210> SEQ ID NO 630
<211> LENGTH: 10
<212> TYPE: PRT
<213> ORGANISM: Homo sapiens

<400> SEQUENCE: 630

Cys Val Ser Leu Leu Cys Arg Pro Met Cys
1               5                   10

<210> SEQ ID NO 631
<211> LENGTH: 10
<212> TYPE: PRT
<213> ORGANISM: Homo sapiens

<400> SEQUENCE: 631

Cys Val Ser Leu Leu Cys Arg Pro Thr Cys
1               5                   10

<210> SEQ ID NO 632
<211> LENGTH: 10
<212> TYPE: PRT
<213> ORGANISM: Homo sapiens

<400> SEQUENCE: 632

Cys Val Ser Leu Leu Cys Arg Pro Val Cys
1               5                   10

<210> SEQ ID NO 633
<211> LENGTH: 10
<212> TYPE: PRT
<213> ORGANISM: Homo sapiens

<400> SEQUENCE: 633

Cys Val Ser Asn Pro Cys Gln Val Thr Cys
1               5                   10

<210> SEQ ID NO 634
<211> LENGTH: 10
<212> TYPE: PRT
```

<213> ORGANISM: Homo sapiens

<400> SEQUENCE: 634

Cys Val Ser Arg Cys Tyr Arg Pro His Cys
1               5                   10

<210> SEQ ID NO 635
<211> LENGTH: 10
<212> TYPE: PRT
<213> ORGANISM: Homo sapiens

<400> SEQUENCE: 635

Cys Val Ser Ser Cys Phe Arg Pro Gln Cys
1               5                   10

<210> SEQ ID NO 636
<211> LENGTH: 10
<212> TYPE: PRT
<213> ORGANISM: Homo sapiens

<400> SEQUENCE: 636

Cys Val Ser Ser Ile Cys Gln Pro Ile Cys
1               5                   10

<210> SEQ ID NO 637
<211> LENGTH: 10
<212> TYPE: PRT
<213> ORGANISM: Homo sapiens

<400> SEQUENCE: 637

Cys Val Ser Ser Pro Cys Gln Pro Thr Cys
1               5                   10

<210> SEQ ID NO 638
<211> LENGTH: 10
<212> TYPE: PRT
<213> ORGANISM: Homo sapiens

<400> SEQUENCE: 638

Cys Val Val Ser Cys Thr Pro Pro Ser Cys
1               5                   10

<210> SEQ ID NO 639
<211> LENGTH: 10
<212> TYPE: PRT
<213> ORGANISM: Homo sapiens

<400> SEQUENCE: 639

Cys Val Val Ser Cys Thr Pro Pro Thr Cys
1               5                   10

<210> SEQ ID NO 640
<211> LENGTH: 10
<212> TYPE: PRT
<213> ORGANISM: Homo sapiens

<400> SEQUENCE: 640

Cys Tyr Cys Pro Lys Asn Ser Ile Phe Cys
1               5                   10

<210> SEQ ID NO 641
<211> LENGTH: 10
<212> TYPE: PRT
<213> ORGANISM: Homo sapiens

```
<400> SEQUENCE: 641

Cys Tyr Glu Pro Cys Leu Pro Arg Gly Cys
1               5                   10

<210> SEQ ID NO 642
<211> LENGTH: 10
<212> TYPE: PRT
<213> ORGANISM: Homo sapiens

<400> SEQUENCE: 642

Cys Tyr Arg Arg Cys Tyr Ser Ser Cys Tyr
1               5                   10

<210> SEQ ID NO 643
<211> LENGTH: 10
<212> TYPE: PRT
<213> ORGANISM: Homo sapiens

<400> SEQUENCE: 643

Gly Cys Cys Gly Tyr Gly Gly Leu Gly Cys
1               5                   10

<210> SEQ ID NO 644
<211> LENGTH: 10
<212> TYPE: PRT
<213> ORGANISM: Homo sapiens

<400> SEQUENCE: 644

Gly Cys Gly Gly Cys Gly Ser Gly Cys Ala
1               5                   10

<210> SEQ ID NO 645
<211> LENGTH: 10
<212> TYPE: PRT
<213> ORGANISM: Homo sapiens

<400> SEQUENCE: 645

Gly Cys Gly Gly Cys Gly Ser Gly Cys Gly
1               5                   10

<210> SEQ ID NO 646
<211> LENGTH: 10
<212> TYPE: PRT
<213> ORGANISM: Homo sapiens

<400> SEQUENCE: 646

Gly Cys Gly Gly Cys Gly Ser Ser Cys Gly
1               5                   10

<210> SEQ ID NO 647
<211> LENGTH: 10
<212> TYPE: PRT
<213> ORGANISM: Homo sapiens

<400> SEQUENCE: 647

Gly Cys Gly Gly Cys Ser Ser Ser Cys Gly
1               5                   10

<210> SEQ ID NO 648
<211> LENGTH: 10
<212> TYPE: PRT
<213> ORGANISM: Homo sapiens

<400> SEQUENCE: 648
```

Gly Cys Gly Gly Ser Gly Ser Ser Cys Cys
1               5                   10

<210> SEQ ID NO 649
<211> LENGTH: 10
<212> TYPE: PRT
<213> ORGANISM: Homo sapiens

<400> SEQUENCE: 649

Gly Cys Gly Ser Gly Cys Ala Gly Cys Gly
1               5                   10

<210> SEQ ID NO 650
<211> LENGTH: 10
<212> TYPE: PRT
<213> ORGANISM: Homo sapiens

<400> SEQUENCE: 650

Gly Cys Gly Ser Gly Cys Gly Gly Cys Gly
1               5                   10

<210> SEQ ID NO 651
<211> LENGTH: 10
<212> TYPE: PRT
<213> ORGANISM: Homo sapiens

<400> SEQUENCE: 651

Gly Cys Gly Ser Gly Cys Gly Gly Cys Ser
1               5                   10

<210> SEQ ID NO 652
<211> LENGTH: 10
<212> TYPE: PRT
<213> ORGANISM: Homo sapiens

<400> SEQUENCE: 652

Gly Cys Gly Ser Ser Cys Gly Gly Cys Asp
1               5                   10

<210> SEQ ID NO 653
<211> LENGTH: 10
<212> TYPE: PRT
<213> ORGANISM: Homo sapiens

<400> SEQUENCE: 653

Gly Cys Gly Ser Ser Cys Gly Gly Cys Gly
1               5                   10

<210> SEQ ID NO 654
<211> LENGTH: 10
<212> TYPE: PRT
<213> ORGANISM: Homo sapiens

<400> SEQUENCE: 654

Gly Cys Gly Ser Ser Cys Ser Gln Cys Ser
1               5                   10

<210> SEQ ID NO 655
<211> LENGTH: 10
<212> TYPE: PRT
<213> ORGANISM: Homo sapiens

<400> SEQUENCE: 655

Gly Cys Gly Tyr Ser Ser Ser Cys Cys Gly
1               5                   10

<210> SEQ ID NO 656
<211> LENGTH: 10
<212> TYPE: PRT
<213> ORGANISM: Homo sapiens

<400> SEQUENCE: 656

Gly Cys Lys Gly Gly Cys Gly Ser Cys Gly
1               5                   10

<210> SEQ ID NO 657
<211> LENGTH: 10
<212> TYPE: PRT
<213> ORGANISM: Homo sapiens

<400> SEQUENCE: 657

Gly Cys Ser Gly Cys Ser Gly Gly Cys Gly
1               5                   10

<210> SEQ ID NO 658
<211> LENGTH: 10
<212> TYPE: PRT
<213> ORGANISM: Homo sapiens

<400> SEQUENCE: 658

Ile Cys Ser Gly Ala Ser Ser Leu Cys Cys
1               5                   10

<210> SEQ ID NO 659
<211> LENGTH: 10
<212> TYPE: PRT
<213> ORGANISM: Homo sapiens

<400> SEQUENCE: 659

Ile Cys Ser Gly Ala Ser Ser Pro Cys Cys
1               5                   10

<210> SEQ ID NO 660
<211> LENGTH: 10
<212> TYPE: PRT
<213> ORGANISM: Homo sapiens

<400> SEQUENCE: 660

Met Cys Cys Asn Tyr Tyr Gly Asn Ser Cys
1               5                   10

<210> SEQ ID NO 661
<211> LENGTH: 10
<212> TYPE: PRT
<213> ORGANISM: Homo sapiens

<400> SEQUENCE: 661

Met Cys Cys Asn Tyr Tyr Arg Asn Ser Cys
1               5                   10

<210> SEQ ID NO 662
<211> LENGTH: 10
<212> TYPE: PRT
<213> ORGANISM: Homo sapiens

<400> SEQUENCE: 662

Met Cys Tyr Gly Tyr Gly Cys Gly Cys Gly
1               5                   10

<210> SEQ ID NO 663
<211> LENGTH: 10
<212> TYPE: PRT
<213> ORGANISM: Homo sapiens

<400> SEQUENCE: 663

Asn Cys Cys Ser Arg Asn Phe Ser Ser Cys
1               5                   10

<210> SEQ ID NO 664
<211> LENGTH: 10
<212> TYPE: PRT
<213> ORGANISM: Homo sapiens

<400> SEQUENCE: 664

Pro Cys Ser Leu Gln Glu Gly Cys Cys Arg
1               5                   10

<210> SEQ ID NO 665
<211> LENGTH: 10
<212> TYPE: PRT
<213> ORGANISM: Homo sapiens

<400> SEQUENCE: 665

Pro Cys Ser Ser Gln Ser Ser Cys Cys Val
1               5                   10

<210> SEQ ID NO 666
<211> LENGTH: 10
<212> TYPE: PRT
<213> ORGANISM: Homo sapiens

<400> SEQUENCE: 666

Ser Cys Cys Ala Pro Ala Ser Ser Cys Gln
1               5                   10

<210> SEQ ID NO 667
<211> LENGTH: 10
<212> TYPE: PRT
<213> ORGANISM: Homo sapiens

<400> SEQUENCE: 667

Ser Cys Cys Ala Pro Ala Ser Thr Cys Gln
1               5                   10

<210> SEQ ID NO 668
<211> LENGTH: 10
<212> TYPE: PRT
<213> ORGANISM: Homo sapiens

<400> SEQUENCE: 668

Ser Cys Cys Ala Pro Thr Ser Ser Cys Gln
1               5                   10

<210> SEQ ID NO 669
<211> LENGTH: 10
<212> TYPE: PRT
<213> ORGANISM: Homo sapiens

<400> SEQUENCE: 669

Ser Cys Cys Gly Tyr Arg Pro Leu Cys Tyr
1               5                   10

<210> SEQ ID NO 670
<211> LENGTH: 10

```
<212> TYPE: PRT
<213> ORGANISM: Homo sapiens

<400> SEQUENCE: 670

Ser Cys Cys Val Pro Ala Ser Ser Cys Gln
1               5                   10

<210> SEQ ID NO 671
<211> LENGTH: 10
<212> TYPE: PRT
<213> ORGANISM: Homo sapiens

<400> SEQUENCE: 671

Ser Cys Cys Val Pro Thr Ser Ser Cys Gln
1               5                   10

<210> SEQ ID NO 672
<211> LENGTH: 10
<212> TYPE: PRT
<213> ORGANISM: Homo sapiens

<400> SEQUENCE: 672

Ser Cys Gly Cys Ser Lys Gly Ala Cys Gly
1               5                   10

<210> SEQ ID NO 673
<211> LENGTH: 10
<212> TYPE: PRT
<213> ORGANISM: Homo sapiens

<400> SEQUENCE: 673

Ser Cys Gly Gly Cys Asp Ser Ser Cys Gly
1               5                   10

<210> SEQ ID NO 674
<211> LENGTH: 10
<212> TYPE: PRT
<213> ORGANISM: Homo sapiens

<400> SEQUENCE: 674

Ser Cys Gly Gly Cys Gly Ser Gly Cys Gly
1               5                   10

<210> SEQ ID NO 675
<211> LENGTH: 10
<212> TYPE: PRT
<213> ORGANISM: Homo sapiens

<400> SEQUENCE: 675

Ser Cys Gly Gly Cys Gly Ser Ser Cys Gly
1               5                   10

<210> SEQ ID NO 676
<211> LENGTH: 10
<212> TYPE: PRT
<213> ORGANISM: Homo sapiens

<400> SEQUENCE: 676

Ser Cys Gly Gly Cys Lys Gly Gly Cys Gly
1               5                   10

<210> SEQ ID NO 677
<211> LENGTH: 10
<212> TYPE: PRT
<213> ORGANISM: Homo sapiens
```

```
<400> SEQUENCE: 677

Ser Cys Gly Gly Ser Lys Gly Cys Cys Gly
1               5                   10

<210> SEQ ID NO 678
<211> LENGTH: 10
<212> TYPE: PRT
<213> ORGANISM: Homo sapiens

<400> SEQUENCE: 678

Ser Cys Gly Ser Gly Cys Arg Gly Cys Gly
1               5                   10

<210> SEQ ID NO 679
<211> LENGTH: 10
<212> TYPE: PRT
<213> ORGANISM: Homo sapiens

<400> SEQUENCE: 679

Ser Cys Tyr Gly Cys Gly Tyr Gly Cys Ile
1               5                   10

<210> SEQ ID NO 680
<211> LENGTH: 10
<212> TYPE: PRT
<213> ORGANISM: Homo sapiens

<400> SEQUENCE: 680

Thr Cys Cys Val Pro Val Pro Ser Cys Gly
1               5                   10

<210> SEQ ID NO 681
<211> LENGTH: 10
<212> TYPE: PRT
<213> ORGANISM: Homo sapiens

<400> SEQUENCE: 681

Thr Cys Ser Asp Asp Ser Gly Ser Cys Cys
1               5                   10

<210> SEQ ID NO 682
<211> LENGTH: 10
<212> TYPE: PRT
<213> ORGANISM: Homo sapiens

<400> SEQUENCE: 682

Thr Cys Ser Glu Asp Ser Ser Ser Cys Cys
1               5                   10

<210> SEQ ID NO 683
<211> LENGTH: 10
<212> TYPE: PRT
<213> ORGANISM: Homo sapiens

<400> SEQUENCE: 683

Thr Cys Ser Glu Asp Ser Tyr Ser Cys Cys
1               5                   10

<210> SEQ ID NO 684
<211> LENGTH: 10
<212> TYPE: PRT
<213> ORGANISM: Homo sapiens

<400> SEQUENCE: 684
```

Thr Cys Ser Glu Ser Ser Pro Ser Cys Cys
1               5                   10

<210> SEQ ID NO 685
<211> LENGTH: 10
<212> TYPE: PRT
<213> ORGANISM: Homo sapiens

<400> SEQUENCE: 685

Thr Cys Ser Glu Ser Ser Ser Ser Cys Cys
1               5                   10

<210> SEQ ID NO 686
<211> LENGTH: 10
<212> TYPE: PRT
<213> ORGANISM: Homo sapiens

<400> SEQUENCE: 686

Thr Cys Ser Lys Asp Ser Ser Ser Cys Cys
1               5                   10

<210> SEQ ID NO 687
<211> LENGTH: 10
<212> TYPE: PRT
<213> ORGANISM: Homo sapiens

<400> SEQUENCE: 687

Thr Cys Ser Arg Leu Ser Ser Ala Cys Cys
1               5                   10

<210> SEQ ID NO 688
<211> LENGTH: 10
<212> TYPE: PRT
<213> ORGANISM: Homo sapiens

<400> SEQUENCE: 688

Val Cys Cys Gln Pro Thr Pro Ile Cys Asp
1               5                   10

<210> SEQ ID NO 689
<211> LENGTH: 10
<212> TYPE: PRT
<213> ORGANISM: Homo sapiens

<400> SEQUENCE: 689

Val Cys Ser Glu Asp Ser Ser Ser Cys Cys
1               5                   10

<210> SEQ ID NO 690
<211> LENGTH: 10
<212> TYPE: PRT
<213> ORGANISM: Homo sapiens

<400> SEQUENCE: 690

Val Cys Ser Gly Ala Ser Ser Leu Cys Cys
1               5                   10

<210> SEQ ID NO 691
<211> LENGTH: 10
<212> TYPE: PRT
<213> ORGANISM: Homo sapiens

<400> SEQUENCE: 691

Val Cys Ser Gly Ala Ser Ser Pro Cys Cys

```
                1               5                   10
```

<210> SEQ ID NO 692
<211> LENGTH: 10
<212> TYPE: PRT
<213> ORGANISM: Homo sapiens

<400> SEQUENCE: 692

```
Val Cys Ser Gly Ala Ser Ser Ser Cys Cys
1               5                   10
```

<210> SEQ ID NO 693
<211> LENGTH: 10
<212> TYPE: PRT
<213> ORGANISM: Homo sapiens

<400> SEQUENCE: 693

```
Val Cys Ser Gly Ala Ser Thr Ser Cys Cys
1               5                   10
```

<210> SEQ ID NO 694
<211> LENGTH: 10
<212> TYPE: PRT
<213> ORGANISM: Homo sapiens

<400> SEQUENCE: 694

```
Val Cys Ser Gly Asp Ser Ser Cys Cys Gln
1               5                   10
```

<210> SEQ ID NO 695
<211> LENGTH: 10
<212> TYPE: PRT
<213> ORGANISM: Homo sapiens

<400> SEQUENCE: 695

```
Val Cys Ser Gly Ile Ser Ser Ser Cys Cys
1               5                   10
```

<210> SEQ ID NO 696
<211> LENGTH: 10
<212> TYPE: PRT
<213> ORGANISM: Homo sapiens

<400> SEQUENCE: 696

```
Tyr Cys Val Pro Ile Pro Ser Cys Cys Ala
1               5                   10
```

<210> SEQ ID NO 697
<211> LENGTH: 10
<212> TYPE: PRT
<213> ORGANISM: Homo sapiens

<400> SEQUENCE: 697

```
Cys Ala Ser Ser Cys Cys Thr Pro Ser Cys
1               5                   10
```

<210> SEQ ID NO 698
<211> LENGTH: 10
<212> TYPE: PRT
<213> ORGANISM: Homo sapiens

<400> SEQUENCE: 698

```
Cys Cys Asp Asn Cys Pro Pro Pro Cys His
1               5                   10
```

<210> SEQ ID NO 699
<211> LENGTH: 10
<212> TYPE: PRT
<213> ORGANISM: Homo sapiens

<400> SEQUENCE: 699

Cys Cys Glu Pro Cys Leu Pro Arg Gly Cys
1               5                   10

<210> SEQ ID NO 700
<211> LENGTH: 10
<212> TYPE: PRT
<213> ORGANISM: Homo sapiens

<400> SEQUENCE: 700

Cys Cys Gly Ala Ala Ser Ser Cys Cys Arg
1               5                   10

<210> SEQ ID NO 701
<211> LENGTH: 10
<212> TYPE: PRT
<213> ORGANISM: Homo sapiens

<400> SEQUENCE: 701

Cys Cys Gly Cys Gly Gly Ser Gly Cys Gly
1               5                   10

<210> SEQ ID NO 702
<211> LENGTH: 10
<212> TYPE: PRT
<213> ORGANISM: Homo sapiens

<400> SEQUENCE: 702

Cys Cys Gly Pro Ser Ser Ser Cys Cys Gln
1               5                   10

<210> SEQ ID NO 703
<211> LENGTH: 10
<212> TYPE: PRT
<213> ORGANISM: Homo sapiens

<400> SEQUENCE: 703

Cys Cys Gly Ser Gly Cys Gly Gly Cys Gly
1               5                   10

<210> SEQ ID NO 704
<211> LENGTH: 10
<212> TYPE: PRT
<213> ORGANISM: Homo sapiens

<400> SEQUENCE: 704

Cys Cys Lys Pro Tyr Cys Ser Gln Cys Ser
1               5                   10

<210> SEQ ID NO 705
<211> LENGTH: 10
<212> TYPE: PRT
<213> ORGANISM: Homo sapiens

<400> SEQUENCE: 705

Cys Cys Met Pro Val Ser Ser Cys Cys Ala
1               5                   10

<210> SEQ ID NO 706

```
<211> LENGTH: 10
<212> TYPE: PRT
<213> ORGANISM: Homo sapiens

<400> SEQUENCE: 706

Cys Cys Asn Tyr Tyr Arg Asn Cys Cys Gly
1               5                   10

<210> SEQ ID NO 707
<211> LENGTH: 10
<212> TYPE: PRT
<213> ORGANISM: Homo sapiens

<400> SEQUENCE: 707

Cys Cys Pro Ser Cys Val Val Ser Ser Cys
1               5                   10

<210> SEQ ID NO 708
<211> LENGTH: 10
<212> TYPE: PRT
<213> ORGANISM: Homo sapiens

<400> SEQUENCE: 708

Cys Cys Pro Ser Tyr Cys Val Ser Ser Cys
1               5                   10

<210> SEQ ID NO 709
<211> LENGTH: 10
<212> TYPE: PRT
<213> ORGANISM: Homo sapiens

<400> SEQUENCE: 709

Cys Cys Gln Pro Ile Cys Gly Ser Ser Cys
1               5                   10

<210> SEQ ID NO 710
<211> LENGTH: 10
<212> TYPE: PRT
<213> ORGANISM: Homo sapiens

<400> SEQUENCE: 710

Cys Cys Gln Pro Ile Cys Val Thr Ser Cys
1               5                   10

<210> SEQ ID NO 711
<211> LENGTH: 10
<212> TYPE: PRT
<213> ORGANISM: Homo sapiens

<400> SEQUENCE: 711

Cys Cys Gln Pro Thr Cys Leu Ser Ser Cys
1               5                   10

<210> SEQ ID NO 712
<211> LENGTH: 10
<212> TYPE: PRT
<213> ORGANISM: Homo sapiens

<400> SEQUENCE: 712

Cys Cys Gln Pro Thr Cys Leu Thr Ser Cys
1               5                   10

<210> SEQ ID NO 713
<211> LENGTH: 10
<212> TYPE: PRT
```

```
<213> ORGANISM: Homo sapiens

<400> SEQUENCE: 713

Cys Cys Gln Pro Thr Cys Val Ala Ser Cys
1               5                   10

<210> SEQ ID NO 714
<211> LENGTH: 10
<212> TYPE: PRT
<213> ORGANISM: Homo sapiens

<400> SEQUENCE: 714

Cys Cys Gln Pro Thr Cys Val Thr Ser Cys
1               5                   10

<210> SEQ ID NO 715
<211> LENGTH: 10
<212> TYPE: PRT
<213> ORGANISM: Homo sapiens

<400> SEQUENCE: 715

Cys Cys Gln Pro Tyr Cys His Pro Thr Cys
1               5                   10

<210> SEQ ID NO 716
<211> LENGTH: 10
<212> TYPE: PRT
<213> ORGANISM: Homo sapiens

<400> SEQUENCE: 716

Cys Cys Gln Gln Ser Ser Cys Val Ser Cys
1               5                   10

<210> SEQ ID NO 717
<211> LENGTH: 10
<212> TYPE: PRT
<213> ORGANISM: Homo sapiens

<400> SEQUENCE: 717

Cys Cys Gln Ser Ser Cys Phe Lys Pro Cys
1               5                   10

<210> SEQ ID NO 718
<211> LENGTH: 10
<212> TYPE: PRT
<213> ORGANISM: Homo sapiens

<400> SEQUENCE: 718

Cys Cys Gln Ser Ser Cys Ser Lys Pro Cys
1               5                   10

<210> SEQ ID NO 719
<211> LENGTH: 10
<212> TYPE: PRT
<213> ORGANISM: Homo sapiens

<400> SEQUENCE: 719

Cys Cys Gln Ser Ser Cys Tyr Lys Pro Cys
1               5                   10

<210> SEQ ID NO 720
<211> LENGTH: 10
<212> TYPE: PRT
<213> ORGANISM: Homo sapiens
```

```
<400> SEQUENCE: 720

Cys Cys Gln Thr Ile Cys Arg Ser Thr Cys
1               5                   10

<210> SEQ ID NO 721
<211> LENGTH: 10
<212> TYPE: PRT
<213> ORGANISM: Homo sapiens

<400> SEQUENCE: 721

Cys Cys Gln Thr Thr Cys His Pro Ser Cys
1               5                   10

<210> SEQ ID NO 722
<211> LENGTH: 10
<212> TYPE: PRT
<213> ORGANISM: Homo sapiens

<400> SEQUENCE: 722

Cys Cys Gln Thr Thr Cys Arg Pro Ser Cys
1               5                   10

<210> SEQ ID NO 723
<211> LENGTH: 10
<212> TYPE: PRT
<213> ORGANISM: Homo sapiens

<400> SEQUENCE: 723

Cys Cys Arg Val Pro Thr Cys Ser Cys Ser
1               5                   10

<210> SEQ ID NO 724
<211> LENGTH: 10
<212> TYPE: PRT
<213> ORGANISM: Homo sapiens

<400> SEQUENCE: 724

Cys Cys Ser Pro Gly Cys Gln Pro Thr Cys
1               5                   10

<210> SEQ ID NO 725
<211> LENGTH: 10
<212> TYPE: PRT
<213> ORGANISM: Homo sapiens

<400> SEQUENCE: 725

Cys Cys Ser Ser Gly Cys Gly Ser Cys
1               5                   10

<210> SEQ ID NO 726
<211> LENGTH: 10
<212> TYPE: PRT
<213> ORGANISM: Homo sapiens

<400> SEQUENCE: 726

Cys Cys Ser Ser Ser Cys Gly Ser Cys Gly
1               5                   10

<210> SEQ ID NO 727
<211> LENGTH: 10
<212> TYPE: PRT
<213> ORGANISM: Homo sapiens

<400> SEQUENCE: 727
```

Cys Cys Thr Gln Glu Gln Asn Cys Cys Glu
1               5                   10

<210> SEQ ID NO 728
<211> LENGTH: 10
<212> TYPE: PRT
<213> ORGANISM: Homo sapiens

<400> SEQUENCE: 728

Cys Cys Val Pro Ile Pro Ser Cys Cys Ala
1               5                   10

<210> SEQ ID NO 729
<211> LENGTH: 10
<212> TYPE: PRT
<213> ORGANISM: Homo sapiens

<400> SEQUENCE: 729

Cys Cys Val Pro Ile Ser Ser Cys Cys Ala
1               5                   10

<210> SEQ ID NO 730
<211> LENGTH: 10
<212> TYPE: PRT
<213> ORGANISM: Homo sapiens

<400> SEQUENCE: 730

Cys Cys Val Pro Val Cys Tyr Gln Cys Lys
1               5                   10

<210> SEQ ID NO 731
<211> LENGTH: 10
<212> TYPE: PRT
<213> ORGANISM: Homo sapiens

<400> SEQUENCE: 731

Cys Cys Val Pro Val Pro Ser Cys Cys Ala
1               5                   10

<210> SEQ ID NO 732
<211> LENGTH: 10
<212> TYPE: PRT
<213> ORGANISM: Homo sapiens

<400> SEQUENCE: 732

Cys Cys Val Pro Val Pro Ser Cys Cys Val
1               5                   10

<210> SEQ ID NO 733
<211> LENGTH: 10
<212> TYPE: PRT
<213> ORGANISM: Homo sapiens

<400> SEQUENCE: 733

Cys Cys Val Pro Val Ser Ser Cys Cys Ala
1               5                   10

<210> SEQ ID NO 734
<211> LENGTH: 10
<212> TYPE: PRT
<213> ORGANISM: Homo sapiens

<400> SEQUENCE: 734

Cys Asp Ser Ser Cys Cys Gln Pro Ser Cys
1               5                   10

<210> SEQ ID NO 735
<211> LENGTH: 10
<212> TYPE: PRT
<213> ORGANISM: Homo sapiens

<400> SEQUENCE: 735

Cys Asp Thr Cys Pro Pro Pro Cys Cys Lys
1               5                   10

<210> SEQ ID NO 736
<211> LENGTH: 10
<212> TYPE: PRT
<213> ORGANISM: Homo sapiens

<400> SEQUENCE: 736

Cys Glu Pro Cys Arg Arg Pro Val Cys Cys
1               5                   10

<210> SEQ ID NO 737
<211> LENGTH: 10
<212> TYPE: PRT
<213> ORGANISM: Homo sapiens

<400> SEQUENCE: 737

Cys Glu Pro Ser Cys Cys Gln Pro Val Cys
1               5                   10

<210> SEQ ID NO 738
<211> LENGTH: 10
<212> TYPE: PRT
<213> ORGANISM: Homo sapiens

<400> SEQUENCE: 738

Cys Glu Pro Ser Cys Cys Ser Ala Val Cys
1               5                   10

<210> SEQ ID NO 739
<211> LENGTH: 10
<212> TYPE: PRT
<213> ORGANISM: Homo sapiens

<400> SEQUENCE: 739

Cys Glu Thr Ser Cys Cys Gln Pro Ser Cys
1               5                   10

<210> SEQ ID NO 740
<211> LENGTH: 10
<212> TYPE: PRT
<213> ORGANISM: Homo sapiens

<400> SEQUENCE: 740

Cys Glu Thr Thr Cys Cys Arg Thr Thr Cys
1               5                   10

<210> SEQ ID NO 741
<211> LENGTH: 10
<212> TYPE: PRT
<213> ORGANISM: Homo sapiens

<400> SEQUENCE: 741

Cys Phe Ser Gly Cys Gly Ser Ser Cys Cys
1               5                   10

```
<210> SEQ ID NO 742
<211> LENGTH: 10
<212> TYPE: PRT
<213> ORGANISM: Homo sapiens

<400> SEQUENCE: 742

Cys Gly Cys Ser Gln Ser Asn Cys Cys Lys
1               5                   10

<210> SEQ ID NO 743
<211> LENGTH: 10
<212> TYPE: PRT
<213> ORGANISM: Homo sapiens

<400> SEQUENCE: 743

Cys Gly Cys Ser Gln Ser Ser Cys Cys Lys
1               5                   10

<210> SEQ ID NO 744
<211> LENGTH: 10
<212> TYPE: PRT
<213> ORGANISM: Homo sapiens

<400> SEQUENCE: 744

Cys Gly Gly Cys Gly Gly Cys Gly Gly Cys
1               5                   10

<210> SEQ ID NO 745
<211> LENGTH: 10
<212> TYPE: PRT
<213> ORGANISM: Homo sapiens

<400> SEQUENCE: 745

Cys Gly Gly Cys Gly Gly Gly Cys Cys Gly
1               5                   10

<210> SEQ ID NO 746
<211> LENGTH: 10
<212> TYPE: PRT
<213> ORGANISM: Homo sapiens

<400> SEQUENCE: 746

Cys Gly Gly Cys Gly Ser Gly Cys Cys Val
1               5                   10

<210> SEQ ID NO 747
<211> LENGTH: 10
<212> TYPE: PRT
<213> ORGANISM: Homo sapiens

<400> SEQUENCE: 747

Cys Gly Gly Cys Gly Ser Ser Cys Cys Val
1               5                   10

<210> SEQ ID NO 748
<211> LENGTH: 10
<212> TYPE: PRT
<213> ORGANISM: Homo sapiens

<400> SEQUENCE: 748

Cys Gly Gly Gly Cys Cys Gly Ser Ser Cys
1               5                   10

<210> SEQ ID NO 749
<211> LENGTH: 10
```

```
<212> TYPE: PRT
<213> ORGANISM: Homo sapiens

<400> SEQUENCE: 749

Cys Gly Gly Ser Cys Cys Gly Ser Ser Cys
1               5                   10

<210> SEQ ID NO 750
<211> LENGTH: 10
<212> TYPE: PRT
<213> ORGANISM: Homo sapiens

<400> SEQUENCE: 750

Cys Gly Gln Ser Cys Cys Arg Pro Ala Cys
1               5                   10

<210> SEQ ID NO 751
<211> LENGTH: 10
<212> TYPE: PRT
<213> ORGANISM: Homo sapiens

<400> SEQUENCE: 751

Cys Gly Gln Ser Cys Cys Arg Pro Val Cys
1               5                   10

<210> SEQ ID NO 752
<211> LENGTH: 10
<212> TYPE: PRT
<213> ORGANISM: Homo sapiens

<400> SEQUENCE: 752

Cys Gly Ser Cys Gly Cys Ser Gln Cys Asn
1               5                   10

<210> SEQ ID NO 753
<211> LENGTH: 10
<212> TYPE: PRT
<213> ORGANISM: Homo sapiens

<400> SEQUENCE: 753

Cys Gly Ser Cys Gly Cys Ser Gln Cys Ser
1               5                   10

<210> SEQ ID NO 754
<211> LENGTH: 10
<212> TYPE: PRT
<213> ORGANISM: Homo sapiens

<400> SEQUENCE: 754

Cys Gly Ser Phe Cys Cys Gln Ser Ser Cys
1               5                   10

<210> SEQ ID NO 755
<211> LENGTH: 10
<212> TYPE: PRT
<213> ORGANISM: Homo sapiens

<400> SEQUENCE: 755

Cys Gly Ser Gly Cys Cys Val Pro Val Cys
1               5                   10

<210> SEQ ID NO 756
<211> LENGTH: 10
<212> TYPE: PRT
<213> ORGANISM: Homo sapiens
```

```
<400> SEQUENCE: 756

Cys Gly Ser Ser Cys Cys Gly Ser Gly Cys
1               5                   10

<210> SEQ ID NO 757
<211> LENGTH: 10
<212> TYPE: PRT
<213> ORGANISM: Homo sapiens

<400> SEQUENCE: 757

Cys Gly Ser Ser Cys Cys Gln Pro Cys Tyr
1               5                   10

<210> SEQ ID NO 758
<211> LENGTH: 10
<212> TYPE: PRT
<213> ORGANISM: Homo sapiens

<400> SEQUENCE: 758

Cys Gly Ser Ser Cys Cys Gln Pro Ile Cys
1               5                   10

<210> SEQ ID NO 759
<211> LENGTH: 10
<212> TYPE: PRT
<213> ORGANISM: Homo sapiens

<400> SEQUENCE: 759

Cys Gly Ser Ser Cys Cys Gln Pro Ser Cys
1               5                   10

<210> SEQ ID NO 760
<211> LENGTH: 10
<212> TYPE: PRT
<213> ORGANISM: Homo sapiens

<400> SEQUENCE: 760

Cys Gly Ser Ser Cys Cys Gln Ser Ser Cys
1               5                   10

<210> SEQ ID NO 761
<211> LENGTH: 10
<212> TYPE: PRT
<213> ORGANISM: Homo sapiens

<400> SEQUENCE: 761

Cys Gly Ser Ser Cys Cys Val Pro Ile Cys
1               5                   10

<210> SEQ ID NO 762
<211> LENGTH: 10
<212> TYPE: PRT
<213> ORGANISM: Homo sapiens

<400> SEQUENCE: 762

Cys Gly Ser Ser Cys Cys Val Pro Val Cys
1               5                   10

<210> SEQ ID NO 763
<211> LENGTH: 10
<212> TYPE: PRT
<213> ORGANISM: Homo sapiens

<400> SEQUENCE: 763
```

```
Cys Gly Ser Ser Cys Ser Gln Cys Ser Cys
1               5                   10
```

<210> SEQ ID NO 764
<211> LENGTH: 10
<212> TYPE: PRT
<213> ORGANISM: Homo sapiens

<400> SEQUENCE: 764

```
Cys Gly Tyr Gly Ser Cys Cys Gly Cys Gly
1               5                   10
```

<210> SEQ ID NO 765
<211> LENGTH: 10
<212> TYPE: PRT
<213> ORGANISM: Homo sapiens

<400> SEQUENCE: 765

```
Cys His Pro Arg Cys Cys Ile Ser Ser Cys
1               5                   10
```

<210> SEQ ID NO 766
<211> LENGTH: 10
<212> TYPE: PRT
<213> ORGANISM: Homo sapiens

<400> SEQUENCE: 766

```
Cys His Pro Ser Cys Cys Glu Ser Ser Cys
1               5                   10
```

<210> SEQ ID NO 767
<211> LENGTH: 10
<212> TYPE: PRT
<213> ORGANISM: Homo sapiens

<400> SEQUENCE: 767

```
Cys His Pro Ser Cys Cys Ile Ser Ser Cys
1               5                   10
```

<210> SEQ ID NO 768
<211> LENGTH: 10
<212> TYPE: PRT
<213> ORGANISM: Homo sapiens

<400> SEQUENCE: 768

```
Cys His Pro Thr Cys Cys Gln Asn Thr Cys
1               5                   10
```

<210> SEQ ID NO 769
<211> LENGTH: 10
<212> TYPE: PRT
<213> ORGANISM: Homo sapiens

<400> SEQUENCE: 769

```
Cys His Pro Thr Cys Cys Gln Thr Ile Cys
1               5                   10
```

<210> SEQ ID NO 770
<211> LENGTH: 10
<212> TYPE: PRT
<213> ORGANISM: Homo sapiens

<400> SEQUENCE: 770

```
Cys His Pro Val Cys Cys Gln Thr Thr Cys
```

```
1               5                   10
```

<210> SEQ ID NO 771
<211> LENGTH: 10
<212> TYPE: PRT
<213> ORGANISM: Homo sapiens

<400> SEQUENCE: 771

```
Cys His Pro Val Cys Lys Ser Thr Cys Cys
1               5                   10
```

<210> SEQ ID NO 772
<211> LENGTH: 10
<212> TYPE: PRT
<213> ORGANISM: Homo sapiens

<400> SEQUENCE: 772

```
Cys His Pro Val Cys Arg Ser Thr Cys Cys
1               5                   10
```

<210> SEQ ID NO 773
<211> LENGTH: 10
<212> TYPE: PRT
<213> ORGANISM: Homo sapiens

<400> SEQUENCE: 773

```
Cys Ile Ser Ser Cys Cys His Pro Ser Cys
1               5                   10
```

<210> SEQ ID NO 774
<211> LENGTH: 10
<212> TYPE: PRT
<213> ORGANISM: Homo sapiens

<400> SEQUENCE: 774

```
Cys Ile Ser Ser Cys Cys Lys Pro Ser Cys
1               5                   10
```

<210> SEQ ID NO 775
<211> LENGTH: 10
<212> TYPE: PRT
<213> ORGANISM: Homo sapiens

<400> SEQUENCE: 775

```
Cys Ile Ser Ser Cys Cys Arg Pro Ser Cys
1               5                   10
```

<210> SEQ ID NO 776
<211> LENGTH: 10
<212> TYPE: PRT
<213> ORGANISM: Homo sapiens

<400> SEQUENCE: 776

```
Cys Ile Ser Ser Cys Thr Pro Ser Cys Cys
1               5                   10
```

<210> SEQ ID NO 777
<211> LENGTH: 10
<212> TYPE: PRT
<213> ORGANISM: Homo sapiens

<400> SEQUENCE: 777

```
Cys Ile Ser Ser Ser Cys Cys Pro Ser Cys
1               5                   10
```

<210> SEQ ID NO 778
<211> LENGTH: 10
<212> TYPE: PRT
<213> ORGANISM: Homo sapiens

<400> SEQUENCE: 778

Cys Lys Ala Val Cys Cys Val Pro Thr Cys
1               5                   10

<210> SEQ ID NO 779
<211> LENGTH: 10
<212> TYPE: PRT
<213> ORGANISM: Homo sapiens

<400> SEQUENCE: 779

Cys Lys Pro Cys Cys Ser Gln Ala Ser Cys
1               5                   10

<210> SEQ ID NO 780
<211> LENGTH: 10
<212> TYPE: PRT
<213> ORGANISM: Homo sapiens

<400> SEQUENCE: 780

Cys Lys Pro Cys Cys Ser Gln Ser Arg Cys
1               5                   10

<210> SEQ ID NO 781
<211> LENGTH: 10
<212> TYPE: PRT
<213> ORGANISM: Homo sapiens

<400> SEQUENCE: 781

Cys Lys Pro Cys Cys Ser Gln Ser Ser Cys
1               5                   10

<210> SEQ ID NO 782
<211> LENGTH: 10
<212> TYPE: PRT
<213> ORGANISM: Homo sapiens

<400> SEQUENCE: 782

Cys Lys Pro Cys Cys Ser Ser Ser Gly Cys
1               5                   10

<210> SEQ ID NO 783
<211> LENGTH: 10
<212> TYPE: PRT
<213> ORGANISM: Homo sapiens

<400> SEQUENCE: 783

Cys Lys Pro Cys Ser Cys Phe Ser Gly Cys
1               5                   10

<210> SEQ ID NO 784
<211> LENGTH: 10
<212> TYPE: PRT
<213> ORGANISM: Homo sapiens

<400> SEQUENCE: 784

Cys Lys Pro Cys Ser Cys Ser Ser Gly Cys
1               5                   10

<210> SEQ ID NO 785

```
<211> LENGTH: 10
<212> TYPE: PRT
<213> ORGANISM: Homo sapiens

<400> SEQUENCE: 785

Cys Lys Pro Cys Tyr Cys Ser Ser Gly Cys
1               5                   10

<210> SEQ ID NO 786
<211> LENGTH: 10
<212> TYPE: PRT
<213> ORGANISM: Homo sapiens

<400> SEQUENCE: 786

Cys Lys Pro Ile Cys Cys Val Pro Val Cys
1               5                   10

<210> SEQ ID NO 787
<211> LENGTH: 10
<212> TYPE: PRT
<213> ORGANISM: Homo sapiens

<400> SEQUENCE: 787

Cys Lys Pro Gln Cys Cys Gln Ser Val Cys
1               5                   10

<210> SEQ ID NO 788
<211> LENGTH: 10
<212> TYPE: PRT
<213> ORGANISM: Homo sapiens

<400> SEQUENCE: 788

Cys Lys Pro Ser Cys Cys Gln Thr Thr Cys
1               5                   10

<210> SEQ ID NO 789
<211> LENGTH: 10
<212> TYPE: PRT
<213> ORGANISM: Homo sapiens

<400> SEQUENCE: 789

Cys Lys Pro Val Cys Cys Ala Pro Thr Cys
1               5                   10

<210> SEQ ID NO 790
<211> LENGTH: 10
<212> TYPE: PRT
<213> ORGANISM: Homo sapiens

<400> SEQUENCE: 790

Cys Lys Pro Val Cys Cys Lys Pro Ile Cys
1               5                   10

<210> SEQ ID NO 791
<211> LENGTH: 10
<212> TYPE: PRT
<213> ORGANISM: Homo sapiens

<400> SEQUENCE: 791

Cys Lys Pro Val Cys Cys Lys Ser Ile Cys
1               5                   10

<210> SEQ ID NO 792
<211> LENGTH: 10
<212> TYPE: PRT
```

<213> ORGANISM: Homo sapiens

<400> SEQUENCE: 792

Cys Lys Pro Val Cys Cys Leu Pro Thr Cys
1               5                   10

<210> SEQ ID NO 793
<211> LENGTH: 10
<212> TYPE: PRT
<213> ORGANISM: Homo sapiens

<400> SEQUENCE: 793

Cys Lys Pro Val Cys Cys Val Pro Thr Cys
1               5                   10

<210> SEQ ID NO 794
<211> LENGTH: 10
<212> TYPE: PRT
<213> ORGANISM: Homo sapiens

<400> SEQUENCE: 794

Cys Lys Pro Val Cys Cys Val Pro Val Cys
1               5                   10

<210> SEQ ID NO 795
<211> LENGTH: 10
<212> TYPE: PRT
<213> ORGANISM: Homo sapiens

<400> SEQUENCE: 795

Cys Lys Pro Val Cys Cys Val Ser Thr Cys
1               5                   10

<210> SEQ ID NO 796
<211> LENGTH: 10
<212> TYPE: PRT
<213> ORGANISM: Homo sapiens

<400> SEQUENCE: 796

Cys Lys Pro Tyr Cys Cys Gln Ser Ser Cys
1               5                   10

<210> SEQ ID NO 797
<211> LENGTH: 10
<212> TYPE: PRT
<213> ORGANISM: Homo sapiens

<400> SEQUENCE: 797

Cys Lys Pro Tyr Cys Ser Gln Cys Ser Cys
1               5                   10

<210> SEQ ID NO 798
<211> LENGTH: 10
<212> TYPE: PRT
<213> ORGANISM: Homo sapiens

<400> SEQUENCE: 798

Cys Lys Ser Asn Cys Cys Lys Pro Val Cys
1               5                   10

<210> SEQ ID NO 799
<211> LENGTH: 10
<212> TYPE: PRT
<213> ORGANISM: Homo sapiens

```
<400> SEQUENCE: 799

Cys Lys Thr Val Cys Cys Lys Pro Val Cys
1               5                   10

<210> SEQ ID NO 800
<211> LENGTH: 10
<212> TYPE: PRT
<213> ORGANISM: Homo sapiens

<400> SEQUENCE: 800

Cys Leu Pro Pro Cys Cys Val Val Ser Cys
1               5                   10

<210> SEQ ID NO 801
<211> LENGTH: 10
<212> TYPE: PRT
<213> ORGANISM: Homo sapiens

<400> SEQUENCE: 801

Cys Leu Thr Ser Cys Cys Gln Pro Ser Cys
1               5                   10

<210> SEQ ID NO 802
<211> LENGTH: 10
<212> TYPE: PRT
<213> ORGANISM: Homo sapiens

<400> SEQUENCE: 802

Cys Asn Pro Cys Cys Ser Gln Ser Ser Cys
1               5                   10

<210> SEQ ID NO 803
<211> LENGTH: 10
<212> TYPE: PRT
<213> ORGANISM: Homo sapiens

<400> SEQUENCE: 803

Cys Pro Glu Ser Cys Cys Glu Leu Pro Cys
1               5                   10

<210> SEQ ID NO 804
<211> LENGTH: 10
<212> TYPE: PRT
<213> ORGANISM: Homo sapiens

<400> SEQUENCE: 804

Cys Pro Glu Ser Cys Cys Glu Pro His Cys
1               5                   10

<210> SEQ ID NO 805
<211> LENGTH: 10
<212> TYPE: PRT
<213> ORGANISM: Homo sapiens

<400> SEQUENCE: 805

Cys Pro Glu Ser Cys Cys Glu Pro Pro Cys
1               5                   10

<210> SEQ ID NO 806
<211> LENGTH: 10
<212> TYPE: PRT
<213> ORGANISM: Homo sapiens

<400> SEQUENCE: 806
```

Cys Pro Phe Ser Cys Pro Thr Thr Cys Cys
1               5                   10

<210> SEQ ID NO 807
<211> LENGTH: 10
<212> TYPE: PRT
<213> ORGANISM: Homo sapiens

<400> SEQUENCE: 807

Cys Pro Gly Asp Cys Phe Thr Cys Cys Thr
1               5                   10

<210> SEQ ID NO 808
<211> LENGTH: 10
<212> TYPE: PRT
<213> ORGANISM: Homo sapiens

<400> SEQUENCE: 808

Cys Pro Ser Cys Val Val Ser Ser Cys Cys
1               5                   10

<210> SEQ ID NO 809
<211> LENGTH: 10
<212> TYPE: PRT
<213> ORGANISM: Homo sapiens

<400> SEQUENCE: 809

Cys Pro Ser Tyr Cys Val Ser Ser Cys Cys
1               5                   10

<210> SEQ ID NO 810
<211> LENGTH: 10
<212> TYPE: PRT
<213> ORGANISM: Homo sapiens

<400> SEQUENCE: 810

Cys Pro Thr Thr Cys Cys Arg Thr Thr Cys
1               5                   10

<210> SEQ ID NO 811
<211> LENGTH: 10
<212> TYPE: PRT
<213> ORGANISM: Homo sapiens

<400> SEQUENCE: 811

Cys Gln Glu Thr Cys Cys Arg Pro Ser Cys
1               5                   10

<210> SEQ ID NO 812
<211> LENGTH: 10
<212> TYPE: PRT
<213> ORGANISM: Homo sapiens

<400> SEQUENCE: 812

Cys Gln His Ala Cys Cys Val Pro Val Cys
1               5                   10

<210> SEQ ID NO 813
<211> LENGTH: 10
<212> TYPE: PRT
<213> ORGANISM: Homo sapiens

<400> SEQUENCE: 813

Cys Gln Asn Thr Cys Cys Arg Thr Thr Cys
1               5                   10

<210> SEQ ID NO 814
<211> LENGTH: 10
<212> TYPE: PRT
<213> ORGANISM: Homo sapiens

<400> SEQUENCE: 814

Cys Gln Pro Ala Cys Cys Gln Pro Thr Cys
1               5                   10

<210> SEQ ID NO 815
<211> LENGTH: 10
<212> TYPE: PRT
<213> ORGANISM: Homo sapiens

<400> SEQUENCE: 815

Cys Gln Pro Ala Cys Cys Thr Ala Ser Cys
1               5                   10

<210> SEQ ID NO 816
<211> LENGTH: 10
<212> TYPE: PRT
<213> ORGANISM: Homo sapiens

<400> SEQUENCE: 816

Cys Gln Pro Ala Cys Cys Thr Ser Ser Cys
1               5                   10

<210> SEQ ID NO 817
<211> LENGTH: 10
<212> TYPE: PRT
<213> ORGANISM: Homo sapiens

<400> SEQUENCE: 817

Cys Gln Pro Ala Cys Cys Thr Thr Ser Cys
1               5                   10

<210> SEQ ID NO 818
<211> LENGTH: 10
<212> TYPE: PRT
<213> ORGANISM: Homo sapiens

<400> SEQUENCE: 818

Cys Gln Pro Ala Cys Cys Val Pro Val Cys
1               5                   10

<210> SEQ ID NO 819
<211> LENGTH: 10
<212> TYPE: PRT
<213> ORGANISM: Homo sapiens

<400> SEQUENCE: 819

Cys Gln Pro Ala Cys Cys Val Ser Ser Cys
1               5                   10

<210> SEQ ID NO 820
<211> LENGTH: 10
<212> TYPE: PRT
<213> ORGANISM: Homo sapiens

<400> SEQUENCE: 820

Cys Gln Pro Cys Cys His Pro Thr Cys Tyr
1               5                   10

```
<210> SEQ ID NO 821
<211> LENGTH: 10
<212> TYPE: PRT
<213> ORGANISM: Homo sapiens

<400> SEQUENCE: 821

Cys Gln Pro Cys Cys Arg Pro Thr Ser Cys
1               5                   10

<210> SEQ ID NO 822
<211> LENGTH: 10
<212> TYPE: PRT
<213> ORGANISM: Homo sapiens

<400> SEQUENCE: 822

Cys Gln Pro Ile Cys Cys Gly Ser Ser Cys
1               5                   10

<210> SEQ ID NO 823
<211> LENGTH: 10
<212> TYPE: PRT
<213> ORGANISM: Homo sapiens

<400> SEQUENCE: 823

Cys Gln Pro Ile Cys Gly Ser Ser Cys Cys
1               5                   10

<210> SEQ ID NO 824
<211> LENGTH: 10
<212> TYPE: PRT
<213> ORGANISM: Homo sapiens

<400> SEQUENCE: 824

Cys Gln Pro Ile Cys Val Thr Ser Cys Cys
1               5                   10

<210> SEQ ID NO 825
<211> LENGTH: 10
<212> TYPE: PRT
<213> ORGANISM: Homo sapiens

<400> SEQUENCE: 825

Cys Gln Pro Asn Cys Cys Arg Pro Ser Cys
1               5                   10

<210> SEQ ID NO 826
<211> LENGTH: 10
<212> TYPE: PRT
<213> ORGANISM: Homo sapiens

<400> SEQUENCE: 826

Cys Gln Pro Arg Cys Cys Glu Thr Ser Cys
1               5                   10

<210> SEQ ID NO 827
<211> LENGTH: 10
<212> TYPE: PRT
<213> ORGANISM: Homo sapiens

<400> SEQUENCE: 827

Cys Gln Pro Ser Cys Cys Arg Pro Ala Cys
1               5                   10

<210> SEQ ID NO 828
<211> LENGTH: 10
```

<212> TYPE: PRT
<213> ORGANISM: Homo sapiens

<400> SEQUENCE: 828

Cys Gln Pro Ser Cys Cys Ser Thr Pro Cys
1               5                   10

<210> SEQ ID NO 829
<211> LENGTH: 10
<212> TYPE: PRT
<213> ORGANISM: Homo sapiens

<400> SEQUENCE: 829

Cys Gln Pro Ser Cys Cys Ser Thr Thr Cys
1               5                   10

<210> SEQ ID NO 830
<211> LENGTH: 10
<212> TYPE: PRT
<213> ORGANISM: Homo sapiens

<400> SEQUENCE: 830

Cys Gln Pro Ser Cys Cys Val Pro Ser Cys
1               5                   10

<210> SEQ ID NO 831
<211> LENGTH: 10
<212> TYPE: PRT
<213> ORGANISM: Homo sapiens

<400> SEQUENCE: 831

Cys Gln Pro Ser Cys Cys Val Ser Ser Cys
1               5                   10

<210> SEQ ID NO 832
<211> LENGTH: 10
<212> TYPE: PRT
<213> ORGANISM: Homo sapiens

<400> SEQUENCE: 832

Cys Gln Pro Thr Cys Cys Gly Ser Ser Cys
1               5                   10

<210> SEQ ID NO 833
<211> LENGTH: 10
<212> TYPE: PRT
<213> ORGANISM: Homo sapiens

<400> SEQUENCE: 833

Cys Gln Pro Thr Cys Cys His Pro Ser Cys
1               5                   10

<210> SEQ ID NO 834
<211> LENGTH: 10
<212> TYPE: PRT
<213> ORGANISM: Homo sapiens

<400> SEQUENCE: 834

Cys Gln Pro Thr Cys Cys Gln Pro Thr Cys
1               5                   10

<210> SEQ ID NO 835
<211> LENGTH: 10
<212> TYPE: PRT
<213> ORGANISM: Homo sapiens

<400> SEQUENCE: 835

Cys Gln Pro Thr Cys Cys Arg Pro Arg Cys
1               5                   10

<210> SEQ ID NO 836
<211> LENGTH: 10
<212> TYPE: PRT
<213> ORGANISM: Homo sapiens

<400> SEQUENCE: 836

Cys Gln Pro Thr Cys Cys Arg Pro Ser Cys
1               5                   10

<210> SEQ ID NO 837
<211> LENGTH: 10
<212> TYPE: PRT
<213> ORGANISM: Homo sapiens

<400> SEQUENCE: 837

Cys Gln Pro Thr Cys Cys Arg Thr Thr Cys
1               5                   10

<210> SEQ ID NO 838
<211> LENGTH: 10
<212> TYPE: PRT
<213> ORGANISM: Homo sapiens

<400> SEQUENCE: 838

Cys Gln Pro Thr Cys Leu Ser Ser Cys Cys
1               5                   10

<210> SEQ ID NO 839
<211> LENGTH: 10
<212> TYPE: PRT
<213> ORGANISM: Homo sapiens

<400> SEQUENCE: 839

Cys Gln Pro Thr Cys Leu Thr Ser Cys Cys
1               5                   10

<210> SEQ ID NO 840
<211> LENGTH: 10
<212> TYPE: PRT
<213> ORGANISM: Homo sapiens

<400> SEQUENCE: 840

Cys Gln Pro Thr Cys Val Ala Ser Cys Cys
1               5                   10

<210> SEQ ID NO 841
<211> LENGTH: 10
<212> TYPE: PRT
<213> ORGANISM: Homo sapiens

<400> SEQUENCE: 841

Cys Gln Pro Thr Cys Val Thr Ser Cys Cys
1               5                   10

<210> SEQ ID NO 842
<211> LENGTH: 10
<212> TYPE: PRT
<213> ORGANISM: Homo sapiens

<400> SEQUENCE: 842

Cys Gln Pro Val Cys Cys Gln Pro Thr Cys
1               5                   10

<210> SEQ ID NO 843
<211> LENGTH: 10
<212> TYPE: PRT
<213> ORGANISM: Homo sapiens

<400> SEQUENCE: 843

Cys Gln Pro Tyr Cys His Pro Thr Cys Cys
1               5                   10

<210> SEQ ID NO 844
<211> LENGTH: 10
<212> TYPE: PRT
<213> ORGANISM: Homo sapiens

<400> SEQUENCE: 844

Cys Gln Gln Ala Cys Cys Met Pro Val Cys
1               5                   10

<210> SEQ ID NO 845
<211> LENGTH: 10
<212> TYPE: PRT
<213> ORGANISM: Homo sapiens

<400> SEQUENCE: 845

Cys Gln Gln Ala Cys Cys Val Pro Ile Cys
1               5                   10

<210> SEQ ID NO 846
<211> LENGTH: 10
<212> TYPE: PRT
<213> ORGANISM: Homo sapiens

<400> SEQUENCE: 846

Cys Gln Gln Ala Cys Cys Val Pro Val Cys
1               5                   10

<210> SEQ ID NO 847
<211> LENGTH: 10
<212> TYPE: PRT
<213> ORGANISM: Homo sapiens

<400> SEQUENCE: 847

Cys Gln Gln Ser Cys Cys Val Pro Val Cys
1               5                   10

<210> SEQ ID NO 848
<211> LENGTH: 10
<212> TYPE: PRT
<213> ORGANISM: Homo sapiens

<400> SEQUENCE: 848

Cys Gln Gln Ser Cys Cys Val Ser Val Cys
1               5                   10

<210> SEQ ID NO 849
<211> LENGTH: 10
<212> TYPE: PRT
<213> ORGANISM: Homo sapiens

<400> SEQUENCE: 849

Cys Gln Ser Met Cys Cys Gln Pro Thr Cys

```
1               5                  10
```

<210> SEQ ID NO 850
<211> LENGTH: 10
<212> TYPE: PRT
<213> ORGANISM: Homo sapiens

<400> SEQUENCE: 850

```
Cys Gln Ser Asn Cys Cys Val Pro Val Cys
1               5                  10
```

<210> SEQ ID NO 851
<211> LENGTH: 10
<212> TYPE: PRT
<213> ORGANISM: Homo sapiens

<400> SEQUENCE: 851

```
Cys Gln Ser Ser Cys Cys Lys Pro Cys Ser
1               5                  10
```

<210> SEQ ID NO 852
<211> LENGTH: 10
<212> TYPE: PRT
<213> ORGANISM: Homo sapiens

<400> SEQUENCE: 852

```
Cys Gln Ser Ser Cys Cys Gln Ser Ser Cys
1               5                  10
```

<210> SEQ ID NO 853
<211> LENGTH: 10
<212> TYPE: PRT
<213> ORGANISM: Homo sapiens

<400> SEQUENCE: 853

```
Cys Gln Ser Ser Cys Cys Val Pro Val Cys
1               5                  10
```

<210> SEQ ID NO 854
<211> LENGTH: 10
<212> TYPE: PRT
<213> ORGANISM: Homo sapiens

<400> SEQUENCE: 854

```
Cys Gln Ser Ser Cys Phe Lys Pro Cys Cys
1               5                  10
```

<210> SEQ ID NO 855
<211> LENGTH: 10
<212> TYPE: PRT
<213> ORGANISM: Homo sapiens

<400> SEQUENCE: 855

```
Cys Gln Ser Ser Cys Ser Lys Pro Cys Cys
1               5                  10
```

<210> SEQ ID NO 856
<211> LENGTH: 10
<212> TYPE: PRT
<213> ORGANISM: Homo sapiens

<400> SEQUENCE: 856

```
Cys Gln Ser Val Cys Cys Gln Pro Thr Cys
1               5                  10
```

<210> SEQ ID NO 857
<211> LENGTH: 10
<212> TYPE: PRT
<213> ORGANISM: Homo sapiens

<400> SEQUENCE: 857

Cys Gln Thr Ile Cys Arg Ser Thr Cys Cys
1               5                   10

<210> SEQ ID NO 858
<211> LENGTH: 10
<212> TYPE: PRT
<213> ORGANISM: Homo sapiens

<400> SEQUENCE: 858

Cys Gln Thr Thr Cys Cys Arg Pro Ser Cys
1               5                   10

<210> SEQ ID NO 859
<211> LENGTH: 10
<212> TYPE: PRT
<213> ORGANISM: Homo sapiens

<400> SEQUENCE: 859

Cys Gln Thr Thr Cys Cys Arg Thr Thr Cys
1               5                   10

<210> SEQ ID NO 860
<211> LENGTH: 10
<212> TYPE: PRT
<213> ORGANISM: Homo sapiens

<400> SEQUENCE: 860

Cys Arg Ala Thr Cys Cys Arg Pro Ser Cys
1               5                   10

<210> SEQ ID NO 861
<211> LENGTH: 10
<212> TYPE: PRT
<213> ORGANISM: Homo sapiens

<400> SEQUENCE: 861

Cys Arg Gly Cys Gly Pro Ser Cys Cys Ala
1               5                   10

<210> SEQ ID NO 862
<211> LENGTH: 10
<212> TYPE: PRT
<213> ORGANISM: Homo sapiens

<400> SEQUENCE: 862

Cys Arg Pro Ala Cys Cys Glu Thr Thr Cys
1               5                   10

<210> SEQ ID NO 863
<211> LENGTH: 10
<212> TYPE: PRT
<213> ORGANISM: Homo sapiens

<400> SEQUENCE: 863

Cys Arg Pro Ala Cys Cys Gln Asn Thr Cys
1               5                   10

<210> SEQ ID NO 864

```
<211> LENGTH: 10
<212> TYPE: PRT
<213> ORGANISM: Homo sapiens

<400> SEQUENCE: 864

Cys Arg Pro Cys Cys Trp Ala Thr Thr Cys
1               5                   10

<210> SEQ ID NO 865
<211> LENGTH: 10
<212> TYPE: PRT
<213> ORGANISM: Homo sapiens

<400> SEQUENCE: 865

Cys Arg Pro Ile Cys Arg Pro Ala Cys Cys
1               5                   10

<210> SEQ ID NO 866
<211> LENGTH: 10
<212> TYPE: PRT
<213> ORGANISM: Homo sapiens

<400> SEQUENCE: 866

Cys Arg Pro Leu Cys Cys Gln Thr Thr Cys
1               5                   10

<210> SEQ ID NO 867
<211> LENGTH: 10
<212> TYPE: PRT
<213> ORGANISM: Homo sapiens

<400> SEQUENCE: 867

Cys Arg Pro Gln Cys Cys Gln Ser Val Cys
1               5                   10

<210> SEQ ID NO 868
<211> LENGTH: 10
<212> TYPE: PRT
<213> ORGANISM: Homo sapiens

<400> SEQUENCE: 868

Cys Arg Pro Gln Cys Cys Gln Thr Thr Cys
1               5                   10

<210> SEQ ID NO 869
<211> LENGTH: 10
<212> TYPE: PRT
<213> ORGANISM: Homo sapiens

<400> SEQUENCE: 869

Cys Arg Pro Arg Cys Cys Ile Ser Ser Cys
1               5                   10

<210> SEQ ID NO 870
<211> LENGTH: 10
<212> TYPE: PRT
<213> ORGANISM: Homo sapiens

<400> SEQUENCE: 870

Cys Arg Pro Ser Cys Cys Glu Ser Ser Cys
1               5                   10

<210> SEQ ID NO 871
<211> LENGTH: 10
<212> TYPE: PRT
```

<213> ORGANISM: Homo sapiens

<400> SEQUENCE: 871

Cys Arg Pro Ser Cys Cys Glu Thr Thr Cys
1               5                   10

<210> SEQ ID NO 872
<211> LENGTH: 10
<212> TYPE: PRT
<213> ORGANISM: Homo sapiens

<400> SEQUENCE: 872

Cys Arg Pro Ser Cys Cys Ile Ser Ser Cys
1               5                   10

<210> SEQ ID NO 873
<211> LENGTH: 10
<212> TYPE: PRT
<213> ORGANISM: Homo sapiens

<400> SEQUENCE: 873

Cys Arg Pro Ser Cys Cys Lys Pro Gln Cys
1               5                   10

<210> SEQ ID NO 874
<211> LENGTH: 10
<212> TYPE: PRT
<213> ORGANISM: Homo sapiens

<400> SEQUENCE: 874

Cys Arg Pro Ser Cys Cys Met Ser Ser Cys
1               5                   10

<210> SEQ ID NO 875
<211> LENGTH: 10
<212> TYPE: PRT
<213> ORGANISM: Homo sapiens

<400> SEQUENCE: 875

Cys Arg Pro Ser Cys Cys Gln Thr Thr Cys
1               5                   10

<210> SEQ ID NO 876
<211> LENGTH: 10
<212> TYPE: PRT
<213> ORGANISM: Homo sapiens

<400> SEQUENCE: 876

Cys Arg Pro Ser Cys Cys Arg Pro Ser Cys
1               5                   10

<210> SEQ ID NO 877
<211> LENGTH: 10
<212> TYPE: PRT
<213> ORGANISM: Homo sapiens

<400> SEQUENCE: 877

Cys Arg Pro Ser Cys Cys Val Ser Arg Cys
1               5                   10

<210> SEQ ID NO 878
<211> LENGTH: 10
<212> TYPE: PRT
<213> ORGANISM: Homo sapiens

<400> SEQUENCE: 878

Cys Arg Pro Ser Cys Cys Val Ser Ser Cys
1               5                   10

<210> SEQ ID NO 879
<211> LENGTH: 10
<212> TYPE: PRT
<213> ORGANISM: Homo sapiens

<400> SEQUENCE: 879

Cys Arg Pro Thr Cys Cys Glu Thr Thr Cys
1               5                   10

<210> SEQ ID NO 880
<211> LENGTH: 10
<212> TYPE: PRT
<213> ORGANISM: Homo sapiens

<400> SEQUENCE: 880

Cys Arg Pro Thr Cys Cys Gln Asn Thr Cys
1               5                   10

<210> SEQ ID NO 881
<211> LENGTH: 10
<212> TYPE: PRT
<213> ORGANISM: Homo sapiens

<400> SEQUENCE: 881

Cys Arg Pro Thr Cys Cys Gln Thr Thr Cys
1               5                   10

<210> SEQ ID NO 882
<211> LENGTH: 10
<212> TYPE: PRT
<213> ORGANISM: Homo sapiens

<400> SEQUENCE: 882

Cys Arg Pro Val Cys Cys Asp Pro Cys Ser
1               5                   10

<210> SEQ ID NO 883
<211> LENGTH: 10
<212> TYPE: PRT
<213> ORGANISM: Homo sapiens

<400> SEQUENCE: 883

Cys Arg Pro Val Cys Cys Gln Thr Thr Cys
1               5                   10

<210> SEQ ID NO 884
<211> LENGTH: 10
<212> TYPE: PRT
<213> ORGANISM: Homo sapiens

<400> SEQUENCE: 884

Cys Arg Pro Val Cys Gln Pro Ala Cys Cys
1               5                   10

<210> SEQ ID NO 885
<211> LENGTH: 10
<212> TYPE: PRT
<213> ORGANISM: Homo sapiens

<400> SEQUENCE: 885

Cys Arg Pro Val Cys Arg Pro Ala Cys Cys
1               5                   10

<210> SEQ ID NO 886
<211> LENGTH: 10
<212> TYPE: PRT
<213> ORGANISM: Homo sapiens

<400> SEQUENCE: 886

Cys Arg Pro Val Cys Arg Pro Thr Cys Cys
1               5                   10

<210> SEQ ID NO 887
<211> LENGTH: 10
<212> TYPE: PRT
<213> ORGANISM: Homo sapiens

<400> SEQUENCE: 887

Cys Arg Pro Val Cys Arg Ser Thr Cys Cys
1               5                   10

<210> SEQ ID NO 888
<211> LENGTH: 10
<212> TYPE: PRT
<213> ORGANISM: Homo sapiens

<400> SEQUENCE: 888

Cys Arg Pro Tyr Cys Cys Glu Ser Ser Cys
1               5                   10

<210> SEQ ID NO 889
<211> LENGTH: 10
<212> TYPE: PRT
<213> ORGANISM: Homo sapiens

<400> SEQUENCE: 889

Cys Arg Arg Pro Val Cys Cys Asp Pro Cys
1               5                   10

<210> SEQ ID NO 890
<211> LENGTH: 10
<212> TYPE: PRT
<213> ORGANISM: Homo sapiens

<400> SEQUENCE: 890

Cys Arg Ser Gln Cys Cys Gln Ser Val Cys
1               5                   10

<210> SEQ ID NO 891
<211> LENGTH: 10
<212> TYPE: PRT
<213> ORGANISM: Homo sapiens

<400> SEQUENCE: 891

Cys Arg Thr Thr Cys Cys His Pro Ser Cys
1               5                   10

<210> SEQ ID NO 892
<211> LENGTH: 10
<212> TYPE: PRT
<213> ORGANISM: Homo sapiens

<400> SEQUENCE: 892

Cys Arg Thr Thr Cys Cys Gln Pro Ile Cys
1               5                   10

<210> SEQ ID NO 893
<211> LENGTH: 10
<212> TYPE: PRT
<213> ORGANISM: Homo sapiens

<400> SEQUENCE: 893

Cys Arg Thr Thr Cys Cys Gln Pro Thr Cys
1               5                   10

<210> SEQ ID NO 894
<211> LENGTH: 10
<212> TYPE: PRT
<213> ORGANISM: Homo sapiens

<400> SEQUENCE: 894

Cys Arg Thr Thr Cys Cys Arg Pro Ser Cys
1               5                   10

<210> SEQ ID NO 895
<211> LENGTH: 10
<212> TYPE: PRT
<213> ORGANISM: Homo sapiens

<400> SEQUENCE: 895

Cys Arg Thr Thr Cys Cys Arg Thr Thr Cys
1               5                   10

<210> SEQ ID NO 896
<211> LENGTH: 10
<212> TYPE: PRT
<213> ORGANISM: Homo sapiens

<400> SEQUENCE: 896

Cys Ser Cys Ser Ser Cys Gly Ser Cys Ala
1               5                   10

<210> SEQ ID NO 897
<211> LENGTH: 10
<212> TYPE: PRT
<213> ORGANISM: Homo sapiens

<400> SEQUENCE: 897

Cys Ser Cys Ser Ser Cys Gly Ser Cys Gly
1               5                   10

<210> SEQ ID NO 898
<211> LENGTH: 10
<212> TYPE: PRT
<213> ORGANISM: Homo sapiens

<400> SEQUENCE: 898

Cys Ser Cys Thr Ser Cys Gly Ser Cys Gly
1               5                   10

<210> SEQ ID NO 899
<211> LENGTH: 10
<212> TYPE: PRT
<213> ORGANISM: Homo sapiens

<400> SEQUENCE: 899

Cys Ser Pro Ala Cys Gln Pro Thr Cys Cys
1               5                   10

```
<210> SEQ ID NO 900
<211> LENGTH: 10
<212> TYPE: PRT
<213> ORGANISM: Homo sapiens

<400> SEQUENCE: 900

Cys Ser Pro Gly Cys Gln Pro Thr Cys Cys
1               5                   10

<210> SEQ ID NO 901
<211> LENGTH: 10
<212> TYPE: PRT
<213> ORGANISM: Homo sapiens

<400> SEQUENCE: 901

Cys Ser Pro Ser Cys Cys Gln Thr Thr Cys
1               5                   10

<210> SEQ ID NO 902
<211> LENGTH: 10
<212> TYPE: PRT
<213> ORGANISM: Homo sapiens

<400> SEQUENCE: 902

Cys Ser Gln Cys Ser Cys Tyr Lys Pro Cys
1               5                   10

<210> SEQ ID NO 903
<211> LENGTH: 10
<212> TYPE: PRT
<213> ORGANISM: Homo sapiens

<400> SEQUENCE: 903

Cys Ser Gln Ser Asn Cys Cys Lys Pro Cys
1               5                   10

<210> SEQ ID NO 904
<211> LENGTH: 10
<212> TYPE: PRT
<213> ORGANISM: Homo sapiens

<400> SEQUENCE: 904

Cys Ser Gln Ser Ser Cys Cys Lys Pro Cys
1               5                   10

<210> SEQ ID NO 905
<211> LENGTH: 10
<212> TYPE: PRT
<213> ORGANISM: Homo sapiens

<400> SEQUENCE: 905

Cys Ser Ser Gly Cys Gly Ser Cys Cys Gln
1               5                   10

<210> SEQ ID NO 906
<211> LENGTH: 10
<212> TYPE: PRT
<213> ORGANISM: Homo sapiens

<400> SEQUENCE: 906

Cys Ser Ser Gly Cys Gly Ser Ser Cys Cys
1               5                   10

<210> SEQ ID NO 907
<211> LENGTH: 10
```

```
<212> TYPE: PRT
<213> ORGANISM: Homo sapiens

<400> SEQUENCE: 907

Cys Ser Ser Gly Cys Gln Pro Ala Cys Cys
1               5                   10

<210> SEQ ID NO 908
<211> LENGTH: 10
<212> TYPE: PRT
<213> ORGANISM: Homo sapiens

<400> SEQUENCE: 908

Cys Ser Ser Ser Cys Cys Gln Pro Ser Cys
1               5                   10

<210> SEQ ID NO 909
<211> LENGTH: 10
<212> TYPE: PRT
<213> ORGANISM: Homo sapiens

<400> SEQUENCE: 909

Cys Ser Thr Pro Cys Cys Gln Pro Thr Cys
1               5                   10

<210> SEQ ID NO 910
<211> LENGTH: 10
<212> TYPE: PRT
<213> ORGANISM: Homo sapiens

<400> SEQUENCE: 910

Cys Ser Thr Thr Cys Cys Gln Pro Ile Cys
1               5                   10

<210> SEQ ID NO 911
<211> LENGTH: 10
<212> TYPE: PRT
<213> ORGANISM: Homo sapiens

<400> SEQUENCE: 911

Cys Thr Ala Val Val Cys Arg Pro Cys Cys
1               5                   10

<210> SEQ ID NO 912
<211> LENGTH: 10
<212> TYPE: PRT
<213> ORGANISM: Homo sapiens

<400> SEQUENCE: 912

Cys Thr Asp Ser Cys Thr Pro Ser Cys Cys
1               5                   10

<210> SEQ ID NO 913
<211> LENGTH: 10
<212> TYPE: PRT
<213> ORGANISM: Homo sapiens

<400> SEQUENCE: 913

Cys Thr Pro Ser Cys Cys Gln Pro Ala Cys
1               5                   10

<210> SEQ ID NO 914
<211> LENGTH: 10
<212> TYPE: PRT
<213> ORGANISM: Homo sapiens
```

<400> SEQUENCE: 914

Cys Thr Arg Pro Ile Cys Glu Pro Cys Cys
1               5                   10

<210> SEQ ID NO 915
<211> LENGTH: 10
<212> TYPE: PRT
<213> ORGANISM: Homo sapiens

<400> SEQUENCE: 915

Cys Thr Ser Ser Cys Thr Pro Ser Cys Cys
1               5                   10

<210> SEQ ID NO 916
<211> LENGTH: 10
<212> TYPE: PRT
<213> ORGANISM: Homo sapiens

<400> SEQUENCE: 916

Cys Val Pro Ala Cys Ser Cys Ser Ser Cys
1               5                   10

<210> SEQ ID NO 917
<211> LENGTH: 10
<212> TYPE: PRT
<213> ORGANISM: Homo sapiens

<400> SEQUENCE: 917

Cys Val Pro Ala Cys Ser Cys Thr Ser Cys
1               5                   10

<210> SEQ ID NO 918
<211> LENGTH: 10
<212> TYPE: PRT
<213> ORGANISM: Homo sapiens

<400> SEQUENCE: 918

Cys Val Pro Val Cys Cys Lys Pro Val Cys
1               5                   10

<210> SEQ ID NO 919
<211> LENGTH: 10
<212> TYPE: PRT
<213> ORGANISM: Homo sapiens

<400> SEQUENCE: 919

Cys Val Pro Val Cys Cys Val Pro Thr Cys
1               5                   10

<210> SEQ ID NO 920
<211> LENGTH: 10
<212> TYPE: PRT
<213> ORGANISM: Homo sapiens

<400> SEQUENCE: 920

Cys Val Pro Val Cys Cys Val Pro Val Cys
1               5                   10

<210> SEQ ID NO 921
<211> LENGTH: 10
<212> TYPE: PRT
<213> ORGANISM: Homo sapiens

<400> SEQUENCE: 921

```
Cys Val Ser Cys Val Ser Ser Pro Cys Cys
1               5                   10
```

<210> SEQ ID NO 922
<211> LENGTH: 10
<212> TYPE: PRT
<213> ORGANISM: Homo sapiens

<400> SEQUENCE: 922

```
Cys Val Ser Arg Cys Cys Arg Pro Gln Cys
1               5                   10
```

<210> SEQ ID NO 923
<211> LENGTH: 10
<212> TYPE: PRT
<213> ORGANISM: Homo sapiens

<400> SEQUENCE: 923

```
Cys Val Ser Ser Cys Cys Lys Pro Gln Cys
1               5                   10
```

<210> SEQ ID NO 924
<211> LENGTH: 10
<212> TYPE: PRT
<213> ORGANISM: Homo sapiens

<400> SEQUENCE: 924

```
Cys Val Ser Ser Cys Cys Gln His Ser Cys
1               5                   10
```

<210> SEQ ID NO 925
<211> LENGTH: 10
<212> TYPE: PRT
<213> ORGANISM: Homo sapiens

<400> SEQUENCE: 925

```
Cys Val Ser Ser Cys Cys Gln Pro Phe Cys
1               5                   10
```

<210> SEQ ID NO 926
<211> LENGTH: 10
<212> TYPE: PRT
<213> ORGANISM: Homo sapiens

<400> SEQUENCE: 926

```
Cys Val Ser Ser Cys Cys Gln Pro Ser Cys
1               5                   10
```

<210> SEQ ID NO 927
<211> LENGTH: 10
<212> TYPE: PRT
<213> ORGANISM: Homo sapiens

<400> SEQUENCE: 927

```
Cys Val Ser Ser Cys Cys Arg Pro Gln Cys
1               5                   10
```

<210> SEQ ID NO 928
<211> LENGTH: 10
<212> TYPE: PRT
<213> ORGANISM: Homo sapiens

<400> SEQUENCE: 928

```
Cys Val Ser Thr Cys Cys Arg Pro Thr Cys
```

```
1               5                   10
```

<210> SEQ ID NO 929
<211> LENGTH: 10
<212> TYPE: PRT
<213> ORGANISM: Homo sapiens

<400> SEQUENCE: 929

```
Cys Val Thr Arg Cys Cys Ser Thr Pro Cys
1               5                   10
```

<210> SEQ ID NO 930
<211> LENGTH: 10
<212> TYPE: PRT
<213> ORGANISM: Homo sapiens

<400> SEQUENCE: 930

```
Cys Val Thr Ser Cys Cys Gln Pro Ala Cys
1               5                   10
```

<210> SEQ ID NO 931
<211> LENGTH: 10
<212> TYPE: PRT
<213> ORGANISM: Homo sapiens

<400> SEQUENCE: 931

```
Cys Val Thr Ser Cys Cys Gln Pro Ser Cys
1               5                   10
```

<210> SEQ ID NO 932
<211> LENGTH: 10
<212> TYPE: PRT
<213> ORGANISM: Homo sapiens

<400> SEQUENCE: 932

```
Cys Val Tyr Ser Cys Cys Gln Pro Phe Cys
1               5                   10
```

<210> SEQ ID NO 933
<211> LENGTH: 10
<212> TYPE: PRT
<213> ORGANISM: Homo sapiens

<400> SEQUENCE: 933

```
Cys Val Tyr Ser Cys Cys Gln Pro Ser Cys
1               5                   10
```

<210> SEQ ID NO 934
<211> LENGTH: 10
<212> TYPE: PRT
<213> ORGANISM: Homo sapiens

<400> SEQUENCE: 934

```
Gly Cys Cys Gly Cys Ser Glu Gly Cys Gly
1               5                   10
```

<210> SEQ ID NO 935
<211> LENGTH: 10
<212> TYPE: PRT
<213> ORGANISM: Homo sapiens

<400> SEQUENCE: 935

```
Gly Cys Cys Gly Cys Ser Gly Gly Cys Gly
1               5                   10
```

```
<210> SEQ ID NO 936
<211> LENGTH: 10
<212> TYPE: PRT
<213> ORGANISM: Homo sapiens

<400> SEQUENCE: 936

Gly Cys Cys Gly Cys Ser Arg Gly Cys Gly
1               5                   10

<210> SEQ ID NO 937
<211> LENGTH: 10
<212> TYPE: PRT
<213> ORGANISM: Homo sapiens

<400> SEQUENCE: 937

Gly Cys Cys Arg Pro Ile Thr Cys Cys Pro
1               5                   10

<210> SEQ ID NO 938
<211> LENGTH: 10
<212> TYPE: PRT
<213> ORGANISM: Homo sapiens

<400> SEQUENCE: 938

Gly Cys Gly Ser Ser Cys Cys Gln Cys Ser
1               5                   10

<210> SEQ ID NO 939
<211> LENGTH: 10
<212> TYPE: PRT
<213> ORGANISM: Homo sapiens

<400> SEQUENCE: 939

Gly Cys Gly Val Pro Val Cys Cys Cys Ser
1               5                   10

<210> SEQ ID NO 940
<211> LENGTH: 10
<212> TYPE: PRT
<213> ORGANISM: Homo sapiens

<400> SEQUENCE: 940

Leu Cys Cys Pro Cys Gln Thr Thr Cys Ser
1               5                   10

<210> SEQ ID NO 941
<211> LENGTH: 10
<212> TYPE: PRT
<213> ORGANISM: Homo sapiens

<400> SEQUENCE: 941

Pro Cys Cys Cys Leu Arg Pro Val Cys Gly
1               5                   10

<210> SEQ ID NO 942
<211> LENGTH: 10
<212> TYPE: PRT
<213> ORGANISM: Homo sapiens

<400> SEQUENCE: 942

Pro Cys Cys Cys Arg Pro Val Thr Cys Gln
1               5                   10

<210> SEQ ID NO 943
```

```
<211> LENGTH: 10
<212> TYPE: PRT
<213> ORGANISM: Homo sapiens

<400> SEQUENCE: 943

Pro Cys Cys Cys Val Arg Pro Val Cys Gly
1               5                   10

<210> SEQ ID NO 944
<211> LENGTH: 10
<212> TYPE: PRT
<213> ORGANISM: Homo sapiens

<400> SEQUENCE: 944

Pro Cys Cys Ser Gln Ala Ser Cys Cys Val
1               5                   10

<210> SEQ ID NO 945
<211> LENGTH: 10
<212> TYPE: PRT
<213> ORGANISM: Homo sapiens

<400> SEQUENCE: 945

Pro Cys Cys Ser Gln Ser Arg Cys Cys Val
1               5                   10

<210> SEQ ID NO 946
<211> LENGTH: 10
<212> TYPE: PRT
<213> ORGANISM: Homo sapiens

<400> SEQUENCE: 946

Pro Cys Cys Ser Gln Ser Ser Cys Cys Lys
1               5                   10

<210> SEQ ID NO 947
<211> LENGTH: 10
<212> TYPE: PRT
<213> ORGANISM: Homo sapiens

<400> SEQUENCE: 947

Pro Cys Cys Ser Gln Ser Ser Cys Cys Val
1               5                   10

<210> SEQ ID NO 948
<211> LENGTH: 10
<212> TYPE: PRT
<213> ORGANISM: Homo sapiens

<400> SEQUENCE: 948

Pro Cys Cys Trp Ala Thr Thr Cys Cys Gln
1               5                   10

<210> SEQ ID NO 949
<211> LENGTH: 10
<212> TYPE: PRT
<213> ORGANISM: Homo sapiens

<400> SEQUENCE: 949

Gln Cys Ser Cys Cys Lys Pro Tyr Cys Ser
1               5                   10

<210> SEQ ID NO 950
<211> LENGTH: 10
<212> TYPE: PRT
```

```
<213> ORGANISM: Homo sapiens

<400> SEQUENCE: 950

Arg Cys Tyr Val Pro Val Cys Cys Cys Lys
1               5                   10

<210> SEQ ID NO 951
<211> LENGTH: 10
<212> TYPE: PRT
<213> ORGANISM: Homo sapiens

<400> SEQUENCE: 951

Ser Cys Cys Ala Pro Val Tyr Cys Cys Lys
1               5                   10

<210> SEQ ID NO 952
<211> LENGTH: 10
<212> TYPE: PRT
<213> ORGANISM: Homo sapiens

<400> SEQUENCE: 952

Ser Cys Cys Ile Ser Ser Ser Cys Cys Pro
1               5                   10

<210> SEQ ID NO 953
<211> LENGTH: 10
<212> TYPE: PRT
<213> ORGANISM: Homo sapiens

<400> SEQUENCE: 953

Ser Cys Cys Val Ser Ser Cys Arg Cys Pro
1               5                   10

<210> SEQ ID NO 954
<211> LENGTH: 10
<212> TYPE: PRT
<213> ORGANISM: Homo sapiens

<400> SEQUENCE: 954

Ser Cys Gly Cys Ser Gln Cys Ser Cys Tyr
1               5                   10

<210> SEQ ID NO 955
<211> LENGTH: 10
<212> TYPE: PRT
<213> ORGANISM: Homo sapiens

<400> SEQUENCE: 955

Ser Cys Gly Leu Glu Asn Cys Cys Cys Pro
1               5                   10

<210> SEQ ID NO 956
<211> LENGTH: 10
<212> TYPE: PRT
<213> ORGANISM: Homo sapiens

<400> SEQUENCE: 956

Val Cys Cys Gly Ala Ser Ser Cys Cys Gln
1               5                   10

<210> SEQ ID NO 957
<211> LENGTH: 10
<212> TYPE: PRT
<213> ORGANISM: Homo sapiens
```

<400> SEQUENCE: 957

Val Cys Cys Gly Asp Ser Ser Cys Cys Gln
1               5                   10

<210> SEQ ID NO 958
<211> LENGTH: 11
<212> TYPE: PRT
<213> ORGANISM: Homo sapiens

<400> SEQUENCE: 958

Cys Ala Ser Ser Cys Cys Thr Pro Ser Cys Cys
1               5                   10

<210> SEQ ID NO 959
<211> LENGTH: 11
<212> TYPE: PRT
<213> ORGANISM: Homo sapiens

<400> SEQUENCE: 959

Cys Cys Cys Pro Ser Cys Val Val Ser Ser Cys
1               5                   10

<210> SEQ ID NO 960
<211> LENGTH: 11
<212> TYPE: PRT
<213> ORGANISM: Homo sapiens

<400> SEQUENCE: 960

Cys Cys Cys Pro Ser Tyr Cys Val Ser Ser Cys
1               5                   10

<210> SEQ ID NO 961
<211> LENGTH: 11
<212> TYPE: PRT
<213> ORGANISM: Homo sapiens

<400> SEQUENCE: 961

Cys Cys Cys Ser Ser Gly Cys Gly Ser Ser Cys
1               5                   10

<210> SEQ ID NO 962
<211> LENGTH: 11
<212> TYPE: PRT
<213> ORGANISM: Homo sapiens

<400> SEQUENCE: 962

Cys Cys Asp Thr Cys Pro Pro Pro Cys Cys Lys
1               5                   10

<210> SEQ ID NO 963
<211> LENGTH: 11
<212> TYPE: PRT
<213> ORGANISM: Homo sapiens

<400> SEQUENCE: 963

Cys Cys Glu Pro His Cys Cys Ala Leu Ser Cys
1               5                   10

<210> SEQ ID NO 964
<211> LENGTH: 11
<212> TYPE: PRT
<213> ORGANISM: Homo sapiens

<400> SEQUENCE: 964

Cys Cys Glu Pro Pro Cys Cys Ala Pro Ser Cys
1               5                   10

<210> SEQ ID NO 965
<211> LENGTH: 11
<212> TYPE: PRT
<213> ORGANISM: Homo sapiens

<400> SEQUENCE: 965

Cys Cys Glu Pro Pro Cys Cys Ala Thr Ser Cys
1               5                   10

<210> SEQ ID NO 966
<211> LENGTH: 11
<212> TYPE: PRT
<213> ORGANISM: Homo sapiens

<400> SEQUENCE: 966

Cys Cys Glu Thr Ser Cys Cys Gln Pro Ser Cys
1               5                   10

<210> SEQ ID NO 967
<211> LENGTH: 11
<212> TYPE: PRT
<213> ORGANISM: Homo sapiens

<400> SEQUENCE: 967

Cys Cys Gly Ser Ser Cys Cys Gly Ser Gly Cys
1               5                   10

<210> SEQ ID NO 968
<211> LENGTH: 11
<212> TYPE: PRT
<213> ORGANISM: Homo sapiens

<400> SEQUENCE: 968

Cys Cys Gly Ser Ser Cys Cys Gly Ser Ser Cys
1               5                   10

<210> SEQ ID NO 969
<211> LENGTH: 11
<212> TYPE: PRT
<213> ORGANISM: Homo sapiens

<400> SEQUENCE: 969

Cys Cys His Pro Arg Cys Cys Ile Ser Ser Cys
1               5                   10

<210> SEQ ID NO 970
<211> LENGTH: 11
<212> TYPE: PRT
<213> ORGANISM: Homo sapiens

<400> SEQUENCE: 970

Cys Cys His Pro Ser Cys Cys Glu Ser Ser Cys
1               5                   10

<210> SEQ ID NO 971
<211> LENGTH: 11
<212> TYPE: PRT
<213> ORGANISM: Homo sapiens

<400> SEQUENCE: 971

Cys Cys His Pro Ser Cys Cys Ile Ser Ser Cys
1               5                   10

```
<210> SEQ ID NO 972
<211> LENGTH: 11
<212> TYPE: PRT
<213> ORGANISM: Homo sapiens

<400> SEQUENCE: 972

Cys Cys His Pro Ser Cys Cys Val Ser Ser Cys
1               5                   10

<210> SEQ ID NO 973
<211> LENGTH: 11
<212> TYPE: PRT
<213> ORGANISM: Homo sapiens

<400> SEQUENCE: 973

Cys Cys His Pro Thr Cys Cys Gln Asn Thr Cys
1               5                   10

<210> SEQ ID NO 974
<211> LENGTH: 11
<212> TYPE: PRT
<213> ORGANISM: Homo sapiens

<400> SEQUENCE: 974

Cys Cys His Pro Thr Cys Cys Gln Thr Ile Cys
1               5                   10

<210> SEQ ID NO 975
<211> LENGTH: 11
<212> TYPE: PRT
<213> ORGANISM: Homo sapiens

<400> SEQUENCE: 975

Cys Cys Ile Ser Ser Cys Cys Lys Pro Ser Cys
1               5                   10

<210> SEQ ID NO 976
<211> LENGTH: 11
<212> TYPE: PRT
<213> ORGANISM: Homo sapiens

<400> SEQUENCE: 976

Cys Cys Ile Ser Ser Cys Cys Arg Pro Ser Cys
1               5                   10

<210> SEQ ID NO 977
<211> LENGTH: 11
<212> TYPE: PRT
<213> ORGANISM: Homo sapiens

<400> SEQUENCE: 977

Cys Cys Ile Ser Ser Ser Cys Cys Pro Ser Cys
1               5                   10

<210> SEQ ID NO 978
<211> LENGTH: 11
<212> TYPE: PRT
<213> ORGANISM: Homo sapiens

<400> SEQUENCE: 978

Cys Cys Lys Ala Val Cys Cys Val Pro Thr Cys
1               5                   10
```

```
<210> SEQ ID NO 979
<211> LENGTH: 11
<212> TYPE: PRT
<213> ORGANISM: Homo sapiens

<400> SEQUENCE: 979

Cys Cys Lys Pro Cys Cys Ser Gln Ala Ser Cys
1               5                   10

<210> SEQ ID NO 980
<211> LENGTH: 11
<212> TYPE: PRT
<213> ORGANISM: Homo sapiens

<400> SEQUENCE: 980

Cys Cys Lys Pro Cys Cys Ser Gln Ser Arg Cys
1               5                   10

<210> SEQ ID NO 981
<211> LENGTH: 11
<212> TYPE: PRT
<213> ORGANISM: Homo sapiens

<400> SEQUENCE: 981

Cys Cys Lys Pro Cys Cys Ser Gln Ser Ser Cys
1               5                   10

<210> SEQ ID NO 982
<211> LENGTH: 11
<212> TYPE: PRT
<213> ORGANISM: Homo sapiens

<400> SEQUENCE: 982

Cys Cys Lys Pro Cys Cys Ser Ser Ser Gly Cys
1               5                   10

<210> SEQ ID NO 983
<211> LENGTH: 11
<212> TYPE: PRT
<213> ORGANISM: Homo sapiens

<400> SEQUENCE: 983

Cys Cys Lys Pro Cys Ser Cys Phe Ser Gly Cys
1               5                   10

<210> SEQ ID NO 984
<211> LENGTH: 11
<212> TYPE: PRT
<213> ORGANISM: Homo sapiens

<400> SEQUENCE: 984

Cys Cys Lys Pro Cys Ser Cys Ser Ser Gly Cys
1               5                   10

<210> SEQ ID NO 985
<211> LENGTH: 11
<212> TYPE: PRT
<213> ORGANISM: Homo sapiens

<400> SEQUENCE: 985

Cys Cys Lys Pro Cys Tyr Cys Ser Ser Gly Cys
1               5                   10

<210> SEQ ID NO 986
<211> LENGTH: 11
```

```
<212> TYPE: PRT
<213> ORGANISM: Homo sapiens

<400> SEQUENCE: 986

Cys Cys Lys Pro Ile Cys Cys Val Pro Val Cys
1               5                   10

<210> SEQ ID NO 987
<211> LENGTH: 11
<212> TYPE: PRT
<213> ORGANISM: Homo sapiens

<400> SEQUENCE: 987

Cys Cys Lys Pro Gln Cys Cys Gln Ser Val Cys
1               5                   10

<210> SEQ ID NO 988
<211> LENGTH: 11
<212> TYPE: PRT
<213> ORGANISM: Homo sapiens

<400> SEQUENCE: 988

Cys Cys Lys Pro Val Cys Cys Lys Pro Ile Cys
1               5                   10

<210> SEQ ID NO 989
<211> LENGTH: 11
<212> TYPE: PRT
<213> ORGANISM: Homo sapiens

<400> SEQUENCE: 989

Cys Cys Lys Pro Tyr Cys Cys Gln Ser Ser Cys
1               5                   10

<210> SEQ ID NO 990
<211> LENGTH: 11
<212> TYPE: PRT
<213> ORGANISM: Homo sapiens

<400> SEQUENCE: 990

Cys Cys Lys Pro Tyr Cys Ser Gln Cys Ser Cys
1               5                   10

<210> SEQ ID NO 991
<211> LENGTH: 11
<212> TYPE: PRT
<213> ORGANISM: Homo sapiens

<400> SEQUENCE: 991

Cys Cys Met Pro Val Cys Cys Lys Pro Val Cys
1               5                   10

<210> SEQ ID NO 992
<211> LENGTH: 11
<212> TYPE: PRT
<213> ORGANISM: Homo sapiens

<400> SEQUENCE: 992

Cys Cys Met Pro Val Cys Cys Lys Thr Val Cys
1               5                   10

<210> SEQ ID NO 993
<211> LENGTH: 11
<212> TYPE: PRT
<213> ORGANISM: Homo sapiens
```

<400> SEQUENCE: 993

Cys Cys Met Ser Ser Cys Cys Lys Pro Gln Cys
1               5                   10

<210> SEQ ID NO 994
<211> LENGTH: 11
<212> TYPE: PRT
<213> ORGANISM: Homo sapiens

<400> SEQUENCE: 994

Cys Cys Asn Pro Cys Cys Ser Gln Ser Ser Cys
1               5                   10

<210> SEQ ID NO 995
<211> LENGTH: 11
<212> TYPE: PRT
<213> ORGANISM: Homo sapiens

<400> SEQUENCE: 995

Cys Cys Pro Gly Asp Cys Phe Thr Cys Cys Thr
1               5                   10

<210> SEQ ID NO 996
<211> LENGTH: 11
<212> TYPE: PRT
<213> ORGANISM: Homo sapiens

<400> SEQUENCE: 996

Cys Cys Pro Ser Cys Val Val Ser Ser Cys Cys
1               5                   10

<210> SEQ ID NO 997
<211> LENGTH: 11
<212> TYPE: PRT
<213> ORGANISM: Homo sapiens

<400> SEQUENCE: 997

Cys Cys Pro Ser Tyr Cys Val Ser Ser Cys Cys
1               5                   10

<210> SEQ ID NO 998
<211> LENGTH: 11
<212> TYPE: PRT
<213> ORGANISM: Homo sapiens

<400> SEQUENCE: 998

Cys Cys Gln Asn Thr Cys Cys Arg Thr Thr Cys
1               5                   10

<210> SEQ ID NO 999
<211> LENGTH: 11
<212> TYPE: PRT
<213> ORGANISM: Homo sapiens

<400> SEQUENCE: 999

Cys Cys Gln Pro Ala Cys Cys Val Ser Ser Cys
1               5                   10

<210> SEQ ID NO 1000
<211> LENGTH: 11
<212> TYPE: PRT
<213> ORGANISM: Homo sapiens

<400> SEQUENCE: 1000

```
Cys Cys Gln Pro Cys Cys His Pro Thr Cys Tyr
1               5                   10

<210> SEQ ID NO 1001
<211> LENGTH: 11
<212> TYPE: PRT
<213> ORGANISM: Homo sapiens

<400> SEQUENCE: 1001

Cys Cys Gln Pro Cys Cys Arg Pro Thr Ser Cys
1               5                   10

<210> SEQ ID NO 1002
<211> LENGTH: 11
<212> TYPE: PRT
<213> ORGANISM: Homo sapiens

<400> SEQUENCE: 1002

Cys Cys Gln Pro Ile Cys Gly Ser Ser Cys Cys
1               5                   10

<210> SEQ ID NO 1003
<211> LENGTH: 11
<212> TYPE: PRT
<213> ORGANISM: Homo sapiens

<400> SEQUENCE: 1003

Cys Cys Gln Pro Ile Cys Val Thr Ser Cys Cys
1               5                   10

<210> SEQ ID NO 1004
<211> LENGTH: 11
<212> TYPE: PRT
<213> ORGANISM: Homo sapiens

<400> SEQUENCE: 1004

Cys Cys Gln Pro Asn Cys Cys Arg Pro Ser Cys
1               5                   10

<210> SEQ ID NO 1005
<211> LENGTH: 11
<212> TYPE: PRT
<213> ORGANISM: Homo sapiens

<400> SEQUENCE: 1005

Cys Cys Gln Pro Ser Cys Cys Glu Thr Ser Cys
1               5                   10

<210> SEQ ID NO 1006
<211> LENGTH: 11
<212> TYPE: PRT
<213> ORGANISM: Homo sapiens

<400> SEQUENCE: 1006

Cys Cys Gln Pro Ser Cys Cys Arg Pro Ala Cys
1               5                   10

<210> SEQ ID NO 1007
<211> LENGTH: 11
<212> TYPE: PRT
<213> ORGANISM: Homo sapiens

<400> SEQUENCE: 1007

Cys Cys Gln Pro Ser Cys Cys Ser Thr Pro Cys
```

-continued

```
1               5                   10

<210> SEQ ID NO 1008
<211> LENGTH: 11
<212> TYPE: PRT
<213> ORGANISM: Homo sapiens

<400> SEQUENCE: 1008

Cys Cys Gln Pro Ser Cys Cys Ser Thr Thr Cys
1               5                   10

<210> SEQ ID NO 1009
<211> LENGTH: 11
<212> TYPE: PRT
<213> ORGANISM: Homo sapiens

<400> SEQUENCE: 1009

Cys Cys Gln Pro Ser Cys Cys Val Pro Ser Cys
1               5                   10

<210> SEQ ID NO 1010
<211> LENGTH: 11
<212> TYPE: PRT
<213> ORGANISM: Homo sapiens

<400> SEQUENCE: 1010

Cys Cys Gln Pro Ser Cys Cys Val Ser Ser Cys
1               5                   10

<210> SEQ ID NO 1011
<211> LENGTH: 11
<212> TYPE: PRT
<213> ORGANISM: Homo sapiens

<400> SEQUENCE: 1011

Cys Cys Gln Pro Thr Cys Cys His Pro Ser Cys
1               5                   10

<210> SEQ ID NO 1012
<211> LENGTH: 11
<212> TYPE: PRT
<213> ORGANISM: Homo sapiens

<400> SEQUENCE: 1012

Cys Cys Gln Pro Thr Cys Cys Gln Pro Thr Cys
1               5                   10

<210> SEQ ID NO 1013
<211> LENGTH: 11
<212> TYPE: PRT
<213> ORGANISM: Homo sapiens

<400> SEQUENCE: 1013

Cys Cys Gln Pro Thr Cys Cys Arg Pro Arg Cys
1               5                   10

<210> SEQ ID NO 1014
<211> LENGTH: 11
<212> TYPE: PRT
<213> ORGANISM: Homo sapiens

<400> SEQUENCE: 1014

Cys Cys Gln Pro Thr Cys Cys Arg Pro Ser Cys
1               5                   10
```

<210> SEQ ID NO 1015
<211> LENGTH: 11
<212> TYPE: PRT
<213> ORGANISM: Homo sapiens

<400> SEQUENCE: 1015

Cys Cys Gln Pro Thr Cys Cys Arg Pro Thr Cys
1               5                   10

<210> SEQ ID NO 1016
<211> LENGTH: 11
<212> TYPE: PRT
<213> ORGANISM: Homo sapiens

<400> SEQUENCE: 1016

Cys Cys Gln Pro Thr Cys Cys Arg Thr Thr Cys
1               5                   10

<210> SEQ ID NO 1017
<211> LENGTH: 11
<212> TYPE: PRT
<213> ORGANISM: Homo sapiens

<400> SEQUENCE: 1017

Cys Cys Gln Pro Thr Cys Leu Ser Ser Cys Cys
1               5                   10

<210> SEQ ID NO 1018
<211> LENGTH: 11
<212> TYPE: PRT
<213> ORGANISM: Homo sapiens

<400> SEQUENCE: 1018

Cys Cys Gln Pro Thr Cys Leu Thr Ser Cys Cys
1               5                   10

<210> SEQ ID NO 1019
<211> LENGTH: 11
<212> TYPE: PRT
<213> ORGANISM: Homo sapiens

<400> SEQUENCE: 1019

Cys Cys Gln Pro Thr Cys Val Ala Ser Cys Cys
1               5                   10

<210> SEQ ID NO 1020
<211> LENGTH: 11
<212> TYPE: PRT
<213> ORGANISM: Homo sapiens

<400> SEQUENCE: 1020

Cys Cys Gln Pro Thr Cys Val Thr Ser Cys Cys
1               5                   10

<210> SEQ ID NO 1021
<211> LENGTH: 11
<212> TYPE: PRT
<213> ORGANISM: Homo sapiens

<400> SEQUENCE: 1021

Cys Cys Gln Pro Tyr Cys His Pro Thr Cys Cys
1               5                   10

<210> SEQ ID NO 1022

```
<211> LENGTH: 11
<212> TYPE: PRT
<213> ORGANISM: Homo sapiens

<400> SEQUENCE: 1022

Cys Cys Gln Ser Met Cys Cys Gln Pro Thr Cys
1               5                   10

<210> SEQ ID NO 1023
<211> LENGTH: 11
<212> TYPE: PRT
<213> ORGANISM: Homo sapiens

<400> SEQUENCE: 1023

Cys Cys Gln Ser Asn Cys Cys Val Pro Val Cys
1               5                   10

<210> SEQ ID NO 1024
<211> LENGTH: 11
<212> TYPE: PRT
<213> ORGANISM: Homo sapiens

<400> SEQUENCE: 1024

Cys Cys Gln Ser Ser Cys Cys Lys Pro Cys Ser
1               5                   10

<210> SEQ ID NO 1025
<211> LENGTH: 11
<212> TYPE: PRT
<213> ORGANISM: Homo sapiens

<400> SEQUENCE: 1025

Cys Cys Gln Ser Ser Cys Cys Lys Pro Ser Cys
1               5                   10

<210> SEQ ID NO 1026
<211> LENGTH: 11
<212> TYPE: PRT
<213> ORGANISM: Homo sapiens

<400> SEQUENCE: 1026

Cys Cys Gln Ser Ser Cys Cys Lys Pro Tyr Cys
1               5                   10

<210> SEQ ID NO 1027
<211> LENGTH: 11
<212> TYPE: PRT
<213> ORGANISM: Homo sapiens

<400> SEQUENCE: 1027

Cys Cys Gln Ser Ser Cys Cys Gln Ser Ser Cys
1               5                   10

<210> SEQ ID NO 1028
<211> LENGTH: 11
<212> TYPE: PRT
<213> ORGANISM: Homo sapiens

<400> SEQUENCE: 1028

Cys Cys Gln Ser Ser Cys Cys Val Pro Val Cys
1               5                   10

<210> SEQ ID NO 1029
<211> LENGTH: 11
<212> TYPE: PRT
```

<213> ORGANISM: Homo sapiens

<400> SEQUENCE: 1029

Cys Cys Gln Ser Ser Cys Phe Lys Pro Cys Cys
1               5                   10

<210> SEQ ID NO 1030
<211> LENGTH: 11
<212> TYPE: PRT
<213> ORGANISM: Homo sapiens

<400> SEQUENCE: 1030

Cys Cys Gln Ser Ser Cys Ser Lys Pro Cys Cys
1               5                   10

<210> SEQ ID NO 1031
<211> LENGTH: 11
<212> TYPE: PRT
<213> ORGANISM: Homo sapiens

<400> SEQUENCE: 1031

Cys Cys Gln Ser Ser Cys Tyr Lys Pro Cys Cys
1               5                   10

<210> SEQ ID NO 1032
<211> LENGTH: 11
<212> TYPE: PRT
<213> ORGANISM: Homo sapiens

<400> SEQUENCE: 1032

Cys Cys Gln Ser Val Cys Cys Gln Pro Thr Cys
1               5                   10

<210> SEQ ID NO 1033
<211> LENGTH: 11
<212> TYPE: PRT
<213> ORGANISM: Homo sapiens

<400> SEQUENCE: 1033

Cys Cys Gln Thr Ile Cys Arg Ser Thr Cys Cys
1               5                   10

<210> SEQ ID NO 1034
<211> LENGTH: 11
<212> TYPE: PRT
<213> ORGANISM: Homo sapiens

<400> SEQUENCE: 1034

Cys Cys Gln Thr Thr Cys Cys Arg Pro Ser Cys
1               5                   10

<210> SEQ ID NO 1035
<211> LENGTH: 11
<212> TYPE: PRT
<213> ORGANISM: Homo sapiens

<400> SEQUENCE: 1035

Cys Cys Gln Thr Thr Cys Cys Arg Thr Thr Cys
1               5                   10

<210> SEQ ID NO 1036
<211> LENGTH: 11
<212> TYPE: PRT
<213> ORGANISM: Homo sapiens

<400> SEQUENCE: 1036

Cys Cys Arg Pro Ala Cys Cys Glu Thr Thr Cys
1               5                   10

<210> SEQ ID NO 1037
<211> LENGTH: 11
<212> TYPE: PRT
<213> ORGANISM: Homo sapiens

<400> SEQUENCE: 1037

Cys Cys Arg Pro Ala Cys Cys Gln Asn Thr Cys
1               5                   10

<210> SEQ ID NO 1038
<211> LENGTH: 11
<212> TYPE: PRT
<213> ORGANISM: Homo sapiens

<400> SEQUENCE: 1038

Cys Cys Arg Pro Leu Cys Cys Gln Thr Thr Cys
1               5                   10

<210> SEQ ID NO 1039
<211> LENGTH: 11
<212> TYPE: PRT
<213> ORGANISM: Homo sapiens

<400> SEQUENCE: 1039

Cys Cys Arg Pro Gln Cys Cys Gln Ser Val Cys
1               5                   10

<210> SEQ ID NO 1040
<211> LENGTH: 11
<212> TYPE: PRT
<213> ORGANISM: Homo sapiens

<400> SEQUENCE: 1040

Cys Cys Arg Pro Gln Cys Cys Gln Thr Thr Cys
1               5                   10

<210> SEQ ID NO 1041
<211> LENGTH: 11
<212> TYPE: PRT
<213> ORGANISM: Homo sapiens

<400> SEQUENCE: 1041

Cys Cys Arg Pro Ser Cys Cys Glu Ser Ser Cys
1               5                   10

<210> SEQ ID NO 1042
<211> LENGTH: 11
<212> TYPE: PRT
<213> ORGANISM: Homo sapiens

<400> SEQUENCE: 1042

Cys Cys Arg Pro Ser Cys Cys Glu Thr Thr Cys
1               5                   10

<210> SEQ ID NO 1043
<211> LENGTH: 11
<212> TYPE: PRT
<213> ORGANISM: Homo sapiens

<400> SEQUENCE: 1043

Cys Cys Arg Pro Ser Cys Gly Ser Ser Cys
1               5                   10

<210> SEQ ID NO 1044
<211> LENGTH: 11
<212> TYPE: PRT
<213> ORGANISM: Homo sapiens

<400> SEQUENCE: 1044

Cys Cys Arg Pro Ser Cys Cys Ile Ser Ser Cys
1               5                   10

<210> SEQ ID NO 1045
<211> LENGTH: 11
<212> TYPE: PRT
<213> ORGANISM: Homo sapiens

<400> SEQUENCE: 1045

Cys Cys Arg Pro Ser Cys Cys Lys Pro Gln Cys
1               5                   10

<210> SEQ ID NO 1046
<211> LENGTH: 11
<212> TYPE: PRT
<213> ORGANISM: Homo sapiens

<400> SEQUENCE: 1046

Cys Cys Arg Pro Ser Cys Cys Gln Thr Thr Cys
1               5                   10

<210> SEQ ID NO 1047
<211> LENGTH: 11
<212> TYPE: PRT
<213> ORGANISM: Homo sapiens

<400> SEQUENCE: 1047

Cys Cys Arg Pro Ser Cys Cys Val Ser Arg Cys
1               5                   10

<210> SEQ ID NO 1048
<211> LENGTH: 11
<212> TYPE: PRT
<213> ORGANISM: Homo sapiens

<400> SEQUENCE: 1048

Cys Cys Arg Pro Ser Cys Cys Val Ser Ser Cys
1               5                   10

<210> SEQ ID NO 1049
<211> LENGTH: 11
<212> TYPE: PRT
<213> ORGANISM: Homo sapiens

<400> SEQUENCE: 1049

Cys Cys Arg Pro Thr Cys Cys Gln Asn Thr Cys
1               5                   10

<210> SEQ ID NO 1050
<211> LENGTH: 11
<212> TYPE: PRT
<213> ORGANISM: Homo sapiens

<400> SEQUENCE: 1050

Cys Cys Arg Pro Thr Cys Cys Gln Thr Thr Cys
1               5                   10

<210> SEQ ID NO 1051
<211> LENGTH: 11
<212> TYPE: PRT
<213> ORGANISM: Homo sapiens

<400> SEQUENCE: 1051

Cys Cys Arg Pro Val Cys Cys Asp Pro Cys Ser
1               5                   10

<210> SEQ ID NO 1052
<211> LENGTH: 11
<212> TYPE: PRT
<213> ORGANISM: Homo sapiens

<400> SEQUENCE: 1052

Cys Cys Arg Thr Thr Cys Cys Gln Pro Thr Cys
1               5                   10

<210> SEQ ID NO 1053
<211> LENGTH: 11
<212> TYPE: PRT
<213> ORGANISM: Homo sapiens

<400> SEQUENCE: 1053

Cys Cys Arg Thr Thr Cys Cys Arg Pro Ser Cys
1               5                   10

<210> SEQ ID NO 1054
<211> LENGTH: 11
<212> TYPE: PRT
<213> ORGANISM: Homo sapiens

<400> SEQUENCE: 1054

Cys Cys Arg Thr Thr Cys Cys Arg Thr Thr Cys
1               5                   10

<210> SEQ ID NO 1055
<211> LENGTH: 11
<212> TYPE: PRT
<213> ORGANISM: Homo sapiens

<400> SEQUENCE: 1055

Cys Cys Ser Cys Ser Ser Cys Gly Ser Cys Ala
1               5                   10

<210> SEQ ID NO 1056
<211> LENGTH: 11
<212> TYPE: PRT
<213> ORGANISM: Homo sapiens

<400> SEQUENCE: 1056

Cys Cys Ser Pro Gly Cys Gln Pro Thr Cys Cys
1               5                   10

<210> SEQ ID NO 1057
<211> LENGTH: 11
<212> TYPE: PRT
<213> ORGANISM: Homo sapiens

<400> SEQUENCE: 1057

Cys Cys Ser Gln Ser Ser Cys Cys Lys Pro Cys
1               5                   10

```
<210> SEQ ID NO 1058
<211> LENGTH: 11
<212> TYPE: PRT
<213> ORGANISM: Homo sapiens

<400> SEQUENCE: 1058

Cys Cys Ser Ser Gly Cys Gly Ser Cys Cys Gln
1               5                   10

<210> SEQ ID NO 1059
<211> LENGTH: 11
<212> TYPE: PRT
<213> ORGANISM: Homo sapiens

<400> SEQUENCE: 1059

Cys Cys Ser Ser Gly Cys Gly Ser Ser Cys Cys
1               5                   10

<210> SEQ ID NO 1060
<211> LENGTH: 11
<212> TYPE: PRT
<213> ORGANISM: Homo sapiens

<400> SEQUENCE: 1060

Cys Cys Ser Thr Pro Cys Cys Gln Pro Thr Cys
1               5                   10

<210> SEQ ID NO 1061
<211> LENGTH: 11
<212> TYPE: PRT
<213> ORGANISM: Homo sapiens

<400> SEQUENCE: 1061

Cys Cys Val Pro Ala Cys Ser Cys Ser Ser Cys
1               5                   10

<210> SEQ ID NO 1062
<211> LENGTH: 11
<212> TYPE: PRT
<213> ORGANISM: Homo sapiens

<400> SEQUENCE: 1062

Cys Cys Val Pro Ala Cys Ser Cys Thr Ser Cys
1               5                   10

<210> SEQ ID NO 1063
<211> LENGTH: 11
<212> TYPE: PRT
<213> ORGANISM: Homo sapiens

<400> SEQUENCE: 1063

Cys Cys Val Pro Ile Cys Cys Lys Pro Ile Cys
1               5                   10

<210> SEQ ID NO 1064
<211> LENGTH: 11
<212> TYPE: PRT
<213> ORGANISM: Homo sapiens

<400> SEQUENCE: 1064

Cys Cys Val Pro Ile Cys Cys Lys Pro Val Cys
1               5                   10

<210> SEQ ID NO 1065
<211> LENGTH: 11
```

```
<212> TYPE: PRT
<213> ORGANISM: Homo sapiens

<400> SEQUENCE: 1065

Cys Cys Val Pro Val Cys Cys Lys Pro Ile Cys
1               5                   10

<210> SEQ ID NO 1066
<211> LENGTH: 11
<212> TYPE: PRT
<213> ORGANISM: Homo sapiens

<400> SEQUENCE: 1066

Cys Cys Val Pro Val Cys Cys Lys Pro Val Cys
1               5                   10

<210> SEQ ID NO 1067
<211> LENGTH: 11
<212> TYPE: PRT
<213> ORGANISM: Homo sapiens

<400> SEQUENCE: 1067

Cys Cys Val Pro Val Cys Cys Lys Ser Asn Cys
1               5                   10

<210> SEQ ID NO 1068
<211> LENGTH: 11
<212> TYPE: PRT
<213> ORGANISM: Homo sapiens

<400> SEQUENCE: 1068

Cys Cys Val Pro Val Cys Cys Lys Thr Val Cys
1               5                   10

<210> SEQ ID NO 1069
<211> LENGTH: 11
<212> TYPE: PRT
<213> ORGANISM: Homo sapiens

<400> SEQUENCE: 1069

Cys Cys Val Pro Val Cys Cys Ser Ser Ser Cys
1               5                   10

<210> SEQ ID NO 1070
<211> LENGTH: 11
<212> TYPE: PRT
<213> ORGANISM: Homo sapiens

<400> SEQUENCE: 1070

Cys Cys Val Pro Val Cys Cys Val Pro Val Cys
1               5                   10

<210> SEQ ID NO 1071
<211> LENGTH: 11
<212> TYPE: PRT
<213> ORGANISM: Homo sapiens

<400> SEQUENCE: 1071

Cys Cys Val Ser Ser Cys Cys Lys Pro Gln Cys
1               5                   10

<210> SEQ ID NO 1072
<211> LENGTH: 11
<212> TYPE: PRT
<213> ORGANISM: Homo sapiens
```

```
<400> SEQUENCE: 1072

Cys Cys Val Ser Ser Cys Cys Gln His Ser Cys
1               5                   10

<210> SEQ ID NO 1073
<211> LENGTH: 11
<212> TYPE: PRT
<213> ORGANISM: Homo sapiens

<400> SEQUENCE: 1073

Cys Cys Val Ser Ser Cys Cys Gln Pro Ser Cys
1               5                   10

<210> SEQ ID NO 1074
<211> LENGTH: 11
<212> TYPE: PRT
<213> ORGANISM: Homo sapiens

<400> SEQUENCE: 1074

Cys Cys Val Ser Ser Cys Cys Arg Pro Gln Cys
1               5                   10

<210> SEQ ID NO 1075
<211> LENGTH: 11
<212> TYPE: PRT
<213> ORGANISM: Homo sapiens

<400> SEQUENCE: 1075

Cys Cys Val Ser Thr Cys Cys Arg Pro Thr Cys
1               5                   10

<210> SEQ ID NO 1076
<211> LENGTH: 11
<212> TYPE: PRT
<213> ORGANISM: Homo sapiens

<400> SEQUENCE: 1076

Cys Cys Val Ser Val Cys Cys Lys Pro Val Cys
1               5                   10

<210> SEQ ID NO 1077
<211> LENGTH: 11
<212> TYPE: PRT
<213> ORGANISM: Homo sapiens

<400> SEQUENCE: 1077

Cys Asp Ser Ser Cys Cys Gln Pro Ser Cys Cys
1               5                   10

<210> SEQ ID NO 1078
<211> LENGTH: 11
<212> TYPE: PRT
<213> ORGANISM: Homo sapiens

<400> SEQUENCE: 1078

Cys Glu Pro Cys Cys Arg Pro Val Cys Cys Asp
1               5                   10

<210> SEQ ID NO 1079
<211> LENGTH: 11
<212> TYPE: PRT
<213> ORGANISM: Homo sapiens

<400> SEQUENCE: 1079
```

Cys Phe Lys Pro Cys Cys Cys Gln Ser Ser Cys
1               5                   10

<210> SEQ ID NO 1080
<211> LENGTH: 11
<212> TYPE: PRT
<213> ORGANISM: Homo sapiens

<400> SEQUENCE: 1080

Cys Gly Asp Gly Cys Cys Pro Ser Cys Tyr
1               5                   10

<210> SEQ ID NO 1081
<211> LENGTH: 11
<212> TYPE: PRT
<213> ORGANISM: Homo sapiens

<400> SEQUENCE: 1081

Cys Gly Gly Gly Cys Cys Gly Ser Ser Cys Cys
1               5                   10

<210> SEQ ID NO 1082
<211> LENGTH: 11
<212> TYPE: PRT
<213> ORGANISM: Homo sapiens

<400> SEQUENCE: 1082

Cys Gly Gly Ser Cys Cys Gly Ser Ser Cys Cys
1               5                   10

<210> SEQ ID NO 1083
<211> LENGTH: 11
<212> TYPE: PRT
<213> ORGANISM: Homo sapiens

<400> SEQUENCE: 1083

Cys Gly Leu Glu Asn Cys Cys Cys Pro Ser Cys
1               5                   10

<210> SEQ ID NO 1084
<211> LENGTH: 11
<212> TYPE: PRT
<213> ORGANISM: Homo sapiens

<400> SEQUENCE: 1084

Cys Gly Gln Ser Cys Cys Arg Pro Ala Cys Cys
1               5                   10

<210> SEQ ID NO 1085
<211> LENGTH: 11
<212> TYPE: PRT
<213> ORGANISM: Homo sapiens

<400> SEQUENCE: 1085

Cys Gly Gln Ser Cys Cys Arg Pro Val Cys Cys
1               5                   10

<210> SEQ ID NO 1086
<211> LENGTH: 11
<212> TYPE: PRT
<213> ORGANISM: Homo sapiens

<400> SEQUENCE: 1086

Cys Gly Ser Cys Cys Gln Ser Ser Cys Cys Asn

```
                1               5                  10
```

<210> SEQ ID NO 1087
<211> LENGTH: 11
<212> TYPE: PRT
<213> ORGANISM: Homo sapiens

<400> SEQUENCE: 1087

```
Cys Gly Ser Cys Gly Cys Ser Gln Cys Asn Cys
1               5                  10
```

<210> SEQ ID NO 1088
<211> LENGTH: 11
<212> TYPE: PRT
<213> ORGANISM: Homo sapiens

<400> SEQUENCE: 1088

```
Cys Gly Ser Cys Gly Cys Ser Gln Cys Ser Cys
1               5                  10
```

<210> SEQ ID NO 1089
<211> LENGTH: 11
<212> TYPE: PRT
<213> ORGANISM: Homo sapiens

<400> SEQUENCE: 1089

```
Cys Gly Ser Gly Cys Cys Gly Pro Val Cys Cys
1               5                  10
```

<210> SEQ ID NO 1090
<211> LENGTH: 11
<212> TYPE: PRT
<213> ORGANISM: Homo sapiens

<400> SEQUENCE: 1090

```
Cys Gly Ser Gly Cys Cys Val Pro Val Cys Cys
1               5                  10
```

<210> SEQ ID NO 1091
<211> LENGTH: 11
<212> TYPE: PRT
<213> ORGANISM: Homo sapiens

<400> SEQUENCE: 1091

```
Cys Gly Ser Asn Cys Cys Gln Pro Cys Cys Arg
1               5                  10
```

<210> SEQ ID NO 1092
<211> LENGTH: 11
<212> TYPE: PRT
<213> ORGANISM: Homo sapiens

<400> SEQUENCE: 1092

```
Cys Gly Ser Ser Cys Cys Gln Pro Cys Cys His
1               5                  10
```

<210> SEQ ID NO 1093
<211> LENGTH: 11
<212> TYPE: PRT
<213> ORGANISM: Homo sapiens

<400> SEQUENCE: 1093

```
Cys Gly Ser Ser Cys Cys Gln Pro Cys Cys Arg
1               5                  10
```

```
<210> SEQ ID NO 1094
<211> LENGTH: 11
<212> TYPE: PRT
<213> ORGANISM: Homo sapiens

<400> SEQUENCE: 1094

Cys Gly Ser Ser Cys Cys Gln Pro Cys Tyr Cys
1               5                   10

<210> SEQ ID NO 1095
<211> LENGTH: 11
<212> TYPE: PRT
<213> ORGANISM: Homo sapiens

<400> SEQUENCE: 1095

Cys Gly Ser Ser Cys Cys Gln Pro Ser Cys Cys
1               5                   10

<210> SEQ ID NO 1096
<211> LENGTH: 11
<212> TYPE: PRT
<213> ORGANISM: Homo sapiens

<400> SEQUENCE: 1096

Cys Gly Ser Ser Cys Cys Gln Ser Ser Cys Cys
1               5                   10

<210> SEQ ID NO 1097
<211> LENGTH: 11
<212> TYPE: PRT
<213> ORGANISM: Homo sapiens

<400> SEQUENCE: 1097

Cys Gly Ser Ser Cys Cys Val Pro Ile Cys Cys
1               5                   10

<210> SEQ ID NO 1098
<211> LENGTH: 11
<212> TYPE: PRT
<213> ORGANISM: Homo sapiens

<400> SEQUENCE: 1098

Cys Gly Ser Ser Cys Cys Val Pro Val Cys Cys
1               5                   10

<210> SEQ ID NO 1099
<211> LENGTH: 11
<212> TYPE: PRT
<213> ORGANISM: Homo sapiens

<400> SEQUENCE: 1099

Cys Gly Ser Ser Cys Ser Gln Cys Ser Cys Cys
1               5                   10

<210> SEQ ID NO 1100
<211> LENGTH: 11
<212> TYPE: PRT
<213> ORGANISM: Homo sapiens

<400> SEQUENCE: 1100

Cys Gly Val Pro Val Cys Cys Cys Ser Cys Ser
1               5                   10

<210> SEQ ID NO 1101
```

```
<211> LENGTH: 11
<212> TYPE: PRT
<213> ORGANISM: Homo sapiens

<400> SEQUENCE: 1101

Cys His Pro Arg Cys Cys Ile Ser Ser Cys Cys
1               5                   10

<210> SEQ ID NO 1102
<211> LENGTH: 11
<212> TYPE: PRT
<213> ORGANISM: Homo sapiens

<400> SEQUENCE: 1102

Cys His Pro Ser Cys Cys Glu Ser Ser Cys Cys
1               5                   10

<210> SEQ ID NO 1103
<211> LENGTH: 11
<212> TYPE: PRT
<213> ORGANISM: Homo sapiens

<400> SEQUENCE: 1103

Cys His Pro Ser Cys Cys Ile Ser Ser Cys Cys
1               5                   10

<210> SEQ ID NO 1104
<211> LENGTH: 11
<212> TYPE: PRT
<213> ORGANISM: Homo sapiens

<400> SEQUENCE: 1104

Cys His Pro Thr Cys Cys Gln Asn Thr Cys Cys
1               5                   10

<210> SEQ ID NO 1105
<211> LENGTH: 11
<212> TYPE: PRT
<213> ORGANISM: Homo sapiens

<400> SEQUENCE: 1105

Cys Ile Ser Ser Cys Cys His Pro Ser Cys Cys
1               5                   10

<210> SEQ ID NO 1106
<211> LENGTH: 11
<212> TYPE: PRT
<213> ORGANISM: Homo sapiens

<400> SEQUENCE: 1106

Cys Ile Ser Ser Cys Cys Lys Pro Ser Cys Cys
1               5                   10

<210> SEQ ID NO 1107
<211> LENGTH: 11
<212> TYPE: PRT
<213> ORGANISM: Homo sapiens

<400> SEQUENCE: 1107

Cys Ile Ser Ser Cys Cys Arg Pro Ser Cys Cys
1               5                   10

<210> SEQ ID NO 1108
<211> LENGTH: 11
<212> TYPE: PRT
```

<213> ORGANISM: Homo sapiens

<400> SEQUENCE: 1108

Cys Ile Ser Ser Ser Cys Cys Pro Ser Cys Cys
1               5                   10

<210> SEQ ID NO 1109
<211> LENGTH: 11
<212> TYPE: PRT
<213> ORGANISM: Homo sapiens

<400> SEQUENCE: 1109

Cys Lys Pro Cys Cys Ser Ser Gly Cys Gly
1               5                   10

<210> SEQ ID NO 1110
<211> LENGTH: 11
<212> TYPE: PRT
<213> ORGANISM: Homo sapiens

<400> SEQUENCE: 1110

Cys Lys Pro Cys Cys Ser Gln Ala Ser Cys Cys
1               5                   10

<210> SEQ ID NO 1111
<211> LENGTH: 11
<212> TYPE: PRT
<213> ORGANISM: Homo sapiens

<400> SEQUENCE: 1111

Cys Lys Pro Cys Cys Ser Gln Ser Arg Cys Cys
1               5                   10

<210> SEQ ID NO 1112
<211> LENGTH: 11
<212> TYPE: PRT
<213> ORGANISM: Homo sapiens

<400> SEQUENCE: 1112

Cys Lys Pro Cys Cys Ser Gln Ser Ser Cys Cys
1               5                   10

<210> SEQ ID NO 1113
<211> LENGTH: 11
<212> TYPE: PRT
<213> ORGANISM: Homo sapiens

<400> SEQUENCE: 1113

Cys Lys Pro Gln Cys Cys Gln Ser Met Cys Cys
1               5                   10

<210> SEQ ID NO 1114
<211> LENGTH: 11
<212> TYPE: PRT
<213> ORGANISM: Homo sapiens

<400> SEQUENCE: 1114

Cys Lys Pro Gln Cys Cys Gln Ser Val Cys Cys
1               5                   10

<210> SEQ ID NO 1115
<211> LENGTH: 11
<212> TYPE: PRT
<213> ORGANISM: Homo sapiens

<400> SEQUENCE: 1115

Cys Lys Pro Val Cys Cys Val Pro Ala Cys
1               5                   10

<210> SEQ ID NO 1116
<211> LENGTH: 11
<212> TYPE: PRT
<213> ORGANISM: Homo sapiens

<400> SEQUENCE: 1116

Cys Lys Pro Val Cys Cys Lys Pro Ile Cys Cys
1               5                   10

<210> SEQ ID NO 1117
<211> LENGTH: 11
<212> TYPE: PRT
<213> ORGANISM: Homo sapiens

<400> SEQUENCE: 1117

Cys Lys Pro Val Cys Cys Met Pro Val Cys Cys
1               5                   10

<210> SEQ ID NO 1118
<211> LENGTH: 11
<212> TYPE: PRT
<213> ORGANISM: Homo sapiens

<400> SEQUENCE: 1118

Cys Lys Pro Val Cys Cys Val Pro Val Cys Cys
1               5                   10

<210> SEQ ID NO 1119
<211> LENGTH: 11
<212> TYPE: PRT
<213> ORGANISM: Homo sapiens

<400> SEQUENCE: 1119

Cys Lys Pro Val Cys Cys Val Ser Val Cys Cys
1               5                   10

<210> SEQ ID NO 1120
<211> LENGTH: 11
<212> TYPE: PRT
<213> ORGANISM: Homo sapiens

<400> SEQUENCE: 1120

Cys Lys Pro Tyr Cys Ser Gln Cys Ser Cys Cys
1               5                   10

<210> SEQ ID NO 1121
<211> LENGTH: 11
<212> TYPE: PRT
<213> ORGANISM: Homo sapiens

<400> SEQUENCE: 1121

Cys Leu Pro Cys Cys Arg Pro Thr Cys Cys Gln
1               5                   10

<210> SEQ ID NO 1122
<211> LENGTH: 11
<212> TYPE: PRT
<213> ORGANISM: Homo sapiens

<400> SEQUENCE: 1122

Cys Leu Thr Ser Cys Cys Gln Pro Ser Cys Cys
1               5                   10

<210> SEQ ID NO 1123
<211> LENGTH: 11
<212> TYPE: PRT
<213> ORGANISM: Homo sapiens

<400> SEQUENCE: 1123

Cys Met Ser Ser Cys Cys Lys Pro Gln Cys Cys
1               5                   10

<210> SEQ ID NO 1124
<211> LENGTH: 11
<212> TYPE: PRT
<213> ORGANISM: Homo sapiens

<400> SEQUENCE: 1124

Cys Asn Pro Cys Cys Ser Gln Ser Ser Cys Cys
1               5                   10

<210> SEQ ID NO 1125
<211> LENGTH: 11
<212> TYPE: PRT
<213> ORGANISM: Homo sapiens

<400> SEQUENCE: 1125

Cys Pro Ala Cys Cys Val Ser Ser Cys Cys Gln
1               5                   10

<210> SEQ ID NO 1126
<211> LENGTH: 11
<212> TYPE: PRT
<213> ORGANISM: Homo sapiens

<400> SEQUENCE: 1126

Cys Pro Glu Ser Cys Cys Glu Pro His Cys Cys
1               5                   10

<210> SEQ ID NO 1127
<211> LENGTH: 11
<212> TYPE: PRT
<213> ORGANISM: Homo sapiens

<400> SEQUENCE: 1127

Cys Pro Glu Ser Cys Cys Glu Pro Pro Cys Cys
1               5                   10

<210> SEQ ID NO 1128
<211> LENGTH: 11
<212> TYPE: PRT
<213> ORGANISM: Homo sapiens

<400> SEQUENCE: 1128

Cys Pro Ser Cys Cys Glu Ser Ser Cys Cys Arg
1               5                   10

<210> SEQ ID NO 1129
<211> LENGTH: 11
<212> TYPE: PRT
<213> ORGANISM: Homo sapiens

<400> SEQUENCE: 1129

Cys Pro Ser Cys Cys Gln Thr Thr Cys Cys Arg
1               5                   10

<210> SEQ ID NO 1130
<211> LENGTH: 11
<212> TYPE: PRT
<213> ORGANISM: Homo sapiens

<400> SEQUENCE: 1130

Cys Pro Ser Cys Cys Val Ser Ser Cys Cys Arg
1               5                   10

<210> SEQ ID NO 1131
<211> LENGTH: 11
<212> TYPE: PRT
<213> ORGANISM: Homo sapiens

<400> SEQUENCE: 1131

Cys Gln Cys Ser Cys Cys Lys Pro Tyr Cys Ser
1               5                   10

<210> SEQ ID NO 1132
<211> LENGTH: 11
<212> TYPE: PRT
<213> ORGANISM: Homo sapiens

<400> SEQUENCE: 1132

Cys Gln Glu Thr Cys Cys Arg Pro Ser Cys Cys
1               5                   10

<210> SEQ ID NO 1133
<211> LENGTH: 11
<212> TYPE: PRT
<213> ORGANISM: Homo sapiens

<400> SEQUENCE: 1133

Cys Gln Asn Thr Cys Cys Arg Thr Thr Cys Cys
1               5                   10

<210> SEQ ID NO 1134
<211> LENGTH: 11
<212> TYPE: PRT
<213> ORGANISM: Homo sapiens

<400> SEQUENCE: 1134

Cys Gln Pro Ala Cys Cys Thr Ala Ser Cys Cys
1               5                   10

<210> SEQ ID NO 1135
<211> LENGTH: 11
<212> TYPE: PRT
<213> ORGANISM: Homo sapiens

<400> SEQUENCE: 1135

Cys Gln Pro Ala Cys Cys Thr Ser Ser Cys Cys
1               5                   10

<210> SEQ ID NO 1136
<211> LENGTH: 11
<212> TYPE: PRT
<213> ORGANISM: Homo sapiens

<400> SEQUENCE: 1136

Cys Gln Pro Ala Cys Cys Thr Thr Ser Cys Cys
1               5                   10

```
<210> SEQ ID NO 1137
<211> LENGTH: 11
<212> TYPE: PRT
<213> ORGANISM: Homo sapiens

<400> SEQUENCE: 1137

Cys Gln Pro Ala Cys Cys Val Pro Val Cys Cys
1               5                   10

<210> SEQ ID NO 1138
<211> LENGTH: 11
<212> TYPE: PRT
<213> ORGANISM: Homo sapiens

<400> SEQUENCE: 1138

Cys Gln Pro Ala Cys Cys Val Ser Ser Cys Cys
1               5                   10

<210> SEQ ID NO 1139
<211> LENGTH: 11
<212> TYPE: PRT
<213> ORGANISM: Homo sapiens

<400> SEQUENCE: 1139

Cys Gln Pro Cys Cys His Pro Thr Cys Cys Gln
1               5                   10

<210> SEQ ID NO 1140
<211> LENGTH: 11
<212> TYPE: PRT
<213> ORGANISM: Homo sapiens

<400> SEQUENCE: 1140

Cys Gln Pro Cys Cys Arg Pro Ala Cys Cys Glu
1               5                   10

<210> SEQ ID NO 1141
<211> LENGTH: 11
<212> TYPE: PRT
<213> ORGANISM: Homo sapiens

<400> SEQUENCE: 1141

Cys Gln Pro Cys Cys Arg Pro Ala Cys Cys Gln
1               5                   10

<210> SEQ ID NO 1142
<211> LENGTH: 11
<212> TYPE: PRT
<213> ORGANISM: Homo sapiens

<400> SEQUENCE: 1142

Cys Gln Pro Cys Cys Arg Pro Thr Cys Cys Gln
1               5                   10

<210> SEQ ID NO 1143
<211> LENGTH: 11
<212> TYPE: PRT
<213> ORGANISM: Homo sapiens

<400> SEQUENCE: 1143

Cys Gln Pro Cys Tyr Cys Pro Ala Cys Cys Val
1               5                   10

<210> SEQ ID NO 1144
<211> LENGTH: 11
```

<212> TYPE: PRT
<213> ORGANISM: Homo sapiens

<400> SEQUENCE: 1144

Cys Gln Pro Ile Cys Cys Gly Ser Ser Cys Cys
1               5                   10

<210> SEQ ID NO 1145
<211> LENGTH: 11
<212> TYPE: PRT
<213> ORGANISM: Homo sapiens

<400> SEQUENCE: 1145

Cys Gln Pro Arg Cys Cys Glu Thr Ser Cys Cys
1               5                   10

<210> SEQ ID NO 1146
<211> LENGTH: 11
<212> TYPE: PRT
<213> ORGANISM: Homo sapiens

<400> SEQUENCE: 1146

Cys Gln Pro Ser Cys Cys Glu Thr Ser Cys Cys
1               5                   10

<210> SEQ ID NO 1147
<211> LENGTH: 11
<212> TYPE: PRT
<213> ORGANISM: Homo sapiens

<400> SEQUENCE: 1147

Cys Gln Pro Ser Cys Cys Arg Pro Ala Cys Cys
1               5                   10

<210> SEQ ID NO 1148
<211> LENGTH: 11
<212> TYPE: PRT
<213> ORGANISM: Homo sapiens

<400> SEQUENCE: 1148

Cys Gln Pro Ser Cys Cys Val Pro Ser Cys Cys
1               5                   10

<210> SEQ ID NO 1149
<211> LENGTH: 11
<212> TYPE: PRT
<213> ORGANISM: Homo sapiens

<400> SEQUENCE: 1149

Cys Gln Pro Ser Cys Cys Val Ser Ser Cys Cys
1               5                   10

<210> SEQ ID NO 1150
<211> LENGTH: 11
<212> TYPE: PRT
<213> ORGANISM: Homo sapiens

<400> SEQUENCE: 1150

Cys Gln Pro Thr Cys Cys Pro Ser Tyr Cys
1               5                   10

<210> SEQ ID NO 1151
<211> LENGTH: 11
<212> TYPE: PRT
<213> ORGANISM: Homo sapiens

<400> SEQUENCE: 1151

Cys Gln Pro Thr Cys Cys Gly Ser Ser Cys Cys
1               5                   10

<210> SEQ ID NO 1152
<211> LENGTH: 11
<212> TYPE: PRT
<213> ORGANISM: Homo sapiens

<400> SEQUENCE: 1152

Cys Gln Pro Thr Cys Cys His Pro Ser Cys Cys
1               5                   10

<210> SEQ ID NO 1153
<211> LENGTH: 11
<212> TYPE: PRT
<213> ORGANISM: Homo sapiens

<400> SEQUENCE: 1153

Cys Gln Pro Thr Cys Cys Gln Pro Thr Cys Cys
1               5                   10

<210> SEQ ID NO 1154
<211> LENGTH: 11
<212> TYPE: PRT
<213> ORGANISM: Homo sapiens

<400> SEQUENCE: 1154

Cys Gln Pro Thr Cys Cys Arg Pro Ser Cys Cys
1               5                   10

<210> SEQ ID NO 1155
<211> LENGTH: 11
<212> TYPE: PRT
<213> ORGANISM: Homo sapiens

<400> SEQUENCE: 1155

Cys Gln Pro Thr Cys Cys Arg Pro Thr Cys Cys
1               5                   10

<210> SEQ ID NO 1156
<211> LENGTH: 11
<212> TYPE: PRT
<213> ORGANISM: Homo sapiens

<400> SEQUENCE: 1156

Cys Gln Pro Thr Cys Cys Arg Thr Thr Cys Cys
1               5                   10

<210> SEQ ID NO 1157
<211> LENGTH: 11
<212> TYPE: PRT
<213> ORGANISM: Homo sapiens

<400> SEQUENCE: 1157

Cys Gln Gln Ala Cys Cys Met Pro Val Cys Cys
1               5                   10

<210> SEQ ID NO 1158
<211> LENGTH: 11
<212> TYPE: PRT
<213> ORGANISM: Homo sapiens

<400> SEQUENCE: 1158

Cys Gln Gln Ala Cys Cys Val Pro Ile Cys Cys
1               5                   10

<210> SEQ ID NO 1159
<211> LENGTH: 11
<212> TYPE: PRT
<213> ORGANISM: Homo sapiens

<400> SEQUENCE: 1159

Cys Gln Gln Ala Cys Cys Val Pro Val Cys Cys
1               5                   10

<210> SEQ ID NO 1160
<211> LENGTH: 11
<212> TYPE: PRT
<213> ORGANISM: Homo sapiens

<400> SEQUENCE: 1160

Cys Gln Gln Ser Cys Cys Val Pro Val Cys Cys
1               5                   10

<210> SEQ ID NO 1161
<211> LENGTH: 11
<212> TYPE: PRT
<213> ORGANISM: Homo sapiens

<400> SEQUENCE: 1161

Cys Gln Gln Ser Cys Cys Val Ser Val Cys Cys
1               5                   10

<210> SEQ ID NO 1162
<211> LENGTH: 11
<212> TYPE: PRT
<213> ORGANISM: Homo sapiens

<400> SEQUENCE: 1162

Cys Gln Ser Asn Cys Cys Val Pro Val Cys Cys
1               5                   10

<210> SEQ ID NO 1163
<211> LENGTH: 11
<212> TYPE: PRT
<213> ORGANISM: Homo sapiens

<400> SEQUENCE: 1163

Cys Gln Ser Ser Cys Cys Cys Pro Ala Ser Cys
1               5                   10

<210> SEQ ID NO 1164
<211> LENGTH: 11
<212> TYPE: PRT
<213> ORGANISM: Homo sapiens

<400> SEQUENCE: 1164

Cys Gln Ser Ser Cys Cys Lys Pro Cys Cys Ser
1               5                   10

<210> SEQ ID NO 1165
<211> LENGTH: 11
<212> TYPE: PRT
<213> ORGANISM: Homo sapiens

<400> SEQUENCE: 1165

Cys Gln Ser Ser Cys Cys Lys Pro Cys Ser Cys

```
1               5                   10
```

<210> SEQ ID NO 1166
<211> LENGTH: 11
<212> TYPE: PRT
<213> ORGANISM: Homo sapiens

<400> SEQUENCE: 1166

```
Cys Gln Ser Ser Cys Cys Lys Pro Tyr Cys Cys
1               5                   10
```

<210> SEQ ID NO 1167
<211> LENGTH: 11
<212> TYPE: PRT
<213> ORGANISM: Homo sapiens

<400> SEQUENCE: 1167

```
Cys Gln Ser Ser Cys Cys Asn Pro Cys Cys Ser
1               5                   10
```

<210> SEQ ID NO 1168
<211> LENGTH: 11
<212> TYPE: PRT
<213> ORGANISM: Homo sapiens

<400> SEQUENCE: 1168

```
Cys Gln Ser Ser Cys Cys Gln Ser Ser Cys Cys
1               5                   10
```

<210> SEQ ID NO 1169
<211> LENGTH: 11
<212> TYPE: PRT
<213> ORGANISM: Homo sapiens

<400> SEQUENCE: 1169

```
Cys Gln Ser Ser Cys Cys Val Pro Val Cys Cys
1               5                   10
```

<210> SEQ ID NO 1170
<211> LENGTH: 11
<212> TYPE: PRT
<213> ORGANISM: Homo sapiens

<400> SEQUENCE: 1170

```
Cys Gln Ser Ser Cys Phe Lys Pro Cys Cys Cys
1               5                   10
```

<210> SEQ ID NO 1171
<211> LENGTH: 11
<212> TYPE: PRT
<213> ORGANISM: Homo sapiens

<400> SEQUENCE: 1171

```
Cys Gln Ser Ser Cys Ser Lys Pro Cys Cys Cys
1               5                   10
```

<210> SEQ ID NO 1172
<211> LENGTH: 11
<212> TYPE: PRT
<213> ORGANISM: Homo sapiens

<400> SEQUENCE: 1172

```
Cys Gln Ser Ser Cys Tyr Lys Pro Cys Cys Cys
1               5                   10
```

<210> SEQ ID NO 1173
<211> LENGTH: 11
<212> TYPE: PRT
<213> ORGANISM: Homo sapiens

<400> SEQUENCE: 1173

Cys Gln Ser Val Cys Cys Gln Pro Thr Cys Cys
1               5                   10

<210> SEQ ID NO 1174
<211> LENGTH: 11
<212> TYPE: PRT
<213> ORGANISM: Homo sapiens

<400> SEQUENCE: 1174

Cys Gln Thr Thr Cys Cys Cys Pro Ser Cys Val
1               5                   10

<210> SEQ ID NO 1175
<211> LENGTH: 11
<212> TYPE: PRT
<213> ORGANISM: Homo sapiens

<400> SEQUENCE: 1175

Cys Gln Thr Thr Cys Cys Arg Pro Ser Cys Cys
1               5                   10

<210> SEQ ID NO 1176
<211> LENGTH: 11
<212> TYPE: PRT
<213> ORGANISM: Homo sapiens

<400> SEQUENCE: 1176

Cys Gln Thr Thr Cys Cys Arg Thr Thr Cys Cys
1               5                   10

<210> SEQ ID NO 1177
<211> LENGTH: 11
<212> TYPE: PRT
<213> ORGANISM: Homo sapiens

<400> SEQUENCE: 1177

Cys Arg Pro Ala Cys Cys Glu Thr Thr Cys Cys
1               5                   10

<210> SEQ ID NO 1178
<211> LENGTH: 11
<212> TYPE: PRT
<213> ORGANISM: Homo sapiens

<400> SEQUENCE: 1178

Cys Arg Pro Ala Cys Cys Gln Asn Thr Cys Cys
1               5                   10

<210> SEQ ID NO 1179
<211> LENGTH: 11
<212> TYPE: PRT
<213> ORGANISM: Homo sapiens

<400> SEQUENCE: 1179

Cys Arg Pro Cys Cys Cys Leu Arg Pro Val Cys
1               5                   10

<210> SEQ ID NO 1180

```
<211> LENGTH: 11
<212> TYPE: PRT
<213> ORGANISM: Homo sapiens

<400> SEQUENCE: 1180

Cys Arg Pro Cys Cys Cys Val Arg Pro Val Cys
1               5                   10

<210> SEQ ID NO 1181
<211> LENGTH: 11
<212> TYPE: PRT
<213> ORGANISM: Homo sapiens

<400> SEQUENCE: 1181

Cys Arg Pro Cys Cys Trp Ala Thr Thr Cys Cys
1               5                   10

<210> SEQ ID NO 1182
<211> LENGTH: 11
<212> TYPE: PRT
<213> ORGANISM: Homo sapiens

<400> SEQUENCE: 1182

Cys Arg Pro Leu Cys Cys Gln Thr Thr Cys Cys
1               5                   10

<210> SEQ ID NO 1183
<211> LENGTH: 11
<212> TYPE: PRT
<213> ORGANISM: Homo sapiens

<400> SEQUENCE: 1183

Cys Arg Pro Gln Cys Cys Gln Ser Val Cys Cys
1               5                   10

<210> SEQ ID NO 1184
<211> LENGTH: 11
<212> TYPE: PRT
<213> ORGANISM: Homo sapiens

<400> SEQUENCE: 1184

Cys Arg Pro Gln Cys Cys Gln Thr Thr Cys Cys
1               5                   10

<210> SEQ ID NO 1185
<211> LENGTH: 11
<212> TYPE: PRT
<213> ORGANISM: Homo sapiens

<400> SEQUENCE: 1185

Cys Arg Pro Arg Cys Cys Ile Ser Ser Cys Cys
1               5                   10

<210> SEQ ID NO 1186
<211> LENGTH: 11
<212> TYPE: PRT
<213> ORGANISM: Homo sapiens

<400> SEQUENCE: 1186

Cys Arg Pro Ser Cys Cys Glu Ser Ser Cys Cys
1               5                   10

<210> SEQ ID NO 1187
<211> LENGTH: 11
<212> TYPE: PRT
```

<213> ORGANISM: Homo sapiens

<400> SEQUENCE: 1187

Cys Arg Pro Ser Cys Cys Ile Ser Ser Cys Cys
1               5                   10

<210> SEQ ID NO 1188
<211> LENGTH: 11
<212> TYPE: PRT
<213> ORGANISM: Homo sapiens

<400> SEQUENCE: 1188

Cys Arg Pro Ser Cys Cys Lys Pro Gln Cys Cys
1               5                   10

<210> SEQ ID NO 1189
<211> LENGTH: 11
<212> TYPE: PRT
<213> ORGANISM: Homo sapiens

<400> SEQUENCE: 1189

Cys Arg Pro Ser Cys Cys Pro Ser Cys Cys Gln
1               5                   10

<210> SEQ ID NO 1190
<211> LENGTH: 11
<212> TYPE: PRT
<213> ORGANISM: Homo sapiens

<400> SEQUENCE: 1190

Cys Arg Pro Ser Cys Cys Gln Thr Thr Cys Cys
1               5                   10

<210> SEQ ID NO 1191
<211> LENGTH: 11
<212> TYPE: PRT
<213> ORGANISM: Homo sapiens

<400> SEQUENCE: 1191

Cys Arg Pro Ser Cys Cys Arg Pro Gln Cys Cys
1               5                   10

<210> SEQ ID NO 1192
<211> LENGTH: 11
<212> TYPE: PRT
<213> ORGANISM: Homo sapiens

<400> SEQUENCE: 1192

Cys Arg Pro Ser Cys Cys Val Ser Arg Cys Cys
1               5                   10

<210> SEQ ID NO 1193
<211> LENGTH: 11
<212> TYPE: PRT
<213> ORGANISM: Homo sapiens

<400> SEQUENCE: 1193

Cys Arg Pro Ser Cys Cys Val Ser Ser Cys Cys
1               5                   10

<210> SEQ ID NO 1194
<211> LENGTH: 11
<212> TYPE: PRT
<213> ORGANISM: Homo sapiens

<400> SEQUENCE: 1194

Cys Arg Pro Thr Cys Cys Gln Asn Thr Cys Cys
1               5                   10

<210> SEQ ID NO 1195
<211> LENGTH: 11
<212> TYPE: PRT
<213> ORGANISM: Homo sapiens

<400> SEQUENCE: 1195

Cys Arg Pro Val Cys Cys Cys Glu Pro Thr Cys
1               5                   10

<210> SEQ ID NO 1196
<211> LENGTH: 11
<212> TYPE: PRT
<213> ORGANISM: Homo sapiens

<400> SEQUENCE: 1196

Cys Arg Pro Val Cys Cys Tyr Ser Cys Glu
1               5                   10

<210> SEQ ID NO 1197
<211> LENGTH: 11
<212> TYPE: PRT
<213> ORGANISM: Homo sapiens

<400> SEQUENCE: 1197

Cys Arg Thr Thr Cys Cys His Pro Ser Cys Cys
1               5                   10

<210> SEQ ID NO 1198
<211> LENGTH: 11
<212> TYPE: PRT
<213> ORGANISM: Homo sapiens

<400> SEQUENCE: 1198

Cys Arg Thr Thr Cys Cys Arg Pro Ser Cys Cys
1               5                   10

<210> SEQ ID NO 1199
<211> LENGTH: 11
<212> TYPE: PRT
<213> ORGANISM: Homo sapiens

<400> SEQUENCE: 1199

Cys Ser Cys Cys Lys Pro Tyr Cys Ser Gln Cys
1               5                   10

<210> SEQ ID NO 1200
<211> LENGTH: 11
<212> TYPE: PRT
<213> ORGANISM: Homo sapiens

<400> SEQUENCE: 1200

Cys Ser Lys Pro Cys Cys Cys Gln Ser Ser Cys
1               5                   10

<210> SEQ ID NO 1201
<211> LENGTH: 11
<212> TYPE: PRT
<213> ORGANISM: Homo sapiens

<400> SEQUENCE: 1201

```
Cys Ser Pro Cys Cys Gln Pro Thr Cys Cys Arg
1               5                   10
```

<210> SEQ ID NO 1202
<211> LENGTH: 11
<212> TYPE: PRT
<213> ORGANISM: Homo sapiens

<400> SEQUENCE: 1202

```
Cys Ser Pro Cys Cys Val Ser Ser Cys Cys Gln
1               5                   10
```

<210> SEQ ID NO 1203
<211> LENGTH: 11
<212> TYPE: PRT
<213> ORGANISM: Homo sapiens

<400> SEQUENCE: 1203

```
Cys Ser Gln Cys Ser Cys Cys Lys Pro Cys Tyr
1               5                   10
```

<210> SEQ ID NO 1204
<211> LENGTH: 11
<212> TYPE: PRT
<213> ORGANISM: Homo sapiens

<400> SEQUENCE: 1204

```
Cys Ser Gln Cys Ser Cys Tyr Lys Pro Cys Cys
1               5                   10
```

<210> SEQ ID NO 1205
<211> LENGTH: 11
<212> TYPE: PRT
<213> ORGANISM: Homo sapiens

<400> SEQUENCE: 1205

```
Cys Ser Gln Ser Asn Cys Cys Lys Pro Cys Cys
1               5                   10
```

<210> SEQ ID NO 1206
<211> LENGTH: 11
<212> TYPE: PRT
<213> ORGANISM: Homo sapiens

<400> SEQUENCE: 1206

```
Cys Ser Gln Ser Ser Cys Cys Lys Pro Cys Cys
1               5                   10
```

<210> SEQ ID NO 1207
<211> LENGTH: 11
<212> TYPE: PRT
<213> ORGANISM: Homo sapiens

<400> SEQUENCE: 1207

```
Cys Ser Ser Ser Cys Cys Gln Pro Ser Cys Cys
1               5                   10
```

<210> SEQ ID NO 1208
<211> LENGTH: 11
<212> TYPE: PRT
<213> ORGANISM: Homo sapiens

<400> SEQUENCE: 1208

```
Cys Thr Pro Ser Cys Cys Gln Pro Ala Cys Cys
1               5                   10
```

```
<210> SEQ ID NO 1209
<211> LENGTH: 11
<212> TYPE: PRT
<213> ORGANISM: Homo sapiens

<400> SEQUENCE: 1209

Cys Val Ala Ser Cys Cys Gln Pro Ser Cys Cys
1               5                   10

<210> SEQ ID NO 1210
<211> LENGTH: 11
<212> TYPE: PRT
<213> ORGANISM: Homo sapiens

<400> SEQUENCE: 1210

Cys Val Pro Ile Cys Cys Cys Lys Pro Val Cys
1               5                   10

<210> SEQ ID NO 1211
<211> LENGTH: 11
<212> TYPE: PRT
<213> ORGANISM: Homo sapiens

<400> SEQUENCE: 1211

Cys Val Pro Ser Cys Cys Gln Pro Cys Cys His
1               5                   10

<210> SEQ ID NO 1212
<211> LENGTH: 11
<212> TYPE: PRT
<213> ORGANISM: Homo sapiens

<400> SEQUENCE: 1212

Cys Val Pro Val Cys Cys Cys Lys Pro Met Cys
1               5                   10

<210> SEQ ID NO 1213
<211> LENGTH: 11
<212> TYPE: PRT
<213> ORGANISM: Homo sapiens

<400> SEQUENCE: 1213

Cys Val Pro Val Cys Cys Cys Lys Pro Val Cys
1               5                   10

<210> SEQ ID NO 1214
<211> LENGTH: 11
<212> TYPE: PRT
<213> ORGANISM: Homo sapiens

<400> SEQUENCE: 1214

Cys Val Pro Val Cys Cys Lys Pro Val Cys Cys
1               5                   10

<210> SEQ ID NO 1215
<211> LENGTH: 11
<212> TYPE: PRT
<213> ORGANISM: Homo sapiens

<400> SEQUENCE: 1215

Cys Val Ser Ser Cys Cys Lys Pro Gln Cys Cys
1               5                   10
```

```
<210> SEQ ID NO 1216
<211> LENGTH: 11
<212> TYPE: PRT
<213> ORGANISM: Homo sapiens

<400> SEQUENCE: 1216

Cys Val Ser Ser Cys Cys Gln His Ser Cys Cys
1               5                   10

<210> SEQ ID NO 1217
<211> LENGTH: 11
<212> TYPE: PRT
<213> ORGANISM: Homo sapiens

<400> SEQUENCE: 1217

Cys Val Ser Ser Cys Cys Gln Pro Cys Cys His
1               5                   10

<210> SEQ ID NO 1218
<211> LENGTH: 11
<212> TYPE: PRT
<213> ORGANISM: Homo sapiens

<400> SEQUENCE: 1218

Cys Val Ser Ser Cys Cys Gln Pro Cys Cys Arg
1               5                   10

<210> SEQ ID NO 1219
<211> LENGTH: 11
<212> TYPE: PRT
<213> ORGANISM: Homo sapiens

<400> SEQUENCE: 1219

Cys Val Ser Ser Cys Cys Gln Pro Phe Cys Cys
1               5                   10

<210> SEQ ID NO 1220
<211> LENGTH: 11
<212> TYPE: PRT
<213> ORGANISM: Homo sapiens

<400> SEQUENCE: 1220

Cys Val Ser Ser Cys Cys Gln Pro Ser Cys Cys
1               5                   10

<210> SEQ ID NO 1221
<211> LENGTH: 11
<212> TYPE: PRT
<213> ORGANISM: Homo sapiens

<400> SEQUENCE: 1221

Cys Val Ser Ser Cys Cys Arg Pro Gln Cys Cys
1               5                   10

<210> SEQ ID NO 1222
<211> LENGTH: 11
<212> TYPE: PRT
<213> ORGANISM: Homo sapiens

<400> SEQUENCE: 1222

Cys Val Thr Arg Cys Cys Ser Thr Pro Cys Cys
1               5                   10

<210> SEQ ID NO 1223
<211> LENGTH: 11
```

```
<212> TYPE: PRT
<213> ORGANISM: Homo sapiens

<400> SEQUENCE: 1223

Cys Val Thr Ser Cys Cys Gln Pro Ala Cys Cys
1               5                   10

<210> SEQ ID NO 1224
<211> LENGTH: 11
<212> TYPE: PRT
<213> ORGANISM: Homo sapiens

<400> SEQUENCE: 1224

Cys Val Thr Ser Cys Cys Gln Pro Ser Cys Cys
1               5                   10

<210> SEQ ID NO 1225
<211> LENGTH: 11
<212> TYPE: PRT
<213> ORGANISM: Homo sapiens

<400> SEQUENCE: 1225

Cys Val Tyr Ser Cys Cys Gln Pro Phe Cys Cys
1               5                   10

<210> SEQ ID NO 1226
<211> LENGTH: 11
<212> TYPE: PRT
<213> ORGANISM: Homo sapiens

<400> SEQUENCE: 1226

Cys Val Tyr Ser Cys Cys Gln Pro Ser Cys Cys
1               5                   10

<210> SEQ ID NO 1227
<211> LENGTH: 11
<212> TYPE: PRT
<213> ORGANISM: Homo sapiens

<400> SEQUENCE: 1227

Cys Tyr Cys Pro Ala Cys Cys Val Ser Ser Cys
1               5                   10

<210> SEQ ID NO 1228
<211> LENGTH: 11
<212> TYPE: PRT
<213> ORGANISM: Homo sapiens

<400> SEQUENCE: 1228

Cys Tyr Lys Pro Cys Cys Cys Gln Ser Ser Cys
1               5                   10

<210> SEQ ID NO 1229
<211> LENGTH: 11
<212> TYPE: PRT
<213> ORGANISM: Homo sapiens

<400> SEQUENCE: 1229

Cys Tyr Lys Pro Cys Cys Cys Ser Ser Gly Cys
1               5                   10

<210> SEQ ID NO 1230
<211> LENGTH: 11
<212> TYPE: PRT
<213> ORGANISM: Homo sapiens
```

<400> SEQUENCE: 1230

Met Cys Cys Cys Val Pro Ala Cys Ser Cys Ser
1               5                   10

<210> SEQ ID NO 1231
<211> LENGTH: 11
<212> TYPE: PRT
<213> ORGANISM: Homo sapiens

<400> SEQUENCE: 1231

Asn Cys Cys Val Pro Val Cys Cys Gln Cys Lys
1               5                   10

<210> SEQ ID NO 1232
<211> LENGTH: 11
<212> TYPE: PRT
<213> ORGANISM: Homo sapiens

<400> SEQUENCE: 1232

Gln Cys Ser Cys Cys Lys Pro Cys Tyr Cys Ser
1               5                   10

<210> SEQ ID NO 1233
<211> LENGTH: 11
<212> TYPE: PRT
<213> ORGANISM: Homo sapiens

<400> SEQUENCE: 1233

Gln Cys Ser Cys Tyr Lys Pro Cys Cys Cys Ser
1               5                   10

<210> SEQ ID NO 1234
<211> LENGTH: 11
<212> TYPE: PRT
<213> ORGANISM: Homo sapiens

<400> SEQUENCE: 1234

Ser Cys Cys Val Pro Ile Cys Cys Gln Cys Lys
1               5                   10

<210> SEQ ID NO 1235
<211> LENGTH: 11
<212> TYPE: PRT
<213> ORGANISM: Homo sapiens

<400> SEQUENCE: 1235

Ser Cys Cys Val Pro Val Cys Cys Gln Cys Lys
1               5                   10

<210> SEQ ID NO 1236
<211> LENGTH: 11
<212> TYPE: PRT
<213> ORGANISM: Homo sapiens

<400> SEQUENCE: 1236

Ser Cys Gly Cys Ser Gln Cys Asn Cys Cys Lys
1               5                   10

<210> SEQ ID NO 1237
<211> LENGTH: 11
<212> TYPE: PRT
<213> ORGANISM: Homo sapiens

<400> SEQUENCE: 1237

```
Ser Cys Gly Cys Ser Gln Cys Ser Cys Lys
1               5                   10

<210> SEQ ID NO 1238
<211> LENGTH: 11
<212> TYPE: PRT
<213> ORGANISM: Homo sapiens

<400> SEQUENCE: 1238

Val Cys Cys Cys Val Pro Ala Cys Ser Cys Ser
1               5                   10

<210> SEQ ID NO 1239
<211> LENGTH: 11
<212> TYPE: PRT
<213> ORGANISM: Homo sapiens

<400> SEQUENCE: 1239

Val Cys Cys Cys Val Pro Ala Cys Ser Cys Thr
1               5                   10
```

PEPTIDE COMPOSITION AND RESPECTIVE USES

CROSS-REFERENCE TO RELATED APPLICATIONS

This application is a U.S. National Stage Application under 35 U.S.C. § 371 of International Patent Application No. PCT/IB2014/065375, filed Oct. 16, 2014 which claims priority to Portugal Application No. 107244, filed Oct. 18, 2013, which are hereby incorporated by reference in their respective entireties.

TECHNICAL DOMAIN

The current application corresponds to a composition that comprises at least one peptide, based on keratin and keratin associated proteins, containing 2 to 5 cysteines with the purpose of treatment and cosmetics of animal hair, in preference human hair.

PRIOR ART

Human hair has a significant social role in most of the various world cultures, particularly for female population. Thus, there is a constant desire to improve and change hair characteristics, such as its natural texture. There are several differences in hair characteristics between different human ethnicities, as well as between individuals of the same ethnicity, such as length, thickness, color and texture.

Hair is composed of approximately 65% to 95% protein. The remaining constituents include water, lipids, pigments and trace elements. The majority of the proteins present in human hair correspond to keratin and keratin-associated proteins.

Human hair fibers structure consists of cuticle, cortex and medulla. The cuticle constitutes about 15% by weight of the hair and consists of overlapping layers of cells, similar to a system of scales, with high content of cysteine. It provides a protective character to the hair fiber. The cortex is the middle region of the hair being responsible for the strength, elasticity and hair color. It is composed of several cell types and represents about 80% of the weight of the hair. The medulla corresponds to a central beam of cells, and is absent in some hairs.

Keratins and mainly keratin-associated proteins have high sulfur content, present in the cysteine amino acid. The presence of sulfur is essential to the hair structure, as it allows the formation of disulfide bonds between amino acids of the polypeptide chains, due to oxidation of cysteine. The existence of these bonds is largely responsible for the structure and texture of the hair.

There are several hair styling methods that involve breakage and reestablishment of disulfide bonds, allowing relaxation and straightening of the hair. However, the most effective methods currently used to modulate hair contain harmful chemicals such as sodium hydroxide, potassium hydroxide, lithium hydroxide, guanidine hydroxide, ammonium thioglycolate or sodium sulfate. These methods can damage the scalp and the hair fiber, leading to its weakening and reducing its tensile strength. Formaldehyde, an extremely toxic chemical, is also used in hair straightening products. Other hair treatments that do not involve so much damage to the hair and the consumer are usually very expensive, time-consuming and/or have low efficacy. Thus there is a constant demand for formulations that efficiently model the hair fiber without damage.

Peptides, proteins, amino acids and its derivatives have also been used in compositions for personal care products, namely hair conditioning and strengthening. For example, the document WO 00/23039 discloses a composition for hair treatment containing intermediate filament proteins, namely artificial keratin. The document EP 0488242 discloses a hair treating agent containing 3% to 10% by weight of cysteine and salts thereof, a polyhydric alcohol or a saccharide containing four to twenty carbon atoms, three or more hydroxyl groups in the molecule and no aldehyde or ketone group.

The current invention is distinguished by the use of peptides, while the other applications refer the use of, respectively, proteins and amino acids in isolation and together with other types of compounds. The peptides in this innovation peptide can penetrate into the human hair in order to improve hair fiber resistance.

The document WO 00/51556 discloses a hair treatment composition that contains four or more discrete amino acids selected from histidine, lysine, methionine, tyrosine, tryptophan or cysteine. This document describes peptides without referring sequences and providing a composition essentially based on histidine, lysine, methionine, tyrosine, tryptophan or cysteine.

The document PT 103484 describes a formulation for cosmetic applications that uses hydrophobic binding domains and/or carbohydrates, in order to enhance its properties and to repair hair damage. The binding domains used are hydrolyzed milk protein, a model of human surfactant protein as well as biologically active and synthetic peptides. The current invention is distinguished by the innovative use of synthetic peptide sequences analogous to keratin proteins instead of surfactant proteins. Furthermore, it does not rely on hydrophobic binding domains and/or carbohydrates, but in other interactions, namely disulfide bonds.

Enzymes have also been used as activating agents for hair treatment, such as in the document WO 00/64405. The document WO 2012/13593 discloses a cosmetic kit for hair conformational change that acts specifically in the disulfide bonds of the hair keratin, through enzyme activating agents and proteolytic enzymes.

As described in the last document there are hair treatments that include actions at the level of the hair disulfide bonds. Below we highlight some examples.

The document WO 97/11672 reports a method for permanent hair processing using tris(2-carboxyethyl)phosphine (TCEP), and other water-soluble tertiary phosphines to break disulfide bonds, whose reaction occurs in acidic environment. The document U.S. Pat. No. 5,635,170 discloses a composition for permanent shaping of hair based on a keratin reducing agent, which contains N-glycyl-L-cysteine and/or L-cysteinyl-glycine. The pH range of this composition is 6.5 to 9.0. The document WO 2008/081348 refers a method and composition for permanent modulation of hair, through the use of 1% to 30% of N-alkyl-2-mercapto acetamide as a keratin reducing agent. It also contains at least one cationic surfactant for permanently shaping hair and the resulting process. The document WO 2006/001536 describes an agent for permanent hair processing that contains a derivative of mercaptocarboxylic acid, which allows processing and reduction of hair keratin in the acidic and neutral range of the pH. The document US 2010/0272666 discloses a hair cosmetic composition for hair treatment, containing 5 to 50 amino acids, without containing cysteine or its derivatives. Thus, this invention is distinguished by the existence of specific amino acid sequences, which contain cysteine, allowing the formation of disulfide bonds that stabilize and protect the hair fiber.

In a previous article by Fernandes et al. (Fernandes, Lima, Loureiro, Gomes, & Cavaco-Paulo, 2012), it is performed the toxicology evaluation of a peptide sequence for hair care use, containing 13 amino acids with two cysteines in its composition. However, in this article it is not mentioned or suggested that the percentage of cysteine in a peptide sequence may have some effect on the resistance of the hair. Also, in the present innovation, the number of amino acids of each peptide sequence is 6 to 12.

General Description

Thus, the present invention aims to provide a composition for treatment of the hair, including animal and human hair, without the use of chemicals harmful to the hair fiber and consumer health and that does not present the drawbacks found in the state of the art.

The compositions described in the current invention, after prolonged use, provide hair with soft, shiny, undamaged texture and with the desired features. The peptide compositions with a specific number of amino acids and cysteines act synergically providing resistance to strength, toughness and elasticity to the hair. Therefore, the compositions of the current invention are particularly relevant for hair treatment, hair dying, hair perms, etc.

The present application describes a peptide composition for hair treatment, in particular human or animal hair, which comprises at least one peptide with 6-12 amino acids length (namely 6, 7, 8, 9, 10, 11, 12 amino acids), where 2-5 of those amino acids correspond to cysteine, preferably 2, 3, 4 or 5 of those amino acids are cysteines and dermatologically suitable excipients, which penetrates the hair, increasing it resistance and reducing it breakage.

In the embodiment, for improved results, the peptide (or peptides) of the peptide composition for hair care can comprise 10-11 amino acids.

In the embodiment of the peptide composition for hair care treatment, the referred peptides can also contain a percentage of hydrophobic amino acids, not higher than 60%, and preferably less than 41% for better results. Preferably, the composition can also comprise at least one hydrophobic amino acid selected from the following list: phenylalanine, alanine, leucine, methionine, isoleucine, tryptophan, proline, valine or their mixtures.

In yet another embodiment, the amount of cysteine of the peptide composition for hair treatment may vary from 10% to 50% of the total of amino acids of the peptide sequence, preferably 20-30%, and even more preferably 25%.

In an embodiment of the composition, with better results of the peptide (or peptides) of the peptide composition for hair treatment, the sequence of peptide(s) can comprise at least one sequence of the following list with a with a degree of homology greater than or equal to 90%: SEQ. ID NO:1-SEQ. ID NO:1239, preferably with a degree of homology greater than or equal to 91%, 92%, 93%, 94%, 95%, 96%, 97%, 98%, 99%, 100%.

In an embodiment, improved results for the peptide (or peptides) of the peptide composition for hair treatment can comprise at least one of the sequences of the following list with a degree of homology equal or greater than 90%: SEQ. ID NO:5, SEQ. ID NO:75; SEQ. ID NO:94; SEQ. ID NO: 409; SEQ. ID NO:411; SEQ. ID NO:412; SEQ ID. NO:432; SEQ. ID NO:618; SEQ. ID NO:717; SEQ. ID NO:951; SEQ. ID NO:1088; SEQ. ID NO:1131; SEQ. ID NO:1149, preferably with a degree of homology equal or greater than 91%, 92%, 93%, 94%, 95%, 96%, 97%, 98%, 99%, 100%.

In other embodiment, the concentration of the peptide of the peptide composition for hair treatment can vary between 0.001%-20% (w/w), preferably 0.01-5% (w/w).

In yet other embodiment, the peptide composition for hair treatment can comprise at least one excipient, selected from the following list: surfactants, emulsifiers, preservatives, thickeners, organic polymers, humectants, silicones, oils, fragrances, vitamins, buffers.

In another embodiment, the peptide composition for hair treatment can comprise at least one anionic surfactant selected from the following list: alkylbenzene sulfonates, ammonium lauryl sulfate, ammonium lauryl sulfate, ammonium xylenesulfonate, sodium C14-16 olefin sulfonate, sodium cocoyl sarcosinate, sodium laureth sulfate, sodium lauryl sulfate, sodium lauryl sulfoacetate, sodium myreth sulfate, sodium xylenesulfonate, TEA-dodecylbenzenesulfonate, ethyl PEG-15 cocamine sulfate, dioctyl sodium sulfosuccinate, or any mixture thereof.

In an embodiment, the peptide composition for hair treatment can comprise at least one amphoteric surfactant selected from the following list: cocamidopropyl betaine, coco betaine, cocoamphoacetate, cocoamphodipropionate, disodium cocoamphodiacetate, disodium cocoamphodipropionate, lauroamphoacetate, sodium cocoyl isethionate, or any mixture thereof.

In other embodiment, the peptide composition for hair treatment can comprise at least one cationic surfactant selected from the following list: quaternary ammonium compounds, behentrimonium chloride, behentrimonium methosulfate, benzalkonium chloride, betrimonium chloride, binnamidopropyltrimonium chloride, cocotrimonium chloride, dicetyldimonium chloride, dicocodimonium chloride, dihydrogenated tallow dimethylammonium chloride, hydrogenated Palm trimethylammonium chloride, laurtrimonium chloride, quaternium-15, quaternium-18 bentonite, quaternium-22 hectonite, stearalkonium chloride, tallowtrimonium chloride, tricetyldimonium chloride, or any mixture thereof.

In yet other embodiment, the peptide composition for hair treatment can comprise at least one non-ionic surfactant selected from the following list: decyl glucoside, laureth-10 (lauryl ether 10), laureth-23, Laureth-4, PEG-10 sorbitan laurate, polysorbate-(20, 21, 40, 60, 61, 65, 80, 81), PPG-1 trideceth-6, sorbitol, steareth-(2, 10, 15, 20), C11-21 pareth-(3-30), C12-20 acid PEG-8 ester, or their mixtures.

In yet other embodiment, the peptide composition for hair treatment can comprise at least one emulsifier selected from the following list: caprylic/capric/diglyceryl succinate, C10-15 pareth-(2,4,6,8) phosphate, C14-16 glycol palmitate, C18-20 glycol isostearate, ceteareth-(4-60), cocamidopropyl lauryl ether, deceth-(3-10), DIPA-hydrogenated cocoate, dipentaerythrityl hydroxystearate, dipentaerythrityl hydroxyisostea rate, dipentaerythrityl hexacaprate/caprylate, dodoxynol-(5,6,7,9,12), nonoxynol-(1-35), octoxynol-(1-70), Octyldodeceth-(2,5,16,20,25), Palm kernel glycerides, or any mixture thereof.

In other embodiment, the peptide composition for hair treatment can comprise at least one preservative selected from the following list: butyl paraben, diazolidinyl urea, DMDM hydantoin, ethyl paraben, imidazolidinyl urea, iodopropynyl butylcarbamate, isobutyl paraben, methyl paraben, methylchloroisothiazolinone, methylisothiazolinone, phenoxyethanol, propyl paraben, sodium benzoate, or any mixture thereof.

In other embodiment, the peptide composition for hair treatment can comprise at least one thickner selected from the following list: aluminum stearates/isostearates/ myristates/laurates/palmitates, glycol distearate, hydrogenated castor oil, hydrogenated castor oil hydroxystearate, hydrogenated castor oil isostearate, hydrogenated castor oil stearate, hydrogenated castor PEG-8 esters, PEG-150 distearate, or any mixture thereof.

In other embodiment, the peptide composition for hair treatment can comprise at least one natural polymer derived selected from the following list: carboxymethyl hydroxyethyl cellulose, carboxymethyl hydroxypropyl guar, cellulose, ethyl cellulose, hydroxybutyl methylcellulose, hydroxyethylcellulose, hydroxymethylcellulose, lauryl polyglucose, or any mixture thereof.

In other embodiment, the peptide composition for hair treatment can comprise at least one humectant selected from the following list: 1,2,6 hexanetriol, dipropylene glycol, glycerin, hexylene glycol, panthenol, phytantriol, propylene glycol, sodium PCA, sorbitol, triethylene glycol, polyglyceryl sorbitol, glucose, fructose, polydextrose, potassium PCA, hydrogenated honey, hyaluronic acid, inositol, hexanediol beeswax, hexanetriol beeswax, hydrolyzed elastin, hydrolyzed collagen, hydrolyzed silk, hydrolyzed keratin, erythritol, capryl glycol, isoceteth-(3-10, 20, 30), isolaureth-(3-10, 20, 30), laneth-(5-50), laureth-(1-30), steareth-(4-20), trideceth-(5-50), or any mixture thereof.

In other embodiment, the peptide composition for hair treatment can comprise at least one cationic polymer selected from the following list: polyquaternium-10, polyquaternium-7, polyquaternium-11m guar hydroxypropyltrimonium chloride, or any mixture thereof.

In other embodiment, the peptide composition for hair treatment can comprise at least one silicone selected from the following list: amodimethicone, amodimethicone, trideceth-12, cetrimonium, chloride mixture, behenoxy, dimethicone sparingly, cetearyl methicone, cetyl dimethicone, cyclomethicone, cyclopentasiloxane, dimethicone, dimethicone copolyol, dimethicone copolyol, dimethiconol, hydrolyzed wheat protein hydroxypropyl polysiloxane, stearoxy dimethicone sparingly, stearyl dimethicone, trimethylsilylamodimethicone, lauryl methicone copolyol, or any mixture thereof.

In yet other embodiment, the peptide composition for hair treatment can comprise at least one organic oil selected from the following list: mineral oil, paraffin, petrolatum, or any mixture thereof.

In yet other embodiment, the peptide composition for hair treatment can comprise at least one protein selected from the following list: cocodimonium hydroxypropyl hydrolyzed casein, cocodimonium hydroxypropyl hydrolyzed collagen, cocodimonium hydroxypropyl hydrolyzed hair keratin, cocodimonium hydroxypropyl hydrolyzed keratin, cocodimonium hydroxypropyl hydrolyzed rice protein, cocodimonium hydroxypropyl hydrolyzed silk, cocodimonium hydroxypropyl hydrolyzed soy protein, cocodimonium hydroxypropyl hydrolyzed wheat protein, cocodimonium hydroxypropyl silk amino acids, cocoyl hydrolyzed collagen, cocoyl hydrolyzed keratin, hydrolyzed keratin, hydrolyzed oat flour, hydrolyzed silk, hydrolyzed silk protein, hydrolyzed soy protein, hydrolyzed wheat protein, hydrolyzed wheat protein, keratin, potassium cocoyl hydrolyzed collagen, TEA-cocoyl hydrolyzed collagen, TEA-cocoyl hydrolyzed soy protein, or any mixture thereof.

In other embodiment, the peptide composition for hair treatment can comprise at least one vitamin selected from the following list: retinol, retinyl palmitate tocopherol acetate, or any mixture thereof.

In other embodiment, the peptide composition for hair treatment can comprise at least one ester emollient selected from the following list: butyl myristate, butyl stearate, C12-15 alkyl benzoate, caprylic/capric triglyceride, cetyl octanoate, cetyl stearate, cetearyl stearate, decyl oleate, dimethyl lauramine isostearate, glyceryl stearate, glyceryl adipate, glyceryl arachidate, glyceryl arachidonate, glyceryl behenate, glyceryl caprate, glyceryl caprylate, glyceryl caprylate/caprate, glyceryl citrate/lactate/linoleate/oleate, glyceryl cocoate, glyceryl diarachidate, glyceryl dibehenate, glyceryl dierucate, glyceryl dihydroxystearate, glyceryl diisopalmitate, glyceryl diisostearate, glyceryl dilaurate, glyceryl dilinoleate, glyceryl dimyristate, glyceryl dioleate, glyceryl dipalmitate, glyceryl dipalmitoleate, glyceryl diricinoleate, glyceryl distearate, glyceryl erucate, glycol stearate, isocetyl stearate, isopropyl myristate, isopropyl palmitate, isopropyl stearate, isostearyl stearate, octyl palmitate, octyl stearate, propylene glycol dicaprylate/dicaprate, sorbitan benzoate, sorbitan caprylate, sorbitan isostearate, Sorbitan laurate, sorbitan tristearate, stearyl stearate, tocopheryl linoleate, or any mixture thereof.

In other embodiment, the peptide composition for hair treatment can comprise at least one alkanolamide selected from the following list: acetamide MEA, cocamide DEA, cocamide MEA, lactamide MEA, lauramide DEA, lauramide DEA, propylene glycol, lauramide MEA, lecithinamide DEA, linoleamide DEA, linoleamide MEA, linoleamide MIPA, myristamide DEA, myristamide MEA, myristamide MIPA, oleamide DEA, oleamide DEA, oleamide MEA, oleamide MIPA, soyamide DEA, stearamide MEA, or any mixture thereof.

In yet other embodiment, the peptide composition for hair treatment can comprise at least one amine selected from the following list: behentamidopropyl dimethylamine, cocamidopropyl dimethylamine, isostearamidopropyl dimethylamine, lauramidopropyl dimethylamine, myristamidopropyl dimethylamine, oleamidopropyl dimethylamine, palmitamidopropyl dimethylamine, stearamidopropyl dimethylamine, tallamidopropyl dimethylamine, or any mixture thereof.

In yet other embodiment, the peptide composition for hair treatment can comprise at least one pH adjuster selected from the following list: ascorbic acid, citric acid, sodium hydroxide, triethanolamine, or any mixture thereof.

In yet other embodiment, the peptide composition for hair treatment can comprise at least one salt selected from the following list: calcium chloride, magnesium chloride, magnesium sulfate, potassium chloride, potassium glycol sulfate, sodium chloride, or any mixture thereof.

In yet other embodiment, the peptide composition for hair treatment can comprise at least one aliphatic alcohol selected from the following list: behenyl alcohol, cetearyl alcohol, cetyl alcohol, isocetyl alcohol, isostearyl alcohol, lauryl alcohol, myristyl alcohol, stearyl alcohol, C30-50 alcohols, lanolin alcohol, or any mixture thereof.

In another embodiment, the peptide composition for hair treatment can comprise at least one UV filter/sunscreen selected from the following list: benzophenone-(2, 3, 4, 5, 6, 7, 8, 9, or 10), benzophenone-4, benzyl salicylate, benzylidene camphor sulfonic acid, bornelone, ethyl cinnamate, ethylhexyl methoxycinnamate (octyl methoxycinnamate), octoxynol-40, octoxynol-20, octyl methoxycinnamate, octyl salicylate, oxybenzone, phenyl ketone, PEG-25 PABA, polyacrylamidomethyl benzylidene camphor, or any mixture thereof.

In other embodiment, the peptide composition for hair treatment can comprise at least one natural oil selected from the following list: coconut oil, jojoba oil, olive oil, palm Oil, safflower oil, sesame seed oil, shea butter, sweet almond oil, wheat germ oil, or any mixture thereof.

In yet other embodiment, the peptide composition for hair treatment can comprise at least one amine oxide selected from the following list: cocamine oxide, lauramine oxide, or any mixture thereof.

In other embodiment, the peptide composition for hair treatment can comprise at least one chelate selected from the following list: diiospropyl oxalate, disodium EDTA, disodium EDTA-copper, HEDTA, oxalic acid, potassium citrate, sodium citrate, dodium oxalate, TEA-EDTA, tetrasodium EDTA, trisodium EDTA, trisodium HEDTA, or any mixture thereof.

In other embodiment, the peptide composition for hair treatment can comprise at least one fatty acid selected from the following list: arichidonic acid, capric acid, coconut fatty acid, lauric acid, linoleic acid, linolenic acid, myristic acid, palmitic acid, pantothenic acid, stearic acid, caproic acid, capryleth-(4, 6, 9) carboxylic acid, isostearic acid, or any mixture thereof.

In other embodiment, the peptide composition for hair treatment can comprise at least one agent antimicrobial/antibacterial selected from the following list: glyoxal, triclosan, or any mixture thereof.

In other embodiment, the peptide composition for hair treatment can comprise at least one PEG-modified material selected from the following list: PEG-150 pentaerythirtyl tetrastearate, PEG-(-2, -3, -4, -6, -8, -12, -20, -32, -50, -150, -175) distearate, PEG-10 castor oil, PEG-10 cocamine, PEG-10 cocoate, PEG-10 coconut oil esters, PEG-10 glyceryl oleate, PEG-10 glyceryl pibsa tallate, PEG-10 glyceryl stearate, PEG-10 hydrogenated lanolin, PEG-10 hydrogenated tallow amine, PEG-10 isolauryl thioether, PEG-10 isostearate, PEG-10 lanolate, PEG-10 lanolin, PEG-10 laurate, PEG-10 oleate, PEG-10 olive glycerides, PEG-10 polyglyceryl-2 laurate, PEG-10 propylene glycol, PEG-10 sorbitan laurate, PEG-10 soya sterol, PEG-10 soyamine, PEG-10 stearamine, PEG-10 stearate, PEG-10 stearyl benzonium chloride, PEG-10 tallate, PEG-10 tallow aminopropylamine, PEG-100, PEG-100 castor oil, PEG-100 hydrogenated castor oil, PEG-100 lanolin, PEG-100 stearate, PEG-40 hydrogenated castor Oil, PEG-60, PEG-55 propylene glycol distearate, or any mixture thereof.

In other embodiment, the peptide composition for hair treatment can comprise at least one polymer selected from the following list: carbomer, dodecanedioic acid/cetearyl alcohol/glycol copolymer, hydrogenated C6-14 olefin polymers, hydrogenated ethylene/propylene/styrene copolymer: polyacrylic acid, polymethyl methacrylate: polymer, polyvinyl acetate, polyvinyl alcohol, PPG, PPG-25-laureth-25, PPG-5 pentaerithrityl ether, PPG-75-PEG-300-hexylene glycol, polyvinylpyrrolidone, PVP/VA (polyvinylpyrrolidone/vinyl acetate copolymer), sodium carbomer, TEA-carbomer, poloxamer (100-407), poloxamine, polyacrylamidomethylpropane sulfonic acid, polyethylene terephthalate, or any mixture thereof.

In other embodiment, the peptide composition for hair treatment can comprise at least one antistatic agent selected from the following list: apricotamidopropyl ethyldimonium ethosulfate, apricotamidopropyl ethyldimonium lactate, cocamidopropyl ethyldimonium ethosulfate, cocamidopropyl ethyldimonium lactate, lauramidopropyl ethyldimonium ethosulfate, lauramidopropyl ethyldimonium lactate, linoleamidopropyl ethyldimonium ethosulfate, linoleamidopropyl ethyldimonium lactate, myristamidopropyl ethyldimonium ethosulfate, myristamidopropyl ethyldimonium lactate, oleamidopropyl ethyldimonium ethosulfate, oleamidopropyl ethyldimonium lactate, stearamidopropyl ethyldimonium ethosulfate, stearamidopropyl ethyldimonium lactate, or any mixture thereof.

In other embodiment, the peptide composition for hair treatment can comprise at least one alcohol selected from the following list: SD alcohol 40, witch hazel, isopropanol, or any mixture thereof.

In yet other embodiment, the peptide composition for hair treatment can comprise fragrances, oils or any mixture thereof.

In other embodiment, the peptide composition for hair treatment can be used in medicine, veterinary and/or for cosmetics, preferably for the treatment of hair, mainly for animal or human, particularly for treating diseases of the scalp, particularly scalp irritation, alopecia areata, lichen planus, folliculitis keloid of the neck, trichorrhexis nodosa, tricodistrophy, pili torti, tricorrexis invaginata, moniletrix, uncombable hair syndrome.

In other embodiment, the composition may comprise a dye agent linked to the N or C-terminal of the referred peptides.

In yet other embodiment is the use of the described composition for hair coloring.

Other aspect of the embodiment is the use of the described composition as a hair strengthener or as fixer of perms and/or curly hairs.

It is also described in this application shampoo, lotion, serum, cream, conditioner, foam, elixir, oil, aerosol or mask comprising the composition presented in this application.

The present application discloses a composition for hair treatment that comprise, in whole or in part, one or more peptide sequences of 6 to 12 amino acid residues based on keratin and keratin-associated proteins having 2 to 5 cysteine residues, preferably having 3 to 5 residues of cysteine, for treatment and cosmetics of the hair, preferably human hair, chemically pre-treated or not. Thus the presence of cysteine in the peptide sequence (higher than 10%, preferably more than 15%) in combination with a percentage of hydrophobic amino acids ensures that the peptides can have a lasting fixation in the hair, improving the human hair properties such as elasticity and strength.

Surprisingly, the described peptide compositions in which the peptide(s) comprising 2 to 5 cysteines allow penetration of the peptide(s) and enhance the properties of hair, preferably 3-5 cysteines. Thus, described peptide(s) containing 2-5 cysteine in order to allow hair penetration and enrichment of the hair properties, such as elasticity, resistance, reduce eventual hair damage, as well as improve and change hair characteristics.

The peptide compositions described in the present application surprisingly enrich and improve the properties and characteristics of the hair, such as elasticity, strength and appearance, repairing damaged keratinous fiber. Therefore, formulation's high cysteine content is used to improve and/or change its characteristics, such as hair curl or uncurl. The sequence of peptides can have also preferably a percentage of hydrophobic amino acids not exceeding 60%, improving even further the results. Examples of hydrophobic amino acids are phenylalanine, alanine, leucine, methionine, isoleucine, tryptophan, proline, valine, and others.

In the context of the present description, the peptide composition can also be applied to the hair and in particular to the human hair as, but not limited to, aqueous solution or conventional shampoo or conditioner. It can also be used as a lotion, foam, aerosol, gel, mask, and application formulation with or without subsequent rinsing.

The concentration of peptide to be used depends on several features such as the condition of the hair, the origin and the formulation of the hair care product.

DETAILED DESCRIPTION

It should be understood that the detailed description and specific examples are indicative of preferred embodiments of the invention and are provided to be illustrative only. This patent is not limited to those mentioned applications.

The present application describes a composition for hair treatment that comprises different peptides, which are based in the structure of keratin and keratin associated proteins.

The compositions described in the present application allow surprisingly the dermo-cosmetic treatment of animal hair, including human hair, chemically pre-treated or not. The composition described in the present invention, through the use of specific peptides, allows the preparation of keratinous fiber damages, due to the high binding capacity of the keratin peptides, including through disulfide bridges.

The described compositions improve the properties and characteristics of the hair, such as elasticity, resistance and appearance, repairing putative damages of the hair.

The peptides here defined are peptide sequences which bind with a certain affinity to the hair. The peptides used in this invention are composed by 6 to 12 amino acids, and are constituted by a minimum of 2 and a maximum of 5 cysteines, preferably 3-5 cysteines.

The peptide composition for hair treatment described allows a resistance increase due to the presence of the cysteine-rich peptide, which leads to the resistance of the hair even after several rinsing.

Every peptide can be used together or separately, as well as all or part of the peptide sequence in the hair composition. Each peptide sequence contains amino acids with sulfur, specifically cysteine, which interacts with the hair and allows the formation of intermolecular cross-linking, stabilizing the keratinous fiber.

The peptide composition described uses a high content on cysteine in order to enrich the hair properties, such as improve elasticity and resistance, reduce putative damage of the hair, improve and/or change hair characteristics. Regarding the interaction with the keratinous fibers, the cysteine is 10% to 50% of the total amount of amino acids of the peptide sequence. Additionally, the number of amino acids of the peptide sequence is preferable from 6 to 12.

The peptides can be used separately or in combination of two or more peptides. The concentration of the peptide to be used depends on several characteristics, such as hair condition, origin and the formulation of the product for hair treatment. The content of the hair composition of the present invention is as example 1-0.001% (w/w) in mass.

The peptides of the present invention can be prepared by conventional methods of peptide synthesis, well known in the state of the art.

Additionally many companies provide customized services for peptide synthesis.

An embodiment of the current invention describes peptides that link to the hair, and which sequence of amino acids includes cysteines where the sequence is selected from the group between the sequences ID NO:1 to sequence ID NO:1239.

The sequence of the 1239 peptides referred is listed in the table of the FIG. 1.

As example of hair, it was used virgin human hair tresses, acquired from the International Hair Importers and Products, Inc. (New York). The term virgin hair is applied to all the hair that was never subject or was at least 10 years without making any chemical treatment. Several different hair samples such as African, Asian and Caucasian hair are commercially available in several companies, such as the company mentioned above. Optionally, the hair samples can be treated, for example, using hydrogen peroxide to bleach the hair, needed for techniques such as hair dying.

In the context of this invention, the peptides can be applied to the hair, such as the human hair in the form of, but not limited to, aqueous or conventional preparation of shampoo or conditioner. It can also be in the form of lotion, foam, spray, gel, mask, formulation applied with or without subsequent rinsing.

This invention can be prepared by peptide coupling with an agent of these preparations directly or via a spacer.

This coupling interaction can be performed by covalent or non-covalent bonds, such as hydrogen bond, electrostatic interactions, hydrophobic interactions or van der Waals interactions. The spacer can be used to separate the peptide from the preparation agent, ensuring that the agent does not interfere with the peptide linkage to the hair.

The present invention can be understood more clearly and accurately by reading the following examples, which are indicative of preferred embodiments of the invention. They are provided for illustration in greater detail of the present invention, without introducing any limitation and without being limited to those applications.

EXAMPLES OF APPLICATIONS

The examples that are within the scope of the claims represent different embodiments of the invention; all other examples are comparative examples.

Example 1

The present application treats human hair through several commercial formulations with and without the use of the peptides from the sequence ID NO: 5. As The hair was supplied from International Hair Importers and Products, Inc. (New York).

The tests were performed with in human hair after 8 treatments of bleaching, at 50° C. in 0.1 M $Na_2CO_3$/$NaHCO_3$ buffer, at pH=9, 10% $H_2O_2$, for 1 hour.

Several formulations were tested:
hair serum with 15% PG;
hair mask.

The mask used in this application was a basic commercial formulation with water, denaturing alcohol, propylene glycol, ether dicaprylic, cetylstearyl alcohol, behentrimonium chloride, cetyl ester, polysorbate 20, hydrolyzed wheat protein, hydrolyzed wheat starch, benzyl alcohol and fragrance.

The hair serum used in this application was a basic commercial formulation with water, denaturing alcohol, propylene glycol, polysorbate 20, hydrolyzed wheat protein, hydrolyzed wheat starch, crosslinked polymer alkyl acrylate/C10-30, triethanolamine, benzyl alcohol, fragrance.

Each of the formulations was tested with and without the peptide sequence ID NO:5, which contains in the sequence 15% of cysteine. The formulations containing the peptide SEQ ID NO:5 had a concentration of peptide of 0.1 mg/mL, in a ratio 1:1 (v/v).

To demonstrate the effect was also tested:
a peptide whose sequence does not contain cysteine, with approximately 41% hydrophobic amino acids;
a peptide which contains in it sequence 8% cysteine, with approximately 58% hydrophobic amino acids.

The hair mask was applied to the hair after 8 bleaching treatments, being left to act for 15 minutes, mimicking the procedure indicated in commercial masks. Posteriorly, the hair was washed. The serum was applied to the hair after 8 bleaching treatments, being left to act for 1 hour at 37° C. Posteriorly, the hair was not washed, as in typical commercial procedures the serum should be applied in dry hair. The hair was also tested after 5 applications.

The peptide from the sequence ID NO: 5 was able to penetrate in the hair fiber for all the formulations.

After the treatment, mechanical tests were performed, using a cell with 2.5 N maximum load and a deformation rate of 1.5 mm/min. Each hair was individually mounted in the tensile jig by means of a paper template with a fixed gauge length of 20 mm.

TABLE 1

Young modulus of virgin hair without treatments and after 8 times bleaching treatments.

| Hair type | Young modulus (MPa) |
|---|---|
| Virgin hair | 6579 |
| Hair after 8 time bleaching | 5294 |
| Serum(with a 15% cysteine and 50% hydrophobic amino acids peptide) | 7149 |
| Serum for comparison(with a 41% hydrophobic amino acid without cysteine peptide) | 6180 |
| Serum for comparison (with a 8% cysteine and 58% hydrophobic amino acid peptide) | 6456 |
| Serum for comparison (without peptide) | 6034 |

TABLE 2

Young modulus for different types of hair treatment. The peptide in these treatments is the peptide from sequence ID NO: 5.

| Type of treatment | Young modulus after 1 application (MPa) | Young modulus after 5 applications (MPa) |
|---|---|---|
| Serum (with a 15% cysteine and 50% hydrophobic amino acid peptide) | 7149 | 7318 |
| Serum for comparison (without peptide) | 6034 | 6112 |
| Mask (with a 15% cysteine and 50% hydrophobic amino acid peptide) | 6175 | 7075 |
| Mask for comparison(without peptide) | 5514 | 5685 |

The formulations which contain the sequence ID NO:5 induce an increase in mechanical resistance of the damaged hair. After 5 applications, the hair treated with the sequence ID NO: 5 maintain the high resistance, having a higher increase in the resistance than without the peptide.

Example 2

This example discloses the treatment of human hair with peptides containing cysteine, and in this case the peptide containing the sequence ID NO: 409, based in the assumption that small peptides are able to penetrate in the hair fiber cuticle.

The hair was supplied from International Hair Importers and Products, Inc. (New York). Hair fibers were pre-treated by bleaching. The formulation was tested in different hair types:

virgin hair washed, with the cuticle intact and absence of chemical damages;

hair after 8 bleaching treatments, at 50° C. in 0.1 M $Na_2CO_3$/$NaHCO_3$ buffer, at pH=9, 10% $H_2O_2$, for 1 hour.

The incorporation of the peptides was performed by direct application in the hair surface. The mechanical resistance tests were performed after the treatment of the hair with the peptide.

The measurements of mechanical resistance were performed using a cell with 2.5 N maximum load and a deformation rate of 1.5 mm/min. Each hair was individually mounted in the tensile jig by means of a paper template with a fixed gauge length of 20 mm.

As for the results obtained for the mechanical test showed that compared to the control, i.e., virgin hair without bleaching or peptide treatment (Young modulus: 4142±590 MPa), bleaching reduced the Young modulus (2478±567 MPa), while the treatment with the peptide sequence ID NO: 409 after bleaching increased the Young modulus to higher valued than the virgin hair with no treatment (5649±1022 MPa).

Example 3

This example discloses the treatment of human hair with a composition comprising peptides. In this example, the peptide with the sequence ID NO: 412 was tested. The hair was supplied from International Hair Importers and Products, Inc. (New York).

The formulation was tested in different hair types:

virgin hair washed, with the cuticle intact and absence of chemical damages;

hair after reduction treatment, at 37° C. in phosphate buffer at pH=8, with 3M GndHCl and 0.05M DTT for 2 hours.

For the treatment with the peptide SEQ ID NO: 412, concentrations of 0.01% (w/w) were used.

The average of the Young modulus for relaxed hair is 3002 MPa, while for relaxed hair fiber after peptide treatment at 0.01% is 4190 MPa. The Young modulus value for virgin hair without treatment is 5214 MPa.

In the maximum load test, for the relaxed hair fiber, the maximum of resistance were 96 MPa, while for the hair fiber relaxed after peptide treatment 126 MPa and for the virgin hair with no treatment 203 MPa.

Regarding hair stretching, the relaxed hair has an average of 51%, while after treatment with the peptide sequence ID NO: 412, has a stretching of 72%. For virgin hair, the average of hair stretching is 58%.

Therefore, it is evident that the peptides are capable to prevent the hair surface degradation and consequently, the hair treated with these peptides has a longer life span.

Example 4

In order to assess the interactions between the keratin and some peptides, a keratin solution was prepared. This procedure was performed by immersing African hair, acquired from the International Hair Importers and Products, Inc. (New York), in a solution containing 8 M urea, 0.2 M sodium dodecyl sulfate and 0.5 M sodium bisulfite. The mixture was heated to 50° C. for 24 h in a shaker bath. The solution was dialyzed for several days against double-distilled water. The keratin solution was then concentrated using AMICON with a 3 kDa cut-off. The keratin was then conjugated with Alexa Fluor 647 carboxylic acid, succinimidyl ester in DMSO anhydrous 5%.

The reaction was incubated for 1 h30 min at room temperature and in the dark. The Alexa Fluor 647 that did not link to the keratin solution was separated by centrifugation in AMICON with a 3 kDa cut-off for 1 h at 25° C. and 5000×g.

The keratin was then diluted to 10 g/mL in blocking buffer (3% BSA in tris-buffered saline (TBS) with 0.05% Tween 20). The peptides tested were SEQ. ID NO:179, SEQ. ID NO:75, SEQ. ID NO:432, SEQ. ID NO:951, SEQ. ID NO:1108, SEQ. ID NO:1131 and a peptide containing 13 amino acids, including 2 cysteines ($X_3CX_5CX_3$), where X represents one of known amino acid residues, with the exception of cysteine residue that is represented by the letter C. This peptide is similar to the one tested in Fernandes et al. (Fernandes, Lima, Loureiro, Gomes, & Cavaco-Paulo, 2012).

Several peptides in a concentration of 15 fmol/mm$^2$, were attached to a glass through a hydrophilic linked moiety, and were then incubated with the keratin, marked with Alexa Fluor 647, for 2 hours at 37° C.

After incubation, the glasses were rinsed in successive washing solutions: TBS+0.1% Tween 20 and blocking buffer with 3% BSA in TBS+0.1% Tween 20, for 3 minutes in each solution.

The imaging of the glasses was performed in Agilent G2565CA Microarray Scanner System. Three replicas of the each peptide incubation were performed and analyzed.

TABLE 1

Normalized intensity levels of peptide sequences.

| Sequence | Number of amino acids | Cysteine content | Hydrophobic amino acids content | Intensity level (average ± standard deviation) |
|---|---|---|---|---|
| SEQ. ID NO: 179 | 10 | 20% | 50% | 0.990 ± 0.014 |
| SEQ. ID NO: 75 | 10 | 30% | 60% | 1.000 ± 0.000 |
| SEQ. ID NO: 432 | 10 | 30% | 40% | 1.000 ± 0.000 |
| SEQ. ID NO: 951 | 10 | 40% | 30% | 1.000 ± 0.000 |
| SEQ. ID NO: 1108 | 11 | 46% | 18% | 1.000 ± 0.000 |
| SEQ. ID NO: 1131 | 11 | 46% | 9% | 1.000 ± 0.000 |
| $X_3CX_5CX_3$ | 13 | 15% | 38% | 0.184 ± 0.084 |

The peptides SEQ. ID NO:75, SEQ. ID NO:432, SEQ. ID NO:951, SEQ. ID NO:1108, SEQ. ID NO:1131, with percentage of cysteine ranging from 30% to 46%, such as and percentage of hydrophobic amino acids ranging from 9% to 60% were able to obtain an intensity of 1, indicating a very high affinity to keratin. The peptide SEQ. ID NO:179, with 20% and 50% of cysteine and hydrophobic content, respectively showed an slightly inferior but still very high intensity (0.990±0.014). These peptides were compared with a peptide similar to the one described in Fernandes et al. (Fernandes, Lima, Loureiro, Gomes, & Cavaco-Paulo, 2012) containing 2 cysteines in a 13 amino acids sequence. The reduced percentage of cysteine (15%) and higher number of amino acids in the sequence (13 amino acids) lead to a decrease in the intensity to 0.184±0.084, showing an inferior affinity to keratin. This suggests that the higher number of amino acids difficult the reaction of the peptide with the hair keratins. This inferior affinity to keratin leads to less fixation of the peptides in the hair in posterior treatments and consequently providing less improvements in the recovery of the hair characteristics.

LIST OF PEPTIDE SEQUENCES

The sequences of peptides are described by one letter code of amino acids. The code is as follows:

| Amino acid-One Letter Code |
|---|
| Histidine-H |
| Arginine-R |
| Lysine-K |
| Isoleucine-I |
| Phenylalanine-F |
| Leucine- L |
| Tryptophan-W |
| Alanine-A |
| Methionine-M |
| Proline-P |
| Valine-V |
| Cysteine-C |
| Asparagine-N |
| Glycine-G |
| Serine-S |
| Glutamine-Q |
| Tyrosine-Y |
| Threonine-T |
| Aspartic acid-D |
| Glutamic acid-E |

| | |
|---|---|
| APCAPRPSCG | SEQ.ID NO: 1 |
| EACVPSVPCP | SEQ.ID NO: 2 |
| ESCGTASGCA | SEQ.ID NO: 3 |
| GLCAGTSACL | SEQ.ID NO: 4 |
| GVCGPSPPCI | SEQ.ID NO: 5 |
| HGCTLPGACN | SEQ.ID NO: 6 |
| HSCTLPGACN | SEQ.ID NO: 7 |
| KDCLQNSLCE | SEQ.ID NO: 8 |
| LPCLPAASCG | SEQ.ID NO: 9 |

| | |
|---|---|
| LPCYFTGSCN | SEQ.ID NO: 10 |
| NFCLPSLSCR | SEQ.ID NO: 11 |
| NPCATTNACD | SEQ.ID NO: 12 |
| NPCATTNACE | SEQ.ID NO: 13 |
| NPCATTNACS | SEQ.ID NO: 14 |
| NPCGLRARCG | SEQ.ID NO: 15 |
| NPCGPRSRCG | SEQ.ID NO: 16 |
| NPCSTPASCT | SEQ.ID NO: 17 |
| NPCSTSPSCV | SEQ.ID NO: 18 |
| PACTSSSPCS | SEQ.ID NO: 19 |
| SKCHESTVCP | SEQ.ID NO: 20 |
| SPCVPRTVCV | SEQ.ID NO: 21 |
| SSCSVETACL | SEQ.ID NO: 22 |
| SVCSSGVNCR | SEQ.ID NO: 23 |
| TACPLPGTCH | SEQ.ID NO: 24 |
| TNCSPRPICV | SEQ.ID NO: 25 |
| TSCVPPAPCT | SEQ.ID NO: 26 |
| TTCTSSNTCE | SEQ.ID NO: 27 |
| VPCVPSVPCT | SEQ.ID NO: 28 |
| ATCGPSACIT | SEQ.ID NO: 29 |
| GPCISNPCGL | SEQ.ID NO: 30 |
| GPCLSNPCTS | SEQ.ID NO: 31 |
| GSCVTNPCGP | SEQ.ID NO: 32 |
| LTCFSITCSS | SEQ.ID NO: 33 |
| NPCSTPSCTT | SEQ.ID NO: 34 |
| PSCVTAPCAP | SEQ.ID NO: 35 |
| SDCSSTHCSP | SEQ.ID NO: 36 |
| SLCLPPTCHT | SEQ.ID NO: 37 |
| SLCNLGSCGP | SEQ.ID NO: 38 |
| SPCLVGNCAW | SEQ.ID NO: 39 |
| TACLPGTCAT | SEQ.ID NO: 40 |
| TSCLPALCLP | SEQ.ID NO: 41 |
| TSCSSRPCVP | SEQ.ID NO: 42 |
| TTCGGGSCGV | SEQ.ID NO: 43 |
| VNCRPELCLG | SEQ.ID NO: 44 |
| YVCQPMACLP | SEQ.ID NO: 45 |
| AFSCISACGP | SEQ.ID NO: 46 |
| GSVCSAPCNG | SEQ.ID NO: 47 |
| GVVCGDLCAS | SEQ.ID NO: 48 |
| GVVCGDLCVS | SEQ.ID NO: 49 |
| LTGCLLPCYF | SEQ.ID NO: 50 |
| NEDCKLPCNP | SEQ.ID NO: 51 |
| NFSCVSACGP | SEQ.ID NO: 52 |
| PPTCHTACPL | SEQ.ID NO: 53 |
| PQPCATACKP | SEQ.ID NO: 54 |
| SEDCKLPCNP | SEQ.ID NO: 55 |
| SLGCRTSCSS | SEQ.ID NO: 56 |
| SLSCRTSCSS | SEQ.ID NO: 57 |
| SSSCPLGCTM | SEQ.ID NO: 58 |
| TGSCNSPCLV | SEQ.ID NO: 59 |
| TSSCPLGCTM | SEQ.ID NO: 60 |
| VGSCGSSCRK | SEQ.ID NO: 61 |

| | |
|---|---|
| VGVCGGSCKR | SEQ.ID NO: 62 |
| VSNCNWFCEG | SEQ.ID NO: 63 |
| ACGPRPGRCC | SEQ.ID NO: 64 |
| ACGPRPSRCC | SEQ.ID NO: 65 |
| CAPRPSCGPC | SEQ.ID NO: 66 |
| CEPCSAYVIC | SEQ.ID NO: 67 |
| CGLRARCGPC | SEQ.ID NO: 68 |
| CGPRPGRCCI | SEQ.ID NO: 69 |
| CGPRPSRCCI | SEQ.ID NO: 70 |
| CGPRSRCGPC | SEQ.ID NO: 71 |
| CGTSQKGCCN | SEQ.ID NO: 72 |
| CHGCTLPGAC | SEQ.ID NO: 73 |
| CHSCTLPGAC | SEQ.ID NO: 74 |
| CLPCLPAASC | SEQ.ID NO: 75 |
| CLPPTCHTAC | SEQ.ID NO: 76 |
| CLSNPCTSCV | SEQ.ID NO: 77 |
| CLVGNCAWCE | SEQ.ID NO: 78 |
| CNPCSTPASC | SEQ.ID NO: 79 |
| CNPCSTPSCT | SEQ.ID NO: 80 |
| CNPCSTSPSC | SEQ.ID NO: 81 |
| CNSPCLVGNC | SEQ.ID NO: 82 |
| CRTSCSSRPC | SEQ.ID NO: 83 |
| CSLKEHCSAC | SEQ.ID NO: 84 |
| CSPRPICVPC | SEQ.ID NO: 85 |
| CSSTMSYSCC | SEQ.ID NO: 86 |
| CSTPASCTSC | SEQ.ID NO: 87 |
| CSTPSCTTCV | SEQ.ID NO: 88 |
| CTSCVPPAPC | SEQ.ID NO: 89 |
| CTSSNTCEPC | SEQ.ID NO: 90 |
| CVPPAPCTPC | SEQ.ID NO: 91 |
| CVPPSCHGCT | SEQ.ID NO: 92 |
| CVPPSCHSCT | SEQ.ID NO: 93 |
| DCKLPCNPCA | SEQ.ID NO: 94 |
| DCKLPCNPCS | SEQ.ID NO: 95 |
| PCGTSQKGCC | SEQ.ID NO: 96 |
| PCLSNPCTSC | SEQ.ID NO: 97 |
| PCLVGNCAWC | SEQ.ID NO: 98 |
| PCNPCSTPSC | SEQ.ID NO: 99 |
| PCSTPSCTTC | SEQ.ID NO: 100 |
| PCTTCGPTCG | SEQ.ID NO: 101 |
| PCVPPSCHGC | SEQ.ID NO: 102 |
| PCVPPSCHSC | SEQ.ID NO: 103 |
| SCCLPSLGCR | SEQ.ID NO: 104 |
| SCSEELQCCQ | SEQ.ID NO: 105 |
| SCSPCSTTCT | SEQ.ID NO: 106 |
| ASCSTSGTCG | SEQ.ID NO: 107 |
| ASCYIPVGCQ | SEQ.ID NO: 108 |
| ASCYVPVSCQ | SEQ.ID NO: 109 |
| AVCTLPSSCQ | SEQ.ID NO: 110 |
| DLCPTSVSCG | SEQ.ID NO: 111 |
| EICWEPTSCQ | SEQ.ID NO: 112 |
| ETCGEPTSCQ | SEQ.ID NO: 113 |

-continued

| | |
|---|---|
| ETCNETTSCQ | SEQ.ID NO: 114 |
| ETCWRPNSCQ | SEQ.ID NO: 115 |
| GYCGYRPFCF | SEQ.ID NO: 116 |
| KTCWEPASCQ | SEQ.ID NO: 117 |
| KTCWEPTSCQ | SEQ.ID NO: 118 |
| LDCVDTTPCK | SEQ.ID NO: 119 |
| LGCGYGSFCG | SEQ.ID NO: 120 |
| NSCGYGSGCG | SEQ.ID NO: 121 |
| NYCPSNTMCE | SEQ.ID NO: 122 |
| PACVTSYSCR | SEQ.ID NO: 123 |
| PDCHVEGTCL | SEQ.ID NO: 124 |
| PDCRVEGTCL | SEQ.ID NO: 125 |
| PICSEPSPCS | SEQ.ID NO: 126 |
| PICYIFKPCQ | SEQ.ID NO: 127 |
| PLCYISNSCQ | SEQ.ID NO: 128 |
| PPCGQPTPCS | SEQ.ID NO: 129 |
| PPCHIPQPCV | SEQ.ID NO: 130 |
| PSCGRLASCG | SEQ.ID NO: 131 |
| PSCSESSICQ | SEQ.ID NO: 132 |
| PSCSEVTSCP | SEQ.ID NO: 133 |
| PSCSTSGTCG | SEQ.ID NO: 134 |
| PSCSVSSGCQ | SEQ.ID NO: 135 |
| PSCTESDSCK | SEQ.ID NO: 136 |
| PSCYQTSSCG | SEQ.ID NO: 137 |
| PTCFLLNSCQ | SEQ.ID NO: 138 |
| PTCSVTSSCQ | SEQ.ID NO: 139 |
| PTCWLLNNCH | SEQ.ID NO: 140 |
| PTCYQRTSCV | SEQ.ID NO: 141 |
| PTCYRRTSCV | SEQ.ID NO: 142 |
| PTCYVVKRCP | SEQ.ID NO: 143 |
| PVCFEATICE | SEQ.ID NO: 144 |
| PVCFEATVCE | SEQ.ID NO: 145 |
| PVCSRPASCS | SEQ.ID NO: 146 |
| PVCSWVPACS | SEQ.ID NO: 147 |
| QTCNESSYCL | SEQ.ID NO: 148 |
| QTCWEPTSCQ | SEQ.ID NO: 149 |
| SFCRLGYGCG | SEQ.ID NO: 150 |
| SFCRRGSGCG | SEQ.ID NO: 151 |
| SLCGYGYGCG | SEQ.ID NO: 152 |
| SLCSTEVSCG | SEQ.ID NO: 153 |
| SNCFGQLNCL | SEQ.ID NO: 154 |
| SPCGQPTPCS | SEQ.ID NO: 155 |
| SSCDQSSSCA | SEQ.ID NO: 156 |
| SSCGQSSSCA | SEQ.ID NO: 157 |
| SVCPEPVSCP | SEQ.ID NO: 158 |
| TFCSFDKSCR | SEQ.ID NO: 159 |
| TICSSDKSCR | SEQ.ID NO: 160 |
| TLCVESSPCH | SEQ.ID NO: 161 |
| TPCYQSSCQ | SEQ.ID NO: 162 |
| VTCSRQTTCI | SEQ.ID NO: 163 |
| YGCGYGSGCG | SEQ.ID NO: 164 |
| YGCGYGSGCR | SEQ.ID NO: 165 |

| Sequence | SEQ ID NO |
|---|---|
| YGCIHSTHCG | 166 |
| AACEPSACQS | 167 |
| AACEPSPCQS | 168 |
| AACTMSVCSS | 169 |
| ADCLGGICLP | 170 |
| ALCLPSSCHS | 171 |
| ALCSPSTCQL | 172 |
| APCLALVCAP | 173 |
| APCLSLVCTP | 174 |
| APCLTLVCTP | 175 |
| APCVALLCRP | 176 |
| ASCGSLLCRP | 177 |
| ASCLSFLCRP | 178 |
| ASCVSLLCRP | 179 |
| AVCEPSPCQS | 180 |
| AVCLPVSCQS | 181 |
| AVCVPVRCQS | 182 |
| AVCVPVSCQS | 183 |
| DLCSPSTCQL | 184 |
| DSCGSSSCGP | 185 |
| DSCVQSNCFP | 186 |
| FNCSTRNCSS | 187 |
| GGCGSYGCSQ | 188 |
| GSCGFGSCYG | 189 |
| GSCSSRKCFS | 190 |
| GVCLPSTCPH | 191 |
| HSCEGYLCYS | 192 |
| IVCAAPSCQS | 193 |
| KTCSTTGCDP | 194 |
| LACVSQPCQS | 195 |
| LGCYGGCGY | 196 |
| LSCGSRSCSS | 197 |
| LVCTPVSCVS | 198 |
| NGCQETYCEP | 199 |
| NSCRSLSCGS | 200 |
| PACVISTCPR | 201 |
| PGCLNQSCGS | 202 |
| PPCGTAPCLT | 203 |
| PPCTTALCRP | 204 |
| PPCYLVSCTP | 205 |
| PRCTRPICEP | 206 |
| PSCPVSSCAQ | 207 |
| PSCQPSVCVP | 208 |
| PSCSVSNCYQ | 209 |
| PSCSVSSCAQ | 210 |
| PSCTSVLCRP | 211 |
| PTCKSPSCEP | 212 |
| PTCVISSCPR | 213 |
| PTCVISTCPR | 214 |
| PTCYQTICFR | 215 |
| PVCGGVSCHT | 216 |
| PVCGRVSCHT | 217 |

| | |
|---|---|
| PVCNKPVCFV | SEQ.ID NO: 218 |
| PVCPTPTCSV | SEQ.ID NO: 219 |
| PVCRSTYCVP | SEQ.ID NO: 220 |
| PVCSKSVCYV | SEQ.ID NO: 221 |
| PVCSRPACYS | SEQ.ID NO: 222 |
| PVCYVPTCSE | SEQ.ID NO: 223 |
| QFCLSKSCQP | SEQ.ID NO: 224 |
| RPCERTACQS | SEQ.ID NO: 225 |
| RSCQTSFCGF | SEQ.ID NO: 226 |
| RSCSSLGCGS | SEQ.ID NO: 227 |
| RSCYSVGCGS | SEQ.ID NO: 228 |
| RVCLPGSCDS | SEQ.ID NO: 229 |
| SFCGFPSCST | SEQ.ID NO: 230 |
| SFCGYPSCST | SEQ.ID NO: 231 |
| SGCDPASCQP | SEQ.ID NO: 232 |
| SGCGGSGCGG | SEQ.ID NO: 233 |
| SGCQPSSCLA | SEQ.ID NO: 234 |
| SHCQPPHCQL | SEQ.ID NO: 235 |
| SICQPATCVA | SEQ.ID NO: 236 |
| SLCVPVSCRP | SEQ.ID NO: 237 |
| SNCLPTSCQP | SEQ.ID NO: 238 |
| SPCLVSSCQP | SEQ.ID NO: 239 |
| SPCQQSSCQE | SEQ.ID NO: 240 |
| SPCQQSYCVP | SEQ.ID NO: 241 |
| SPCSPAVCVS | SEQ.ID NO: 242 |
| SRCQQPSCQP | SEQ.ID NO: 243 |
| SRCYRPHCGQ | SEQ.ID NO: 244 |
| SSCAPIYCRR | SEQ.ID NO: 245 |
| SSCAPVYCRR | SEQ.ID NO: 246 |
| SSCGKGGCGS | SEQ.ID NO: 247 |
| SSCGKRGCGS | SEQ.ID NO: 248 |
| SSCLPVSCRP | SEQ.ID NO: 249 |
| SSCQPAYCTS | SEQ.ID NO: 250 |
| SSCQPSYCRQ | SEQ.ID NO: 251 |
| SSCQPVVCEP | SEQ.ID NO: 252 |
| SSCTAVVCRP | SEQ.ID NO: 253 |
| SSCYQPFCRS | SEQ.ID NO: 254 |
| SSCYRPICGS | SEQ.ID NO: 255 |
| SSCYRPTCGS | SEQ.ID NO: 256 |
| SVCMSGSCQA | SEQ.ID NO: 257 |
| SVCSDQGCDQ | SEQ.ID NO: 258 |
| SVCSDQGCGL | SEQ.ID NO: 259 |
| SVCSDQGCGQ | SEQ.ID NO: 260 |
| SVCSDQGCSQ | SEQ.ID NO: 261 |
| SVCSDQSCGQ | SEQ.ID NO: 262 |
| SVCSHQGCGQ | SEQ.ID NO: 263 |
| SVCSHQGCGR | SEQ.ID NO: 264 |
| SVCVPVSCRP | SEQ.ID NO: 265 |
| SYCRQASCVS | SEQ.ID NO: 266 |
| TACEPSACQS | SEQ.ID NO: 267 |
| TICTASPCQP | SEQ.ID NO: 268 |
| TSCPETSCLP | SEQ.ID NO: 269 |

| Sequence | SEQ ID NO |
|---|---|
| TSCQMTNCEQ | SEQ.ID NO: 270 |
| TSCQPVHCET | SEQ.ID NO: 271 |
| TSCQPVLCKS | SEQ.ID NO: 272 |
| TSCQPVLCVP | SEQ.ID NO: 273 |
| TSCVGFVCQP | SEQ.ID NO: 274 |
| TSCVSNPCQV | SEQ.ID NO: 275 |
| TTCFQPTCVS | SEQ.ID NO: 276 |
| TTCFQPTCVT | SEQ.ID NO: 277 |
| TTCFQPTCVY | SEQ.ID NO: 278 |
| TTCISNPCST | SEQ.ID NO: 279 |
| TWCQGSSCQP | SEQ.ID NO: 280 |
| VGCQSSVCVP | SEQ.ID NO: 281 |
| VPCQPSTCVF | SEQ.ID NO: 282 |
| VSCEPSPCQS | SEQ.ID NO: 283 |
| VSCGGPICLP | SEQ.ID NO: 284 |
| VSCKPVLCVA | SEQ.ID NO: 285 |
| VSCPSTSCRP | SEQ.ID NO: 286 |
| VSCQSSVCMP | SEQ.ID NO: 287 |
| VSCTRIVCVA | SEQ.ID NO: 288 |
| VTCEPSPCQS | SEQ.ID NO: 289 |
| VTCQTTVCRP | SEQ.ID NO: 290 |
| YGCGYEGCRY | SEQ.ID NO: 291 |
| AGSCQPSCSE | SEQ.ID NO: 292 |
| ALLCRPLCGV | SEQ.ID NO: 293 |
| ALVCEPVCLR | SEQ.ID NO: 294 |
| ATICEPSCSV | SEQ.ID NO: 295 |
| ATTCEPSCSV | SEQ.ID NO: 296 |
| ATVCEPSCSV | SEQ.ID NO: 297 |
| EGTCLPPCYL | SEQ.ID NO: 298 |
| FSTCRPSCSG | SEQ.ID NO: 299 |
| GFVCQPMCSH | SEQ.ID NO: 300 |
| GLDCYGCGY | SEQ.ID NO: 301 |
| GLGCYGCGY | SEQ.ID NO: 302 |
| GLGCSYGCGH | SEQ.ID NO: 303 |
| GLGCSYGCGL | SEQ.ID NO: 304 |
| GSGCYGCGY | SEQ.ID NO: 305 |
| GTGCYGCGY | SEQ.ID NO: 306 |
| GVSCHTTCYR | SEQ.ID NO: 307 |
| GYACNFPCSY | SEQ.ID NO: 308 |
| GYGCYGCGF | SEQ.ID NO: 309 |
| HSPCQASCYV | SEQ.ID NO: 310 |
| HTSCSPACQP | SEQ.ID NO: 311 |
| HTSCSSGCQP | SEQ.ID NO: 312 |
| IRWCHPDCHV | SEQ.ID NO: 313 |
| IRWCRPDCRV | SEQ.ID NO: 314 |
| ISSCGTGCGI | SEQ.ID NO: 315 |
| KGGCGSGCGG | SEQ.ID NO: 316 |
| KGGCGSSCSQ | SEQ.ID NO: 317 |
| LVTCQDSCGS | SEQ.ID NO: 318 |
| LVTCQESCQP | SEQ.ID NO: 319 |
| MSICSSACTD | SEQ.ID NO: 320 |
| MSICSSACTN | SEQ.ID NO: 321 |

| | |
|---|---|
| MSVCSSACSD | SEQ.ID NO: 322 |
| PAICEPSCSV | SEQ.ID NO: 323 |
| PASCQKSCYR | SEQ.ID NO: 324 |
| PIYCRRTCYH | SEQ.ID NO: 325 |
| PNSCQTLCVE | SEQ.ID NO: 326 |
| PQPCVPTCFL | SEQ.ID NO: 327 |
| PSACQSGCTS | SEQ.ID NO: 328 |
| PSPCEPSCSE | SEQ.ID NO: 329 |
| PSPCQASCYI | SEQ.ID NO: 330 |
| PSPCQSGCIS | SEQ.ID NO: 331 |
| PSPCQSGCTD | SEQ.ID NO: 332 |
| PSPCQSGCTS | SEQ.ID NO: 333 |
| PTACQPTCYQ | SEQ.ID NO: 334 |
| PTACQPTCYR | SEQ.ID NO: 335 |
| PTPCSTTCRT | SEQ.ID NO: 336 |
| PTSCQKSCYR | SEQ.ID NO: 337 |
| PTSCQPSCES | SEQ.ID NO: 338 |
| PTSCQTSCTL | SEQ.ID NO: 339 |
| PVICEPSCSV | SEQ.ID NO: 340 |
| PVSCVPVCSG | SEQ.ID NO: 341 |
| PVTCVPRCTR | SEQ.ID NO: 342 |
| PVYCRRTCYH | SEQ.ID NO: 343 |
| PVYCRRTCYY | SEQ.ID NO: 344 |
| PVYCVPVCSG | SEQ.ID NO: 345 |
| QPGCESPCEP | SEQ.ID NO: 346 |
| QQSCVSSCRR | SEQ.ID NO: 347 |
| QTSCGSSCGQ | SEQ.ID NO: 348 |
| QTTCHPSCGM | SEQ.ID NO: 349 |
| QTTCRPSCGV | SEQ.ID NO: 350 |
| RGGCGSGCGG | SEQ.ID NO: 351 |
| RLACYSLCSG | SEQ.ID NO: 352 |
| RPACYRPCYS | SEQ.ID NO: 353 |
| RPFCFRRCYS | SEQ.ID NO: 354 |
| RPICRPICSG | SEQ.ID NO: 355 |
| RPLCYRRCYS | SEQ.ID NO: 356 |
| RSPCQASCYV | SEQ.ID NO: 357 |
| RVSCHTTCYR | SEQ.ID NO: 358 |
| SAICRPTCPR | SEQ.ID NO: 359 |
| SDSCKRDCKK | SEQ.ID NO: 360 |
| SEGCGSGCGG | SEQ.ID NO: 361 |
| SFLCRPACSR | SEQ.ID NO: 362 |
| SGGCGSGCGG | SEQ.ID NO: 363 |
| SGGCGSSCGG | SEQ.ID NO: 364 |
| SGSCQAACGQ | SEQ.ID NO: 365 |
| SLLCHPVCKS | SEQ.ID NO: 366 |
| SLLCHPVCRS | SEQ.ID NO: 367 |
| SLLCRPACSP | SEQ.ID NO: 368 |
| SLLCRPACSR | SEQ.ID NO: 369 |
| SLLCRPICRP | SEQ.ID NO: 370 |
| SLLCRPMCSR | SEQ.ID NO: 371 |
| SLLCRPTCSR | SEQ.ID NO: 372 |
| SLLCRPVCQP | SEQ.ID NO: 373 |

| Sequence | SEQ ID NO |
|---|---|
| SLLCRPVCRP | SEQ.ID NO: 374 |
| SLLCRPVCRS | SEQ.ID NO: 375 |
| SLLCRPVCSR | SEQ.ID NO: 376 |
| SNPCQVTCSR | SEQ.ID NO: 377 |
| SRGCGSGCGG | SEQ.ID NO: 378 |
| SRSCQSPCYR | SEQ.ID NO: 379 |
| SRSCQSSCYR | SEQ.ID NO: 380 |
| SSGCGYGCGY | SEQ.ID NO: 381 |
| SSGCPMACPG | SEQ.ID NO: 382 |
| SSICQPICSE | SEQ.ID NO: 383 |
| SSPCHTSCYY | SEQ.ID NO: 384 |
| SSPCQPTCYV | SEQ.ID NO: 385 |
| SSPCQQSCYV | SEQ.ID NO: 386 |
| SSPCQTSCYR | SEQ.ID NO: 387 |
| SSSCQQSCRV | SEQ.ID NO: 388 |
| STVCQPACGV | SEQ.ID NO: 389 |
| TDNCQETCGE | SEQ.ID NO: 390 |
| TQPCYEPCLP | SEQ.ID NO: 391 |
| TSSCGTGCGI | SEQ.ID NO: 392 |
| TSSCQPSCGR | SEQ.ID NO: 393 |
| TSSCTTPCYQ | SEQ.ID NO: 394 |
| TSVCLPGCLN | SEQ.ID NO: 395 |
| TTVCLPGCLN | SEQ.ID NO: 396 |
| VANCQAPCST | SEQ.ID NO: 397 |
| VDDCPESCWP | SEQ.ID NO: 398 |
| VKRCPSVCPE | SEQ.ID NO: 399 |
| VSSCQPSCSE | SEQ.ID NO: 400 |
| YEGCRYGCGH | SEQ.ID NO: 401 |
| YGRCRHGCHS | SEQ.ID NO: 402 |
| YGYCRPSCYG | SEQ.ID NO: 403 |
| YRDCQKTCWE | SEQ.ID NO: 404 |
| YRGCQEICWE | SEQ.ID NO: 405 |
| YRGCQETCWR | SEQ.ID NO: 406 |
| YRGCQQTCWE | SEQ.ID NO: 407 |
| YRSCRPSCYG | SEQ.ID NO: 408 |
| GGVCGPSPPC | SEQ.ID NO: 409 |
| GVCGPSPPCI | SEQ.ID NO: 410 |
| VCGPSPPCIT | SEQ.ID NO: 411 |
| CGPSPPCITT | SEQ.ID NO: 412 |
| CAPIYCRRTC | SEQ.ID NO: 413 |
| CAPSPCQASC | SEQ.ID NO: 414 |
| CAPSPCQPAC | SEQ.ID NO: 415 |
| CAPVYCRRTC | SEQ.ID NO: 416 |
| CASSPCQQAC | SEQ.ID NO: 417 |
| CASSSCQPAC | SEQ.ID NO: 418 |
| CASSSCQQSC | SEQ.ID NO: 419 |
| CCGNFSSHSC | SEQ.ID NO: 420 |
| CCGYGGLGCG | SEQ.ID NO: 421 |
| CCNYYGNSCG | SEQ.ID NO: 422 |
| CCNYYRNSCG | SEQ.ID NO: 423 |
| CCSRNFSSCS | SEQ.ID NO: 424 |
| CDAGSCQPSC | SEQ.ID NO: 425 |

| Sequence | SEQ ID NO |
|---|---|
| CDPCSLQEGC | SEQ.ID NO: 426 |
| CDPSPCEPSC | SEQ.ID NO: 427 |
| CDPVICEPSC | SEQ.ID NO: 428 |
| CDQGLCQETC | SEQ.ID NO: 429 |
| CEATTCEPSC | SEQ.ID NO: 430 |
| CELPCGTPSC | SEQ.ID NO: 431 |
| CEPAICEPSC | SEQ.ID NO: 432 |
| CEPPCGTAPC | SEQ.ID NO: 433 |
| CEPPCSAPSC | SEQ.ID NO: 434 |
| CEPRSCASSC | SEQ.ID NO: 435 |
| CEPSACQSGC | SEQ.ID NO: 436 |
| CEPSCSVSNC | SEQ.ID NO: 437 |
| CEPSCSVSSC | SEQ.ID NO: 438 |
| CEPSPCQSGC | SEQ.ID NO: 439 |
| CEPTACQPTC | SEQ.ID NO: 440 |
| CEPTSCQTSC | SEQ.ID NO: 441 |
| CEPVCLRPVC | SEQ.ID NO: 442 |
| CETSSCQPRC | SEQ.ID NO: 443 |
| CETTCFQPTC | SEQ.ID NO: 444 |
| CFQPTCVSSC | SEQ.ID NO: 445 |
| CFQPTCVTSC | SEQ.ID NO: 446 |
| CFQPTCVYSC | SEQ.ID NO: 447 |
| CGCGFRRLGC | SEQ.ID NO: 448 |
| CGCGYRGLDC | SEQ.ID NO: 449 |
| CGCNGYYGCY | SEQ.ID NO: 450 |
| CGFGSCYGCG | SEQ.ID NO: 451 |
| CGGSGCGGSC | SEQ.ID NO: 452 |
| CGGSGSSCCV | SEQ.ID NO: 453 |
| CGGVSCHTTC | SEQ.ID NO: 454 |
| CGKGGCGSCG | SEQ.ID NO: 455 |
| CGKRGCGSCG | SEQ.ID NO: 456 |
| CGQDLCQETC | SEQ.ID NO: 457 |
| CGQTSCGSSC | SEQ.ID NO: 458 |
| CGQVLCQETC | SEQ.ID NO: 459 |
| CGRDLCQETC | SEQ.ID NO: 460 |
| CGRVSCHTTC | SEQ.ID NO: 461 |
| CGSCGFGSCY | SEQ.ID NO: 462 |
| CGSCGGSKGC | SEQ.ID NO: 463 |
| CGSGCGVPVC | SEQ.ID NO: 464 |
| CGSLLCRPTC | SEQ.ID NO: 465 |
| CGSRCYVPVC | SEQ.ID NO: 466 |
| CGSSSCGPQC | SEQ.ID NO: 467 |
| CGSVCSDQGC | SEQ.ID NO: 468 |
| CGSVCSDQSC | SEQ.ID NO: 469 |
| CGSVCSHQGC | SEQ.ID NO: 470 |
| CGSYGCSQCS | SEQ.ID NO: 471 |
| CGVCLPSTCP | SEQ.ID NO: 472 |
| CGYEGCRYGC | SEQ.ID NO: 473 |
| CGYGCYGCG | SEQ.ID NO: 474 |
| CGYGGCGYGC | SEQ.ID NO: 475 |
| CGYGSFCGCG | SEQ.ID NO: 476 |
| CGYGSGCGCG | SEQ.ID NO: 477 |

| | |
|---|---|
| CHPSCGMSSC | SEQ.ID NO: 478 |
| CHPSCSISSC | SEQ.ID NO: 479 |
| CHPTCYQTIC | SEQ.ID NO: 480 |
| CHTSCSPACQ | SEQ.ID NO: 481 |
| CHTSCSSGCQ | SEQ.ID NO: 482 |
| CHTTCYRPAC | SEQ.ID NO: 483 |
| CHTTCYRPTC | SEQ.ID NO: 484 |
| CIHSPCQASC | SEQ.ID NO: 485 |
| CIHSTHCGCN | SEQ.ID NO: 486 |
| CIRSPCQASC | SEQ.ID NO: 487 |
| CISSCYRPQC | SEQ.ID NO: 488 |
| CISSPCQQSC | SEQ.ID NO: 489 |
| CKPCSSQSSC | SEQ.ID NO: 490 |
| CKPSCSQSSC | SEQ.ID NO: 491 |
| CKPVCFKPIC | SEQ.ID NO: 492 |
| CKPVCYVPTC | SEQ.ID NO: 493 |
| CKPVSCVPVC | SEQ.ID NO: 494 |
| CKPVYCVPVC | SEQ.ID NO: 495 |
| CKTVYCKPIC | SEQ.ID NO: 496 |
| CLNQSCGSNC | SEQ.ID NO: 497 |
| CLNQSCGSSC | SEQ.ID NO: 498 |
| CLPGCLNQSC | SEQ.ID NO: 499 |
| CLPGSCDSCS | SEQ.ID NO: 500 |
| CLPPCYLVSC | SEQ.ID NO: 501 |
| CLPTSCQPSC | SEQ.ID NO: 502 |
| CLSFLCRPAC | SEQ.ID NO: 503 |
| CLVSSCQPSC | SEQ.ID NO: 504 |
| CMPSPCQPAC | SEQ.ID NO: 505 |
| CMSGSCQAAC | SEQ.ID NO: 506 |
| CNESSYCLPC | SEQ.ID NO: 507 |
| CPASCVSLLC | SEQ.ID NO: 508 |
| CPMACPGSPC | SEQ.ID NO: 509 |
| CPSSCTAVVC | SEQ.ID NO: 510 |
| CPVTCEPSPC | SEQ.ID NO: 511 |
| CQAACEPSAC | SEQ.ID NO: 512 |
| CQAACEPSPC | SEQ.ID NO: 513 |
| CQAACGQSVC | SEQ.ID NO: 514 |
| CQAPCSTKNC | SEQ.ID NO: 515 |
| CQAVCEPSPC | SEQ.ID NO: 516 |
| CQDSCGSSSC | SEQ.ID NO: 517 |
| CQHSSCQPTC | SEQ.ID NO: 518 |
| CQISSCGTGC | SEQ.ID NO: 519 |
| CQKSSCQPAC | SEQ.ID NO: 520 |
| CQPMCSHAAC | SEQ.ID NO: 521 |
| CQPPCTTALC | SEQ.ID NO: 522 |
| CQPSCESSFC | SEQ.ID NO: 523 |
| CQPSCSESTC | SEQ.ID NO: 524 |
| CQPSCTSVLC | SEQ.ID NO: 525 |
| CQPTCGGSSC | SEQ.ID NO: 526 |
| CQPTCSRPSC | SEQ.ID NO: 527 |
| CQPVCPTPTC | SEQ.ID NO: 528 |
| CQPVLCKSSC | SEQ.ID NO: 529 |

| Sequence | ID |
|---|---|
| CQPVVCEPSC | SEQ.ID NO: 530 |
| CQQPSCQPAC | SEQ.ID NO: 531 |
| CQQSCRVPVC | SEQ.ID NO: 532 |
| CQQSCYVPVC | SEQ.ID NO: 533 |
| CQQSGCQPAC | SEQ.ID NO: 534 |
| CQQSSCHPAC | SEQ.ID NO: 535 |
| CQQSSCKPAC | SEQ.ID NO: 536 |
| CQQSSCQLAC | SEQ.ID NO: 537 |
| CQQSSCQPAC | SEQ.ID NO: 538 |
| CQQSSCQPTC | SEQ.ID NO: 539 |
| CQQSSCQSAC | SEQ.ID NO: 540 |
| CQQSSCVSCV | SEQ.ID NO: 541 |
| CQQSYCVPVC | SEQ.ID NO: 542 |
| CQSGCISSCT | SEQ.ID NO: 543 |
| CQSGCTDSCT | SEQ.ID NO: 544 |
| CQSGCTSSCT | SEQ.ID NO: 545 |
| CQSSCYRPTC | SEQ.ID NO: 546 |
| CQSVCYQPTC | SEQ.ID NO: 547 |
| CQSVYCQPTC | SEQ.ID NO: 548 |
| CQTACEPSAC | SEQ.ID NO: 549 |
| CQTSSCGTGC | SEQ.ID NO: 550 |
| CQTTCHPSCG | SEQ.ID NO: 551 |
| CQTTCRPSCG | SEQ.ID NO: 552 |
| CQTTCYRTTC | SEQ.ID NO: 553 |
| CQTTRCRTTC | SEQ.ID NO: 554 |
| CQVTCEPSPC | SEQ.ID NO: 555 |
| CRNTSCQPTC | SEQ.ID NO: 556 |
| CRPACSPLAC | SEQ.ID NO: 557 |
| CRPACSRLAC | SEQ.ID NO: 558 |
| CRPACSRPAC | SEQ.ID NO: 559 |
| CRPMCSRPAC | SEQ.ID NO: 560 |
| CRPSCGQTTC | SEQ.ID NO: 561 |
| CRPSCGVSSC | SEQ.ID NO: 562 |
| CRPSCSISSC | SEQ.ID NO: 563 |
| CRPSCSQTTC | SEQ.ID NO: 564 |
| CRPSYCGQSC | SEQ.ID NO: 565 |
| CRPSYCISSC | SEQ.ID NO: 566 |
| CRPSYCQTTC | SEQ.ID NO: 567 |
| CRPTCSRLAC | SEQ.ID NO: 568 |
| CRPTCSSGSC | SEQ.ID NO: 569 |
| CRPTSCQNTC | SEQ.ID NO: 570 |
| CRPVCRSTYC | SEQ.ID NO: 571 |
| CRPVCSRPAC | SEQ.ID NO: 572 |
| CRPVTCVPRC | SEQ.ID NO: 573 |
| CRQSSCQPAC | SEQ.ID NO: 574 |
| CRTTCFHPIC | SEQ.ID NO: 575 |
| CRTTCFQPTC | SEQ.ID NO: 576 |
| CRTTCYRPSC | SEQ.ID NO: 577 |
| CRTTYCRPSC | SEQ.ID NO: 578 |
| CRVTCEPSPC | SEQ.ID NO: 579 |
| CRYGCGHRGC | SEQ.ID NO: 580 |
| CSAPCVALLC | SEQ.ID NO: 581 |

| Sequence | SEQ ID NO |
|---|---|
| CSDDSGSCCQ | SEQ.ID NO: 582 |
| CSEDSSSCCQ | SEQ.ID NO: 583 |
| CSEDSYSCCQ | SEQ.ID NO: 584 |
| CSEGCGSGCG | SEQ.ID NO: 585 |
| CSESSPSCCQ | SEQ.ID NO: 586 |
| CSESSSSCCQ | SEQ.ID NO: 587 |
| CSFDKSCRCG | SEQ.ID NO: 588 |
| CSGASSLCCQ | SEQ.ID NO: 589 |
| CSGASSPCCQ | SEQ.ID NO: 590 |
| CSGASSSCCQ | SEQ.ID NO: 591 |
| CSGASTSCCQ | SEQ.ID NO: 592 |
| CSGGCGSGCG | SEQ.ID NO: 593 |
| CSGGCGSSCG | SEQ.ID NO: 594 |
| CSGISSSCCQ | SEQ.ID NO: 595 |
| CSKDSSSCCQ | SEQ.ID NO: 596 |
| CSKGACGSCG | SEQ.ID NO: 597 |
| CSLSCGSRSC | SEQ.ID NO: 598 |
| CSQDLCQETC | SEQ.ID NO: 599 |
| CSRGCGSGCG | SEQ.ID NO: 600 |
| CSRLSSACCG | SEQ.ID NO: 601 |
| CSSCGKGGCG | SEQ.ID NO: 602 |
| CSSCGKRGCG | SEQ.ID NO: 603 |
| CSSDKSCRCG | SEQ.ID NO: 604 |
| CSSGNFSSCC | SEQ.ID NO: 605 |
| CSSSGCGSFC | SEQ.ID NO: 606 |
| CSSSGCGSSC | SEQ.ID NO: 607 |
| CSTPCYQPIC | SEQ.ID NO: 608 |
| CSTTCRTSSC | SEQ.ID NO: 609 |
| CSWVPACSCT | SEQ.ID NO: 610 |
| CTFSPCQQAC | SEQ.ID NO: 611 |
| CTMSVCSSAC | SEQ.ID NO: 612 |
| CTRPICEPCR | SEQ.ID NO: 613 |
| CTSSPCQHAC | SEQ.ID NO: 614 |
| CTSSPCQQAC | SEQ.ID NO: 615 |
| CTSSPCQQSC | SEQ.ID NO: 616 |
| CTSSSCQQAC | SEQ.ID NO: 617 |
| CVALLCRPLC | SEQ.ID NO: 618 |
| CVALVCEPVC | SEQ.ID NO: 619 |
| CVFSSCNTTC | SEQ.ID NO: 620 |
| CVGFVCQPMC | SEQ.ID NO: 621 |
| CVPRCTRPIC | SEQ.ID NO: 622 |
| CVPSPCQVAC | SEQ.ID NO: 623 |
| CVPSRCQASC | SEQ.ID NO: 624 |
| CVPSSCQASC | SEQ.ID NO: 625 |
| CVPVCNKPVC | SEQ.ID NO: 626 |
| CVPVCSKSVC | SEQ.ID NO: 627 |
| CVPVRCKPVC | SEQ.ID NO: 628 |
| CVSLLCRPAC | SEQ.ID NO: 629 |
| CVSLLCRPMC | SEQ.ID NO: 630 |
| CVSLLCRPTC | SEQ.ID NO: 631 |
| CVSLLCRPVC | SEQ.ID NO: 632 |
| CVSNPCQVTC | SEQ.ID NO: 633 |

| | |
|---|---|
| CVSRCYRPHC | SEQ.ID NO: 634 |
| CVSSCFRPQC | SEQ.ID NO: 635 |
| CVSSICQPIC | SEQ.ID NO: 636 |
| CVSSPCQPTC | SEQ.ID NO: 637 |
| CVVSCTPPSC | SEQ.ID NO: 638 |
| CVVSCTPPTC | SEQ.ID NO: 639 |
| CYCPKNSIFC | SEQ.ID NO: 640 |
| CYEPCLPRGC | SEQ.ID NO: 641 |
| CYRRCYSSCY | SEQ.ID NO: 642 |
| GCCGYGGLGC | SEQ.ID NO: 643 |
| GCGGCGSGCA | SEQ.ID NO: 644 |
| GCGGCGSGCG | SEQ.ID NO: 645 |
| GCGGCGSSCG | SEQ.ID NO: 646 |
| GCGGCSSSCG | SEQ.ID NO: 647 |
| GCGGSGSSCC | SEQ.ID NO: 648 |
| GCGSGCAGCG | SEQ.ID NO: 649 |
| GCGSGCGGCG | SEQ.ID NO: 650 |
| GCGSGCGGCS | SEQ.ID NO: 651 |
| GCGSSCGGCD | SEQ.ID NO: 652 |
| GCGSSCGGCG | SEQ.ID NO: 653 |
| GCGSSCSQCS | SEQ.ID NO: 654 |
| GCGYSSSCCG | SEQ.ID NO: 655 |
| GCKGGCGSCG | SEQ.ID NO: 656 |
| GCSGCSGGCG | SEQ.ID NO: 657 |
| ICSGASSLCC | SEQ.ID NO: 658 |
| ICSGASSPCC | SEQ.ID NO: 659 |
| MCCNYYGNSC | SEQ.ID NO: 660 |
| MCCNYYRNSC | SEQ.ID NO: 661 |
| MCYGYGCGCG | SEQ.ID NO: 662 |
| NCCSRNFSSC | SEQ.ID NO: 663 |
| PCSLQEGCCR | SEQ.ID NO: 664 |
| PCSSQSSCCV | SEQ.ID NO: 665 |
| SCCAPASSCQ | SEQ.ID NO: 666 |
| SCCAPASTCQ | SEQ.ID NO: 667 |
| SCCAPTSSCQ | SEQ.ID NO: 668 |
| SCCGYRPLCY | SEQ.ID NO: 669 |
| SCCVPASSCQ | SEQ.ID NO: 670 |
| SCCVPTSSCQ | SEQ.ID NO: 671 |
| SCGCSKGACG | SEQ.ID NO: 672 |
| SCGGCDSSCG | SEQ.ID NO: 673 |
| SCGGCGSGCG | SEQ.ID NO: 674 |
| SCGGCGSSCG | SEQ.ID NO: 675 |
| SCGGCKGGCG | SEQ.ID NO: 676 |
| SCGGSKGCCG | SEQ.ID NO: 677 |
| SCGSGCRGCG | SEQ.ID NO: 678 |
| SCYGCYGCI | SEQ.ID NO: 679 |
| TCCVPVPSCG | SEQ.ID NO: 680 |
| TCSDDSGSCC | SEQ.ID NO: 681 |
| TCSEDSSSCC | SEQ.ID NO: 682 |
| TCSEDSYSCC | SEQ.ID NO: 683 |
| TCSESSPSCC | SEQ.ID NO: 684 |
| TCSESSSSCC | SEQ.ID NO: 685 |

| Sequence | SEQ ID NO |
|---|---|
| TCSKDSSSCC | SEQ.ID NO: 686 |
| TCSRLSSACC | SEQ.ID NO: 687 |
| VCCQPTPICD | SEQ.ID NO: 688 |
| VCSEDSSSCC | SEQ.ID NO: 689 |
| VCSGASSLCC | SEQ.ID NO: 690 |
| VCSGASSPCC | SEQ.ID NO: 691 |
| VCSGASSSCC | SEQ.ID NO: 692 |
| VCSGASTSCC | SEQ.ID NO: 693 |
| VCSGDSSCCQ | SEQ.ID NO: 694 |
| VCSGISSSCC | SEQ.ID NO: 695 |
| YCVPIPSCCA | SEQ.ID NO: 696 |
| CASSCCTPSC | SEQ.ID NO: 697 |
| CCDNCPPPCH | SEQ.ID NO: 698 |
| CCEPCLPRGC | SEQ.ID NO: 699 |
| CCGAASSCCR | SEQ.ID NO: 700 |
| CCGCGGSGCG | SEQ.ID NO: 701 |
| CCGPSSSCCQ | SEQ.ID NO: 702 |
| CCGSGCGGCG | SEQ.ID NO: 703 |
| CCKPYCSQCS | SEQ.ID NO: 704 |
| CCMPVSSCCA | SEQ.ID NO: 705 |
| CCNYYRNCCG | SEQ.ID NO: 706 |
| CCPSCVVSSC | SEQ.ID NO: 707 |
| CCPSYCVSSC | SEQ.ID NO: 708 |
| CCQPICGSSC | SEQ.ID NO: 709 |
| CCQPICVTSC | SEQ.ID NO: 710 |
| CCQPTCLSSC | SEQ.ID NO: 711 |
| CCQPTCLTSC | SEQ.ID NO: 712 |
| CCQPTCVASC | SEQ.ID NO: 713 |
| CCQPTCVTSC | SEQ.ID NO: 714 |
| CCQPYCHPTC | SEQ.ID NO: 715 |
| CCQQSSCVSC | SEQ.ID NO: 716 |
| CCQSSCFKPC | SEQ.ID NO: 717 |
| CCQSSCSKPC | SEQ.ID NO: 718 |
| CCQSSCYKPC | SEQ.ID NO: 719 |
| CCQTICRSTC | SEQ.ID NO: 720 |
| CCQTTCHPSC | SEQ.ID NO: 721 |
| CCQTTCRPSC | SEQ.ID NO: 722 |
| CCRVPTCSCS | SEQ.ID NO: 723 |
| CCSPGCQPTC | SEQ.ID NO: 724 |
| CCSSGCGSSC | SEQ.ID NO: 725 |
| CCSSSCGSCG | SEQ.ID NO: 726 |
| CCTQEQNCCE | SEQ.ID NO: 727 |
| CCVPIPSCCA | SEQ.ID NO: 728 |
| CCVPISSCCA | SEQ.ID NO: 729 |
| CCVPVCYQCK | SEQ.ID NO: 730 |
| CCVPVPSCCA | SEQ.ID NO: 731 |
| CCVPVPSCCV | SEQ.ID NO: 732 |
| CCVPVSSCCA | SEQ.ID NO: 733 |
| CDSSCCQPSC | SEQ.ID NO: 734 |
| CDTCPPPCCK | SEQ.ID NO: 735 |
| CEPCRRPVCC | SEQ.ID NO: 736 |
| CEPSCCQPVC | SEQ.ID NO: 737 |

| Sequence | SEQ ID NO |
|---|---|
| CEPSCCSAVC | SEQ.ID NO: 738 |
| CETSCCQPSC | SEQ.ID NO: 739 |
| CETTCCRTTC | SEQ.ID NO: 740 |
| CFSGCGSSCC | SEQ.ID NO: 741 |
| CGCSQSNCCK | SEQ.ID NO: 742 |
| CGCSQSSCCK | SEQ.ID NO: 743 |
| CGGCGGCGGC | SEQ.ID NO: 744 |
| CGGCGGGCCG | SEQ.ID NO: 745 |
| CGGCGSGCCV | SEQ.ID NO: 746 |
| CGGCGSSCCV | SEQ.ID NO: 747 |
| CGGGCCGSSC | SEQ.ID NO: 748 |
| CGGSCCGSSC | SEQ.ID NO: 749 |
| CGQSCCRPAC | SEQ.ID NO: 750 |
| CGQSCCRPVC | SEQ.ID NO: 751 |
| CGSCGCSQCN | SEQ.ID NO: 752 |
| CGSCGCSQCS | SEQ.ID NO: 753 |
| CGSFCCQSSC | SEQ.ID NO: 754 |
| CGSGCCVPVC | SEQ.ID NO: 755 |
| CGSSCCGSGC | SEQ.ID NO: 756 |
| CGSSCCQPCY | SEQ.ID NO: 757 |
| CGSSCCQPIC | SEQ.ID NO: 758 |
| CGSSCCQPSC | SEQ.ID NO: 759 |
| CGSSCCQSSC | SEQ.ID NO: 760 |
| CGSSCCVPIC | SEQ.ID NO: 761 |
| CGSSCCVPVC | SEQ.ID NO: 762 |
| CGSSCSQCSC | SEQ.ID NO: 763 |
| CGYGSCCGCG | SEQ.ID NO: 764 |
| CHPRCCISSC | SEQ.ID NO: 765 |
| CHPSCCESSC | SEQ.ID NO: 766 |
| CHPSCCISSC | SEQ.ID NO: 767 |
| CHPTCCQNTC | SEQ.ID NO: 768 |
| CHPTCCQTIC | SEQ.ID NO: 769 |
| CHPVCCQTTC | SEQ.ID NO: 770 |
| CHPVCKSTCC | SEQ.ID NO: 771 |
| CHPVCRSTCC | SEQ.ID NO: 772 |
| CISSCCHPSC | SEQ.ID NO: 773 |
| CISSCCKPSC | SEQ.ID NO: 774 |
| CISSCCRPSC | SEQ.ID NO: 775 |
| CISSCTPSCC | SEQ.ID NO: 776 |
| CISSSCCPSC | SEQ.ID NO: 777 |
| CKAVCCVPTC | SEQ.ID NO: 778 |
| CKPCCSQASC | SEQ.ID NO: 779 |
| CKPCCSQSRC | SEQ.ID NO: 780 |
| CKPCCSQSSC | SEQ.ID NO: 781 |
| CKPCCSSSGC | SEQ.ID NO: 782 |
| CKPCSCFSGC | SEQ.ID NO: 783 |
| CKPCSCSSGC | SEQ.ID NO: 784 |
| CKPCYCSSGC | SEQ.ID NO: 785 |
| CKPICCVPVC | SEQ.ID NO: 786 |
| CKPQCCQSVC | SEQ.ID NO: 787 |
| CKPSCCQTTC | SEQ.ID NO: 788 |
| CKPVCCAPTC | SEQ.ID NO: 789 |

| Sequence | SEQ ID NO |
|---|---|
| CKPVCCKPIC | SEQ.ID NO: 790 |
| CKPVCCKSIC | SEQ.ID NO: 791 |
| CKPVCCLPTC | SEQ.ID NO: 792 |
| CKPVCCVPTC | SEQ.ID NO: 793 |
| CKPVCCVPVC | SEQ.ID NO: 794 |
| CKPVCCVSTC | SEQ.ID NO: 795 |
| CKPYCCQSSC | SEQ.ID NO: 796 |
| CKPYCSQCSC | SEQ.ID NO: 797 |
| CKSNCCKPVC | SEQ.ID NO: 798 |
| CKTVCCKPVC | SEQ.ID NO: 799 |
| CLPPCCVVSC | SEQ.ID NO: 800 |
| CLTSCCQPSC | SEQ.ID NO: 801 |
| CNPCCSQSSC | SEQ.ID NO: 802 |
| CPESCCELPC | SEQ.ID NO: 803 |
| CPESCCEPHC | SEQ.ID NO: 804 |
| CPESCCEPPC | SEQ.ID NO: 805 |
| CPFSCPTTCC | SEQ.ID NO: 806 |
| CPGDCFTCCT | SEQ.ID NO: 807 |
| CPSCVVSSCC | SEQ.ID NO: 808 |
| CPSYCVSSCC | SEQ.ID NO: 809 |
| CPTTCCRTTC | SEQ.ID NO: 810 |
| CQETCCRPSC | SEQ.ID NO: 811 |
| CQHACCVPVC | SEQ.ID NO: 812 |
| CQNTCCRTTC | SEQ.ID NO: 813 |
| CQPACCQPTC | SEQ.ID NO: 814 |
| CQPACCTASC | SEQ.ID NO: 815 |
| CQPACCTSSC | SEQ.ID NO: 816 |
| CQPACCTTSC | SEQ.ID NO: 817 |
| CQPACCVPVC | SEQ.ID NO: 818 |
| CQPACCVSSC | SEQ.ID NO: 819 |
| CQPCCHPTCY | SEQ.ID NO: 820 |
| CQPCCRPTSC | SEQ.ID NO: 821 |
| CQPICCGSSC | SEQ.ID NO: 822 |
| CQPICGSSCC | SEQ.ID NO: 823 |
| CQPICVTSCC | SEQ.ID NO: 824 |
| CQPNCCRPSC | SEQ.ID NO: 825 |
| CQPRCCETSC | SEQ.ID NO: 826 |
| CQPSCCRPAC | SEQ.ID NO: 827 |
| CQPSCCSTPC | SEQ.ID NO: 828 |
| CQPSCCSTTC | SEQ.ID NO: 829 |
| CQPSCCVPSC | SEQ.ID NO: 830 |
| CQPSCCVSSC | SEQ.ID NO: 831 |
| CQPTCCGSSC | SEQ.ID NO: 832 |
| CQPTCCHPSC | SEQ.ID NO: 833 |
| CQPTCCQPTC | SEQ.ID NO: 834 |
| CQPTCCRPRC | SEQ.ID NO: 835 |
| CQPTCCRPSC | SEQ.ID NO: 836 |
| CQPTCCRTTC | SEQ.ID NO: 837 |
| CQPTCLSSCC | SEQ.ID NO: 838 |
| CQPTCLTSCC | SEQ.ID NO: 839 |
| CQPTCVASCC | SEQ.ID NO: 840 |
| CQPTCVTSCC | SEQ.ID NO: 841 |

| Sequence | SEQ ID NO |
|---|---|
| CQPVCCQPTC | SEQ.ID NO: 842 |
| CQPYCHPTCC | SEQ.ID NO: 843 |
| CQQACCMPVC | SEQ.ID NO: 844 |
| CQQACCVPIC | SEQ.ID NO: 845 |
| CQQACCVPVC | SEQ.ID NO: 846 |
| CQQSCCVPVC | SEQ.ID NO: 847 |
| CQQSCCVSVC | SEQ.ID NO: 848 |
| CQSMCCQPTC | SEQ.ID NO: 849 |
| CQSNCCVPVC | SEQ.ID NO: 850 |
| CQSSCCKPCS | SEQ.ID NO: 851 |
| CQSSCCQSSC | SEQ.ID NO: 852 |
| CQSSCCVPVC | SEQ.ID NO: 853 |
| CQSSCFKPCC | SEQ.ID NO: 854 |
| CQSSCSKPCC | SEQ.ID NO: 855 |
| CQSVCCQPTC | SEQ.ID NO: 856 |
| CQTICRSTCC | SEQ.ID NO: 857 |
| CQTTCCRPSC | SEQ.ID NO: 858 |
| CQTTCCRTTC | SEQ.ID NO: 859 |
| CRATCCRPSC | SEQ.ID NO: 860 |
| CRGCGPSCCA | SEQ.ID NO: 861 |
| CRPACCETTC | SEQ.ID NO: 862 |
| CRPACCQNTC | SEQ.ID NO: 863 |
| CRPCCWATTC | SEQ.ID NO: 864 |
| CRPICRPACC | SEQ.ID NO: 865 |
| CRPLCCQTTC | SEQ.ID NO: 866 |
| CRPQCCQSVC | SEQ.ID NO: 867 |
| CRPQCCQTTC | SEQ.ID NO: 868 |
| CRPRCCISSC | SEQ.ID NO: 869 |
| CRPSCCESSC | SEQ.ID NO: 870 |
| CRPSCCETTC | SEQ.ID NO: 871 |
| CRPSCCISSC | SEQ.ID NO: 872 |
| CRPSCCKPQC | SEQ.ID NO: 873 |
| CRPSCCMSSC | SEQ.ID NO: 874 |
| CRPSCCQTTC | SEQ.ID NO: 875 |
| CRPSCCRPSC | SEQ.ID NO: 876 |
| CRPSCCVSRC | SEQ.ID NO: 877 |
| CRPSCCVSSC | SEQ.ID NO: 878 |
| CRPTCCETTC | SEQ.ID NO: 879 |
| CRPTCCQNTC | SEQ.ID NO: 880 |
| CRPTCCQTTC | SEQ.ID NO: 881 |
| CRPVCCDPCS | SEQ.ID NO: 882 |
| CRPVCCQTTC | SEQ.ID NO: 883 |
| CRPVCQPACC | SEQ.ID NO: 884 |
| CRPVCRPACC | SEQ.ID NO: 885 |
| CRPVCRPTCC | SEQ.ID NO: 886 |
| CRPVCRSTCC | SEQ.ID NO: 887 |
| CRPYCCESSC | SEQ.ID NO: 888 |
| CRRPVCCDPC | SEQ.ID NO: 889 |
| CRSQCCQSVC | SEQ.ID NO: 890 |
| CRTTCCHPSC | SEQ.ID NO: 891 |
| CRTTCCQPIC | SEQ.ID NO: 892 |
| CRTTCCQPTC | SEQ.ID NO: 893 |

| Sequence | SEQ ID NO |
|---|---|
| CRTTCCRPSC | SEQ.ID NO: 894 |
| CRTTCCRTTC | SEQ.ID NO: 895 |
| CSCSSCGSCA | SEQ.ID NO: 896 |
| CSCSSCGSCG | SEQ.ID NO: 897 |
| CSCTSCGSCG | SEQ.ID NO: 898 |
| CSPACQPTCC | SEQ.ID NO: 899 |
| CSPGCQPTCC | SEQ.ID NO: 900 |
| CSPSCCQTTC | SEQ.ID NO: 901 |
| CSQCSCYKPC | SEQ.ID NO: 902 |
| CSQSNCCKPC | SEQ.ID NO: 903 |
| CSQSSCCKPC | SEQ.ID NO: 904 |
| CSSGCGSCCQ | SEQ.ID NO: 905 |
| CSSGCGSSCC | SEQ.ID NO: 906 |
| CSSGCQPACC | SEQ.ID NO: 907 |
| CSSSCCQPSC | SEQ.ID NO: 908 |
| CSTPCCQPTC | SEQ.ID NO: 909 |
| CSTTCCQPIC | SEQ.ID NO: 910 |
| CTAVVCRPCC | SEQ.ID NO: 911 |
| CTDSCTPSCC | SEQ.ID NO: 912 |
| CTPSCCQPAC | SEQ.ID NO: 913 |
| CTRPICEPCC | SEQ.ID NO: 914 |
| CTSSCTPSCC | SEQ.ID NO: 915 |
| CVPACSCSSC | SEQ.ID NO: 916 |
| CVPACSCTSC | SEQ.ID NO: 917 |
| CVPVCCKPVC | SEQ.ID NO: 918 |
| CVPVCCVPTC | SEQ.ID NO: 919 |
| CVPVCCVPVC | SEQ.ID NO: 920 |
| CVSCVSSPCC | SEQ.ID NO: 921 |
| CVSRCCRPQC | SEQ.ID NO: 922 |
| CVSSCCKPQC | SEQ.ID NO: 923 |
| CVSSCCQHSC | SEQ.ID NO: 924 |
| CVSSCCQPFC | SEQ.ID NO: 925 |
| CVSSCCQPSC | SEQ.ID NO: 926 |
| CVSSCCRPQC | SEQ.ID NO: 927 |
| CVSTCCRPTC | SEQ.ID NO: 928 |
| CVTRCCSTPC | SEQ.ID NO: 929 |
| CVTSCCQPAC | SEQ.ID NO: 930 |
| CVTSCCQPSC | SEQ.ID NO: 931 |
| CVYSCCQPFC | SEQ.ID NO: 932 |
| CVYSCCQPSC | SEQ.ID NO: 933 |
| GCCGCSEGCG | SEQ.ID NO: 934 |
| GCCGCSGGCG | SEQ.ID NO: 935 |
| GCCGCSRGCG | SEQ.ID NO: 936 |
| GCCRPITCCP | SEQ.ID NO: 937 |
| GCGSSCCQCS | SEQ.ID NO: 938 |
| GCGVPVCCCS | SEQ.ID NO: 939 |
| LCCPCQTTCS | SEQ.ID NO: 940 |
| PCCCLRPVCG | SEQ.ID NO: 941 |
| PCCCRPVTCQ | SEQ.ID NO: 942 |
| PCCCVRPVCG | SEQ.ID NO: 943 |
| PCCSQASCCV | SEQ.ID NO: 944 |
| PCCSQSRCCV | SEQ.ID NO: 945 |

| Sequence | SEQ ID NO |
|---|---|
| PCCSQSSCCK | SEQ.ID NO: 946 |
| PCCSQSSCCV | SEQ.ID NO: 947 |
| PCCWATTCCQ | SEQ.ID NO: 948 |
| QCSCCKPYCS | SEQ.ID NO: 949 |
| RCYVPVCCCK | SEQ.ID NO: 950 |
| SCCAPVYCCK | SEQ.ID NO: 951 |
| SCCISSSCCP | SEQ.ID NO: 952 |
| SCCVSSCRCP | SEQ.ID NO: 953 |
| SCGCSQCSCY | SEQ.ID NO: 954 |
| SCGLENCCCP | SEQ.ID NO: 955 |
| VCCGASSCCQ | SEQ.ID NO: 956 |
| VCCGDSSCCQ | SEQ.ID NO: 957 |
| CASSCCTPSCC | SEQ.ID NO: 958 |
| CCCPSCVVSSC | SEQ.ID NO: 959 |
| CCCPSYCVSSC | SEQ.ID NO: 960 |
| CCCSSGCGSSC | SEQ.ID NO: 961 |
| CCDTCPPPCCK | SEQ.ID NO: 962 |
| CCEPHCCALSC | SEQ.ID NO: 963 |
| CCEPPCCAPSC | SEQ.ID NO: 964 |
| CCEPPCCATSC | SEQ.ID NO: 965 |
| CCETSCCQPSC | SEQ.ID NO: 966 |
| CCGSSCCGSGC | SEQ.ID NO: 967 |
| CCGSSCCGSSC | SEQ.ID NO: 968 |
| CCHPRCCISSC | SEQ.ID NO: 969 |
| CCHPSCCESSC | SEQ.ID NO: 970 |
| CCHPSCCISSC | SEQ.ID NO: 971 |
| CCHPSCCVSSC | SEQ.ID NO: 972 |
| CCHPTCCQNTC | SEQ.ID NO: 973 |
| CCHPTCCQTIC | SEQ.ID NO: 974 |
| CCISSCCKPSC | SEQ.ID NO: 975 |
| CCISSCCRPSC | SEQ.ID NO: 976 |
| CCISSSCCPSC | SEQ.ID NO: 977 |
| CCKAVCCVPTC | SEQ.ID NO: 978 |
| CCKPCCSQASC | SEQ.ID NO: 979 |
| CCKPCCSQSRC | SEQ.ID NO: 980 |
| CCKPCCSQSSC | SEQ.ID NO: 981 |
| CCKPCCSSSGC | SEQ.ID NO: 982 |
| CCKPCSCFSGC | SEQ.ID NO: 983 |
| CCKPCSCSSGC | SEQ.ID NO: 984 |
| CCKPCYCSSGC | SEQ.ID NO: 985 |
| CCKPICCVPVC | SEQ.ID NO: 986 |
| CCKPQCCQSVC | SEQ.ID NO: 987 |
| CCKPVCCKPIC | SEQ.ID NO: 988 |
| CCKPYCCQSSC | SEQ.ID NO: 989 |
| CCKPYCSQCSC | SEQ.ID NO: 990 |
| CCMPVCCKPVC | SEQ.ID NO: 991 |
| CCMPVCCKTVC | SEQ.ID NO: 992 |
| CCMSSCCKPQC | SEQ.ID NO: 993 |
| CCNPCCSQSSC | SEQ.ID NO: 994 |
| CCPGDCFTCCT | SEQ.ID NO: 995 |
| CCPSCVVSSCC | SEQ.ID NO: 996 |
| CCPSYCVSSCC | SEQ.ID NO: 997 |

| | |
|---|---|
| CCQNTCCRTTC | SEQ.ID NO: 998 |
| CCQPACCVSSC | SEQ.ID NO: 999 |
| CCQPCCHPTCY | SEQ.ID NO: 1000 |
| CCQPCCRPTSC | SEQ.ID NO: 1001 |
| CCQPICGSSCC | SEQ.ID NO: 1002 |
| CCQPICVTSCC | SEQ.ID NO: 1003 |
| CCQPNCCRPSC | SEQ.ID NO: 1004 |
| CCQPSCCETSC | SEQ.ID NO: 1005 |
| CCQPSCCRPAC | SEQ.ID NO: 1006 |
| CCQPSCCSTPC | SEQ.ID NO: 1007 |
| CCQPSCCSTTC | SEQ.ID NO: 1008 |
| CCQPSCCVPSC | SEQ.ID NO: 1009 |
| CCQPSCCVSSC | SEQ.ID NO: 1010 |
| CCQPTCCHPSC | SEQ.ID NO: 1011 |
| CCQPTCCQPTC | SEQ.ID NO: 1012 |
| CCQPTCCRPRC | SEQ.ID NO: 1013 |
| CCQPTCCRPSC | SEQ.ID NO: 1014 |
| CCQPTCCRPTC | SEQ.ID NO: 1015 |
| CCQPTCCRTTC | SEQ.ID NO: 1016 |
| CCQPTCLSSCC | SEQ.ID NO: 1017 |
| CCQPTCLTSCC | SEQ.ID NO: 1018 |
| CCQPTCVASCC | SEQ.ID NO: 1019 |
| CCQPTCVTSCC | SEQ.ID NO: 1020 |
| CCQPYCHPTCC | SEQ.ID NO: 1021 |
| CCQSMCCQPTC | SEQ.ID NO: 1022 |
| CCQSNCCVPVC | SEQ.ID NO: 1023 |
| CCQSSCCKPCS | SEQ.ID NO: 1024 |
| CCQSSCCKPSC | SEQ.ID NO: 1025 |
| CCQSSCCKPYC | SEQ.ID NO: 1026 |
| CCQSSCCQSSC | SEQ.ID NO: 1027 |
| CCQSSCCVPVC | SEQ.ID NO: 1028 |
| CCQSSCFKPCC | SEQ.ID NO: 1029 |
| CCQSSCSKPCC | SEQ.ID NO: 1030 |
| CCQSSCYKPCC | SEQ.ID NO: 1031 |
| CCQSVCCQPTC | SEQ.ID NO: 1032 |
| CCQTICRSTCC | SEQ.ID NO: 1033 |
| CCQTTCCRPSC | SEQ.ID NO: 1034 |
| CCQTTCCRTTC | SEQ.ID NO: 1035 |
| CCRPACCETTC | SEQ.ID NO: 1036 |
| CCRPACCQNTC | SEQ.ID NO: 1037 |
| CCRPLCCQTTC | SEQ.ID NO: 1038 |
| CCRPQCCQSVC | SEQ.ID NO: 1039 |
| CCRPQCCQTTC | SEQ.ID NO: 1040 |
| CCRPSCCESSC | SEQ.ID NO: 1041 |
| CCRPSCCETTC | SEQ.ID NO: 1042 |
| CCRPSCCGSSC | SEQ.ID NO: 1043 |
| CCRPSCCISSC | SEQ.ID NO: 1044 |
| CCRPSCCKPQC | SEQ.ID NO: 1045 |
| CCRPSCCQTTC | SEQ.ID NO: 1046 |
| CCRPSCCVSRC | SEQ.ID NO: 1047 |
| CCRPSCCVSSC | SEQ.ID NO: 1048 |
| CCRPTCCQNTC | SEQ.ID NO: 1049 |

| | |
|---|---|
| CCRPTCCQTTC | SEQ.ID NO: 1050 |
| CCRPVCCDPCS | SEQ.ID NO: 1051 |
| CCRTTCCQPTC | SEQ.ID NO: 1052 |
| CCRTTCCRPSC | SEQ.ID NO: 1053 |
| CCRTTCCRTTC | SEQ.ID NO: 1054 |
| CCSCSSCGSCA | SEQ.ID NO: 1055 |
| CCSPGCQPTCC | SEQ.ID NO: 1056 |
| CCSQSSCCKPC | SEQ.ID NO: 1057 |
| CCSSGCGSCCQ | SEQ.ID NO: 1058 |
| CCSSGCGSSCC | SEQ.ID NO: 1059 |
| CCSTPCCQPTC | SEQ.ID NO: 1060 |
| CCVPACSCSSC | SEQ.ID NO: 1061 |
| CCVPACSCTSC | SEQ.ID NO: 1062 |
| CCVPICCKPIC | SEQ.ID NO: 1063 |
| CCVPICCKPVC | SEQ.ID NO: 1064 |
| CCVPVCCKPIC | SEQ.ID NO: 1065 |
| CCVPVCCKPVC | SEQ.ID NO: 1066 |
| CCVPVCCKSNC | SEQ.ID NO: 1067 |
| CCVPVCCKTVC | SEQ.ID NO: 1068 |
| CCVPVCCSSSC | SEQ.ID NO: 1069 |
| CCVPVCCVPVC | SEQ.ID NO: 1070 |
| CCVSSCCKPQC | SEQ.ID NO: 1071 |
| CCVSSCCQHSC | SEQ.ID NO: 1072 |
| CCVSSCCQPSC | SEQ.ID NO: 1073 |
| CCVSSCCRPQC | SEQ.ID NO: 1074 |
| CCVSTCCRPTC | SEQ.ID NO: 1075 |
| CCVSVCCKPVC | SEQ.ID NO: 1076 |
| CDSSCCQPSCC | SEQ.ID NO: 1077 |
| CEPCCRPVCCD | SEQ.ID NO: 1078 |
| CFKPCCCQSSC | SEQ.ID NO: 1079 |
| CGDGCCCPSCY | SEQ.ID NO: 1080 |
| CGGGCCGSSCC | SEQ.ID NO: 1081 |
| CGGSCCGSSCC | SEQ.ID NO: 1082 |
| CGLENCCCPSC | SEQ.ID NO: 1083 |
| CGQSCCRPACC | SEQ.ID NO: 1084 |
| CGQSCCRPVCC | SEQ.ID NO: 1085 |
| CGSCCQSSCCN | SEQ.ID NO: 1086 |
| CGSCGCSQCNC | SEQ.ID NO: 1087 |
| CGSCGCSQCSC | SEQ.ID NO: 1088 |
| CGSGCCGPVCC | SEQ.ID NO: 1089 |
| CGSGCCVPVCC | SEQ.ID NO: 1090 |
| CGSNCCQPCCR | SEQ.ID NO: 1091 |
| CGSSCCQPCCH | SEQ.ID NO: 1092 |
| CGSSCCQPCCR | SEQ.ID NO: 1093 |
| CGSSCCQPCYC | SEQ.ID NO: 1094 |
| CGSSCCQPSCC | SEQ.ID NO: 1095 |
| CGSSCCQSSCC | SEQ.ID NO: 1096 |
| CGSSCCVPICC | SEQ.ID NO: 1097 |
| CGSSCCVPVCC | SEQ.ID NO: 1098 |
| CGSSCSQCSCC | SEQ.ID NO: 1099 |
| CGVPVCCCSCS | SEQ.ID NO: 1100 |
| CHPRCCISSCC | SEQ.ID NO: 1101 |

| | |
|---|---|
| CHPSCCESSCC | SEQ.ID NO: 1102 |
| CHPSCCISSCC | SEQ.ID NO: 1103 |
| CHPTCCQNTCC | SEQ.ID NO: 1104 |
| CISSCCHPSCC | SEQ.ID NO: 1105 |
| CISSCCKPSCC | SEQ.ID NO: 1106 |
| CISSCCRPSCC | SEQ.ID NO: 1107 |
| CISSSCCPSCC | SEQ.ID NO: 1108 |
| CKPCCCSSGCG | SEQ.ID NO: 1109 |
| CKPCCSQASCC | SEQ.ID NO: 1110 |
| CKPCCSQSRCC | SEQ.ID NO: 1111 |
| CKPCCSQSSCC | SEQ.ID NO: 1112 |
| CKPQCCQSMCC | SEQ.ID NO: 1113 |
| CKPQCCQSVCC | SEQ.ID NO: 1114 |
| CKPVCCCVPAC | SEQ.ID NO: 1115 |
| CKPVCCKPICC | SEQ.ID NO: 1116 |
| CKPVCCMPVCC | SEQ.ID NO: 1117 |
| CKPVCCVPVCC | SEQ.ID NO: 1118 |
| CKPVCCVSVCC | SEQ.ID NO: 1119 |
| CKPYCSQCSCC | SEQ.ID NO: 1120 |
| CLPCCRPTCCQ | SEQ.ID NO: 1121 |
| CLTSCCQPSCC | SEQ.ID NO: 1122 |
| CMSSCCKPQCC | SEQ.ID NO: 1123 |
| CNPCCSQSSCC | SEQ.ID NO: 1124 |
| CPACCVSSCCQ | SEQ.ID NO: 1125 |
| CPESCCEPHCC | SEQ.ID NO: 1126 |
| CPESCCEPPCC | SEQ.ID NO: 1127 |
| CPSCCESSCCR | SEQ.ID NO: 1128 |
| CPSCCQTTCCR | SEQ.ID NO: 1129 |
| CPSCCVSSCCR | SEQ.ID NO: 1130 |
| CQCSCCKPYCS | SEQ.ID NO: 1131 |
| CQETCCRPSCC | SEQ.ID NO: 1132 |
| CQNTCCRTTCC | SEQ.ID NO: 1133 |
| CQPACCTASCC | SEQ.ID NO: 1134 |
| CQPACCTSSCC | SEQ.ID NO: 1135 |
| CQPACCTTSCC | SEQ.ID NO: 1136 |
| CQPACCVPVCC | SEQ.ID NO: 1137 |
| CQPACCVSSCC | SEQ.ID NO: 1138 |
| CQPCCHPTCCQ | SEQ.ID NO: 1139 |
| CQPCCRPACCE | SEQ.ID NO: 1140 |
| CQPCCRPACCQ | SEQ.ID NO: 1141 |
| CQPCCRPTCCQ | SEQ.ID NO: 1142 |
| CQPCYCPACCV | SEQ.ID NO: 1143 |
| CQPICCGSSCC | SEQ.ID NO: 1144 |
| CQPRCCETSCC | SEQ.ID NO: 1145 |
| CQPSCCETSCC | SEQ.ID NO: 1146 |
| CQPSCCRPACC | SEQ.ID NO: 1147 |
| CQPSCCVPSCC | SEQ.ID NO: 1148 |
| CQPSCCVSSCC | SEQ.ID NO: 1149 |
| CQPTCCCPSYC | SEQ.ID NO: 1150 |
| CQPTCCGSSCC | SEQ.ID NO: 1151 |
| CQPTCCHPSCC | SEQ.ID NO: 1152 |
| CQPTCCQPTCC | SEQ.ID NO: 1153 |

| | |
|---|---|
| CQPTCCRPSCC | SEQ.ID NO: 1154 |
| CQPTCCRPTCC | SEQ.ID NO: 1155 |
| CQPTCCRTTCC | SEQ.ID NO: 1156 |
| CQQACCMPVCC | SEQ.ID NO: 1157 |
| CQQACCVPICC | SEQ.ID NO: 1158 |
| CQQACCVPVCC | SEQ.ID NO: 1159 |
| CQQSCCVPVCC | SEQ.ID NO: 1160 |
| CQQSCCVSVCC | SEQ.ID NO: 1161 |
| CQSNCCVPVCC | SEQ.ID NO: 1162 |
| CQSSCCCPASC | SEQ.ID NO: 1163 |
| CQSSCCKPCCS | SEQ.ID NO: 1164 |
| CQSSCCKPCSC | SEQ.ID NO: 1165 |
| CQSSCCKPYCC | SEQ.ID NO: 1166 |
| CQSSCCNPCCS | SEQ.ID NO: 1167 |
| CQSSCCQSSCC | SEQ.ID NO: 1168 |
| CQSSCCVPVCC | SEQ.ID NO: 1169 |
| CQSSCFKPCCC | SEQ.ID NO: 1170 |
| CQSSCSKPCCC | SEQ.ID NO: 1171 |
| CQSSCYKPCCC | SEQ.ID NO: 1172 |
| CQSVCCQPTCC | SEQ.ID NO: 1173 |
| CQTTCCCPSCV | SEQ.ID NO: 1174 |
| CQTTCCRPSCC | SEQ.ID NO: 1175 |
| CQTTCCRTTCC | SEQ.ID NO: 1176 |
| CRPACCETTCC | SEQ.ID NO: 1177 |
| CRPACCQNTCC | SEQ.ID NO: 1178 |
| CRPCCCLRPVC | SEQ.ID NO: 1179 |
| CRPCCCVRPVC | SEQ.ID NO: 1180 |
| CRPCCWATTCC | SEQ.ID NO: 1181 |
| CRPLCCQTTCC | SEQ.ID NO: 1182 |
| CRPQCCQSVCC | SEQ.ID NO: 1183 |
| CRPQCCQTTCC | SEQ.ID NO: 1184 |
| CRPRCCISSCC | SEQ.ID NO: 1185 |
| CRPSCCESSCC | SEQ.ID NO: 1186 |
| CRPSCCISSCC | SEQ.ID NO: 1187 |
| CRPSCCKPQCC | SEQ.ID NO: 1188 |
| CRPSCCPSCCQ | SEQ.ID NO: 1189 |
| CRPSCCQTTCC | SEQ.ID NO: 1190 |
| CRPSCCRPQCC | SEQ.ID NO: 1191 |
| CRPSCCVSRCC | SEQ.ID NO: 1192 |
| CRPSCCVSSCC | SEQ.ID NO: 1193 |
| CRPTCCQNTCC | SEQ.ID NO: 1194 |
| CRPVCCCEPTC | SEQ.ID NO: 1195 |
| CRPVCCCYSCE | SEQ.ID NO: 1196 |
| CRTTCCHPSCC | SEQ.ID NO: 1197 |
| CRTTCCRPSCC | SEQ.ID NO: 1198 |
| CSCCKPYCSQC | SEQ.ID NO: 1199 |
| CSKPCCCQSSC | SEQ.ID NO: 1200 |
| CSPCCQPTCCR | SEQ.ID NO: 1201 |
| CSPCCVSSCCQ | SEQ.ID NO: 1202 |
| CSQCSCCKPCY | SEQ.ID NO: 1203 |
| CSQCSCYKPCC | SEQ.ID NO: 1204 |
| CSQSNCCKPCC | SEQ.ID NO: 1205 |

| Sequence | SEQ ID NO |
|---|---|
| CSQSSCCKPCC | SEQ.ID NO: 1206 |
| CSSSCCQPSCC | SEQ.ID NO: 1207 |
| CTPSCCQPACC | SEQ.ID NO: 1208 |
| CVASCCQPSCC | SEQ.ID NO: 1209 |
| CVPICCCKPVC | SEQ.ID NO: 1210 |
| CVPSCCQPCCH | SEQ.ID NO: 1211 |
| CVPVCCCKPMC | SEQ.ID NO: 1212 |
| CVPVCCCKPVC | SEQ.ID NO: 1213 |
| CVPVCCKPVCC | SEQ.ID NO: 1214 |
| CVSSCCKPQCC | SEQ.ID NO: 1215 |
| CVSSCCQHSCC | SEQ.ID NO: 1216 |
| CVSSCCQPCCH | SEQ.ID NO: 1217 |
| CVSSCCQPCCR | SEQ.ID NO: 1218 |
| CVSSCCQPFCC | SEQ.ID NO: 1219 |
| CVSSCCQPSCC | SEQ.ID NO: 1220 |
| CVSSCCRPQCC | SEQ.ID NO: 1221 |
| CVTRCCSTPCC | SEQ.ID NO: 1222 |
| CVTSCCQPACC | SEQ.ID NO: 1223 |
| CVTSCCQPSCC | SEQ.ID NO: 1224 |
| CVYSCCQPFCC | SEQ.ID NO: 1225 |
| CVYSCCQPSCC | SEQ.ID NO: 1226 |
| CYCPACCVSSC | SEQ.ID NO: 1227 |
| CYKPCCCQSSC | SEQ.ID NO: 1228 |
| CYKPCCCSSGC | SEQ.ID NO: 1229 |
| MCCCVPACSCS | SEQ.ID NO: 1230 |
| NCCVPVCCQCK | SEQ.ID NO: 1231 |
| QCSCCKPCYCS | SEQ.ID NO: 1232 |
| QCSCYKPCCCS | SEQ.ID NO: 1233 |
| SCCVPICCQCK | SEQ.ID NO: 1234 |
| SCCVPVCCQCK | SEQ.ID NO: 1235 |
| SCGCSQCNCCK | SEQ.ID NO: 1236 |
| SCGCSQCSCCK | SEQ.ID NO: 1237 |
| VCCCVPACSCS | SEQ.ID NO: 1238 |
| VCCCVPACSCT | SEQ.ID NO: 1239 |

The present invention is of course in any way restricted to the embodiments herein described and one with ordinary skill in the area can provide many possibilities to modifications and substitutions of technical characteristics by equivalent ones, depending on each situation, as defined in the claims.

The preferred embodiments described above may obviously be combined. The following claims define further preferred embodiments.

---

The invention claimed is:

1. A peptide composition for hair treatment comprising at least one peptide with a sequence length of 6-12 amino acids, where 2-5 of those amino acids are cysteines, and at least one dermatologically adequate excipient, wherein the at least one peptide comprises at least 90% sequence identity to one of the sequences selected from the group consisting of: SEQ.ID NO:75, SEQ.ID NO:412, and SEQ.ID NO:1131, and wherein the at least one dermatologically adequate excipient comprises at least one emulsifier selected from the group consisting of: C10-15 pareth-(2,4,6,8) phosphate, ceteareth-(4-60), cocamidopropyl lauryl ether, deceth-(3-10), DIPA-hydrogenated cocoate, dipentaerythrityl hydroxystearate, dipentaerythrityl hydroxyisostearate, dipentaerythrityl hexacaprate/caprylate, dodoxynol-(5,6,7,9,12), nonoxynol-(1-35), octoxynol-(1-70) and Octyldodeceth-(2, 5,16,20,25).

2. The composition of claim 1, wherein the at least one peptide comprises at least one of the sequences selected from the group consisting of SEQ.ID NO:75; SEQ.ID NO:412; and SEQ.ID NO:1131.

3. The composition of claim 1, wherein the concentration of peptide is between 0.001%-5% (w/w) of the total composition.

4. The composition of claim 1, further comprising at least one of the excipients selected from the group consisting of buffer/s, naturally derived polymer, organic oil, protein, emollient ester, alkanolamide, amine, pH adjustor, salt, aliphatic alcohol, UV filter, amine oxide, chelate, fatty acid, polyethylene glycol (PEG) material, polymer, anti-static agent and alcohol.

5. The composition of claim 1, further comprising at least one surfactant selected from the following list: anionic surfactant, amphoteric surfactant, cationic surfactant or a non-ionic surfactant.

6. The composition of claim 1, further comprising fragrance, oil or any mixture thereof.

7. The composition of claim 1, further comprising a dying agent or dye linked to the N or C terminal of the peptides.

8. The composition of claim 1, formulated as a hair treatment.

9. The composition of claim 1, formulated in a cosmetic, hair coloring agent, hair curl or uncurl agent, shampoo, lotion, serum, cream, conditioner, foam, elixir, oil, aerosol, mask, or combinations thereof.

10. The composition of claim 1, wherein the at least one dermatologically adequate excipient further comprises at least one compound selected from the group consisting of: amodimethicone, trideceth-12, cetrimonium, chloride mixture, behenoxy, dimethicone, cetearyl methicone, cetyl dimethicone, cyclomethicone, cyclopentasiloxane, dimethicone, dimethicone copolyol, dimethiconol, hydrolyzed wheat protein, hydroxypropyl polysiloxane, stearoxy dimethicone, stearyl dimethicone, trimethylsilylamodimethicone, and lauryl methiconecopolyol.

11. The composition of claim 1, wherein the at least one dermatologically adequate excipient further comprises at least one compound selected from the group consisting of: alkylbenzene sulfonates, ammonium lauryl sulfate, ammonium xylenesulfonate, sodium C14-16 olefin sulfonate, sodium cocoyl sarcosinate, sodium laureth sulfate, sodium lauryl sulfate, sodium lauryl sulfoacetate, sodium myreth sulfate, sodium xylenesulfonate, TEA-dodecylbenzenesulfonate, ethyl PEG-15 cocamine sulfate, dioctyl sodium sulfosuccinate, cocamidopropyl betaine, coco betaine, cocoamphoacetate, cocoamphodipropionate, disodium cocoamphodiacetate, disodium cocoamphodipropionate, lauroamphoacetate, sodium cocoyl isethionate, quaternary ammonium compounds, behentrimonium chloride, behentrimonium methosulfate, benzalkonium chloride, betrimonium chloride, binnamidopropyltrimonium chloride, cocotrimonium chloride, dicetyldimonium chloride, dicocodimonium chloride, dihydrogenated tallow dimethylammonium chloride, hydrogenated Palm trimethylammonium chloride, laurtrimonium chloride, quaternium-15, quaternium-18 bentonite, quatemnium-22 hectonite, stearalkonium chloride, tallowtrimonium chloride, ticetyldimonium chloride, decyl glucoside, laureth-10 (lauryl ether 10), laureth-23, Laureth-4, PEG-10 sorbitan laurate, polysorbate-(20, 21, 40, 60, 61, 65, 80, 81), PPG-1 trideceth-6, sorbitol, steareth-(2, 10, 15, 20), C 11-21 pareth-(3-30) and C 12-20 acid PEG-8 ester.

* * * * *